US012692221B2

(12) United States Patent
Nichols

(10) Patent No.: US 12,692,221 B2
(45) Date of Patent: Jul. 28, 2026

(54) 5-METHOXYMETHYL AND 5-HYDROXYMETHYL PHENETHYLAMINES

(71) Applicant: 2A Biosciences, Inc., New York, NY (US)

(72) Inventor: David E. Nichols, Chapel Hill, NC (US)

(73) Assignee: 2A Biosciences, Inc., New York, NY (US)

( * ) Notice: Subject to any disclaimer, the term of this patent is extended or adjusted under 35 U.S.C. 154(b) by 0 days.

(21) Appl. No.: 19/212,649

(22) Filed: May 19, 2025

(65) Prior Publication Data

US 2025/0353808 A1 Nov. 20, 2025

Related U.S. Application Data

(60) Provisional application No. 63/649,104, filed on May 17, 2024.

(51) Int. Cl.

| | |
|---|---|
| ***C07C 217/60*** | (2006.01) |
| ***A61K 31/137*** | (2006.01) |
| ***A61P 25/00*** | (2006.01) |
| ***C07C 215/52*** | (2006.01) |
| ***C07C 217/48*** | (2006.01) |

(52) U.S. Cl.

CPC .......... *C07C 217/60* (2013.01); *A61K 31/137* (2013.01); *A61P 25/00* (2018.01); *C07C 215/52* (2013.01); *C07C 217/48* (2013.01); *C07C 2601/02* (2017.05)

(58) Field of Classification Search

CPC ...... C07C 217/60; A61K 31/137; A61P 25/00

See application file for complete search history.

(56) References Cited

U.S. PATENT DOCUMENTS

| | | | |
|---|---|---|---|
| 2003/0207927 A1 | 11/2003 | Malamas et al. |
| 2008/0045588 A1 | 2/2008 | Gant et al. |
| 2021/0137908 A1 | 5/2021 | Kristensen et al. |

FOREIGN PATENT DOCUMENTS

| | | |
|---|---|---|
| WO | 2015074137 A1 | 5/2015 |
| WO | 2020210823 A1 | 10/2020 |
| WO | 2023010000 | 2/2023 |
| WO | 2023023351 A1 | 2/2023 |
| WO | 2023156453 A1 | 8/2023 |
| WO | 2024010765 A1 | 1/2024 |
| WO | 2024107445 A1 | 5/2024 |
| WO | 2024243599 A1 | 11/2024 |
| WO | 2025059373 A1 | 3/2025 |
| WO | 2025122979 A1 | 6/2025 |

OTHER PUBLICATIONS

PubChem CID 55254859 (created date: Jan. 24, 2012).*

Kanamori et al. A study of the metabolism of methamphetamine and 4-bromo-2,5-dimethoxyphenethylamine (2C-B) in isolated rat hepatocytes. Forensic Sci Int. 2005;148(2-3):131-137.

Kanamori et al. Analysis of 4-bromo-2,5-dimethoxyphenethylamine abuser's urine: identification and quantitation of urinary metabolites. J Forensic Sci. 2013;58(1):279-287.

Kanamori et al. Excretory Profile of 4-Bromo-2,5-dimethoxyphenethylamine (2C-B) in Rat. Journal of Health Science. 2003;49(2):166-169.

Kanamori et al. In vivo metabolism of 4-bromo-2,5-dimethoxyphenethylamine (2C-B) in the rat: identification of urinary metabolites. J Anal Toxicol. 2002;26(2):61-66.

Kim et al. In Vitro Metabolism of 25B-NBF, 2-(4-Bromo-2,5-Dimethoxyphenyl)-N-(2-Fluorobenzyl)ethanamine, in Human Hepatocytes Using Liquid Chromatography Mass Spectrometry. Molecules. 2019;24(4):818.

Klein et al. Investigation of the Structure-Activity Relationships of Psilocybin Analogues. ACS Pharmacol Transl Sci. 2020;4(2):533-542.

Klein et al. Receptor binding profiles and behavioral pharmacology of ring-substituted N,N-diallyltryptamine analogs. Neuropharmacology. 2018;142:231-239.

Kulkarni. Scratching response induced in mice by mescaline and related amphetamine derivatives. Biol Psychiatry. 1973;6(2):177-180.

Lein et al. Genome-wide atlas of gene expression in the adult mouse brain. Nature. 2007;445:168-176.

(Continued)

*Primary Examiner* — Bong-Sook Baek

(74) *Attorney, Agent, or Firm* — CALYX LAW LLP; Graham Pechenik

(57) ABSTRACT

Novel compounds, such as phenethylamines having a 5-methoxymethyl or 5-hydroxymethyl substituent, are provided. In some aspects, pharmaceutical compositions comprising the compounds, methods of synthesizing the compounds, and methods of using such compounds, including their administration to subjects, are also provided. In some aspects, useful features of the compounds include neuromodulatory and/or anti-inflammatory activity, for example via activation of serotonin receptors. In some further aspects, the compounds are useful as therapeutic agents for treating medical conditions, such as psychiatric disorders and inflammatory conditions, including inflammation and inflammatory diseases and disorders.

Formula (1)

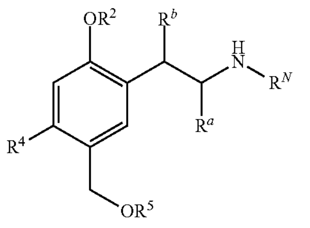

9 Claims, 10 Drawing Sheets

(56) References Cited

OTHER PUBLICATIONS

Leth-Petersen et al. 5-HT2A/5-HT2C Receptor Pharmacology and Intrinsic Clearance of N-Benzylphenethylamines Modified at the Primary Site of Metabolism. ACS Chem Neurosci. 2016;7(11):1614-1619.
Leth-Petersen et al. Metabolic Fate of Hallucinogenic NBOMes. Chemical Research in Toxicology. 2015;29(1).
Letinski et al. Inter-laboratory comparison of water solubility methods applied to difficult-to-test substances. BMC Chem. 2021;15(1):52.
Loewe & Muischnek. Über Kombinationswirkungen. Archiv für Experimentelle Pathologie Und Pharmakologie. 1926;114(5-6):313-326. doi:10.1007/bf01952257.
Loftsson & Hreinsdottir. Determination of aqueous solubility by heating and equilibration: A technical note. AAPS PharmSciTech. 2006;7(1):E29-E32.
Luethi D & Liechti ME, Designer drugs: mechanism of action and adverse effects, Arch. Toxicol., 2020; 94, 1085-133.
Luo et al. Normal Reference Intervals of Neutrophil-To-Lymphocyte Ratio, Platelet-To-Lymphocyte Ratio, Lymphocyte-To-Monocyte Ratio, and Systemic Immune Inflammation Index in Healthy Adults: a Large Multi-Center Study from Western China . Clin Lab. 2019 1;65(3).
Ly et al. Psychedelics Promote Structural and Functional Neural Plasticity. Cell Rep. 2018;23(11):3170-3182.
Ly et al. Transient Stimulation with Psychoplastogens Is Sufficient to Initiate Neuronal Growth. ACS Pharmacol Transl Sci. 2020;4(2):452-460.
Malamas et al. Design and synthesis of aryl diphenolic azoles as potent and selective estrogen receptor-beta ligands. J Med Chem. 2004;47(21):5021-5040.
Mithoefer et al. A Manual for MDMA-Assisted Psychotherapy in the Treatment of Posttraumatic Stress Disorder.; 2015.
Morin et al. Investigating neuronal activity with planar microelectrode arrays: achievements and new perspectives. J Biosci Bioeng. 2005;100(2):131-143.
Nakahara et al. Basics and recent advances in the pathophysiology of atopic dermatitis. J Dermatol. 2021;48(2):130-139.
Nau et al. Serotonin 5-$HT_2$ receptor activation prevents allergic asthma in a mouse model. Am J Physiol Lung Cell Mol Physiol. 2015;308(2):L191-L198.
Nau et al. Serotonin 5-HT2A receptor activation blocks TNF-α mediated inflammation in vivo. PLoS One. 2013;8(10):e75426.
NCT04747808. Study of LL-BMT1 in Patients With Elevated Intraocular Pressure. MediPrint Ophthalmics, Inc. Jun. 8, 2022.
Nichols CD. Serotonin 5-HT2A Receptor Function as a Contributing Factor to Both Neuropsychiatric and Cardiovascular Diseases. Cardiovasc Psychiatry Neurol. 2009:475108.
Nichols DE, Psychedelics, Pharmacological Reviews, 2016; 68(2):264-355.
Nichols. Psychedelics as potent anti-inflammatory therapeutics. Neuropharmacology. 2022;219:109232.
Obien et al. Revealing neuronal function through microelectrode array recordings. Front Neurosci. 2015;8:423.
Olson. Psychoplastogens: A Promising Class of Plasticity-Promoting Neurotherapeutics. J Exp Neurosci. 2018;12:1179069518800508.
Petry et al. "Prize reinforcement contingency management for cocaine dependence: integration with group therapy in a methadone clinic." Journal of consulting and clinical psychology. 2005;73(2):354.
Renert-Yuval. Biomarkers in atopic dermatitis—a review on behalf of the International Eczema Council. J Allergy Clin Immunol. 2021;147(4):1174-1190.e1.
Richardson et al. Efficiency in Drug Discovery: Liver S9 Fraction Assay as a Screen for Metabolic Stability. Drug Metab Lett. 2016;10(2):83-90.
Rohsenhow et al, Brief coping skills treatment for cocaine abuse: 12-month substance use outcomes. J. Consul. Clin. Psychol. 2000; 68(3): 515-2.
Schenberg EE, Psychedelic-Assisted Psychotherapy: A Paradigm Shift in Psychiatric Research and Development. Frontiers in Pharmacology, 2018;9:733.
Seggel et al. A structure-affinity study of the binding of 4-substituted analogs of 1-(2,5-dimethoxyphenyl)-2-aminopropane at 5-HT2 serotonin receptors. Journal of Medicinal Chemistry. 1990;33(3).
Shulgin & Shulgin. Pihkal: A Chemical Love Story, 1992 Transform Press, Berkeley CA.
Shulgin & Shulgin. Tihkal: The Continuation, 1997 Transform Press.
Sroka-Tomaszewska & Trzeciak. Molecular Mechanisms of Atopic Dermatitis Pathogenesis. Int J Mol Sci. 2021;22(8):4130.
Stefulj et al. mRNA expression of serotonin receptors in cells of the immune tissues of the rat. Brain Behav Immun. 2000;14(3):219-224.
Stotts et al. Motivational interviewing with cocaine-dependent patients: a pilot study. J Consult Clin Psychol. Oct. 2001;69(5):858-62.
Szabo & Slavish. Measuring salivary markers of inflammation in health research: A review of methodological considerations and best practices. Psychoneuroendocrinology. 2021;124:105069.
Thakur et al. QSAR studies on psychotomimetic phenylalkylamines. Bioorganic & Medicinal Chemistry. 2004;12(4):825-831.
Theobald et al. Studies on the toxicological detection of the designer drug 4-bromo-2,5-dimethoxy-beta-phenethylamine (2C-B) in rat urine using gas chromatography-mass spectrometry. J Chromatogr B Analyt Technol Biomed Life Sci. 2007;846(1-2):374-377.
Toro-Sazo et al. 5-HT2 receptor binding, functional activity and selectivity in N-benzyltryptamines. PLoS One. 2019;14(1):e0209804.
Vaidyanathan et al. Persistent Corneal Epithelial Defects: A Review Article. Med Hypothesis Discov Innov Ophthalmol. 2019;8(3):163-176.
Watanabe & Arumugam. Japanese Kampo medicines for the treatment of common diseases: Focus on inflammation. Academic Press; 2017.
Wollenberg et al. Immunological and molecular targets of atopic dermatitis treatment. Br J Dermatol. 2014;170 Suppl 1:7-11.
Yu et al. Serotonin 5-hydroxytryptamine(2A) receptor activation suppresses tumor necrosis factor-alpha-induced inflammation with extraordinary potency. J Pharmacol Exp Ther. 2008;327(2):316-323.
Zhang et al. Cytokines, inflammation, and pain. Int Anesthesiol Clin. 2007;45(2):27-37.
Adams et al. Contingency management for patients with cooccurring disorders: evaluation of a case study and recommendations for practitioners. Case Rep Psychiatry. 2012;2012:731638.
Ahmad et al. Photostability and Photostabilization of Drugs and Drug Products. International Journal of Photoenergy. 2016;8135609:19.
Ahmed. An overview of inflammation: mechanism and consequences. Frontier in Biology. 2011;6:274-281.
Ahn et al. Recent advances in atopic dermatitis. Curr Opin Immunol. 2020;66:14-21.
Allain et al. In-Use Photostability Practice and Regulatory Evaluation for Pharmaceutical Products in an Age of Light-Emitting Diode Light Sources. J Pharm Sci. 2019;108(3):1172-1176.
Armstrong R. What causes neurodegenerative disease?. Folia Neuropathol. 2020;58(2):93-112.
Barry et al. Comparable efficacy of contingency management for cocaine dependence among African American, Hispanic, and White methadone maintenance clients. Psychol Addict Behav. 2009;23(1):168-174.
Beck et al. Type 2 Inflammation Contributes to Skin Barrier Dysfunction in Atopic Dermatitis. JID Innov. 2022;2(5):100131.
Berankova et al. Distribution profile of 2,5-dimethoxy-4-bromoamphetamine (DOB) in rats after oral and subcutaneous doses. Forensic Sci Int. 2007;170(2-3):94-99.
Berankova et al. Study on metabolites of 2,5-dimethoxy-4-bromamphetamine (DOB) in human urine using gas chromatography-mass spectrometry. Biomed Pap Med Fac Univ Palacky Olomouc Czech Repub. 2005;149(2):465-468.
Beuerle et al. Three-dimensional Quantitative Structure-Activity Relationships of Hallucinogenic Phenylalkanamine and Tryptamine

(56) References Cited

OTHER PUBLICATIONS

Derivatives: Studies using Comparative Molecular Field Analysis (CoMFA). Quantitative Structure-Activity Relationships. 1997;16(6):447-458.
Bitch et al. Determining the water solubility of difficult-to-test substances: A tutorial review. Anal Chim Acta. 2019;1086:16-28.
Bourne et al. Causes of vision loss worldwide, 1990-2010: a systematic analysis. Lancet Glob Health. 2013;1(6):e339-e349.
Calder et al. A consideration of biomarkers to be used for evaluation of inflammation in human nutritional studies. Br J Nutr. 2013;109 Suppl 1:S1-S34.
Chou & Talalay. Quantitative analysis of dose-effect relationships: the combined effects of multiple drugs or enzyme inhibitors. Adv Enzyme Regul. 1984;22:27-55.
Cloez-Tayarani et al. Differential effect of serotonin on cytokine production in lipopolysaccharide-stimulated human peripheral blood mononuclear cells: involvement of 5-hydroxytryptamine2A receptors. Int Immunol. 2003;15(2):233-240.
Coelho et al. Photostabilization strategies of photosensitive drugs. Int J Pharm. 2018;541(1-2):19-25.
Crits-Christoph et al. Psychosocial treatments for cocaine dependence: National Institute on Drug Abuse Collaborative Cocaine Treatment Study. Arch Gen Psychiatry. 1999;56(6):493-502.
De Jager et al. Ultraviolet Light Induced Generation of Reactive Oxygen Species. Adv Exp Med Biol. 2017;996:15-23.
De La Fuente et al. Automated quantification of head-twitch response in mice via ear tag reporter coupled with biphasic detection. J Neurosci Methods. Published online Jan. 16, 2020.
De La Fuente et al. Fully automated head-twitch detection system for the study of 5-HT2A receptor pharmacology in vivo. Sci Rep. 2019;9(1):14247.
Dean et al. 2C or not 2C: phenethylamine designer drug review. J Med Toxicol. 2013;9(2):172-178.
Djuric et al. Genetically transmitted cholinergic hyperresponsiveness predisposes to experimental asthma. Brain Behav Immun. 1998;12(4):272-284.
Dugger & Dickson. Pathology of Neurodegenerative Diseases. Cold Spring Harb Perspect Biol. 2017;9(7):a028035. Published Jul. 5, 2017. doi:10.1101/cshperspect.a028035.
Fallon et al. A homozygous frameshift mutation in the mouse Flg gene facilitates enhanced percutaneous allergen priming. Nat Genet. 2009;41(5):602-608.
Flanagan & Nichols. Psychedelics as anti-inflammatory agents. Int Rev Psychiatry. 2018;30(4):363-375.
Flanagan et al. Nichols CD. 5-HT2 receptor activation alleviates airway inflammation and structural remodeling in a chronic mouse asthma model. Life Sci. 2019;236:116790.
Flanagan et al. Serotonin-2 Receptor Agonists Produce Anti-inflammatory Effects through Functionally Selective Mechanisms That Involve the Suppression of Disease-Induced Arginase 1 Expression. ACS Pharmacol Transl Sci. 2024;7(2):478-492.
Flanagan et al. Structure-Activity Relationship Analysis of Psychedelics in a Rat Model of Asthma Reveals the Anti-Inflammatory Pharmacophore. ACS Pharmacol Transl Sci. 2020;4(2):488-502.
Foster et al. Virus-induced serotonin production correlates with severity of inflammation-associated ocular disease: Therapeutic potential of 5HT2A receptor agonists. ARVO Annual Meeting Abstract. 2020;61(7):429.
Franco & De Marco. Contact Lenses as Ophthalmic Drug Delivery Systems: A Review. Polymers. 2021;13(7):1102.
Fung et al. Local delivery of corticosteroids in clinical ophthalmology: A review. Clin Exp Ophthalmol. 2020;48(3):366-401.
Furue et al. Pathogenesis of Atopic Dermatitis: Current Paradigm. Iran J Immunol. 2019;16(2):97-107.
Germolec et al. Markers of Inflammation. Methods Mol Biol. 2018;1803:57-79.
Ghasemi et al. Roles of IL-8 in ocular inflammations: a review. Ocul Immunol Inflamm. 2011;19(6):401-412.
Ghasemi. Roles of IL-6 in Ocular Inflammation: A Review. Ocul Immunol Inflamm. 2018;26(1):37-50.
Glatfelter et al. Automated Computer Software Assessment of 5-Hydroxytryptamine 2A Receptor-Mediated Head Twitch Responses from Video Recordings of Mice. ACS Pharmacol Transl Sci. 2022;5(5):321-330.
Glennon & Seggel. Interaction of Phenylisopropylamines with Central 5-HT2 Receptors. ACS Symposium Series. 1989;18:264-280.
Glennon R, Arylalkylamine Drugs of Abuse: An Overview of Drug Discrimination Studies, Pharmacology Biochemistry and Behavior, 1999; 64, 251-56.
Grob CS & Grigsby J, Handbook of Medical Hallucinogens, 2021.
Halberstadt & Geyer. Characterization of the head-twitch response induced by hallucinogens in mice: detection of the behavior based on the dynamics of head movement. Psychopharmacology (Berl). 2013;227(4):727-739.
Halberstadt et al. Differential contributions of serotonin receptors to the behavioral effects of indoleamine hallucinogens in mice. J Psychopharmacol. 2011;25(11):1548-1561.
Halberstadt et al. Pharmacological characterization of the LSD analog N-ethyl-N-cyclopropyl lysergamide (ECPLA) [published correction appears in Psychopharmacology (Berl). Nov. 15, 2018;:]. Psychopharmacology (Berl). 2019;236(2):799-808.
Hamelmann et al. Noninvasive measurement of airway responsiveness in allergic mice using barometric plethysmography. Am J Respir Crit Care Med. 1997;156(3 Pt 1):766-775.
Holford & Sheiner. Understanding the dose-effect relationship: clinical application of pharmacokinetic-pharmacodynamic models. Clin Pharmacokinet. 1981;6(6):429-453.
Huang et al. Isobologram Analysis: A Comprehensive Review of Methodology and Current Research. Front Pharmacol. Oct. 29, 2019;10:1222.
Hutcheson et al. Serotonin receptors and heart valve disease—it was meant 2B. Pharmacol Ther. 2011;132(2):146-157.
ICH Harmonised Tripartite Guideline. Stability Testing: Photostability Testing of New Drug Substances and Products Q1B. Nov. 6, 1996.
Johnson et al. Human hallucinogen research: guidelines for safety. J Psychopharmacol. 2008;22(6):603-620.
Kanamori et al. A model system for prediction of the in vivo metabolism of designer drugs using three-dimensional culture of rat and human hepatocytes. Forensic Toxicology. 2011;29:142-151.
Henry et al. Can light absorption and photostability data be used to assess the photosafety risks in patients for a new drug molecule?. J Photochem Photobiol B. 2009;96(1):57-62.
US Food and Drug Administration. S10 photosafety evaluation of pharmaceuticals: guidance for industry. Silver Spring, MD: US Food and Drug Administration; Jan. 2015.
Wallach et al. Identification of 5-HT2A receptor signaling pathways associated with psychedelic potential. Nat Commun. 2023;14(1):8221.
Chemical Abstract Service. Database accession No. 1380139-24-1. Jul. 3, 2025.
Chemical Abstract Service. Database accession No. 1551614-14-2. Jul. 3, 2025.
Chemical Abstract Service. Database accession No. 1898274-23-1. Jul. 3, 2025.
Chemical Abstract Service. Database accession No. 2110281-24-6. Jul. 3, 2025.
Chemical Abstract Service. Database accession No. 2185527-15-3. Jul. 3, 2025.
Chemical Abstract Service. Database accession No. 2383762-58-9. Jul. 3, 2025.
Chemical Abstract Service. Database accession No. 2384025-73-2. Jul. 3, 2025.
Chemical Abstract Service. Database accession No. 3088642-63-8. Jul. 3, 2025.
PCT/US2025/030080. International Search Report Sep. 9, 2025.
PCT/US2025/030080. Search Strategy. Sep. 9, 2025.
PCT/US2025/030080. Written Opinion of the International Searching Authority. Sep. 9, 2025.

* cited by examiner

5-METHOXYMETHYL AND 5-HYDROXYMETHYL PHENETHYLAMINES

CROSS-REFERENCE

Priority is claimed under PCT Article 8(1) and Rule 4.10 to U.S. Provisional Application No. 63/649,104, filed May 17, 2024 and hereby incorporated by reference in its entirety for all purposes.

FIELD OF THE INVENTION

This disclosure relates to novel compounds, such as phenethylamines having a 5-methoxymethyl or 5-hydroxymethyl substituent. It also relates to compositions of the compounds, methods of synthesizing the compounds, and methods of using such compounds, including their administration to subjects. In some aspects, useful features of the compounds include neuromodulatory and/or anti-inflammatory activity, for example via activation of serotonin receptors. In some aspects, the compounds are useful as therapeutic agents for treating medical conditions, such as psychiatric disorders and inflammatory conditions.

BACKGROUND OF THE INVENTION

Psychedelics such as psilocybin and LSD, and entactogens such as MDMA, are being investigated for various medical uses, owing to their psychedelic, anxiolytic, and antidepressant effects. Beyond mental health, psychedelics and related serotonin receptor agonists may also hold promise for treating inflammatory conditions, especially neuroinflammation associated with neurological and neurodegenerative diseases. However, there remains an ongoing need for novel therapeutic compounds capable of treating a broad range of indications, especially chronic inflammatory and neuroinflammatory conditions that lack effective and well-tolerated treatments, and of avoiding the drawbacks of current therapies, like generalized immunosuppression.

Provided herein are compounds, compositions, methods, uses, and kits to meet these needs and others, having such advantages and improvements as will become readily apparent through the disclosure.

INCORPORATION BY REFERENCE

Each cited patent, publication, and non-patent literature is incorporated by reference in its entirety, as if each was incorporated by reference individually, and as if each is fully set forth herein. However, no such citation is as an admission that a cited reference comes from an area that is analogous or directly applicable to the invention, nor should any citation be construed as an admission that a document or underlying information, in any jurisdiction, is prior art or is part of the common general knowledge in the art.

BRIEF SUMMARY OF THE INVENTION

The following presents a simplified summary of some embodiments of the invention in order to provide a basic understanding thereof. It is not an extensive overview of the invention nor intended to identify key or critical elements of the invention or to delineate its full scope. Its sole purpose is to present some embodiments of the invention in a simplified form as a prelude to the more detailed description that is presented later.

In some aspects are provided compounds of Formula (1):

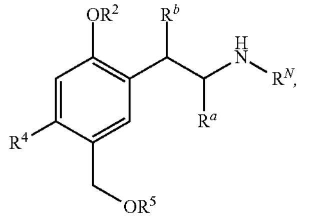

(1)

wherein: $R^2$ is H or $C_1$-$C_6$ alkyl; $R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or $-(CH_2)_{0\text{-}3}-C(O)-O-C_1$-$C_6$ alkyl; $R^5$ is H or $C_1$-$C_6$ alkyl; and $R^N$ is H or $-CH_2-Ar$; wherein Ar is 6- to 12-membered heterocyclyl or $C_6$-$C_{12}$ aryl optionally substituted by F, Cl, Br, I, OH, $C_1$-$C_6$ alkoxy, or phenyl; and $R^a$ is H or $C_1$-$C_6$ alkyl, and $R^b$ is H; or $R^a$ and $R^b$ together with the intervening atoms form a 3- to 6-membered cycloalkyl; or $R^N$ and $R^b$ together with the intervening atoms form a 4- to 8-membered heterocyclyl, and $R^a$ is H or $C_1$-$C_6$ alkyl; or a pharmaceutically acceptable salt, stereoisomer, hydrate, solvate, or isotopic derivative thereof.

In some embodiments of the compound of Formula (1), $R^2$ is H. In some embodiments of the compound of Formula (1), $R^2$ is $C_1$-$C_6$ alkyl. In some embodiments of the compound of Formula (1), $R^2$ is methyl. In some embodiments of the compound of Formula (1), $R^5$ is H. In some embodiments of the compound of Formula (1), $R^5$ is $C_1$-$C_6$ alkyl. In some embodiments of the compound of Formula (1), $R^5$ is methyl. In some embodiments of the compound of Formula (1), $R^a$ is H. In some embodiments of the compound of Formula (1), $R^a$ is $C_1$-$C_6$ alkyl. In some embodiments of the compound of Formula (1), $R^a$ is methyl. In some embodiments of the compound of Formula (1), $R^a$ is ethyl. In some embodiments of the compound of Formula (1), $R^4$ is F, Cl, Br, or I. In some embodiments of the compound of Formula (1), $R^4$ is Br. In some embodiments of the compound of Formula (1), $R^4$ is I. In some embodiments of the compound of Formula (1), $R^4$ is $C_1$-$C_6$ alkyl. In some embodiments of the compound of Formula (1), $R^4$ is ethyl. In some embodiments of the compound of Formula (1), $R^4$ is isobutyl. In some embodiments of the compound of Formula (1), $R^4$ is $-(CH_2)_{0\text{-}3}-C(O)-O-C_1$-$C_6$ alkyl. In some embodiments of the compound of Formula (1), $R^4$ is $-CH_2COOCH_3$. In some embodiments of the compound of Formula (1), $R^4$ is $-CH_2COOCH_2CH_3$. In some embodiments of the compound of Formula (1), $R^4$ is $C_1$-$C_6$ alkenyl. In some embodiments of the compound of Formula (1), $R^4$ is allyl. In some embodiments of the compound of Formula (1), $R^4$ is $C_1$-$C_6$ alkynyl. In some embodiments of the compound of Formula (1), $R^4$ is propargyl. In some embodiments of the compound of Formula (1), $R^N$ is H. In some embodiments of the compound of Formula (1), $R^N$ is $-CH_2-Ar$.

(2)

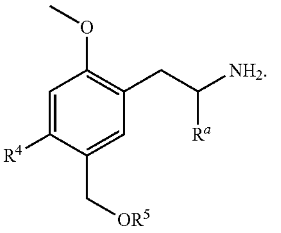

In some further aspects are provided compounds of Formula (2):

In some further aspects are provided compounds of Formula (3):

(3)

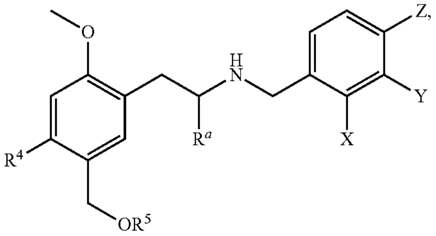

wherein: X, Y, and Z are each independently H, F, Cl, Br, I, OH, $C_1$-$C_6$ alkoxy, or phenyl; or X and Y are taken together to form a 4- to 6-membered heterocyclyl, and Z is H, F, Cl, Br, I, OH, $C_1$-$C_6$ alkoxy, $C_3$-$C_6$ cycloalkyl, or phenyl; or Y and Z are taken together to form a 4- to 6-membered heterocyclyl, and X is H, F, Cl, Br, I, OH, $C_1$-$C_6$ alkoxy, $C_3$-$C_6$ cycloalkyl, or phenyl.

In some embodiments of the compound of Formula (3), X is OH. In some embodiments of the compound of Formula (3), X is methoxy. In some embodiments of the compound of Formula (3), X is F, Cl, Br, or I. In some embodiments of the compound of Formula (3), X is phenyl. In some embodiments of the compound of Formula (3), X is $C_3$-$C_6$ cycloalkyl. In some embodiments of the compound of Formula (3), X is cyclopropyl. In some embodiments of the compound of Formula (3), X and Z are H. In some embodiments of the compound of Formula (3), X and Y are taken together to form

(methylenedioxy), wherein * and ** indicate the points of connection between X and the rest of the compound, and between Y and the rest of the compound, respectively.

In some embodiments of the compound of Formula (3), X and Y are taken together to form a dihydrofuranyl. In some embodiments of the compound of Formula (3), X and Y are taken together to form

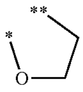 or 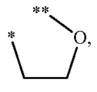, wherein * and ** indicate the points of connection between X and the rest of the compound, and between Y and the rest of the compound, respectively. In some embodiments of the compound of Formula (3), X and Y are taken together to form a furanyl. In some embodiments of the compound of Formula (3), X and Y are taken together to form

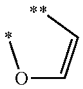 or 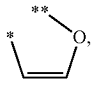, wherein * and ** indicate the points of connection between X and the rest of the compound, and Y and the rest of the compound, respectively.

In some embodiments, the compound has the structure of Formula (I):

(I)

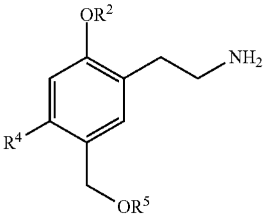

In some embodiments of the compound of Formula (I), $R^2$ is H or methyl. In some embodiments of the compound of Formula (I), $R^5$ is H or methyl. In some embodiments of the compound of Formula (I), $R^4$ is F, Cl, Br, or I. In some embodiments of the compound of Formula (I), $R^4$ is $C_1$-$C_6$ alkyl.

In some embodiments, the compound has the structure of any of Formulas (IV), (VII), (XX), and ((XI):

(IV)

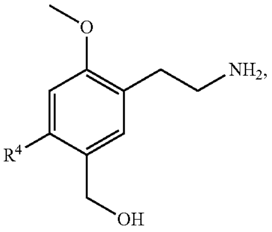

(VII)

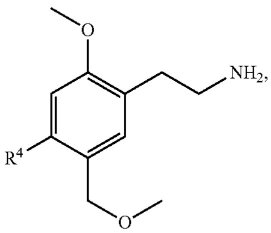

-continued (XX)

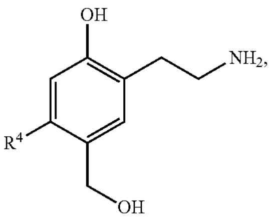

and (XXI)

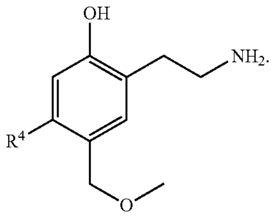

In some embodiments of the compound of any of Formulas (IV), (VII), (XX), and (XXI), $R^4$ is Br.

In some embodiments of the compound of any of Formulas (IV), (VII), (XX), and (XXI), $R^4$ is isobutyl.

In some embodiments, the compound has the structure:

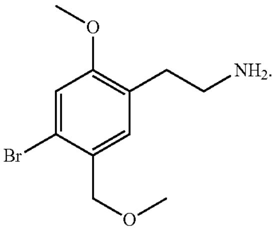

In some embodiments, the compound has the structure:

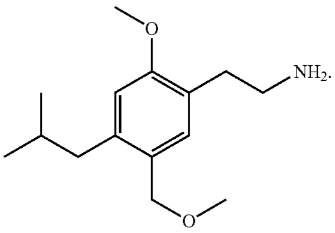 [SMILES: COCc1cc(CCN)c(OC)cc1CC(C)C]

In some embodiments, the compound has the structure:

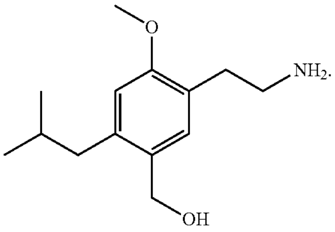 [SMILES: COc1cc(CC(C)C)c(CO)cc1CCN]

In some embodiments, the compound has the structure:

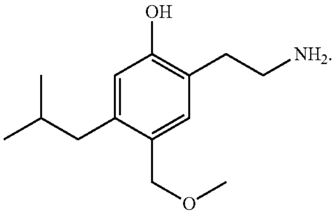 [SMILES: COCc1cc(CCN)c(O)cc1CC(C)C]

In some embodiments, the compound is selected from the compounds in Table 1 herein.

In some embodiments, the compound is selected from the compounds defined herein as Group A.

In some embodiments, the compound is selected from the compounds defined herein as Group B.

In some embodiments, the compound is selected from the compounds defined herein as Group C.

In some further aspects are provided pharmaceutical compositions comprising a therapeutically effective amount of the compound of claim 1, and a pharmaceutically acceptable carrier, diluent, or excipient. In some embodiments, the composition is suitable for oral, buccal, sublingual, intranasal, injectable, subcutaneous, intravenous, topical, transdermal, ocular, ophthalmic, intraocular, or periocular administration. In embodiments, the composition is in a unit dosage form. In some embodiments, the composition comprises the compound in a total amount of between about 0.01 and about 100 mg. In some embodiments, the composition is formulated for topical or ophthalmic administration. In some embodiments, the composition is formulated for topical administration. In some embodiments, the composition is formulated for ophthalmic administration.

In some embodiments, the composition is formulated as an aerosol, emulsion, spray, ointment, salve, gel, paste, lotion, liniment, oil, or cream. In some embodiments, the composition comprises one or more pharmaceutically acceptable excipients selected from the group consisting of penetration enhancers, carriers, diluents, emulsifiers, stabilizers, solvents and cosolvents, viscosity modifying agents (e.g., thickeners), adhesion modifying agents (e.g., tackifiers), preservatives, antioxidants, adhesive polymers, solubilizing agents, colorants, binders, humectants, surfactants, and gelling agents. In embodiments, the composition further comprises a therapeutically effective amount of an additional active compound, or a pharmaceutically acceptable salt, stereoisomer, hydrate, solvate, or isotopic derivative thereof.

In further aspects are provided methods of modulating neurotransmission, increasing neuroplasticity, and/or treating a medical condition in a subject, comprising administering to the subject a disclosed compound or pharmaceutical composition. In some further aspects are provided methods of modulating neurotransmission in a subject, comprising administering to the subject a disclosed compound or pharmaceutical composition. In some further aspects are provided methods of increasing neuroplasticity in a subject, comprising administering to the subject a disclosed compound or pharmaceutical composition. In some further aspects are provided methods of treating a medical condition in a subject, comprising administering to the subject a disclosed compound or pharmaceutical composition. In some embodiments, the medical condition is a disorder linked to dysregulation or inadequate functioning of serotonergic neurotransmission. In some embodiments, the medical condition is a mental, behavioral, or neurodevelopmental disorder. In some embodiments, the medical condition is inflammation or an inflammatory disorder. In embodiments, the medical condition is an ophthalmic disorder. In embodiments, the ophthalmic disorder is an inflammatory disorder. In embodiments, the medical condition is a neurodegenerative disorder.

In some further aspects are provided compounds and compositions for use in modulating neurotransmission, increasing neuroplasticity, and/or treating a medical condition. In some further aspects are provided the use of the disclosed compounds and compositions for the manufacture of a medicament for modulating neurotransmission, increasing neuroplasticity, and/or treating a medical condition.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims. The headings herein are used only to facilitate review by a reader. They should not be construed as limiting the disclosure in any manner.

BRIEF DESCRIPTION OF THE FIGURES

To further clarify various aspects of the invention, certain exemplary embodiments are illustrated in the figures. The figures depict only illustrated embodiments of the invention and should not be considered limiting of its scope. Certain aspects of the invention are therefore further described and explained with additional specificity and detail, but still by way of example only, with reference to the accompanying figures in which.

DETAILED DESCRIPTION OF THE INVENTION

Figure 1A:
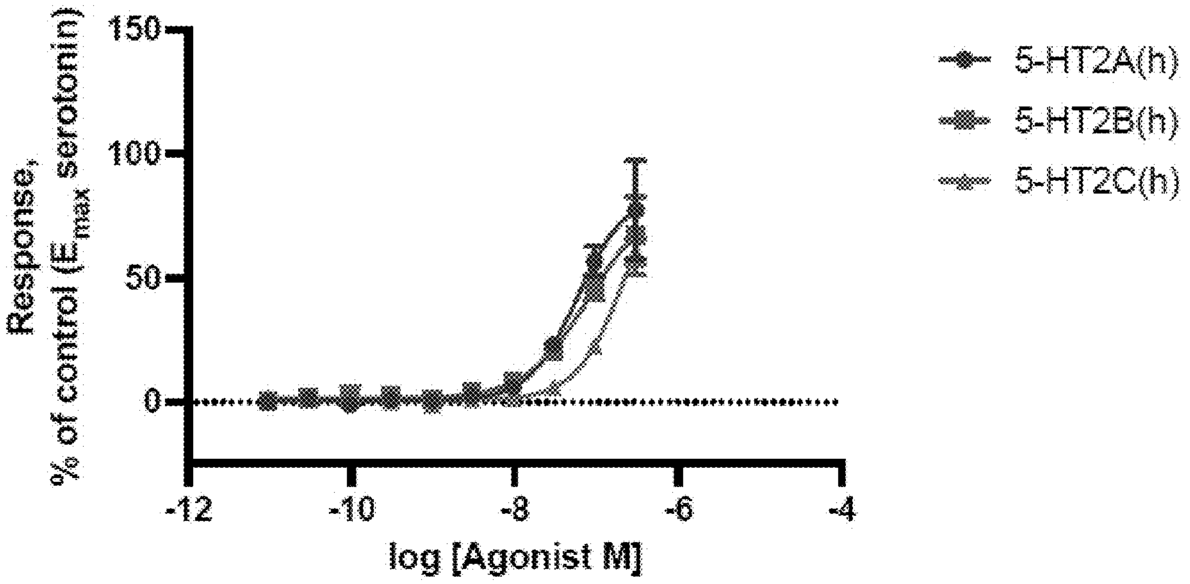
FIG. 1A shows the dose-response curve for inositol monophosphate (IP-1) accumulation induced by exemplary compound 2CB-5MM (Compound 4) at human serotonin (5-HT) receptor subtypes 5-$HT_{2A}$, 5-$HT_{2B}$, and 5-$HT_{2C}$, as described in Example 6.
Figure 1B:
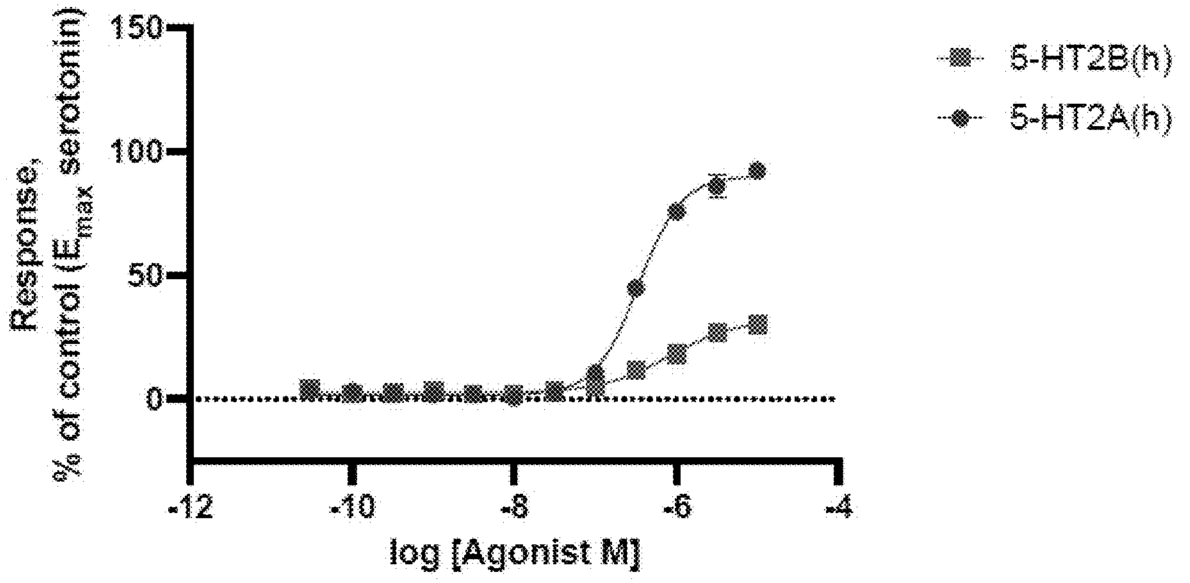
FIG. 1B shows the dose-response curve for IP-1 accumulation induced by exemplary compound 2CIB-5MM (Compound 8) at human 5-HT receptor subtypes 5-$HT_{2A}$ and 5-$HT_{2B}$, as described in Example 6.
Figure 1C:
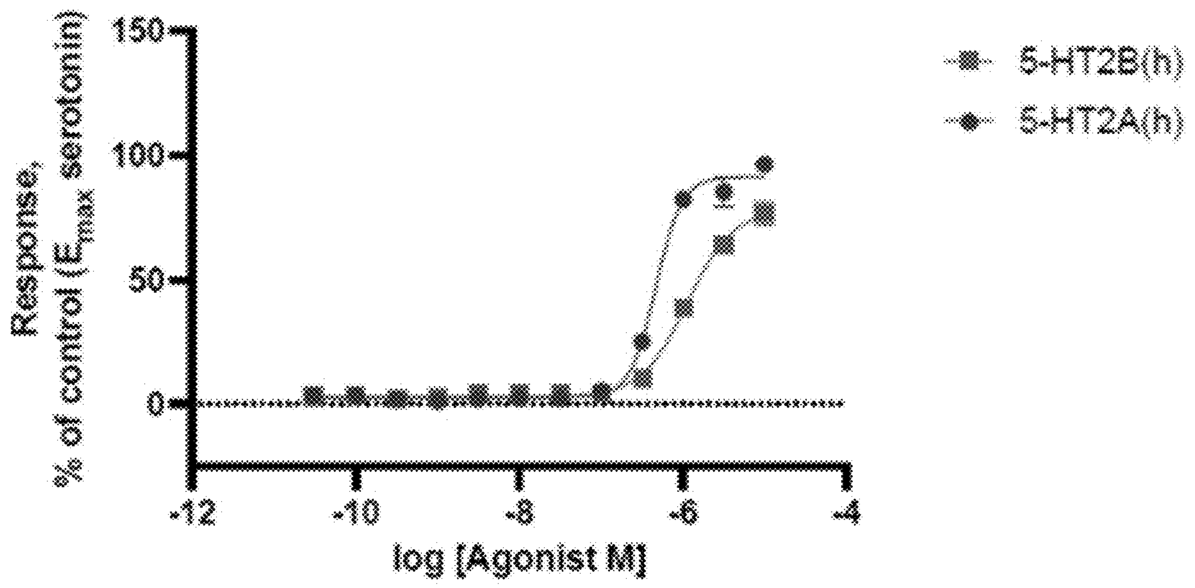
FIG. 1C shows the dose-response curve for IP-1 accumulation induced by exemplary compound 2CIB-5HM (Compound 26) at human 5-HT receptor subtypes 5-$HT_{2A}$ and 5-$HT_{2B}$, as described in Example 6.
Figure 1D:
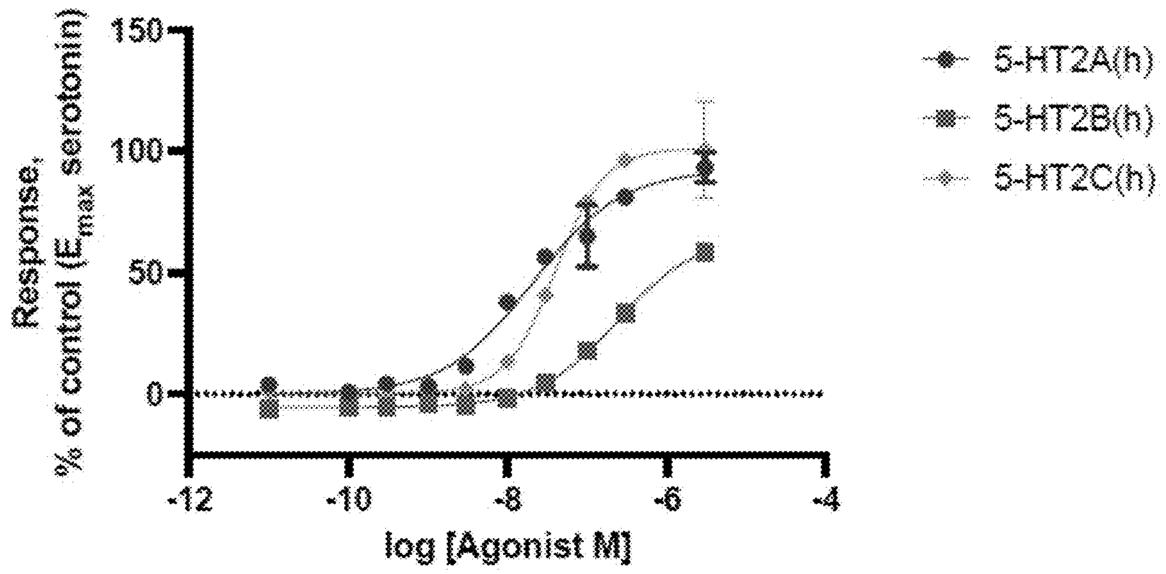
FIG. 1D shows the dose-response curve for IP-1 accumulation induced by reference compound 2C-B at human serotonin receptor subtypes 5-$HT_{2A}$, 5-$HT_{2B}$, and 5-$HT_{2C}$, as described in Example 6.
Figure 1E:
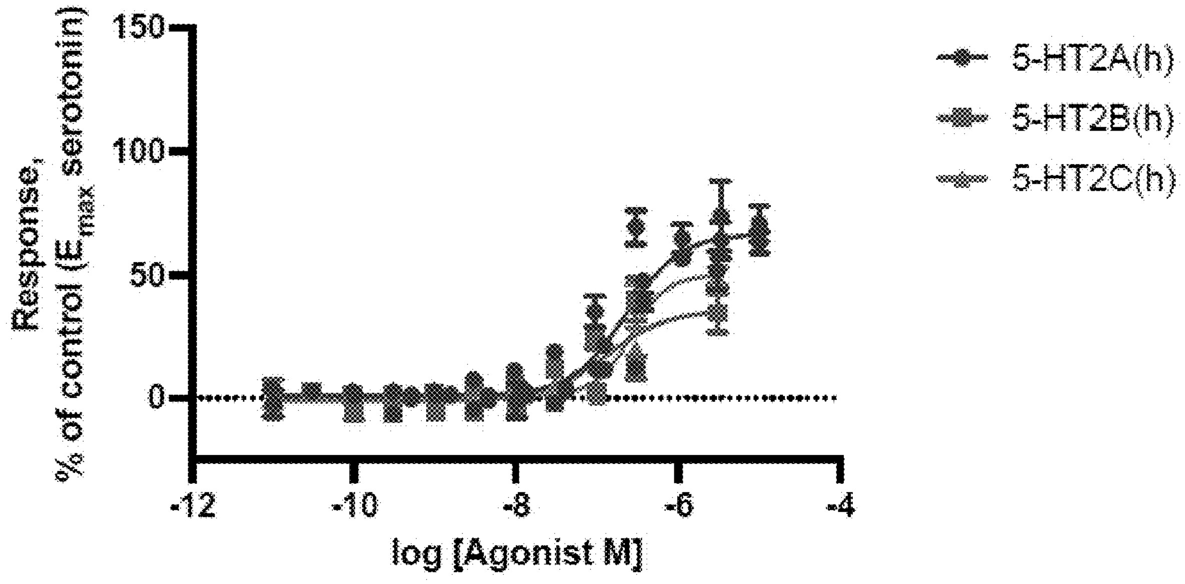
FIG. 1E shows the dose-response curve for IP-1 accumulation induced by reference compound 2CB-5ME at human serotonin receptor subtypes 5-$HT_{2A}$, 5-$HT_{2B}$, and 5-$HT_{2C}$, as described in Example 6.
Figure 2A:
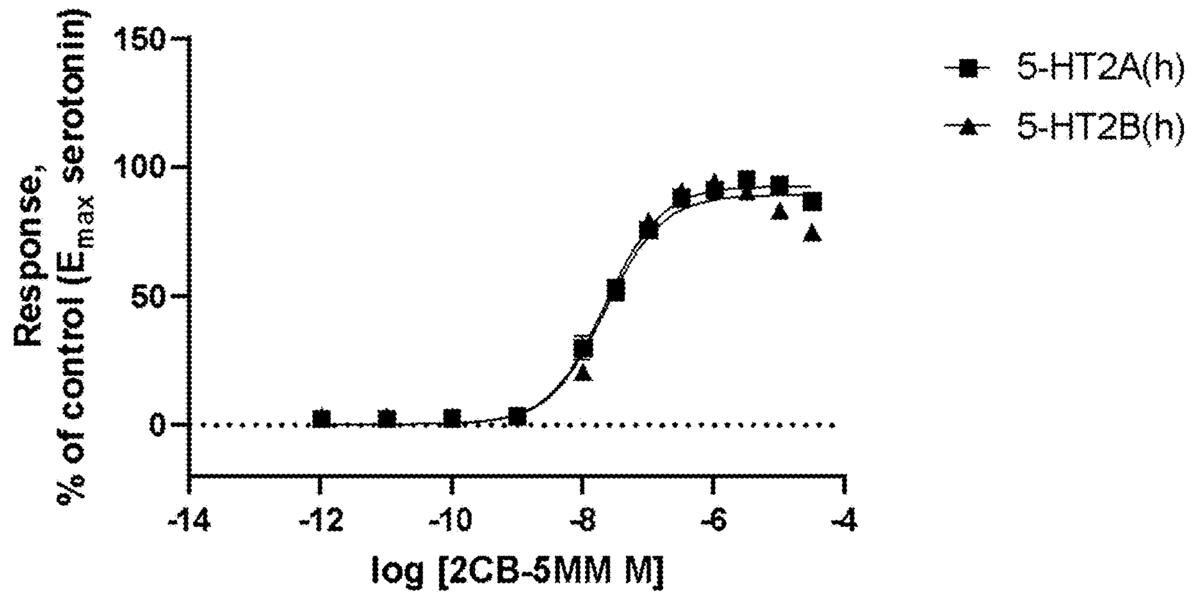
FIG. 2A shows the dose-response curve from a cell-based agonist calcium flux assay for exemplary compound 2CB-5MM at 5-$HT_{2A}$ and 5-$HT_{2B}$, as described in Example 7.
Figure 2B:
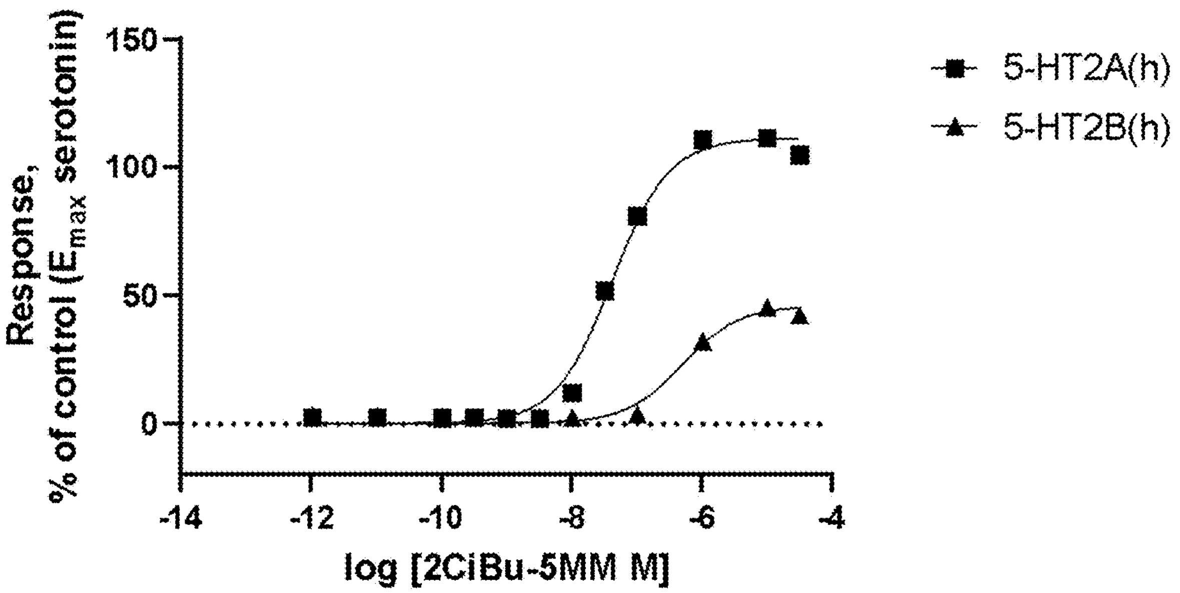
FIG. 2B shows the dose-response curve from a cell-based agonist calcium flux assay for exemplary compound 2C-iBU-5MM at 5-$HT_{2A}$ and 5-$HT_{2B}$, as described in Example 7.
Figure 2C:
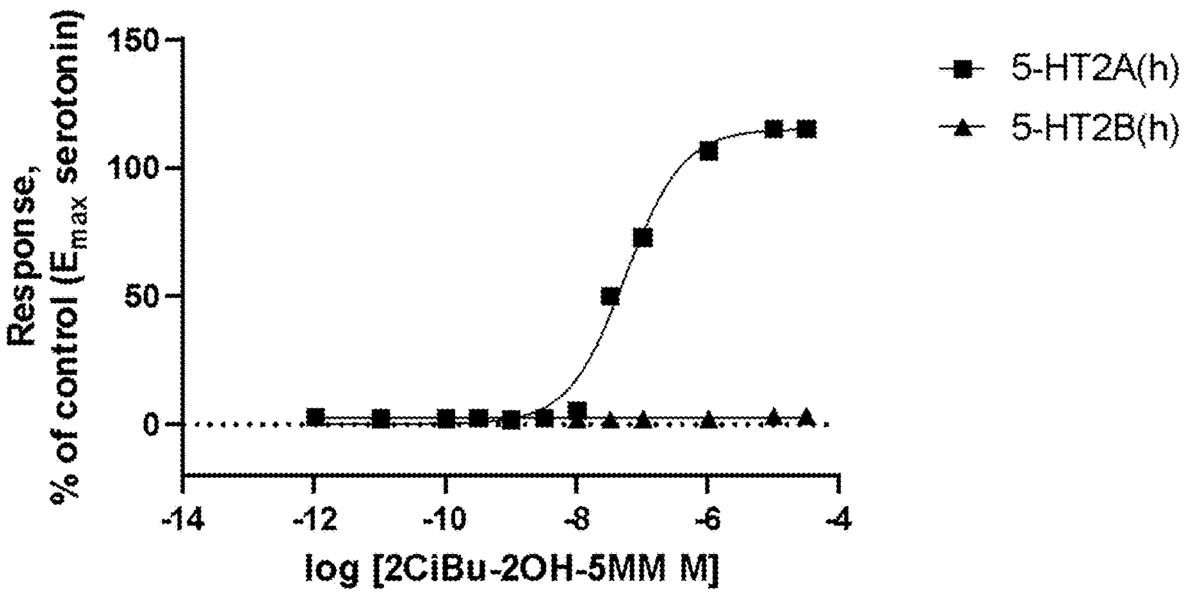
FIG. 2C shows the dose-response curve from a cell-based agonist calcium flux assay for exemplary compound 2C-iBU-2OH-5MM at 5-$HT_{2A}$ and 5-$HT_{2B}$, as described in Example 7.
Figure 2D:
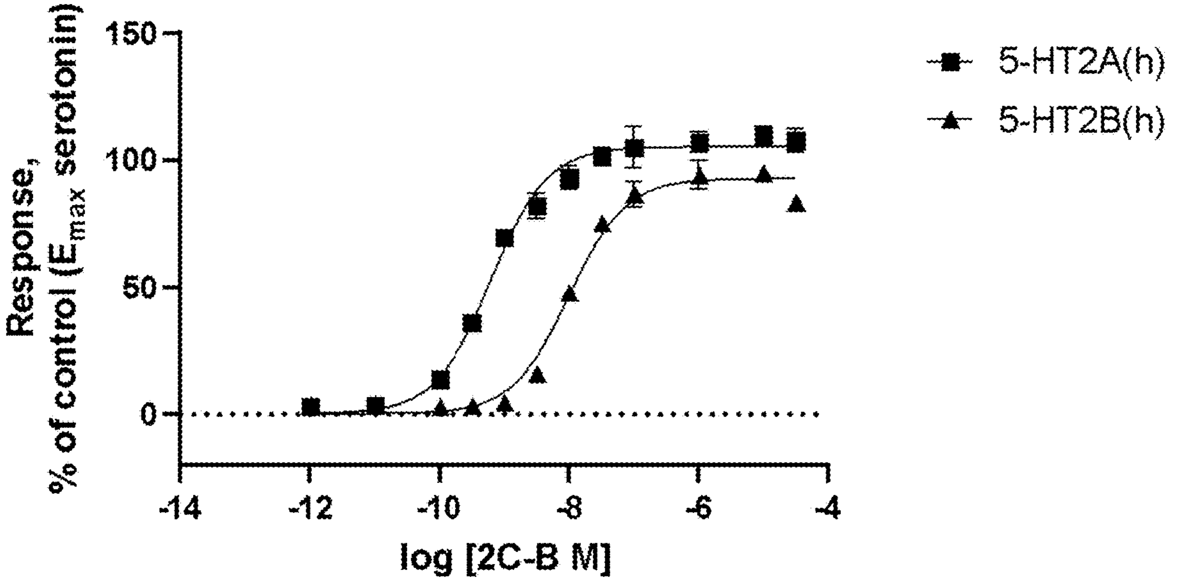
FIG. 2D shows the dose-response curve from a cell-based agonist calcium flux assay for reference compound 2C-B at 5-$HT_{2A}$ and 5-$HT_{2B}$, as described in Example 7.
Figure 2E:
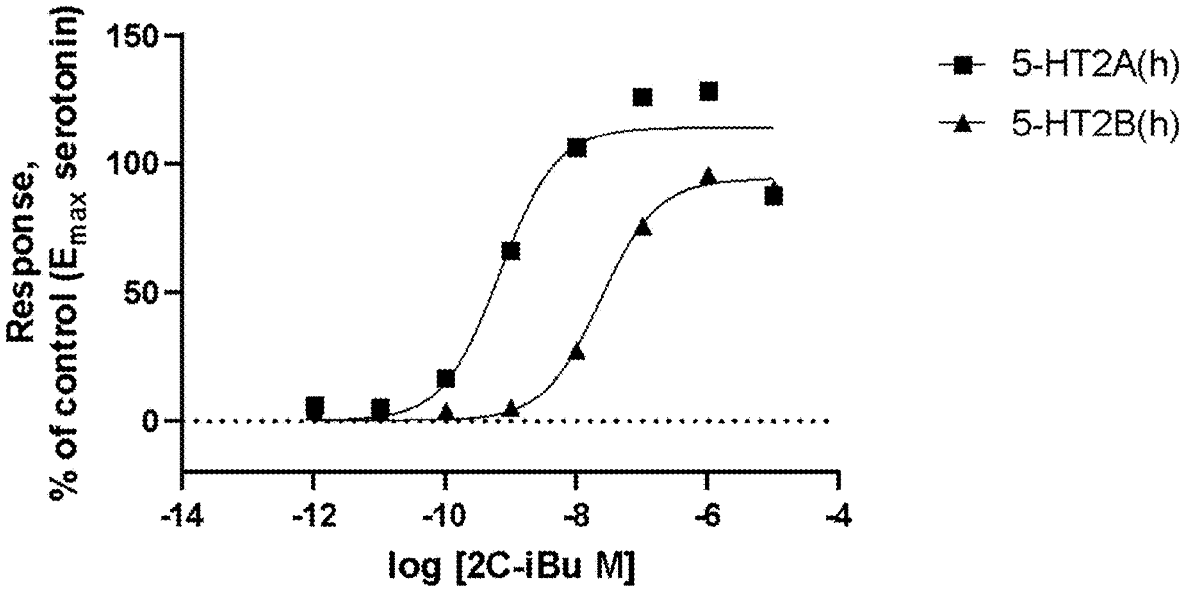
FIG. 2E shows the dose-response curve from a cell-based agonist calcium flux assay for reference compound 2C-iBU at 5-$HT_{2A}$ and 5-$HT_{2B}$, as described in Example 7.

While various aspects and features of certain embodiments are summarized above, the following detailed description illustrates some exemplary embodiments in further detail to enable one having ordinary skill in the art to which the invention belongs (equivalently as shorthand, "one of skill" or "those of skill") to practice such embodiments and to make and use the full scope of the invention claimed.

Many modifications, substitutions, changes, and variations in the described examples, embodiments, applications, and details of the invention illustrated herein can be made by one of skill without departing from the spirit of the invention, or the scope of the invention as claimed, and the general principles herein may be applied to a wide range of aspects. The invention is not limited to the aspects presented, and should be accorded the widest scope consistent with the principles and features disclosed. The description will make such scope apparent to one of skill, and many further embodiments will be both readily cognizable and readily creatable without undue experimentation, based on the teachings herein and the general knowledge in the art.

A. GENERAL DEFINITIONS AND TERMS

As used in the specification and claims, the singular forms "a," "an," and "the" include plural referents unless the context clearly dictates otherwise. Thus, for example, "an active agent" includes a combination of two or more active agents, and "an excipient" includes a combination of two or more excipients. While the term "one or more" may be used, its absence (or its replacement by the singular) does not signify the singular only, but simply underscores the possibility of, for example, multiple agents or ingredients in some embodiments.

"Or" means, and is interchangeable with, "and/or" unless context clearly indicates otherwise. The specific use of the term "and/or" does not signify that any uses of "or" are disjunctive only; rather, such use simply underscores the possibility that the term "and/or" may be conjunctive in particular embodiments, but otherwise may be disjunctive, like "or." The term "and" will be understood to be conjunctive.

The terms "comprising," "including," "such as," and "having" are inclusive and not exclusive (i.e., they do not limit lists to recited elements), and are interchangeable with the phrase "including but not limited to."

Where ranges are used, the disclosure includes embodiments in which the endpoints are included, embodiments in which both endpoints are excluded, and embodiments in which one endpoint is included and the other is excluded. It should be assumed that both endpoints are included unless indicated otherwise. It is also understood that unless otherwise indicated or otherwise evident from the context and understanding of one of skill, values that are expressed as ranges can assume any specific value or subrange within the stated ranges in different embodiments, to the tenth of the unit of the lower limit of the range, unless the context clearly dictates otherwise. It is further understood that where a series of numerical values is stated herein, the disclosure includes embodiments that relate analogously to any intervening value or range defined by any two values in the series, and that the lowest value may be taken as a minimum and the greatest value may be taken as a maximum. Numerical values, as used herein, include values expressed as percentages.

Unless otherwise indicated, all numbers expressing quantities of ingredients, properties such as concentration, reaction conditions, and so forth, will be understood as being modified in some instances by the term "about," even where not so stated explicitly. In alternative embodiments, such numbers will be understood as not being modified by the term "about." In embodiments, the numerical parameters are approximations that can vary depending on the particular embodiment or the properties sought to be obtained. In embodiments, "about" includes numbers that fall within a range of ±10% of a number, in embodiments within ±5% of a number, in embodiments within ±2% of a number, in embodiments within ±1% of a number, in embodiments within ±0.5% of a number, and in embodiments within ±0.1% of a number, unless otherwise stated or evident from the context (such as where a number would impermissibly exceed 100% of a possible value).

Where "about" is used to modify one number in a series or range, it should be understood to modify all numbers in the series or range, including, for a range, both the upper and lower bounds of the range. Thus, "about 1, 2, or 3" means "about 1, about 2, or about 3" and "about 1 to 10" means "about 1 to about 10."

"Substantially," when used to modify a feature or limitation, must be interpreted in the context of the disclosure and in light of the knowledge in the art to provide the appropriate certainty, such as by using an art-recognized standard to understand it as a term of degree, or by ascertaining the scope as would one of skill.

Numerical parameters should be construed in light of the number of reported significant digits and by applying ordinary rounding techniques. Notwithstanding that the numerical ranges and parameters setting forth the broad scope of embodiments are approximations, the numerical values set forth in the examples are reported as precisely as practicable. Numerical values in some embodiments may contain certain errors necessarily resulting from the standard deviation found in their respective testing measurements.

A comprehensive list of the abbreviations used by organic chemists of ordinary skill in the art appears in the first issue of each volume of the Journal of Organic Chemistry, typically presented in a table entitled Standard List of Abbreviations; the current list as of the date of this filing is incorporated by reference.

Generally, the nomenclature and terminology used and the procedures performed herein are those known in fields relating to that of one or more aspects of the disclosure, such as biology, pharmacology, neuroscience, organic chemistry, synthetic chemistry, and/or medicinal chemistry, and are those that will be well known and commonly employed in such fields. Standard techniques and procedures are those generally performed according to conventional methods in the art. While any materials and methods similar or equivalent to those described can be used in some embodiments, certain materials and methods are described herein.

Unless explicitly defined otherwise, all technical and scientific terms herein have the meaning as commonly understood by one of skill. Further definitions that may assist a reader in understanding the disclosed and exemplary embodiments are below; however, it will be appreciated that such definitions are not intended to limit the scope of the disclosure, which shall be properly interpreted and understood by reference to the full specification (as well as any plain meaning known to one of skill) in view of the language used in the claims. Terminology is for the purpose of describing particular embodiments and not intended to be limiting.

Terms having a specific meaning within the regulatory law of a jurisdiction in which this application is filed or may be in force generally should be given such meaning unless context dictates otherwise.

"In embodiments" is equivalent to, and used only as shorthand for, "in some embodiments."

"Alkyl" will be understood to include straight or branched radicals having any degree or level of saturation, i.e., groups having exclusively single carbon-carbon bonds, groups having one or more double carbon-carbon (C═C) bonds, groups having one or more triple carbon-carbon (C≡C) bonds and groups having mixtures of single, double, and triple carbon-carbon bonds. Where a specific level of saturation is intended, the expressions "alkanyl," "alkenyl," and "alkynyl" can be used. In embodiments, an alkyl group comprises from 1 to 10 carbon atoms, from 1 to 6 carbon atoms, from 1 to 4 carbon atoms, or from 1 to 3 carbon atoms. For any alkyl, the alkyl may be optionally substituted at one or more positions by deuterium, halogen, alkyl, alkenyl, alkynyl, alkyl ester, hydroxy, alkoxy, carboxy, formyl, aryl, cycloalkyl, cycloalkenyl, heterocycloalkyl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —OP(O)$(OH)_2$, —OC(O)H, —$OSO_2OH$, —OC(O)$NH_2$, and —$SONH_2$. In embodiments, an alkyl group will be optionally substituted. In embodiments, an alkyl group will be substituted at one or more positions. In embodiments, an alkyl group will not be substituted at any positions.

"Alkenyl" refers to an unsaturated branched, straight-chain, or cyclic alkyl radical having at least one C═C double bond derived by the removal of one H atom from a single C atom of a parent alkene. The group may be in either the cis or trans conformation about the double bond(s). Typical alkenyl groups include ethenyl; propenyls such as prop-1-en-1-yl, prop-1-en-2-yl, prop-2-en-1-yl (allyl), prop-2-en-2-yl, cycloprop-1-en-1-yl, and cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2yl, buta-1,3-dien-1-yl, buta-1,3-dien-2-yl, cyclobut-1-en-1-yl, cyclobut-1-en-3-yl, and cyclobuta-1,3-dien-1-yl; and the like. An alkenyl group can be substituted or unsubstituted.

"Alkynyl" refers to an unsaturated branched, straight-chain, or cyclic alkyl radical having at least one C≡C triple bond derived by the removal of one H atom from a single C atom of a parent alkyne. Typical alkynyl groups include ethynyl; propynyls such as prop-1-yn-1-yl, and prop-2-yn-1-yl; butynyls such as but-1-yn-1-yl, but-1-yn-3-yl, and but-3-yn-1-yl; and the like. An alkynyl group can be substituted or unsubstituted.

"Aryl" refers to a monovalent aromatic hydrocarbon radical derived by the removal of one hydrogen atom from a single carbon atom of a parent aromatic ring system. Typical aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, an aryl group comprises from 6-20 carbon atoms, or between 6-12 carbon atoms. An aryl group can be substituted or unsubstituted.

"Cycloalkyl" refers to a saturated monocyclic, bicyclic, fused bicyclic or bridged polycyclic ring assembly containing from 3-12 ring atoms, or the number of atoms indicated. Cycloalkyl can include any number of carbons, such as 3-6 carbon atoms, 4-6 carbon atoms, 5-6 carbon atoms, 3-8 carbon atoms, 4-8 carbon atoms, 5-8 carbon atoms, 6-8 carbon atoms, 7-8 carbon atoms, 3-9 carbon atoms, 4-9 carbon atoms, 5-9 carbon atoms, 6-9 carbon atoms, 7-9 carbon atoms, 8-9 carbon atoms, 3-10 carbon atoms, 4-10 carbon atoms, 5-10 carbon atoms, 6-10 carbon atoms, 7-10 carbon atoms, 8-10 carbon atoms, 9-10 carbon atoms, 3-11 carbon atoms, 4-11 carbon atoms, 5-11 carbon atoms, 6-11 carbon atoms, 7-11 carbon atoms, 8-11 carbon atoms, 9-11 carbon atoms, 10-11 carbon atoms, 3-12 carbon atoms, 4-12 carbon atoms, 5-12 carbon atoms, 6-12 carbon atoms, 7-12 carbon atoms, 8-12 carbon atoms, 9-12 carbon atoms, 10-12 carbon atoms, and 11-12 carbon atoms. Monocyclic cycloalkyl rings include cyclopropyl, cyclobutyl, cyclopentyl, cyclohexyl, and cyclooctyl. Bicyclic compounds include spirocyclic compounds, fused bicyclic compounds and bridged bicyclic compounds. Bicyclic and polycyclic cycloalkyl rings include norbornane, bicyclooctane, decahydronaphthalene, and adamantane. When cycloalkyl is a monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a monocyclic $C_{3-6}$cycloalkyl, exemplary groups include cyclopropyl, cyclobutyl, cyclopentyl, and cyclohexyl. A cycloalkyl group can be substituted or unsubstituted.

"Cycloalkenyl" refers to a mono- or multi-cyclic hydrocarbon ring system that contains one or more double bonds in at least one ring. However, if there is more than one double bond, the double bonds cannot form a fully delocalized pi-electron system throughout all the rings (otherwise the group would be "aryl," as defined herein). When composed of two or more rings, the rings may be connected together in a fused fashion. Cycloalkenyl can include any number of carbons, such as 3-6 carbon atoms, 4-6 carbon atoms, 5-6 carbon atoms, 3-8 carbon atoms, 4-8 carbon atoms, 5-8 carbon atoms, 6-8 carbon atoms, 7-8 carbon atoms, 3-9 carbon atoms, 4-9 carbon atoms, 5-9 carbon atoms, 6-9 carbon atoms, 7-9 carbon atoms, 8-9 carbon atoms, 3-10 carbon atoms, 4-10 carbon atoms, 5-10 carbon atoms, 6-10 carbon atoms, 7-10 carbon atoms, 8-10 carbon atoms, 9-10 carbon atoms, 3-11 carbon atoms, 4-11 carbon atoms, 5-11 carbon atoms, 6-11 carbon atoms, 7-11 carbon atoms, 8-11 carbon atoms, 9-11 carbon atoms, 10-11 carbon atoms, 3-12 carbon atoms, 4-12 carbon atoms, 5-12 carbon atoms, 6-12 carbon atoms, 7-12 carbon atoms, 8-12 carbon atoms, 9-12 carbon atoms, 10-12 carbon atoms, and 11-12 carbon atoms. Representative Cycloalkenyl groups include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. A cycloalkenyl group may be unsubstituted or substituted.

"Cycloalkylmethyl" refers to a radical having a methylene component and a cycloalkyl component, where the methylene component links the cycloalkyl component to the point of attachment. The cycloalkyl component is as defined above, and can include any number of carbons, such as 3-6 carbon atoms (i.e., a $C_3$-$C_6$ cycloalkylmethyl), 4-6 carbon atoms, 5-6 carbon atoms, 3-8 carbon atoms, 4-8 carbon atoms, 5-8 carbon atoms, 6-8 carbon atoms, 7-8 carbon atoms, 3-9 carbon atoms, 4-9 carbon atoms, 5-9 carbon atoms, 6-9 carbon atoms, 7-9 carbon atoms, 8-9 carbon atoms, 3-10 carbon atoms, 4-10 carbon atoms, 5-10 carbon atoms, 6-10 carbon atoms, 7-10 carbon atoms, 8-10 carbon atoms, 9-10 carbon atoms, 3-11 carbon atoms, 4-11 carbon atoms, 5-11 carbon atoms, 6-11 carbon atoms, 7-11 carbon atoms, 8-11 carbon atoms, 9-11 carbon atoms, 10-11 carbon atoms, 3-12 carbon atoms, 4-12 carbon atoms, 5-12 carbon atoms, 6-12 carbon atoms, 7-12 carbon atoms, 8-12 carbon atoms, 9-12 carbon atoms, 10-12 carbon atoms, and 11-12 carbon atoms. In embodiments, the cyclo-alkylmethyl group is a cyclopropylmethyl group. A cycloalkylmethyl group can be substituted or unsubstituted.

"Halogen" refers to fluorine, chlorine, bromine, and iodine.

"Heterocycloalkyl" refers to a cycloalkyl as defined above, having from 3 to 12 ring members and from 1 to 4 heteroatoms of N, O and S. Heterocycloalkyl includes bicyclic compounds which include a heteroatom. Bicyclic compounds includes spirocyclic compounds, fused bicyclic compounds, and bridged bicyclic compounds The heteroatoms can also be oxidized, such as, but not limited to, —S(O)— and —$S(O)_2$—. Heterocycloalkyl groups can include any number of ring atoms, such as, 3-6, 4-6, 5-6, 3-8, 4-8, 5-8, 6-8, 3-9, 3-10, 3-11, or 3-12 ring members. Any suitable number of heteroatoms can be included in the heterocycloalkyl groups, such as 1, 2, 3, or 4, or 1-2, 1-3, 1-4, 2-3, 2-4, or 3-4. The heterocycloalkyl group can include groups such as aziridine, azetidinyl, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including indoline. Heterocycloalkyl groups can be unsubstituted or substituted. For example, heterocycloalkyl groups can be substituted with C1-6 alkyl or oxo (═O), among many others.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as C1-2, C1-3, C1-4, C1-5, C1-6, C2-3, C2-4, C2-5, C2-6, C3-4, C3-5, C3-6, C4-5, C4-6 and C5-6. In some instances, the alkyl component can be absent. The heterocycloalkyl component is as defined herein. Alkyl-heterocycloalkyl groups can be substituted or unsubstituted.

"Heteroaryl" refers to a monocyclic or fused bicyclic or tricyclic aromatic ring assembly containing 5-16 ring atoms, where from 1-5 of the ring atoms are a heteroatom such as N, O or S. Heteroaryl groups can include any number of ring atoms, such as, 5-6, 3-8, 4-8, 5-8, 6-8, 3-9, 3-10, 3-11, or 3-12 ring members. Any suitable number of heteroatoms can be included in the heteroaryl groups, such as 1, 2, 3, 4, or 5, or 1-2, 1-3, 1-4, 1-5, 2-3, 2-4, 2-5, 3-4, or 3-5. Heteroaryl groups can have from 5-8 ring members and from 1-4 heteroatoms, or from 5-8 ring members and from 1-3 heteroatoms, or from 5-6 ring members and from 1-4 heteroatoms, or from 5-6 ring members and from 1-3 heteroatoms. A heteroaryl includes groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as C0-6, C1-2, C1-3, C1-4, C1-5, C1-6, C2-3, C2-4, C2-5, C2-6, C3-4, C3-5, C3-6, C4-5, C4-6 and C5- 6. The alkyl component can be absent. "Heteroaryl" is as defined within. Alkyl-heteroaryl groups can be substituted or unsubstituted.

"Alkoxy" refers to the formula —OR, wherein R is an alkyl, an alkenyl, an alkynyl, a cycloalkyl, a cycloalkenyl, aryl, or heterocyclyl, as defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

"Alkylthio" or "thioalkyl" refers to the formula —SR, wherein R is an alkyl, an alkenyl, an alkynyl, a cycloalkyl, a cycloalkenyl, aryl, or heterocyclyl, as defined herein. A non-limiting list of alkylthio are methylthio, ethylthio, n-propylthio, isopropylthio, n-butylthio, iso-butylthio, sec-butylthio, phenylthio, and benzylthio. An alkylthio may be substituted or unsubstituted.

"Acyl" refers to a hydrogen, an alkyl, an alkenyl, an alkynyl, a cycloalkyl, a cycloalkenyl, aryl, or heterocyclyl, connected via a carbonyl group as a substituent. Examples include formyl, acetyl, propanoyl, benzoyl, and acryl. An acyl may be substituted or unsubstituted.

"Haloalkyl" refers to any alkyl group as defined above, wherein one or more hydrogen atoms are replaced by a halogen (e.g., a fluorine, a chlorine, a bromine, or an iodine). Where an alkyl radical is substituted by more than one halogen, it may be referred to using a prefix corresponding to the number of halogen substitutions. For example, dihaloalkyl refers to an alkyl substituted by two halo groups, which may be, but are not necessarily, the same halogen. Examples of haloalkyl groups include difluoromethyl (—$CHF_2$), bromofluoromethyl (—CHBrF), trifluoromethyl (—$CF_3$), and 2-fluoroethyl (—$CH_2CH_2F$). Additional examples of haloalkyl groups include —$CHF_2$, —$CH_2F$, —$CH_2CF_3$, —$CH_2CHF_2$, —$CH_2CH_2F$, —$CH(CH_3)(CF_3)$, —$CH(CH_3)(CHF_2)$, and —$CH(CH_3)(CH_2F)$. A haloalkyl may be substituted or unsubstituted.

"Haloalkylthio" refers to any alkylthio group as defined above, wherein one or more hydrogen atoms are replaced by a halogen (e.g., a fluorine, a chlorine, a bromine, or an iodine). Where an alkylthio radical is substituted by more than one halogen, it may be referred to using a prefix corresponding to the number of halogen substitutions. For example, dihaloalkylthio refers to an alkylthio substituted by two halo groups, which may be, but are not necessarily, the same halogen. Examples of haloalkylthio groups include —$SCF_3$, —$CHF_2$, —$CH_2F$, —$CH_2CF_3$, —$CH_2CHF_2$, —$CH_2CH_2F$, —$CH(CH_3)(CF_3)$, —$CH(CH_3)(CHF_2)$, and —$CH(CH_3)(CH_2F)$. A haloalkyl may be substituted or unsubstituted.

"Hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxy-propyl, 2-hydroxypropyl and 2,2-dihydroxyethyl. A hydroxyalkyl may be substituted or unsubstituted.

"Haloalkoxy" refers to an —O-alkyl group in which one or more of the hydrogen atoms are replaced by a halogen (e.g., mono-haloalkoxy, di-haloalkoxy and tri-haloalkoxy). The halogens may be the same or different in each instance. Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

"Sulfenyl" refers to an —SR group in which R can be hydrogen, alkyl, alkenyl, alkynyl, cycloalkyl, cycloalkenyl, aryl, or heterocyclyl, as defined herein. A sulfenyl may be substituted or unsubstituted.

"Sulfinyl" refers to an —S(═O)—R group in which R can be the same as defined with respect to sulfenyl. A sulfinyl may be substituted or unsubstituted.

"Sulfonyl" refers to an —$SO_2$R group in which R can be the same as defined with respect to sulfenyl. A sulfonyl may be substituted or unsubstituted.

"O-carboxy" refers to a —RC(═O)O— group in which R can be hydrogen, alkyl, alkenyl, alkynyl, cyclo-alkyl, cycloalkenyl, aryl, or heterocyclyl, as defined herein. An O-carboxy may be substituted or unsubstituted.

"Ester" and "C-carboxy" refer to a —C(═O)OR group in which R can be the same as defined with respect to O-carboxy. Ester and C-carboxy groups may be substituted or unsubstituted.

"Thiocarbonyl" refers to a —C(═S)R group in which R can be the same as defined with respect to O-carboxy. A thiocarbonyl may be substituted or unsubstituted.

"Trihalomethanesulfonyl" refers to an $X_3CSO_2$— group wherein each X is a halogen.

"Trihalomethanesulfonamido" refers to an $X_3CS(O)_2N(R_A)$— group wherein each X is a halogen, and $R_A$ is hydrogen, alkyl, alkenyl, alkynyl, cycloalkyl, cycloalkenyl, aryl, or heterocyclyl, as defined herein.

"S-sulfonamido" refers to a —$SO_2N(R_AR_B)$ group in which $R_A$ and $R_B$ can be independently hydrogen, alkyl, alkenyl, alkynyl, cycloalkyl, cycloalkenyl, aryl, or heterocyclyl, as defined herein. An S-sulfonamido may be substituted or unsubstituted.

"N-sulfonamido" refers to a $RSO_2N(R_A)$— group in which R and $R_A$ can be independently hydrogen, alkyl, alkenyl, alkynyl, cycloalkyl, cycloalkenyl, aryl, or heterocyclyl, as defined herein. An N-sulfonamido may be substituted or unsubstituted.

"O-carbamyl" refers to a —OC(═O)N($R_AR_B$) group in which $R_A$ and $R_B$ can be independently hydrogen, alkyl, alkenyl, alkynyl, cycloalkyl, cycloalkenyl, aryl, or heterocyclyl, as defined herein. An O-carbamyl may be substituted or unsubstituted.

"N-carbamyl" refers to an ROC(═O)N($R_A$)— group in which R and $R_A$ can be independently hydrogen, alkyl, alkenyl, alkynyl, cycloalkyl, cycloalkenyl, aryl, or heterocyclyl, as defined herein. An N-carbamyl may be substituted or unsubstituted.

"O-thiocarbamyl" refers to a —OC(═S)—N($R_AR_B$) group in which $R_A$ and $R_B$ can be independently hydrogen, alkyl, alkenyl, alkynyl, cycloalkyl, cycloalkenyl, aryl, or heterocyclyl, as defined herein. An O-thiocarbamyl may be substituted or unsubstituted.

"N-thiocarbamyl" refers to an ROC(═S)N($R_A$)— group in which R and $R_A$ can be independently hydrogen, alkyl, alkenyl, alkynyl, cycloalkyl, cycloalkenyl, aryl, or heterocyclyl, as defined herein. An N-thiocarbamyl may be substituted or unsubstituted.

"C-amido" group refers to a —C(═O)N($R_AR_B$) group in which $R_A$ and $R_B$ can be independently hydrogen, alkyl, alkenyl, alkynyl, cycloalkyl, cycloalkenyl, aryl, or heterocyclyl, as defined herein. A C-amido may be substituted or unsubstituted.

"N-amido" refers to a RC(═O)N($R_A$)— group in which R and $R_A$ can be independently hydrogen, alkyl, alkenyl, alkynyl, cycloalkyl, cycloalkenyl, aryl, or heterocyclyl, as defined herein. An N-amido may be substituted or unsubstituted.

Even where not expressly stated, any group above can be substituted or unsubstituted. In some embodiments, a group is substituted. In other embodiments, a group is unsubstituted. In other embodiments, a group is optionally substituted.

"Optionally substituted" unless otherwise specified means that a group may be unsubstituted, or substituted by one or more of the substituents listed for that group. Likewise, when a group is described as being "unsubstituted or substituted" if substituted, the substituent(s) may be selected from one or more of the indicated substituents. When there are more than one substituents, the substituents may be the same or different. In some embodiments, an optionally substituted group has one substituent. In another embodiment, an optionally substituted group has two substituents. In another embodiment, an optionally substituted group has three substituents. In another embodiment, an optionally substituted group has four substituents. If no substituents are indicated for an "optionally substituted" or "substituted" group, it is meant that the indicated "optionally substituted" or "substituted" group may be substituted with one or more group(s) individually and independently selected from alkyl, alkenyl, alkynyl, cycloalkyl, cycloalkenyl, aryl, heteroaryl, heterocyclyl, aryl(alkyl), heteroaryl(alkyl), (heterocyclyl) alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group, a di-substituted amino group, and a tri-substituted amino group.

Even where not expressly stated, any group having a definition may be interpreted as defined herein.

Still additional definitions and abbreviations are provided elsewhere herein.

B. COMPOUNDS

The phenethylamine pharmacophore is one of the most well-known chemical scaffolds found in biologically active molecules, such as neurotransmitters (e.g., dopamine) and psychoactive drugs (e.g., the entactogen 3,4-methylenedioxymethamphetamine, also known as MDMA).

One class of phenethylamine compounds, known as the "2C" or "2C-x" compounds, are ring-substituted phenethylamines containing methoxy groups on the 2 and 5 positions of the benzene ring, and an additional (often lipophilic) substituent at the 4-position. Many 2C compounds are potent and selective 5-$HT_{2A}$ receptor agonists, and have been historically studied as pharmacophores in SAR studies of psychedelic drugs. Certain 2C compounds have effects similar to those of entactogens such as MDMA, as well as effects similar to those of "classic" psychedelics such as psilocybin. Although some 2C compounds are generally well-tolerated within certain dose ranges, adverse sympathomimetic effects have been reported, including agitation, excited delirium, aggression, violence, dysphoria, hypertension, tachycardia, seizures, and hyperthermia, and many 2C compounds are known to be associated with heavy "body load" and GI effects (see, e.g., Dean et al., *J Med Toxicol,* 2013; 9(2):172-178). For these and other reasons, among the ongoing needs for new chemical entities that are addressed by the disclosure are the disclosure of compounds that retain advantages of certain phenethylamines, while also providing new advantageous properties and biochemical functionalities, and/or mitigating one or more downsides (above and others) of known compounds.

In some aspects, the disclosure provides and relates to compounds of Formula (1):

(1)

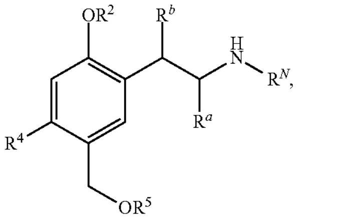

wherein:

$R^2$ is H or $C_1$-$C_6$ alkyl;

$R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or —$(CH_2)_{0-3}$—C(O)—O—$C_1$-$C_6$ alkyl;

$R^5$ is H or $C_1$-$C_6$ alkyl; and $R^N$ is H or —$CH_2$—Ar; wherein Ar is 6- to 12-membered heterocyclyl or $C_6$-$C_{12}$ aryl optionally substituted by F, Cl, Br, I, OH, $C_1$-$C_6$ alkoxy, or phenyl; and $R^a$ is H or $C_1$-$C_6$ alkyl, and $R^b$ is H;

or $R^a$ and $R^b$ together with the intervening atoms form a 3- to 6-membered cycloalkyl;

or $R^N$ and $R^b$ together with the intervening atoms form a 4- to 8-membered heterocyclyl, and $R^a$ is H or $C_1$-$C_6$ alkyl; or a pharmaceutically acceptable salt, stereoisomer, hydrate, solvate, or isotopic derivative thereof.

In some embodiments of Formula (1), $R^2$ is H or $C_1$-$C_6$ alkyl. In some embodiments, $R^2$ is H. In some embodiments, $R^2$ is $C_1$-$C_6$ alkyl. In some embodiments, $R^2$ is methyl.

In some embodiments of Formula (1), $R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or —$(CH_2)_{0-3}$—C(O)—O—$C_1$-$C_6$ alkyl. In embodiments, $R^4$ is H. In embodiments, $R^4$ is F. In embodiments, $R^4$ is Cl. In embodiments, $R^4$ is Br. In embodiments, $R^4$ is I. In embodiments, $R^4$ is CN. In embodiments, $R^4$ is $NO_2$. In embodiments, $R^4$ is $C_1$-$C_6$ alkyl. In embodiments, $R^4$ is methyl. In embodiments, $R^4$ is ethyl. In embodiments, $R^4$ is propyl. In embodiments, $R^4$ is butyl. In embodiments, $R^4$ is isobutyl. In embodiments, $R^4$ is pentyl. In embodiments, $R^4$ is neopentyl. In embodiments, $R^4$ is $C_2$-$C_6$ alkenyl. In embodiments, $R^4$ is vinyl. In embodiments, $R^4$ is allyl. In embodiments, $R^4$ is $C_2$-$C_6$ alkynyl. In embodiments, $R^4$ is ethynyl. In embodiments, $R^4$ is $C_1$-$C_6$ haloalkyl. In embodiments, $R^4$ is trifluoromethyl. In embodiments, $R^4$ is $C_1$-$C_6$ alkoxy. In embodiments, $R^4$ is methoxy. In embodiments, $R^4$ is $C_1$-$C_6$ haloalkylthio. In embodiments, $R^4$ is 2-fluoro-ethylthio. In embodiments, $R^4$ is $C_1$-$C_6$ alkylthio. In embodiments, $R^4$ is methylthio. In embodiments, $R^4$ is ethylthio. In embodiments, $R^4$ is propylthio. In embodiments, $R^4$ is butylthio. In embodiments, $R^4$ is isobutylthio. In embodiments, $R^4$ is $C_3$-$C_6$ cycloalkylmethyl. In embodiments, $R^4$ is cyclopropylmethyl. In embodiments, $R^4$ is —$(CH_2)_{0-3}$—C(O)—O—$C_1$-$C_6$ alkyl. In embodiments, $R^4$ is —COO—$C_1$-$C_6$ alkyl. In embodiments, $R^4$ is —$CH_2$COO—$C_1$-$C_6$ alkyl. In embodiments, $R^4$ is —$(CH_2)_2$COO—$C_1$-$C_6$ alkyl. In embodiments, $R^4$ is —$(CH_2)_3$COO—$C_1$-$C_6$ alkyl. In embodiments, $R^4$ is —$CH_2COOCH_3$. In embodiments, $R^4$ is —$CH_2COOCH_2CH_3$.

In some embodiments of Formula (1), $R^5$ is H or $C_1$-$C_6$ alkyl. In some embodiments, $R^5$ is H. In some embodiments, $R^5$ is $C_1$-$C_6$ alkyl. In some embodiments, $R^5$ is methyl.

In some embodiments of Formula (1), $R^a$ is H or $C_1$-$C_6$ alkyl. In some embodiments, $R^a$ is H. In some embodiments, $R^a$ is $C_1$-$C_6$ alkyl. In some embodiments, $R^a$ is methyl. In some embodiments, $R^a$ is ethyl.

In some embodiments of Formula (1), $R^N$ is H or —$CH_2$—Ar, wherein Ar is 6- to 12-membered heterocyclyl or $C_6$-$C_{12}$ aryl optionally substituted by F, Cl, Br, I, OH, $C_1$-$C_6$ alkoxy, or phenyl. In embodiments, $R^N$ is H. In embodiments, $R^N$ is —$CH_2$—Ar. In embodiments, $R^N$ is —$CH_2$—Ar, and Ar is 6- to 12-membered heterocyclyl optionally substituted by F, Cl, Br, I, OH, $C_1$-$C_6$ alkoxy, or phenyl. In embodiments, $R^N$ is —$CH_2$—Ar, and Ar is unsubstituted 6- to 12-membered heterocyclyl. In embodiments, $R^N$ is —$CH_2$—Ar, and Ar is 6- to 12-membered heterocyclyl substituted by F, Cl, Br, I, OH, $C_1$-$C_6$ alkoxy, or phenyl. In embodiments, $R^N$ is —$CH_2$—Ar, and Ar is benzodioxolyl (e.g., 1,3-benzodioxolyl). In embodiments, $R^N$ is —$CH_2$—Ar, and Ar is benzo-furanyl (e.g., 1-benzofuranyl). In embodiments, $R^N$ is —$CH_2$—Ar, and Ar is $C_6$-$C_{12}$ aryl optionally substituted by F, Cl, Br, I, OH, $C_1$-$C_6$ alkoxy, or phenyl. In embodiments, $R^N$ is —$CH_2$—Ar, and Ar is unsubstituted $C_6$-$C_{12}$ aryl. In embodiments, $R^N$ is —$CH_2$—Ar, and Ar is phenyl. In embodiments, $R^N$ is —$CH_2$—Ar, and Ar is naphthyl. In embodiments, $R^N$ is —$CH_2$—Ar, and Ar is $C_6$-$C_{12}$ aryl substituted by F, Cl, Br, I, OH, $C_1$-$C_6$ alkoxy, or phenyl. In embodiments, $R^N$ is —$CH_2$—Ar, and Ar is phenyl substituted by F, Cl, Br, or I. In embodiments, $R^N$ is —$CH_2$—Ar, and Ar is 2-fluorophenyl, 2-chlorophenyl, 2-bromophenyl, or 2-iodophenyl. In embodiments, $R^N$ is —$CH_2$—Ar, and Ar is 3-fluorophenyl, 3-chlorophenyl, 3-bromophenyl, or 3-iodophenyl. In embodiments, $R^N$ is —$CH_2$—Ar, and Ar is phenyl substituted by OH. In embodiments, $R^N$ is —$CH_2$—Ar, and Ar is 2-hydroxyphenyl. In embodiments, $R^N$ is —$CH_2$—Ar, and Ar is phenyl substituted by $C_1$-$C_6$ alkoxy. In embodiments, $R^N$ is —$CH_2$—Ar, and Ar is 2-methoxyphenyl. In embodiments, $R^N$ is —$CH_2$—Ar, and Ar is phenyl substituted by phenyl. In embodiments, $R^N$ is —$CH_2$—Ar, and Ar is biphenyl (e.g., 2-biphenyl). In embodiments, $R^N$ is —$CH_2$—Ar, and Ar is 2-(4-hydroxyphenyl)phenyl. In embodiments, $R^N$ is —$CH_2$—Ar, and Ar is phenyl substituted by $C_3$-$C_6$ cycloalkyl. In embodiments, $R^N$ is —$CH_2$—Ar, and Ar is phenyl substituted by cyclopropyl (e.g., 2-cyclopropylphenyl).

In some embodiments of Formula (1), $R^b$ is H.

In some embodiments of Formula (1), $R^b$ and $R^N$ together with the intervening atoms form a 4- to 8-membered heterocyclyl. In some embodiments, $R^b$ and $R^N$ together with the intervening atoms form an azetidinyl. In some embodiments, $R^b$ and $R^N$ together with the intervening atoms form a pyrrolidinyl. In some embodiments, $R^b$ and $R^N$ together with the intervening atoms form a piperidinyl. In some embodiments, $R^b$ and $R^N$ together with the intervening atoms form an azepanyl.

In some embodiments of Formula (1), $R^a$ and $R^b$ together with the intervening atoms form a 3- to 6-membered cycloalkyl. In some embodiments, $R^a$ and $R^b$ together with the intervening atoms form a cyclopropyl. In some embodiments, $R^a$ and $R^b$ together with the intervening atoms form a cyclobutyl. In some embodiments, $R^a$ and $R^b$ together with the intervening atoms form a cyclopentyl. In some embodiments, $R^a$ and $R^b$ together with the intervening atoms form a cyclohexyl.

In some embodiments, the compound has the structure of Formula (2):

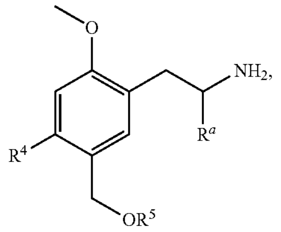

(2)

wherein:

$R^a$ is H or $C_1$-$C_6$ alkyl;

$R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or —$(CH_2)_{0-3}$—C(O)—O—$C_1$-$C_6$ alkyl; and $R^5$ is H or $C_1$-$C_6$ alkyl;

or a pharmaceutically acceptable salt, stereoisomer, hydrate, solvate, or isotopic derivative thereof.

In some embodiments of Formula (2), $R^a$ is H or $C_1$-$C_6$ alkyl. In some embodiments, $R^a$ is H. In some embodiments, $R^a$ is $C_1$-$C_6$ alkyl. In some embodiments, $R^a$ is methyl. In some embodiments, $R^a$ is ethyl.

In some embodiments of Formula (2), $R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or —$(CH_2)_{0-3}$—C(O)—O—$C_1$-$C_6$ alkyl. In embodiments, $R^4$ is H. In embodiments, $R^4$ is F. In embodiments, $R^4$ is Cl. In embodiments, $R^4$ is Br. In embodiments, $R^4$ is I. In embodiments, $R^4$ is CN. In embodiments, $R^4$ is $NO_2$. In embodiments, $R^4$ is $C_1$-$C_6$ alkyl. In embodiments, $R^4$ is methyl. In embodiments, $R^4$ is ethyl. In embodiments, $R^4$ is propyl. In embodiments, $R^4$ is butyl. In embodiments, $R^4$ is isobutyl. In embodiments, $R^4$ is pentyl. In embodiments, $R^4$ is neopentyl. In embodiments, $R^4$ is $C_2$-$C_6$ alkenyl. In embodiments, $R^4$ is vinyl. In embodiments, $R^4$ is allyl. In embodiments, $R^4$ is $C_2$-$C_6$ alkynyl. In embodiments, $R^4$ is ethynyl. In embodiments, $R^4$ is $C_1$-$C_6$ haloalkyl. In embodiments, $R^4$ is trifluoromethyl. In embodiments, $R^4$ is $C_1$-$C_6$ alkoxy. In embodiments, $R^4$ is methoxy. In embodiments, $R^4$ is $C_1$-$C_6$ haloalkylthio. In embodiments, $R^4$ is 2-fluoro-ethylthio. In embodiments, $R^4$ is $C_1$-$C_6$ alkylthio. In embodiments, $R^4$ is methylthio. In embodiments, $R^4$ is ethylthio. In embodiments, $R^4$ is propylthio. In embodiments, $R^4$ is butylthio. In embodiments, $R^4$ is isobutylthio. In embodiments, $R^4$ is $C_3$-$C_6$ cycloalkylmethyl. In embodiments, $R^4$ is cyclopropylmethyl. In embodiments, $R^4$ is —$(CH_2)_{0-3}$—C(O)—O—$C_1$-$C_6$ alkyl. In embodiments, $R^4$ is —COO—$C_1$-$C_6$ alkyl. In embodiments, $R^4$ is —$CH_2$COO—$C_1$-$C_6$ alkyl. In embodiments, $R^4$ is —$(CH_2)_2$COO—$C_1$-$C_6$ alkyl. In embodiments, $R^4$ is —$(CH_2)_3$COO—$C_1$-$C_6$ alkyl. In embodiments, $R^4$ is —$CH_2COOCH_3$. In embodiments, $R^4$ is —$CH_2COOCH_2CH_3$.

In some embodiments of Formula (2), $R^5$ is H or $C_1$-$C_6$ alkyl. In some embodiments, $R^5$ is H. In some embodiments, $R^5$ is $C_1$-$C_6$ alkyl. In some embodiments, $R^5$ is methyl.

In some embodiments, the compound has the structure of Formula (3):

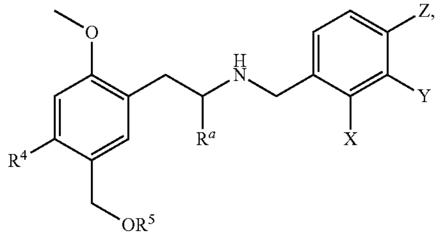

(3)

wherein:

$R^a$ is H or $C_1$-$C_6$ alkyl;

$R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or —$(CH_2)_{0-3}$—C(O)—O—$C_1$-$C_6$ alkyl;

$R^5$ is H or $C_1$-$C_6$ alkyl; and

X, Y, and Z are each independently H, F, Cl, Br, I, OH, $C_1$-$C_6$ alkoxy, or phenyl; or X and Y are taken together to form a 4- to 6-membered heterocyclyl, and Z is H, F, Cl, Br, I, OH, $C_1$-$C_6$ alkoxy, $C_3$-$C_6$ cycloalkyl, or phenyl; or Y and Z are taken together to form a 4- to 6-membered heterocyclyl, and X is H, F, Cl, Br, I, OH, $C_1$-$C_6$ alkoxy, $C_3$-$C_6$ cycloalkyl, or phenyl.

In some embodiments of Formula (3), $R^a$ is H or $C_1$-$C_6$ alkyl. In some embodiments, $R^a$ is H. In some embodiments, $R^a$ is $C_1$-$C_6$ alkyl. In some embodiments, $R^a$ is methyl. In some embodiments, $R^a$ is ethyl.

In some embodiments of Formula (3), $R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or —$(CH_2)_{0-3}$—C(O)—O—$C_1$-$C_6$ alkyl. In embodiments, $R^4$ is H. In embodiments, $R^4$ is F. In embodiments, $R^4$ is Cl. In embodiments, $R^4$ is Br. In embodiments, $R^4$ is I. In embodiments, $R^4$ is CN. In embodiments, $R^4$ is $NO_2$. In embodiments, $R^4$ is $C_1$-$C_6$ alkyl. In embodiments, $R^4$ is methyl. In embodiments, $R^4$ is ethyl. In embodiments, $R^4$ is propyl. In embodiments, $R^4$ is butyl. In embodiments, $R^4$ is isobutyl. In embodiments, $R^4$ is pentyl. In embodiments, $R^4$ is neopentyl. In embodiments, $R^4$ is $C_2$-$C_6$ alkenyl. In embodiments, $R^4$ is vinyl. In embodiments, $R^4$ is allyl. In embodiments, $R^4$ is $C_2$-$C_6$ alkynyl. In embodiments, $R^4$ is ethynyl. In embodiments, $R^4$ is $C_1$-$C_6$ haloalkyl. In embodiments, $R^4$ is trifluoromethyl. In embodiments, $R^4$ is $C_1$-$C_6$ alkoxy. In embodiments, $R^4$ is methoxy. In embodiments, $R^4$ is $C_1$-$C_6$ haloalkylthio. In embodiments, $R^4$ is 2-fluoro-ethylthio. In embodiments, $R^4$ is $C_1$-$C_6$ alkylthio. In embodiments, $R^4$ is methylthio. In embodiments, $R^4$ is ethylthio. In embodiments, $R^4$ is propylthio. In embodiments, $R^4$ is butylthio. In embodiments, $R^4$ is isobutylthio. In embodiments, $R^4$ is $C_3$-$C_6$ cycloalkylmethyl. In embodiments, $R^4$ is cyclopropylmethyl. In embodiments, $R^4$ is $—(CH_2)_{0-3}—C(O)—O—C_1$-$C_6$ alkyl. In embodiments, $R^4$ is $—COO—C_1$-$C_6$ alkyl. In embodiments, $R^4$ is $—CH_2COO—C_1$-$C_6$ alkyl. In embodiments, $R^4$ is $—(CH_2)_2COO—C_1$-$C_6$ alkyl. In embodiments, $R^4$ is $—(CH_2)_3COO—C_1$-$C_6$ alkyl. In embodiments, $R^4$ is $—CH_2COOCH_3$. In embodiments, $R^4$ is $—CH_2COOCH_2CH_3$.

In some embodiments of Formula (3), $R^5$ is H or $C_1$-$C_6$ alkyl. In some embodiments, $R^5$ is H. In some embodiments, $R^5$ is $C_1$-$C_6$ alkyl. In some embodiments, $R^5$ is methyl. In some embodiments, $R^5$ is H or methyl.

In some embodiments of Formula (3), X, Y, and Z are each independently H, F, Cl, Br, I, OH, $C_1$-$C_6$ alkoxy, or phenyl. In embodiments, X is F, Cl, Br, I, OH, $C_1$-$C_6$ alkoxy, or phenyl; and Y and Z are both H. In embodiments, Y is F, Cl, Br, I, OH, $C_1$-$C_6$ alkoxy, or phenyl; and X and Z are both H. In embodiments, Z is F, Cl, Br, I, OH, $C_1$-$C_6$ alkoxy, or phenyl; and X and Y are both H. In embodiments, X and Y are each independently F, Cl, Br, I, OH, $C_1$-$C_6$ alkoxy, or phenyl; and Z is H. In embodiments, X and Z are each independently F, Cl, Br, I, OH, $C_1$-$C_6$ alkoxy, or phenyl; and Y is H. In embodiments, Y and Z are each independently F, Cl, Br, I, OH, $C_1$-$C_6$ alkoxy, or phenyl; and X is H.

In some embodiments of Formula (3), X is H, F, Cl, Br, I, OH, $C_1$-$C_6$ alkoxy, or phenyl. In embodiments, X is F, Cl, Br, or I. In embodiments, X is H. In embodiments, X is F. In embodiments, X is Cl. In embodiments, X is Br. In embodiments, X is I. In embodiments, X is OH. In embodiments, X is $C_1$-$C_6$ alkoxy. In embodiments, X is methoxy. In embodiments, X is phenyl. In embodiments, X is 4-hydroxyphenyl. In embodiments, X is $C_3$-$C_6$ cycloalkyl. In embodiments, X is cyclopropyl.

In some embodiments of Formula (3), Y is H, F, Cl, Br, I, OH, $C_1$-$C_6$ alkoxy, or phenyl. In embodiments, Y is F, Cl, Br, or I. In embodiments, Y is H. In embodiments, Y is F. In embodiments, Y is Cl. In embodiments, Y is Br. In embodiments, Y is I. In embodiments, Y is OH. In embodiments, Y is $C_1$-$C_6$ alkoxy. In embodiments, Y is methoxy. In embodiments, Y is phenyl. In embodiments, Y is 4-hydroxyphenyl. In embodiments, Y is $C_3$-$C_6$ cycloalkyl. In embodiments, Y is cyclopropyl.

In some embodiments of Formula (3), Z is H, F, Cl, Br, I, OH, $C_1$-$C_6$ alkoxy, or phenyl. In embodiments, Z is F, Cl, Br, or I. In embodiments, Z is H. In embodiments, Z is F. In embodiments, Z is Cl. In embodiments, Z is Br. In embodiments, Z is I. In embodiments, Z is OH. In embodiments, Z is $C_1$-$C_6$ alkoxy. In embodiments, Z is methoxy. In embodiments, Z is phenyl. In embodiments, Z is 4-hydroxyphenyl. In embodiments, Z is $C_3$-$C_6$ cycloalkyl. In embodiments, Z is cyclopropyl.

In some embodiments of Formula (3), X and Y are taken together to form a 4- to 6-membered heterocyclyl. In embodiments, X and Y are taken together to form

(methylenedioxy), wherein * and ** indicate the points of connection between X and the rest of the compound, and between Y and the rest of the compound, respectively. In embodiments, X and Y are taken together to form a dihydrofuranyl. In embodiments, X and Y are taken together to form

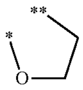

or

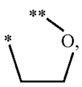

, wherein * and ** indicate the points of connection between X and the rest of the compound, and between Y and the rest of the compound, respectively. In embodiments, X and Y are taken together to form a furanyl. In embodiments, X and Y are taken together to form

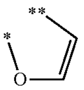

or

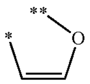

wherein * and ** indicate the points of connection between X and the rest of the compound, and between Y and the rest of the compound, respectively.

In some embodiments of Formula (3), Y and Z are taken together to form a 4- to 6-membered heterocyclyl. In embodiments, Y and Z are taken together to form

(methylenedioxy), wherein * and ** indicate the points of connection between Y and the rest of the compound, and between Z and the rest of the compound, respectively. In embodiments, Y and Z are taken together to form a dihydrofuranyl. In embodiments, Y and Z are taken together to form

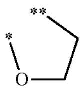

or

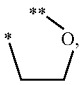

, wherein * and ** indicate the points of connection between Y and the rest of the compound, and between Z and the rest of the compound, respectively. In embodiments, Y and Z are taken together to form a furanyl. In embodiments, Y and Z are taken together to form

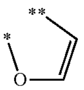

or

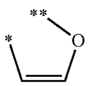

wherein * and ** indicate the points of connection between Y and the rest of the compound, and between Z and the rest of the compound, respectively.

In some embodiments of Formula (3), $R^a$ is H or $C_1$-$C_6$ alkyl. In embodiments, $R^a$ is H. In embodiments, $R^a$ is $C_1$-$C_6$ alkyl. In embodiments, $R^a$ is methyl. In embodiments, $R^a$ is ethyl.

In some embodiments, the compound has the structure of any of Formulae (I)-(III):

(I)

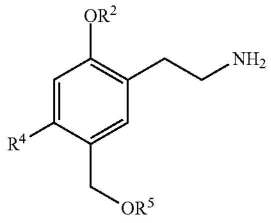

(II)

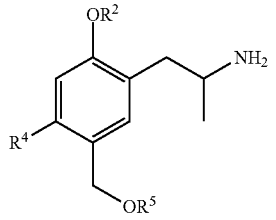

(III)

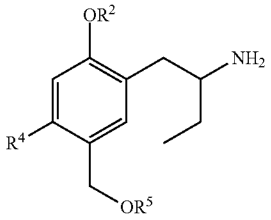

For each of the Formulae (I)-(III), $R^2$, $R^4$, and $R^5$ are as defined for Formula (1), including for each of the separate individual listed embodiments of Formulae (1) and (2), and as otherwise disclosed herein.

In some embodiments, the compound has the structure of any of Formulae (IV)-(XXI), wherein for each of the Formulae (IV)-(XXI), $R^4$ is as defined for Formula (1), including for each of the separate individual listed embodiments of Formulae (1) and (2), and as otherwise disclosed herein:

(IV)

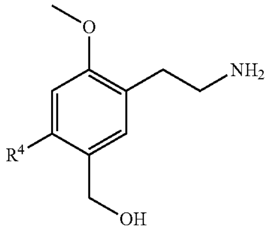

(V)

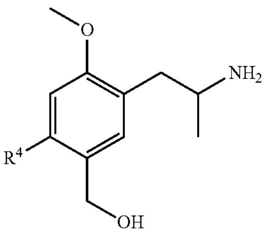

-continued (VI)

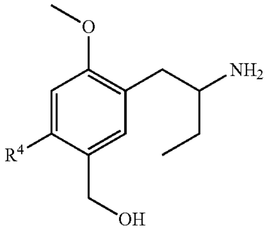

(VII)

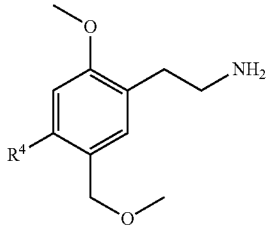

(VIII)

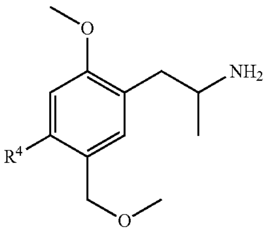

(IX)

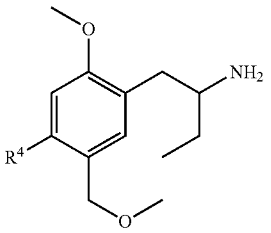

(X)

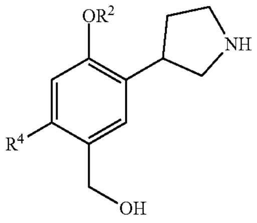

(XI)

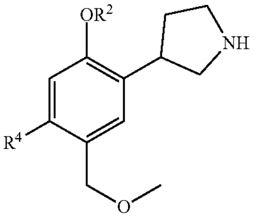

-continued (XII)

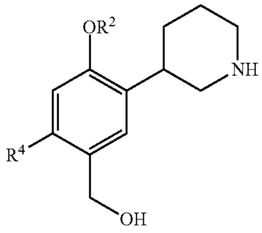

(XIII)

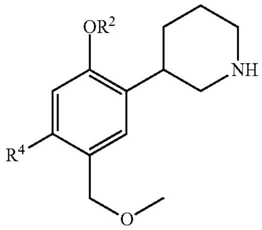

(XIV)

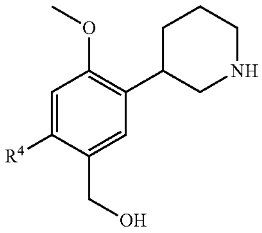

(XV)

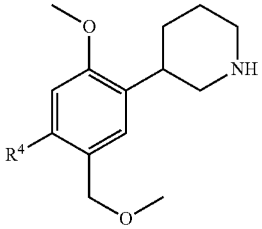

(XVI)

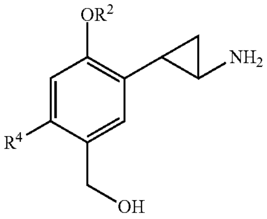

(XVII)

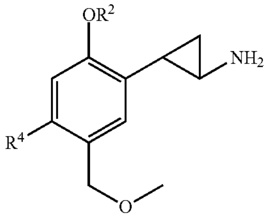

(XVIII)

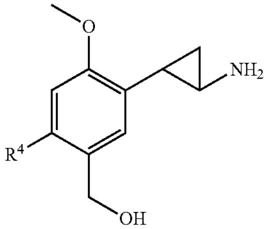

-continued (XIX)

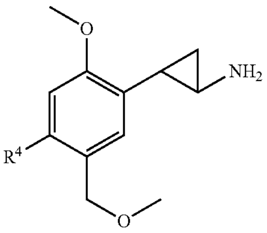

(XX)

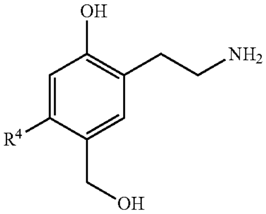

(XXI)

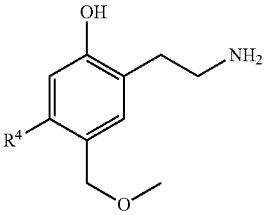

In some embodiments, the compound is selected from Table 1, or a pharmaceutically acceptable salt, stereoisomer, hydrate, solvate, or isotopic derivative thereof. In the embodiments of Table 1, and elsewhere as will be appreciated by those of skill, the following variables will have the following abbreviations:

| Structure, wherein * indicates the point of connection | 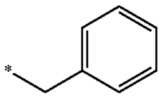 | 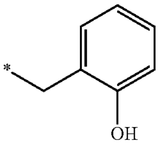 |
|---|---|---|
| Abbreviation | NB | NBOH |
| 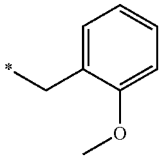 | 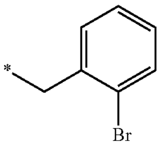 | 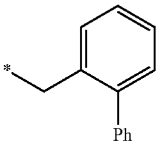 |
| NBOMe | NBBr | NBPh |
| 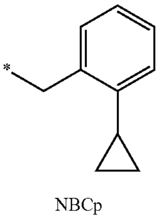 | 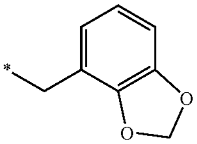 | |
| NBCp | NBMD | |

-continued

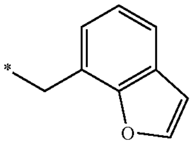

NMe7BF

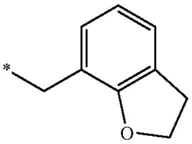

NMe7DHBF

In embodiments, the compound is any one of compounds 1-144 in Table 1. In embodiments, the compound is any one of compounds 145-180 in Table 1. In embodiments, the compound is any one of compounds 181-216 in Table 1. In embodiments, the compound is any one of compounds 217-252 in Table 1. In embodiments, the compound is any one of compounds 253-288 in Table 1. In embodiments, the compound is any one of compounds 289-324 in Table 1. In embodiments, the compound is any one of compounds 325-360 in Table 1. In embodiments, the compound is any one of compounds 361-396 in Table 1. In embodiments, the compound is any one of compounds 397-432 in Table 1. In embodiments, the compound is any one of compounds 433-468 in Table 1. For each of the foregoing embodiments, in some embodiments the compound is a pharmaceutically acceptable salt, stereoisomer, hydrate, solvate, or isotopic derivative thereof.

TABLE 1

Exemplary Compounds of Formula (1)

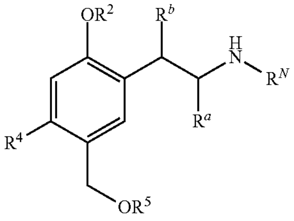

| No. | $R^2$ | $R^4$ | $R^5$ | $R^a$ | $R^b$ | $R^N$ |
|---|---|---|---|---|---|---|
| 1 | $—CH_3$ | —H | $—CH_3$ | —H | —H | —H |
| 2 | $—CH_3$ | —F | $—CH_3$ | —H | —H | —H |
| 3 | $—CH_3$ | —Cl | $—CH_3$ | —H | —H | —H |
| 4 | $—CH_3$ | —Br | $—CH_3$ | —H | —H | —H |
| 5 | $—CH_3$ | —I | $—CH_3$ | —H | —H | —H |
| 6 | $—CH_3$ | $—CH_3$ | $—CH_3$ | —H | —H | —H |
| 7 | $—CH_3$ | $—CH_2CH_3$ | $—CH_3$ | —H | —H | —H |
| 8 | $—CH_3$ | $—CH_2CH(CH_3)_2$ | $—CH_3$ | —H | —H | —H |
| 9 | $—CH_3$ | $—CH_2CH{=}CH_2$ | $—CH_3$ | —H | —H | —H |
| 10 | $—CH_3$ | —CN | $—CH_3$ | —H | —H | —H |
| 11 | $—CH_3$ | $—NO_2$ | $—CH_3$ | —H | —H | —H |
| 12 | $—CH_3$ | $—CF_3$ | $—CH_3$ | —H | —H | —H |
| 13 | $—CH_3$ | $—OCH_3$ | $—CH_3$ | —H | —H | —H |
| 14 | $—CH_3$ | $—SCH_3$ | $—CH_3$ | —H | —H | —H |
| 15 | $—CH_3$ | $—SCH_2CH_3$ | $—CH_3$ | —H | —H | —H |
| 16 | $—CH_3$ | $—SCH_2CH_2F$ | $—CH_3$ | —H | —H | —H |
| 17 | $—CH_3$ | $—CH_2Cp$ | $—CH_3$ | —H | —H | —H |
| 18 | $—CH_3$ | $—CH_2COOCH_3$ | $—CH_3$ | —H | —H | —H |
| 19 | $—CH_3$ | —H | —H | —H | —H | —H |
| 20 | $—CH_3$ | —F | —H | —H | —H | —H |
| 21 | $—CH_3$ | —Cl | —H | —H | —H | —H |
| 22 | $—CH_3$ | —Br | —H | —H | —H | —H |
| 23 | $—CH_3$ | —I | —H | —H | —H | —H |
| 24 | $—CH_3$ | $—CH_3$ | —H | —H | —H | —H |
| 25 | $—CH_3$ | $—CH_2CH_3$ | —H | —H | —H | —H |
| 26 | $—CH_3$ | $—CH_2CH(CH_3)_2$ | —H | —H | —H | —H |
| 27 | $—CH_3$ | $—CH_2CH{=}CH_2$ | —H | —H | —H | —H |
| 28 | $—CH_3$ | —CN | —H | —H | —H | —H |
| 29 | $—CH_3$ | $—NO_2$ | —H | —H | —H | —H |
| 30 | $—CH_3$ | $—CF_3$ | —H | —H | —H | —H |
| 31 | $—CH_3$ | $—OCH_3$ | —H | —H | —H | —H |

TABLE 1-continued

Exemplary Compounds of Formula (1)

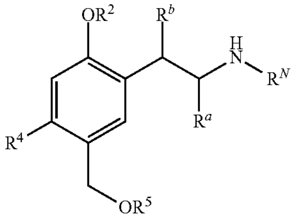

| No. | $R^2$ | $R^4$ | $R^5$ | $R^a$ | $R^b$ | $R^N$ |
|---|---|---|---|---|---|---|
| 32 | $—CH_3$ | $—SCH_3$ | —H | —H | —H | —H |
| 33 | $—CH_3$ | $—SCH_2CH_3$ | —H | —H | —H | —H |
| 34 | $—CH_3$ | $—SCH_2CH_2F$ | —H | —H | —H | —H |
| 35 | $—CH_3$ | $—CH_2Cp$ | —H | —H | —H | —H |
| 36 | $—CH_3$ | $—CH_2COOCH_3$ | —H | —H | —H | —H |
| 37 | $—CH_3$ | —H | $—CH_3$ | $—CH_3$ | —H | —H |
| 38 | $—CH_3$ | —F | $—CH_3$ | $—CH_3$ | —H | —H |
| 39 | $—CH_3$ | —Cl | $—CH_3$ | $—CH_3$ | —H | —H |
| 40 | $—CH_3$ | —Br | $—CH_3$ | $—CH_3$ | —H | —H |
| 41 | $—CH_3$ | —I | $—CH_3$ | $—CH_3$ | —H | —H |
| 42 | $—CH_3$ | $—CH_3$ | $—CH_3$ | $—CH_3$ | —H | —H |
| 43 | $—CH_3$ | $—CH_2CH_3$ | $—CH_3$ | $—CH_3$ | —H | —H |
| 44 | $—CH_3$ | $—CH_2CH(CH_3)_2$ | $—CH_3$ | $—CH_3$ | —H | —H |
| 45 | $—CH_3$ | $—CH_2CH{=}CH_2$ | $—CH_3$ | $—CH_3$ | —H | —H |
| 46 | $—CH_3$ | —CN | $—CH_3$ | $—CH_3$ | —H | —H |
| 47 | $—CH_3$ | $—NO_2$ | $—CH_3$ | $—CH_3$ | —H | —H |
| 48 | $—CH_3$ | $—CF_3$ | $—CH_3$ | $—CH_3$ | —H | —H |
| 49 | $—CH_3$ | $—OCH_3$ | $—CH_3$ | $—CH_3$ | —H | —H |
| 50 | $—CH_3$ | $—SCH_3$ | $—CH_3$ | $—CH_3$ | —H | —H |
| 51 | $—CH_3$ | $—SCH_2CH_3$ | $—CH_3$ | $—CH_3$ | —H | —H |
| 52 | $—CH_3$ | $—SCH_2CH_2F$ | $—CH_3$ | $—CH_3$ | —H | —H |
| 53 | $—CH_3$ | $—CH_2Cp$ | $—CH_3$ | $—CH_3$ | —H | —H |
| 54 | $—CH_3$ | $—CH_2COOCH_3$ | $—CH_3$ | $—CH_3$ | —H | —H |
| 55 | $—CH_3$ | —H | —H | $—CH_3$ | —H | —H |
| 56 | $—CH_3$ | —F | —H | $—CH_3$ | —H | —H |
| 57 | $—CH_3$ | —Cl | —H | $—CH_3$ | —H | —H |
| 58 | $—CH_3$ | —Br | —H | $—CH_3$ | —H | —H |
| 59 | $—CH_3$ | —I | —H | $—CH_3$ | —H | —H |
| 60 | $—CH_3$ | $—CH_3$ | —H | $—CH_3$ | —H | —H |
| 61 | $—CH_3$ | $—CH_2CH_3$ | —H | $—CH_3$ | —H | —H |
| 62 | $—CH_3$ | $—CH_2CH(CH_3)_2$ | —H | $—CH_3$ | —H | —H |
| 63 | $—CH_3$ | $—CH_2CH{=}CH_2$ | —H | $—CH_3$ | —H | —H |
| 64 | $—CH_3$ | —CN | —H | $—CH_3$ | —H | —H |
| 65 | $—CH_3$ | $—NO_2$ | —H | $—CH_3$ | —H | —H |
| 66 | $—CH_3$ | $—CF_3$ | —H | $—CH_3$ | —H | —H |
| 67 | $—CH_3$ | $—OCH_3$ | —H | $—CH_3$ | —H | —H |
| 68 | $—CH_3$ | $—SCH_3$ | —H | $—CH_3$ | —H | —H |
| 69 | $—CH_3$ | $—SCH_2CH_3$ | —H | $—CH_3$ | —H | —H |
| 70 | $—CH_3$ | $—SCH_2CH_2F$ | —H | $—CH_3$ | —H | —H |
| 71 | $—CH_3$ | $—CH_2Cp$ | —H | $—CH_3$ | —H | —H |
| 72 | $—CH_3$ | $—CH_2COOCH_3$ | —H | $—CH_3$ | —H | —H |
| 73 | $—CH_3$ | —H | $—CH_3$ | $—CH_2CH_3$ | —H | —H |
| 74 | $—CH_3$ | —F | $—CH_3$ | $—CH_2CH_3$ | —H | —H |
| 75 | $—CH_3$ | —Cl | $—CH_3$ | $—CH_2CH_3$ | —H | —H |
| 76 | $—CH_3$ | —Br | $—CH_3$ | $—CH_2CH_3$ | —H | —H |
| 77 | $—CH_3$ | —I | $—CH_3$ | $—CH_2CH_3$ | —H | —H |
| 78 | $—CH_3$ | $—CH_3$ | $—CH_3$ | $—CH_2CH_3$ | —H | —H |
| 79 | $—CH_3$ | $—CH_2CH_3$ | $—CH_3$ | $—CH_2CH_3$ | —H | —H |
| 80 | $—CH_3$ | $—CH_2CH(CH_3)_2$ | $—CH_3$ | $—CH_2CH_3$ | —H | —H |
| 81 | $—CH_3$ | $—CH_2CH{=}CH_2$ | $—CH_3$ | $—CH_2CH_3$ | —H | —H |
| 82 | $—CH_3$ | —CN | $—CH_3$ | $—CH_2CH_3$ | —H | —H |
| 83 | $—CH_3$ | $—NO_2$ | $—CH_3$ | $—CH_2CH_3$ | —H | —H |
| 84 | $—CH_3$ | $—CF_3$ | $—CH_3$ | $—CH_2CH_3$ | —H | —H |
| 85 | $—CH_3$ | $—OCH_3$ | $—CH_3$ | $—CH_2CH_3$ | —H | —H |
| 86 | $—CH_3$ | $—SCH_3$ | $—CH_3$ | $—CH_2CH_3$ | —H | —H |
| 87 | $—CH_3$ | $—SCH_2CH_3$ | $—CH_3$ | $—CH_2CH_3$ | —H | —H |
| 88 | $—CH_3$ | $—SCH_2CH_2F$ | $—CH_3$ | $—CH_2CH_3$ | —H | —H |
| 89 | $—CH_3$ | $—CH_2Cp$ | $—CH_3$ | $—CH_2CH_3$ | —H | —H |
| 90 | $—CH_3$ | $—CH_2COOCH_3$ | $—CH_3$ | $—CH_2CH_3$ | —H | —H |
| 91 | $—CH_3$ | —H | —H | $—CH_2CH_3$ | —H | —H |
| 92 | $—CH_3$ | —F | —H | $—CH_2CH_3$ | —H | —H |
| 93 | $—CH_3$ | —Cl | —H | $—CH_2CH_3$ | —H | —H |
| 94 | $—CH_3$ | —Br | —H | $—CH_2CH_3$ | —H | —H |
| 95 | $—CH_3$ | —I | —H | $—CH_2CH_3$ | —H | —H |
| 96 | $—CH_3$ | $—CH_3$ | —H | $—CH_2CH_3$ | —H | —H |

TABLE 1-continued

Exemplary Compounds of Formula (1)

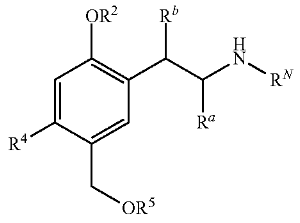

| No. | $R^2$ | $R^4$ | $R^5$ | $R^a$ | $R^b$ | $R^N$ |
|---|---|---|---|---|---|---|
| 97 | —$CH_3$ | —$CH_2CH_3$ | —H | —$CH_2CH_3$ | —H | —H |
| 98 | —$CH_3$ | —$CH_2CH(CH_3)_2$ | —H | —$CH_2CH_3$ | —H | —H |
| 99 | —$CH_3$ | —$CH_2CH{=}CH_2$ | —H | —$CH_2CH_3$ | —H | —H |
| 100 | —$CH_3$ | —CN | —H | —$CH_2CH_3$ | —H | —H |
| 101 | —$CH_3$ | —$NO_2$ | —H | —$CH_2CH_3$ | —H | —H |
| 102 | —$CH_3$ | —$CF_3$ | —H | —$CH_2CH_3$ | —H | —H |
| 103 | —$CH_3$ | —$OCH_3$ | —H | —$CH_2CH_3$ | —H | —H |
| 104 | —$CH_3$ | —$SCH_3$ | —H | —$CH_2CH_3$ | —H | —H |
| 105 | —$CH_3$ | —$SCH_2CH_3$ | —H | —$CH_2CH_3$ | —H | —H |
| 106 | —$CH_3$ | —$SCH_2CH_2F$ | —H | —$CH_2CH_3$ | —H | —H |
| 107 | —$CH_3$ | —$CH_2Cp$ | —H | —$CH_2CH_3$ | —H | —H |
| 108 | —$CH_3$ | —$CH_2COOCH_3$ | —H | —$CH_2CH_3$ | —H | —H |
| 109 | —H | —H | —$CH_3$ | —H | —H | —H |
| 110 | —H | —F | —$CH_3$ | —H | —H | —H |
| 111 | —H | —Cl | —$CH_3$ | —H | —H | —H |
| 112 | —H | —Br | —$CH_3$ | —H | —H | —H |
| 113 | —H | —I | —$CH_3$ | —H | —H | —H |
| 114 | —H | —$CH_3$ | —$CH_3$ | —H | —H | —H |
| 115 | —H | —$CH_2CH_3$ | —$CH_3$ | —H | —H | —H |
| 116 | —H | —$CH_2CH(CH_3)_2$ | —$CH_3$ | —H | —H | —H |
| 117 | —H | —$CH_2CH{=}CH_2$ | —$CH_3$ | —H | —H | —H |
| 118 | —H | —CN | —$CH_3$ | —H | —H | —H |
| 119 | —H | —$NO_2$ | —$CH_3$ | —H | —H | —H |
| 120 | —H | —$CF_3$ | —$CH_3$ | —H | —H | —H |
| 121 | —H | —$OCH_3$ | —$CH_3$ | —H | —H | —H |
| 122 | —H | —$SCH_3$ | —$CH_3$ | —H | —H | —H |
| 123 | —H | —$SCH_2CH_3$ | —$CH_3$ | —H | —H | —H |
| 124 | —H | —$SCH_2CH_2F$ | —$CH_3$ | —H | —H | —H |
| 125 | —H | —$CH_2Cp$ | —$CH_3$ | —H | —H | —H |
| 126 | —H | —$CH_2COOCH_3$ | —$CH_3$ | —H | —H | —H |
| 127 | —H | —H | —H | —H | —H | —H |
| 128 | —H | —F | —H | —H | —H | —H |
| 129 | —H | —Cl | —H | —H | —H | —H |
| 130 | —H | —Br | —H | —H | —H | —H |
| 131 | —H | —I | —H | —H | —H | —H |
| 132 | —H | —$CH_3$ | —H | —H | —H | —H |
| 133 | —H | —$CH_2CH_3$ | —H | —H | —H | —H |
| 134 | —H | —$CH_2CH(CH_3)_2$ | —H | —H | —H | —H |
| 135 | —H | —$CH_2CH{=}CH_2$ | —H | —H | —H | —H |
| 136 | —H | —CN | —H | —H | —H | —H |
| 137 | —H | —$NO_2$ | —H | —H | —H | —H |
| 138 | —H | —$CF_3$ | —H | —H | —H | —H |
| 139 | —H | —$OCH_3$ | —H | —H | —H | —H |
| 140 | —H | —$SCH_3$ | —H | —H | —H | —H |
| 141 | —H | —$SCH_2CH_3$ | —H | —H | —H | —H |
| 142 | —H | —$SCH_2CH_2F$ | —H | —H | —H | —H |
| 143 | —H | —$CH_2Cp$ | —H | —H | —H | —H |
| 144 | —H | —$CH_2COOCH_3$ | —H | —H | —H | —H |
| 145 | —$CH_3$ | —H | —$CH_3$ | —H | —H | NB |
| 146 | —$CH_3$ | —F | —$CH_3$ | —H | —H | NB |
| 147 | —$CH_3$ | —Cl | —$CH_3$ | —H | —H | NB |
| 148 | —$CH_3$ | —Br | —$CH_3$ | —H | —H | NB |
| 149 | —$CH_3$ | —I | —$CH_3$ | —H | —H | NB |
| 150 | —$CH_3$ | —$CH_3$ | —$CH_3$ | —H | —H | NB |
| 151 | —$CH_3$ | —$CH_2CH_3$ | —$CH_3$ | —H | —H | NB |
| 152 | —$CH_3$ | —$CH_2CH(CH_3)_2$ | —$CH_3$ | —H | —H | NB |
| 153 | —$CH_3$ | —$CH_2CH{=}CH_2$ | —$CH_3$ | —H | —H | NB |
| 154 | —$CH_3$ | —CN | —$CH_3$ | —H | —H | NB |
| 155 | —$CH_3$ | —$NO_2$ | —$CH_3$ | —H | —H | NB |
| 156 | —$CH_3$ | —$CF_3$ | —$CH_3$ | —H | —H | NB |
| 157 | —$CH_3$ | —$OCH_3$ | —$CH_3$ | —H | —H | NB |
| 158 | —$CH_3$ | —$SCH_3$ | —$CH_3$ | —H | —H | NB |
| 159 | —$CH_3$ | —$SCH_2CH_3$ | —$CH_3$ | —H | —H | NB |
| 160 | —$CH_3$ | —$SCH_2CH_2F$ | —$CH_3$ | —H | —H | NB |
| 161 | —$CH_3$ | —$CH_2Cp$ | —$CH_3$ | —H | —H | NB |

TABLE 1-continued

Exemplary Compounds of Formula (1)

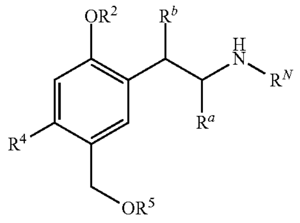

| No. | $R^2$ | $R^4$ | $R^5$ | $R^a$ | $R^b$ | $R^N$ |
|---|---|---|---|---|---|---|
| 162 | —$CH_3$ | —$CH_2COOCH_3$ | —$CH_3$ | —H | —H | NB |
| 163 | —$CH_3$ | —H | —H | —H | —H | NB |
| 164 | —$CH_3$ | —F | —H | —H | —H | NB |
| 165 | —$CH_3$ | —Cl | —H | —H | —H | NB |
| 166 | —$CH_3$ | —Br | —H | —H | —H | NB |
| 167 | —$CH_3$ | —I | —H | —H | —H | NB |
| 168 | —$CH_3$ | —$CH_3$ | —H | —H | —H | NB |
| 169 | —$CH_3$ | —$CH_2CH_3$ | —H | —H | —H | NB |
| 170 | —$CH_3$ | —$CH_2CH(CH_3)_2$ | —H | —H | —H | NB |
| 171 | —$CH_3$ | —$CH_2CH{=}CH_2$ | —H | —H | —H | NB |
| 172 | —$CH_3$ | —CN | —H | —H | —H | NB |
| 173 | —$CH_3$ | —$NO_2$ | —H | —H | —H | NB |
| 174 | —$CH_3$ | —$CF_3$ | —H | —H | —H | NB |
| 175 | —$CH_3$ | —$OCH_3$ | —H | —H | —H | NB |
| 176 | —$CH_3$ | —$SCH_3$ | —H | —H | —H | NB |
| 177 | —$CH_3$ | —$SCH_2CH_3$ | —H | —H | —H | NB |
| 178 | —$CH_3$ | —$SCH_2CH_2F$ | —H | —H | —H | NB |
| 179 | —$CH_3$ | —$CH_2Cp$ | —H | —H | —H | NB |
| 180 | —$CH_3$ | —$CH_2COOCH_3$ | —H | —H | —H | NB |
| 181 | —$CH_3$ | —H | —$CH_3$ | —H | —H | NBOH |
| 182 | —$CH_3$ | —F | —$CH_3$ | —H | —H | NBOH |
| 183 | —$CH_3$ | —Cl | —$CH_3$ | —H | —H | NBOH |
| 184 | —$CH_3$ | —Br | —$CH_3$ | —H | —H | NBOH |
| 185 | —$CH_3$ | —I | —$CH_3$ | —H | —H | NBOH |
| 186 | —$CH_3$ | —$CH_3$ | —$CH_3$ | —H | —H | NBOH |
| 187 | —$CH_3$ | —$CH_2CH_3$ | —$CH_3$ | —H | —H | NBOH |
| 188 | —$CH_3$ | —$CH_2CH(CH_3)_2$ | —$CH_3$ | —H | —H | NBOH |
| 189 | —$CH_3$ | —$CH_2CH{=}CH_2$ | —$CH_3$ | —H | —H | NBOH |
| 190 | —$CH_3$ | —CN | —$CH_3$ | —H | —H | NBOH |
| 191 | —$CH_3$ | —$NO_2$ | —$CH_3$ | —H | —H | NBOH |
| 192 | —$CH_3$ | —$CF_3$ | —$CH_3$ | —H | —H | NBOH |
| 193 | —$CH_3$ | —$OCH_3$ | —$CH_3$ | —H | —H | NBOH |
| 194 | —$CH_3$ | —$SCH_3$ | —$CH_3$ | —H | —H | NBOH |
| 195 | —$CH_3$ | —$SCH_2CH_3$ | —$CH_3$ | —H | —H | NBOH |
| 196 | —$CH_3$ | —$SCH_2CH_2F$ | —$CH_3$ | —H | —H | NBOH |
| 197 | —$CH_3$ | —$CH_2Cp$ | —$CH_3$ | —H | —H | NBOH |
| 198 | —$CH_3$ | —$CH_2COOCH_3$ | —$CH_3$ | —H | —H | NBOH |
| 199 | —$CH_3$ | —H | —H | —H | —H | NBOH |
| 200 | —$CH_3$ | —F | —H | —H | —H | NBOH |
| 201 | —$CH_3$ | —Cl | —H | —H | —H | NBOH |
| 202 | —$CH_3$ | —Br | —H | —H | —H | NBOH |
| 203 | —$CH_3$ | —I | —H | —H | —H | NBOH |
| 204 | —$CH_3$ | —$CH_3$ | —H | —H | —H | NBOH |
| 205 | —$CH_3$ | —$CH_2CH_3$ | —H | —H | —H | NBOH |
| 206 | —$CH_3$ | —$CH_2CH(CH_3)_2$ | —H | —H | —H | NBOH |
| 207 | —$CH_3$ | —$CH_2CH{=}CH_2$ | —H | —H | —H | NBOH |
| 208 | —$CH_3$ | —CN | —H | —H | —H | NBOH |
| 209 | —$CH_3$ | —$NO_2$ | —H | —H | —H | NBOH |
| 210 | —$CH_3$ | —$CF_3$ | —H | —H | —H | NBOH |
| 211 | —$CH_3$ | —$OCH_3$ | —H | —H | —H | NBOH |
| 212 | —$CH_3$ | —$SCH_3$ | —H | —H | —H | NBOH |
| 213 | —$CH_3$ | —$SCH_2CH_3$ | —H | —H | —H | NBOH |
| 214 | —$CH_3$ | —$SCH_2CH_2F$ | —H | —H | —H | NBOH |
| 215 | —$CH_3$ | —$CH_2Cp$ | —H | —H | —H | NBOH |
| 216 | —$CH_3$ | —$CH_2COOCH_3$ | —H | —H | —H | NBOH |
| 217 | —$CH_3$ | —H | —$CH_3$ | —H | —H | NBOMe |
| 218 | —$CH_3$ | —F | —$CH_3$ | —H | —H | NBOMe |
| 219 | —$CH_3$ | —Cl | —$CH_3$ | —H | —H | NBOMe |
| 220 | —$CH_3$ | —Br | —$CH_3$ | —H | —H | NBOMe |
| 221 | —$CH_3$ | —I | —$CH_3$ | —H | —H | NBOMe |
| 222 | —$CH_3$ | —$CH_3$ | —$CH_3$ | —H | —H | NBOMe |
| 223 | —$CH_3$ | —$CH_2CH_3$ | —$CH_3$ | —H | —H | NBOMe |
| 224 | —$CH_3$ | —$CH_2CH(CH_3)_2$ | —$CH_3$ | —H | —H | NBOMe |
| 225 | —$CH_3$ | —$CH_2CH{=}CH_2$ | —$CH_3$ | —H | —H | NBOMe |
| 226 | —$CH_3$ | —CN | —$CH_3$ | —H | —H | NBOMe |

TABLE 1-continued

Exemplary Compounds of Formula (1)

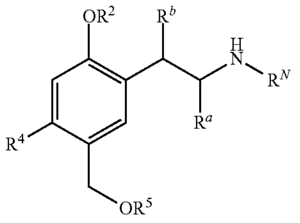

| No. | $R^2$ | $R^4$ | $R^5$ | $R^a$ | $R^b$ | $R^N$ |
|---|---|---|---|---|---|---|
| 227 | —$CH_3$ | —$NO_2$ | —$CH_3$ | —H | —H | NBOMe |
| 228 | —$CH_3$ | —$CF_3$ | —$CH_3$ | —H | —H | NBOMe |
| 229 | —$CH_3$ | —$OCH_3$ | —$CH_3$ | —H | —H | NBOMe |
| 230 | —$CH_3$ | —$SCH_3$ | —$CH_3$ | —H | —H | NBOMe |
| 231 | —$CH_3$ | —$SCH_2CH_3$ | —$CH_3$ | —H | —H | NBOMe |
| 232 | —$CH_3$ | —$SCH_2CH_2F$ | —$CH_3$ | —H | —H | NBOMe |
| 233 | —$CH_3$ | —$CH_2Cp$ | —$CH_3$ | —H | —H | NBOMe |
| 234 | —$CH_3$ | —$CH_2COOCH_3$ | —$CH_3$ | —H | —H | NBOMe |
| 235 | —$CH_3$ | —H | —H | —H | —H | NBOMe |
| 236 | —$CH_3$ | —F | —H | —H | —H | NBOMe |
| 237 | —$CH_3$ | —Cl | —H | —H | —H | NBOMe |
| 238 | —$CH_3$ | —Br | —H | —H | —H | NBOMe |
| 239 | —$CH_3$ | —I | —H | —H | —H | NBOMe |
| 240 | —$CH_3$ | —$CH_3$ | —H | —H | —H | NBOMe |
| 241 | —$CH_3$ | —$CH_2CH_3$ | —H | —H | —H | NBOMe |
| 242 | —$CH_3$ | —$CH_2CH(CH_3)_2$ | —H | —H | —H | NBOMe |
| 243 | —$CH_3$ | —$CH_2CH{=}CH_2$ | —H | —H | —H | NBOMe |
| 244 | —$CH_3$ | —CN | —H | —H | —H | NBOMe |
| 245 | —$CH_3$ | —$NO_2$ | —H | —H | —H | NBOMe |
| 246 | —$CH_3$ | —$CF_3$ | —H | —H | —H | NBOMe |
| 247 | —$CH_3$ | —$OCH_3$ | —H | —H | —H | NBOMe |
| 248 | —$CH_3$ | —$SCH_3$ | —H | —H | —H | NBOMe |
| 249 | —$CH_3$ | —$SCH_2CH_3$ | —H | —H | —H | NBOMe |
| 250 | —$CH_3$ | —$SCH_2CH_2F$ | —H | —H | —H | NBOMe |
| 251 | —$CH_3$ | —$CH_2Cp$ | —H | —H | —H | NBOMe |
| 252 | —$CH_3$ | —$CH_2COOCH_3$ | —H | —H | —H | NBOMe |
| 253 | —$CH_3$ | —H | —$CH_3$ | —H | —H | NBBr |
| 254 | —$CH_3$ | —F | —$CH_3$ | —H | —H | NBBr |
| 255 | —$CH_3$ | —Cl | —$CH_3$ | —H | —H | NBBr |
| 256 | —$CH_3$ | —Br | —$CH_3$ | —H | —H | NBBr |
| 257 | —$CH_3$ | —I | —$CH_3$ | —H | —H | NBBr |
| 258 | —$CH_3$ | —$CH_3$ | —$CH_3$ | —H | —H | NBBr |
| 259 | —$CH_3$ | —$CH_2CH_3$ | —$CH_3$ | —H | —H | NBBr |
| 260 | —$CH_3$ | —$CH_2CH(CH_3)_2$ | —$CH_3$ | —H | —H | NBBr |
| 261 | —$CH_3$ | —$CH_2CH{=}CH_2$ | —$CH_3$ | —H | —H | NBBr |
| 262 | —$CH_3$ | —CN | —$CH_3$ | —H | —H | NBBr |
| 263 | —$CH_3$ | —$NO_2$ | —$CH_3$ | —H | —H | NBBr |
| 264 | —$CH_3$ | —$CF_3$ | —$CH_3$ | —H | —H | NBBr |
| 265 | —$CH_3$ | —$OCH_3$ | —$CH_3$ | —H | —H | NBBr |
| 266 | —$CH_3$ | —$SCH_3$ | —$CH_3$ | —H | —H | NBBr |
| 267 | —$CH_3$ | —$SCH_2CH_3$ | —$CH_3$ | —H | —H | NBBr |
| 268 | —$CH_3$ | —$SCH_2CH_2F$ | —$CH_3$ | —H | —H | NBBr |
| 269 | —$CH_3$ | —$CH_2Cp$ | —$CH_3$ | —H | —H | NBBr |
| 270 | —$CH_3$ | —$CH_2COOCH_3$ | —$CH_3$ | —H | —H | NBBr |
| 271 | —$CH_3$ | —H | —H | —H | —H | NBBr |
| 272 | —$CH_3$ | —F | —H | —H | —H | NBBr |
| 273 | —$CH_3$ | —Cl | —H | —H | —H | NBBr |
| 274 | —$CH_3$ | —Br | —H | —H | —H | NBBr |
| 275 | —$CH_3$ | —I | —H | —H | —H | NBBr |
| 276 | —$CH_3$ | —$CH_3$ | —H | —H | —H | NBBr |
| 277 | —$CH_3$ | —$CH_2CH_3$ | —H | —H | —H | NBBr |
| 278 | —$CH_3$ | —$CH_2CH(CH_3)_2$ | —H | —H | —H | NBBr |
| 279 | —$CH_3$ | —$CH_2CH{=}CH_2$ | —H | —H | —H | NBBr |
| 280 | —$CH_3$ | —CN | —H | —H | —H | NBBr |
| 281 | —$CH_3$ | —$NO_2$ | —H | —H | —H | NBBr |
| 282 | —$CH_3$ | —$CF_3$ | —H | —H | —H | NBBr |
| 283 | —$CH_3$ | —$OCH_3$ | —H | —H | —H | NBBr |
| 284 | —$CH_3$ | —$SCH_3$ | —H | —H | —H | NBBr |
| 285 | —$CH_3$ | —$SCH_2CH_3$ | —H | —H | —H | NBBr |
| 286 | —$CH_3$ | —$SCH_2CH_2F$ | —H | —H | —H | NBBr |
| 287 | —$CH_3$ | —$CH_2Cp$ | —H | —H | —H | NBBr |
| 288 | —$CH_3$ | —$CH_2COOCH_3$ | —H | —H | —H | NBBr |
| 289 | —$CH_3$ | —H | —$CH_3$ | —H | —H | NBPh |
| 290 | —$CH_3$ | —F | —$CH_3$ | —H | —H | NBPh |
| 291 | —$CH_3$ | —Cl | —$CH_3$ | —H | —H | NBPh |

TABLE 1-continued

Exemplary Compounds of Formula (1)

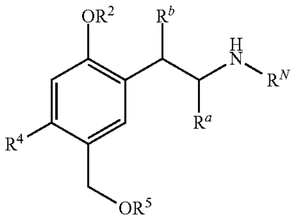

| No. | $R^2$ | $R^4$ | $R^5$ | $R^a$ | $R^b$ | $R^N$ |
|---|---|---|---|---|---|---|
| 292 | —$CH_3$ | —Br | —$CH_3$ | —H | —H | NBPh |
| 293 | —$CH_3$ | —I | —$CH_3$ | —H | —H | NBPh |
| 294 | —$CH_3$ | —$CH_3$ | —$CH_3$ | —H | —H | NBPh |
| 295 | —$CH_3$ | —$CH_2CH_3$ | —$CH_3$ | —H | —H | NBPh |
| 296 | —$CH_3$ | —$CH_2CH(CH_3)_2$ | —$CH_3$ | —H | —H | NBPh |
| 297 | —$CH_3$ | —$CH_2CH{=}CH_2$ | —$CH_3$ | —H | —H | NBPh |
| 298 | —$CH_3$ | —CN | —$CH_3$ | —H | —H | NBPh |
| 299 | —$CH_3$ | —$NO_2$ | —$CH_3$ | —H | —H | NBPh |
| 300 | —$CH_3$ | —$CF_3$ | —$CH_3$ | —H | —H | NBPh |
| 301 | —$CH_3$ | —$OCH_3$ | —$CH_3$ | —H | —H | NBPh |
| 302 | —$CH_3$ | —$SCH_3$ | —$CH_3$ | —H | —H | NBPh |
| 303 | —$CH_3$ | —$SCH_2CH_3$ | —$CH_3$ | —H | —H | NBPh |
| 304 | —$CH_3$ | —$SCH_2CH_2F$ | —$CH_3$ | —H | —H | NBPh |
| 305 | —$CH_3$ | —$CH_2Cp$ | —$CH_3$ | —H | —H | NBPh |
| 306 | —$CH_3$ | —$CH_2COOCH_3$ | —$CH_3$ | —H | —H | NBPh |
| 307 | —$CH_3$ | —H | —H | —H | —H | NBPh |
| 308 | —$CH_3$ | —F | —H | —H | —H | NBPh |
| 309 | —$CH_3$ | —Cl | —H | —H | —H | NBPh |
| 310 | —$CH_3$ | —Br | —H | —H | —H | NBPh |
| 311 | —$CH_3$ | —I | —H | —H | —H | NBPh |
| 312 | —$CH_3$ | —$CH_3$ | —H | —H | —H | NBPh |
| 313 | —$CH_3$ | —$CH_2CH_3$ | —H | —H | —H | NBPh |
| 314 | —$CH_3$ | —$CH_2CH(CH_3)_2$ | —H | —H | —H | NBPh |
| 315 | —$CH_3$ | —$CH_2CH{=}CH_2$ | —H | —H | —H | NBPh |
| 316 | —$CH_3$ | —CN | —H | —H | —H | NBPh |
| 317 | —$CH_3$ | —$NO_2$ | —H | —H | —H | NBPh |
| 318 | —$CH_3$ | —$CF_3$ | —H | —H | —H | NBPh |
| 319 | —$CH_3$ | —$OCH_3$ | —H | —H | —H | NBPh |
| 320 | —$CH_3$ | —$SCH_3$ | —H | —H | —H | NBPh |
| 321 | —$CH_3$ | —$SCH_2CH_3$ | —H | —H | —H | NBPh |
| 322 | —$CH_3$ | —$SCH_2CH_2F$ | —H | —H | —H | NBPh |
| 323 | —$CH_3$ | —$CH_2Cp$ | —H | —H | —H | NBPh |
| 324 | —$CH_3$ | —$CH_2COOCH_3$ | —H | —H | —H | NBPh |
| 325 | —$CH_3$ | —H | —$CH_3$ | —H | —H | NBCp |
| 326 | —$CH_3$ | —F | —$CH_3$ | —H | —H | NBCp |
| 327 | —$CH_3$ | —Cl | —$CH_3$ | —H | —H | NBCp |
| 328 | —$CH_3$ | —Br | —$CH_3$ | —H | —H | NBCp |
| 329 | —$CH_3$ | —I | —$CH_3$ | —H | —H | NBCp |
| 330 | —$CH_3$ | —$CH_3$ | —$CH_3$ | —H | —H | NBCp |
| 331 | —$CH_3$ | —$CH_2CH_3$ | —$CH_3$ | —H | —H | NBCp |
| 332 | —$CH_3$ | —$CH_2CH(CH_3)_2$ | —$CH_3$ | —H | —H | NBCp |
| 333 | —$CH_3$ | —$CH_2CH{=}CH_2$ | —$CH_3$ | —H | —H | NBCp |
| 334 | —$CH_3$ | —CN | —$CH_3$ | —H | —H | NBCp |
| 335 | —$CH_3$ | —$NO_2$ | —$CH_3$ | —H | —H | NBCp |
| 336 | —$CH_3$ | —$CF_3$ | —$CH_3$ | —H | —H | NBCp |
| 337 | —$CH_3$ | —$OCH_3$ | —$CH_3$ | —H | —H | NBCp |
| 338 | —$CH_3$ | —$SCH_3$ | —$CH_3$ | —H | —H | NBCp |
| 339 | —$CH_3$ | —$SCH_2CH_3$ | —$CH_3$ | —H | —H | NBCp |
| 340 | —$CH_3$ | —$SCH_2CH_2F$ | —$CH_3$ | —H | —H | NBCp |
| 341 | —$CH_3$ | —$CH_2Cp$ | —$CH_3$ | —H | —H | NBCp |
| 342 | —$CH_3$ | —$CH_2COOCH_3$ | —$CH_3$ | —H | —H | NBCp |
| 343 | —$CH_3$ | —H | —H | —H | —H | NBCp |
| 344 | —$CH_3$ | —F | —H | —H | —H | NBCp |
| 345 | —$CH_3$ | —Cl | —H | —H | —H | NBCp |
| 346 | —$CH_3$ | —Br | —H | —H | —H | NBCp |
| 347 | —$CH_3$ | —I | —H | —H | —H | NBCp |
| 348 | —$CH_3$ | —$CH_3$ | —H | —H | —H | NBCp |
| 349 | —$CH_3$ | —$CH_2CH_3$ | —H | —H | —H | NBCp |
| 350 | —$CH_3$ | —$CH_2CH(CH_3)_2$ | —H | —H | —H | NBCp |
| 351 | —$CH_3$ | —$CH_2CH{=}CH_2$ | —H | —H | —H | NBCp |
| 352 | —$CH_3$ | —CN | —H | —H | —H | NBCp |
| 353 | —$CH_3$ | —$NO_2$ | —H | —H | —H | NBCp |
| 354 | —$CH_3$ | —$CF_3$ | —H | —H | —H | NBCp |
| 355 | —$CH_3$ | —$OCH_3$ | —H | —H | —H | NBCp |
| 356 | —$CH_3$ | —$SCH_3$ | —H | —H | —H | NBCp |

TABLE 1-continued

Exemplary Compounds of Formula (1)

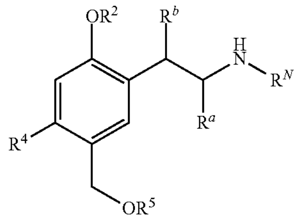

| No. | $R^2$ | $R^4$ | $R^5$ | $R^a$ | $R^b$ | $R^N$ |
|---|---|---|---|---|---|---|
| 357 | —$CH_3$ | —$SCH_2CH_3$ | —H | —H | —H | NBCp |
| 358 | —$CH_3$ | —$SCH_2CH_2F$ | —H | —H | —H | NBCp |
| 359 | —$CH_3$ | —$CH_2Cp$ | —H | —H | —H | NBCp |
| 360 | —$CH_3$ | —$CH_2COOCH_3$ | —H | —H | —H | NBCp |
| 361 | —$CH_3$ | —H | —$CH_3$ | —H | —H | NBMD |
| 362 | —$CH_3$ | —F | —$CH_3$ | —H | —H | NBMD |
| 363 | —$CH_3$ | —Cl | —$CH_3$ | —H | —H | NBMD |
| 364 | —$CH_3$ | —Br | —$CH_3$ | —H | —H | NBMD |
| 365 | —$CH_3$ | —I | —$CH_3$ | —H | —H | NBMD |
| 366 | —$CH_3$ | —$CH_3$ | —$CH_3$ | —H | —H | NBMD |
| 367 | —$CH_3$ | —$CH_2CH_3$ | —$CH_3$ | —H | —H | NBMD |
| 368 | —$CH_3$ | —$CH_2CH(CH_3)_2$ | —$CH_3$ | —H | —H | NBMD |
| 369 | —$CH_3$ | —$CH_2CH{=}CH_2$ | —$CH_3$ | —H | —H | NBMD |
| 370 | —$CH_3$ | —CN | —$CH_3$ | —H | —H | NBMD |
| 371 | —$CH_3$ | —$NO_2$ | —$CH_3$ | —H | —H | NBMD |
| 372 | —$CH_3$ | —$CF_3$ | —$CH_3$ | —H | —H | NBMD |
| 373 | —$CH_3$ | —$OCH_3$ | —$CH_3$ | —H | —H | NBMD |
| 374 | —$CH_3$ | —$SCH_3$ | —$CH_3$ | —H | —H | NBMD |
| 375 | —$CH_3$ | —$SCH_2CH_3$ | —$CH_3$ | —H | —H | NBMD |
| 376 | —$CH_3$ | —$SCH_2CH_2F$ | —$CH_3$ | —H | —H | NBMD |
| 377 | —$CH_3$ | —$CH_2Cp$ | —$CH_3$ | —H | —H | NBMD |
| 378 | —$CH_3$ | —$CH_2COOCH_3$ | —$CH_3$ | —H | —H | NBMD |
| 379 | —$CH_3$ | —H | —H | —H | —H | NBMD |
| 380 | —$CH_3$ | —F | —H | —H | —H | NBMD |
| 381 | —$CH_3$ | —Cl | —H | —H | —H | NBMD |
| 382 | —$CH_3$ | —Br | —H | —H | —H | NBMD |
| 383 | —$CH_3$ | —I | —H | —H | —H | NBMD |
| 384 | —$CH_3$ | —$CH_3$ | —H | —H | —H | NBMD |
| 385 | —$CH_3$ | —$CH_2CH_3$ | —H | —H | —H | NBMD |
| 386 | —$CH_3$ | —$CH_2CH(CH_3)_2$ | —H | —H | —H | NBMD |
| 387 | —$CH_3$ | —$CH_2CH{=}CH_2$ | —H | —H | —H | NBMD |
| 388 | —$CH_3$ | —CN | —H | —H | —H | NBMD |
| 389 | —$CH_3$ | —$NO_2$ | —H | —H | —H | NBMD |
| 390 | —$CH_3$ | —$CF_3$ | —H | —H | —H | NBMD |
| 391 | —$CH_3$ | —$OCH_3$ | —H | —H | —H | NBMD |
| 392 | —$CH_3$ | —$SCH_3$ | —H | —H | —H | NBMD |
| 393 | —$CH_3$ | —$SCH_2CH_3$ | —H | —H | —H | NBMD |
| 394 | —$CH_3$ | —$SCH_2CH_2F$ | —H | —H | —H | NBMD |
| 395 | —$CH_3$ | —$CH_2Cp$ | —H | —H | —H | NBMD |
| 396 | —$CH_3$ | —$CH_2COOCH_3$ | —H | —H | —H | NBMD |
| 397 | —$CH_3$ | —H | —$CH_3$ | —H | —H | NMe7BF |
| 398 | —$CH_3$ | —F | —$CH_3$ | —H | —H | NMe7BF |
| 399 | —$CH_3$ | —Cl | —$CH_3$ | —H | —H | NMe7BF |
| 400 | —$CH_3$ | —Br | —$CH_3$ | —H | —H | NMe7BF |
| 401 | —$CH_3$ | —I | —$CH_3$ | —H | —H | NMe7BF |
| 402 | —$CH_3$ | —$CH_3$ | —$CH_3$ | —H | —H | NMe7BF |
| 403 | —$CH_3$ | —$CH_2CH_3$ | —$CH_3$ | —H | —H | NMe7BF |
| 404 | —$CH_3$ | —$CH_2CH(CH_3)_2$ | —$CH_3$ | —H | —H | NMe7BF |
| 405 | —$CH_3$ | —$CH_2CH{=}CH_2$ | —$CH_3$ | —H | —H | NMe7BF |
| 406 | —$CH_3$ | —CN | —$CH_3$ | —H | —H | NMe7BF |
| 407 | —$CH_3$ | —$NO_2$ | —$CH_3$ | —H | —H | NMe7BF |
| 408 | —$CH_3$ | —$CF_3$ | —$CH_3$ | —H | —H | NMe7BF |
| 409 | —$CH_3$ | —$OCH_3$ | —$CH_3$ | —H | —H | NMe7BF |
| 410 | —$CH_3$ | —$SCH_3$ | —$CH_3$ | —H | —H | NMe7BF |
| 411 | —$CH_3$ | —$SCH_2CH_3$ | —$CH_3$ | —H | —H | NMe7BF |
| 412 | —$CH_3$ | —$SCH_2CH_2F$ | —$CH_3$ | —H | —H | NMe7BF |
| 413 | —$CH_3$ | —$CH_2Cp$ | —$CH_3$ | —H | —H | NMe7BF |
| 414 | —$CH_3$ | —$CH_2COOCH_3$ | —$CH_3$ | —H | —H | NMe7BF |
| 415 | —$CH_3$ | —H | —H | —H | —H | NMe7BF |
| 416 | —$CH_3$ | —F | —H | —H | —H | NMe7BF |
| 417 | —$CH_3$ | —Cl | —H | —H | —H | NMe7BF |
| 418 | —$CH_3$ | —Br | —H | —H | —H | NMe7BF |
| 419 | —$CH_3$ | —I | —H | —H | —H | NMe7BF |
| 420 | —$CH_3$ | —$CH_3$ | —H | —H | —H | NMe7BF |
| 421 | —$CH_3$ | —$CH_2CH_3$ | —H | —H | —H | NMe7BF |

TABLE 1-continued

Exemplary Compounds of Formula (1)

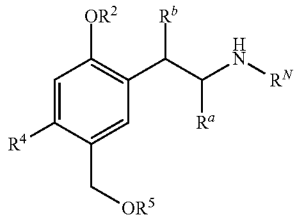

| No. | $R^2$ | $R^4$ | $R^5$ | $R^a$ | $R^b$ | $R^N$ |
|---|---|---|---|---|---|---|
| 422 | —$CH_3$ | —$CH_2CH(CH_3)_2$ | —H | —H | —H | NMe7BF |
| 423 | —$CH_3$ | —$CH_2CH{=}CH_2$ | —H | —H | —H | NMe7BF |
| 424 | —$CH_3$ | —CN | —H | —H | —H | NMe7BF |
| 425 | —$CH_3$ | —$NO_2$ | —H | —H | —H | NMe7BF |
| 426 | —$CH_3$ | —$CF_3$ | —H | —H | —H | NMe7BF |
| 427 | —$CH_3$ | —$OCH_3$ | —H | —H | —H | NMe7BF |
| 428 | —$CH_3$ | —$SCH_3$ | —H | —H | —H | NMe7BF |
| 429 | —$CH_3$ | —$SCH_2CH_3$ | —H | —H | —H | NMe7BF |
| 430 | —$CH_3$ | —$SCH_2CH_2F$ | —H | —H | —H | NMe7BF |
| 431 | —$CH_3$ | —$CH_2Cp$ | —H | —H | —H | NMe7BF |
| 432 | —$CH_3$ | —$CH_2COOCH_3$ | —H | —H | —H | NMe7BF |
| 433 | —$CH_3$ | —H | —$CH_3$ | —H | —H | NMe7DHBF |
| 434 | —$CH_3$ | —F | —$CH_3$ | —H | —H | NMe7DHBF |
| 435 | —$CH_3$ | —Cl | —$CH_3$ | —H | —H | NMe7DHBF |
| 436 | —$CH_3$ | —Br | —$CH_3$ | —H | —H | NMe7DHBF |
| 437 | —$CH_3$ | —I | —$CH_3$ | —H | —H | NMe7DHBF |
| 438 | —$CH_3$ | —$CH_3$ | —$CH_3$ | —H | —H | NMe7DHBF |
| 439 | —$CH_3$ | —$CH_2CH_3$ | —$CH_3$ | —H | —H | NMe7DHBF |
| 440 | —$CH_3$ | —$CH_2CH(CH_3)_2$ | —$CH_3$ | —H | —H | NMe7DHBF |
| 441 | —$CH_3$ | —$CH_2CH{=}CH_2$ | —$CH_3$ | —H | —H | NMe7DHBF |
| 442 | —$CH_3$ | —CN | —$CH_3$ | —H | —H | NMe7DHBF |
| 443 | —$CH_3$ | —$NO_2$ | —$CH_3$ | —H | —H | NMe7DHBF |
| 444 | —$CH_3$ | —$CF_3$ | —$CH_3$ | —H | —H | NMe7DHBF |
| 445 | —$CH_3$ | —$OCH_3$ | —$CH_3$ | —H | —H | NMe7DHBF |
| 446 | —$CH_3$ | —$SCH_3$ | —$CH_3$ | —H | —H | NMe7DHBF |
| 447 | —$CH_3$ | —$SCH_2CH_3$ | —$CH_3$ | —H | —H | NMe7DHBF |
| 448 | —$CH_3$ | —$SCH_2CH_2F$ | —$CH_3$ | —H | —H | NMe7DHBF |
| 449 | —$CH_3$ | —$CH_2Cp$ | —$CH_3$ | —H | —H | NMe7DHBF |
| 450 | —$CH_3$ | —$CH_2COOCH_3$ | —$CH_3$ | —H | —H | NMe7DHBF |
| 451 | —$CH_3$ | —H | —H | —H | —H | NMe7DHBF |
| 452 | —$CH_3$ | —F | —H | —H | —H | NMe7DHBF |
| 453 | —$CH_3$ | —Cl | —H | —H | —H | NMe7DHBF |
| 454 | —$CH_3$ | —Br | —H | —H | —H | NMe7DHBF |
| 455 | —$CH_3$ | —I | —H | —H | —H | NMe7DHBF |
| 456 | —$CH_3$ | —$CH_3$ | —H | —H | —H | NMe7DHBF |
| 457 | —$CH_3$ | —$CH_2CH_3$ | —H | —H | —H | NMe7DHBF |
| 458 | —$CH_3$ | —$CH_2CH(CH_3)_2$ | —H | —H | —H | NMe7DHBF |
| 459 | —$CH_3$ | —$CH_2CH{=}CH_2$ | —H | —H | —H | NMe7DHBF |
| 460 | —$CH_3$ | —CN | —H | —H | —H | NMe7DHBF |
| 461 | —$CH_3$ | —$NO_2$ | —H | —H | —H | NMe7DHBF |
| 462 | —$CH_3$ | —$CF_3$ | —H | —H | —H | NMe7DHBF |
| 463 | —$CH_3$ | —$OCH_3$ | —H | —H | —H | NMe7DHBF |
| 464 | —$CH_3$ | —$SCH_3$ | —H | —H | —H | NMe7DHBF |
| 465 | —$CH_3$ | —$SCH_2CH_3$ | —H | —H | —H | NMe7DHBF |
| 466 | —$CH_3$ | —$SCH_2CH_2F$ | —H | —H | —H | NMe7DHBF |
| 467 | —$CH_3$ | —$CH_2Cp$ | —H | —H | —H | NMe7DHBF |
| 468 | —$CH_3$ | —$CH_2COOCH_3$ | —H | —H | —H | NMe7DHBF |

For any of the exemplary compounds in Table 1, additional compounds include those in which the substituent on the phenyl ring at $R^N$ is located at a different position on the ring. For example, while in some embodiments the phenyl ring comprises a substituent (e.g., a hydroxy or methoxy group) in the ortho position relative to the point of substitution indicated by the asterisk, in other embodiments the substituent is located at the meta or para position. Thus, a 2-hydroxybenzyl (NBOH) may in other embodiments be a 3-hydroxybenzyl (NB3OH) or a 4-hydroxybenzyl (NB4OH). Likewise, a 2-methoxybenzyl (NBOMe) may in other embodiments be a 3-methoxybenzyl (NB3OMe) or a4-methoxybenzyl (NB4OMe). Similarly, a 2-bromobenzyl (NBBr) may in other embodiments be a 3-bromobenzyl (NB3Br) or a 4-bromobenzyl (NB4B3r), and the bromine in any of the foregoing may in other embodiments be another halogen. Similarly, polycyclic and fused-ring benzyls such as a 2,3-methylenedioxybenzyl (NBMD) may in other embodiments be a 3,4-methylenedioxybenzyl (NB34MD) or a 4,5-methylenedioxybenzyl (NB45MD). Other exemplary compounds include the cyclopropyl replaced with another cycloalkyl or alkyl (at any of the 2, 3, or 4-position); the methoxy replaced with another alkoxy (at any of the 2, 3, or 4-position), e.g., NBOEt or NB3OEt; di-substituted and multi-substituted benzyls; and the like.

For any compound where $R^N$ is NMe7BF, i.e., X and Y are taken together to form

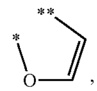
, in other embodiments X and Y are taken together to form

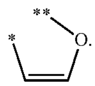

For any compound where $R^N$ is NMe7DHBF, i.e., X and Y are taken together to form

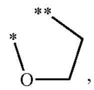
, in other embodiments X and Y are taken together to form

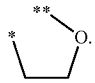

In some embodiments, the compound is a 2-hydroxy (2-HO) or 2-methoxy (2-MeO), 5-hydroxymethyl ("5-HM") compound. In embodiments, the compound is a 2-hydroxy, 5-hydroxymethyl compound. In embodiments, the compound is a 2-methoxy, 5-hydroxymethyl compound.

In some embodiments, the compound is a 2-hydroxy or 2-methoxy, 5-methoxymethyl ("5-MM") compound. In some embodiments, the compound is a 2-hydroxy, 5-methoxymethyl compound. In some embodiments, the compound is a 2-methoxy, 5-methoxymethyl compound.

In some embodiments, the 2-HO or 2-MeO, 5-HM compound is selected from the group consisting of:

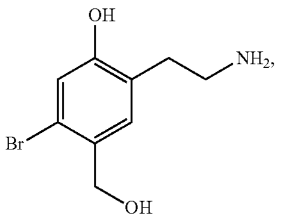

-continued

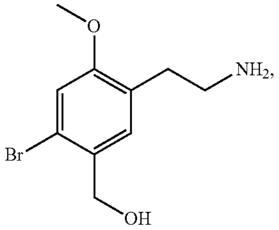

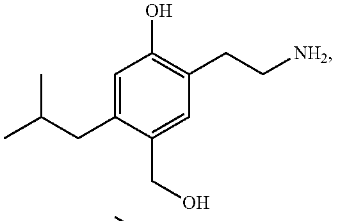

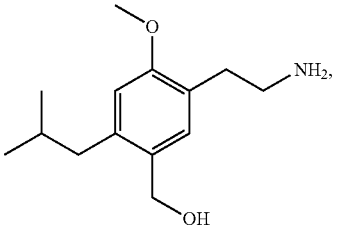

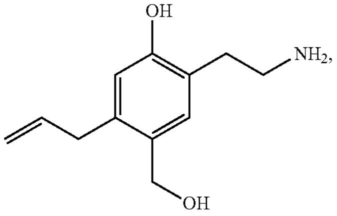

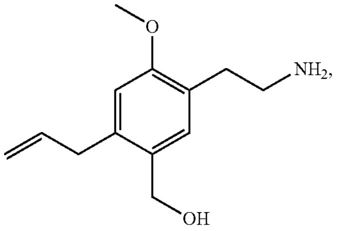

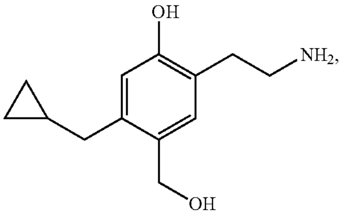
and

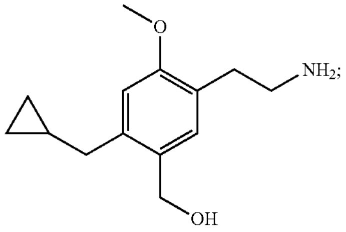

or a pharmaceutically acceptable salt, stereoisomer, hydrate, solvate, or isotopic derivative thereof.

In some such embodiments, the compound is any of the 2-HO, 5-HM compounds. In other such embodiments, the compound is any of the 2-MeO, 5-HM compounds.

In some embodiments, the 2-HO or 2-MeO, 5-MM compound is selected from the group consisting of:

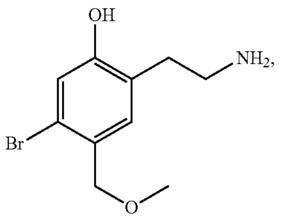
,

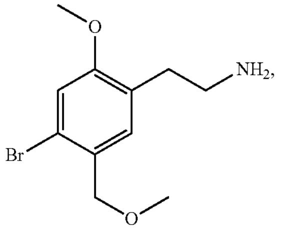
,

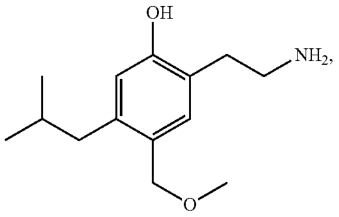
,

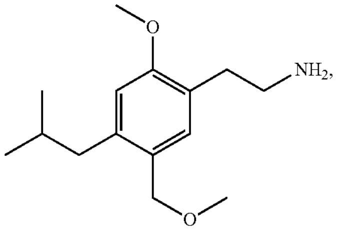
,

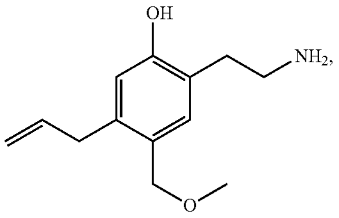
,

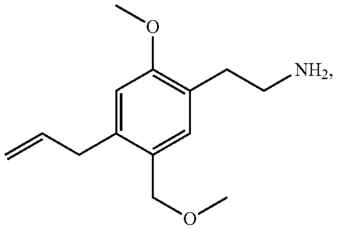
,

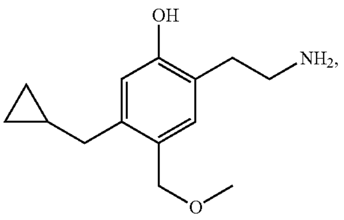
, and

-continued

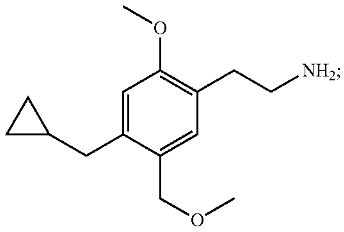
;

or a pharmaceutically acceptable salt, stereoisomer, hydrate, solvate, or isotopic derivative thereof.

In some such embodiments, the compound is any of the 2-HO, 5-MM compounds. In other such embodiments, the compound is any of the 2-MeO, 5-MM compounds.

In some embodiments, the compound is a 2-HO or 2-MeO, 5-hydroxymethyl piperidine compound. In embodiments, the compound is a 2-HO, 5-hydroxymethyl piperidine compound. In some embodiments, the compound is a 2-MeO, 5-hydroxymethyl piperidine compound.

In some embodiments, the 2-HO, 5-HM piperidine compound is selected from the group consisting of:

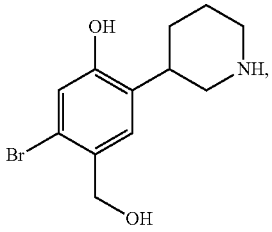
,

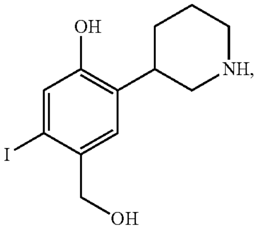
,

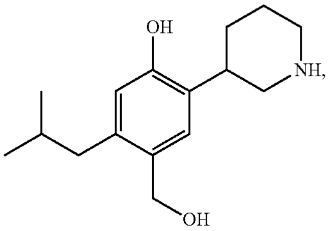
,

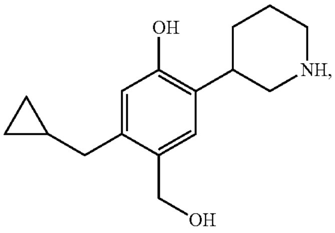
, and

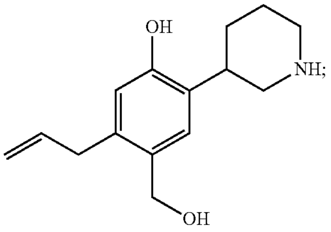
;

or a pharmaceutically acceptable salt, stereoisomer, hydrate, solvate, or isotopic derivative thereof.

In some embodiments, the 2-MeO, 5-HM piperidine compound is selected from the group consisting of:

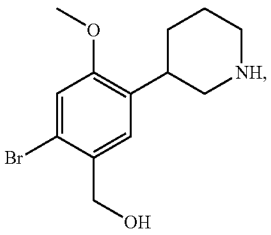

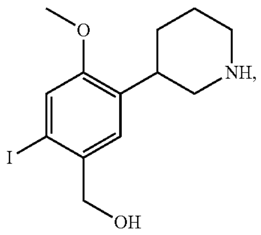

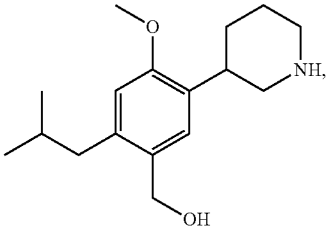

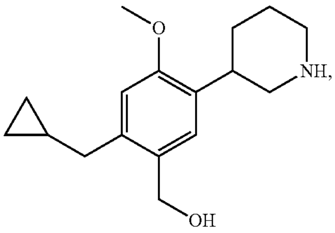 and

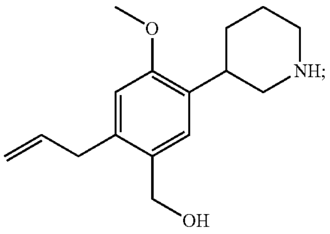

or a pharmaceutically acceptable salt, stereoisomer, hydrate, solvate, or isotopic derivative thereof.

In some embodiments, the compound is a 2-HO or 2-MeO, 5-methoxymethyl piperidine compound. In embodiments, the compound is a 2-HO, 5-methoxymethyl piperidine compound. In some embodiments, the compound is a 2-MeO, 5-methoxymethyl piperidine compound.

In some embodiments, the 2-HO, 5-MM piperidine compound is selected from the group consisting of:

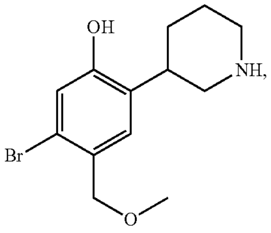

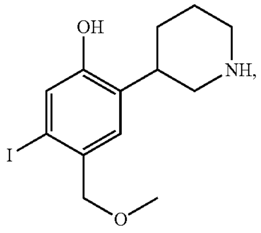

-continued

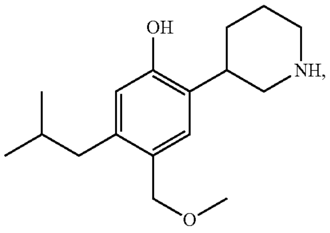

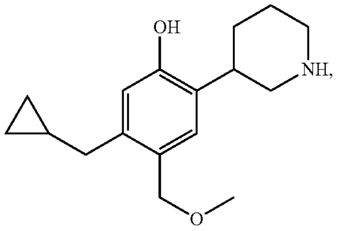 and

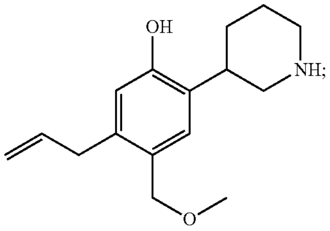

or a pharmaceutically acceptable salt, stereoisomer, hydrate, solvate, or isotopic derivative thereof.

In some embodiments, the 2-MeO, 5-MM piperidine compound is selected from the group consisting of:

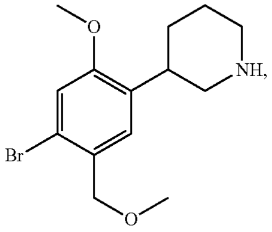

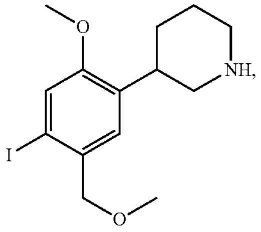

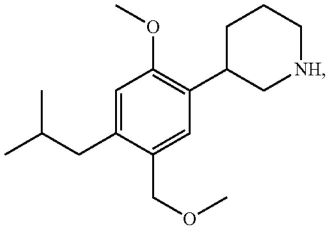

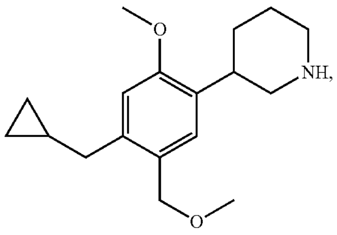 and

-continued

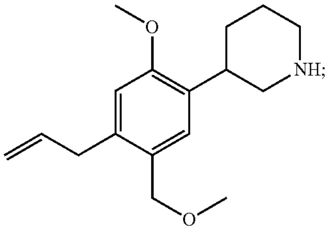

or a pharmaceutically acceptable salt, stereoisomer, hydrate, solvate, or isotopic derivative thereof.

In some embodiments, the compound is a 2-HO or 2-MeO, 5-HM cyclopropyl compound. In embodiments, the compound is a 2-HO, 5-HM cyclopropyl compound. In some embodiments, the compound is a 2-MeO, 5-HM cyclopropyl compound. In some embodiments, the 2-HO or 2-MeO, 5-HM cyclopropyl compound is selected from the group consisting of:

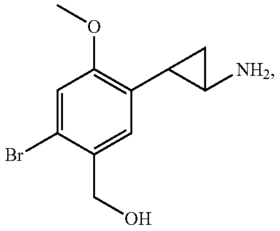

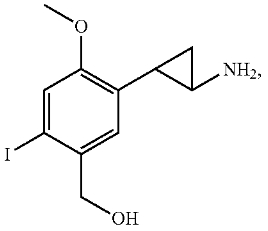

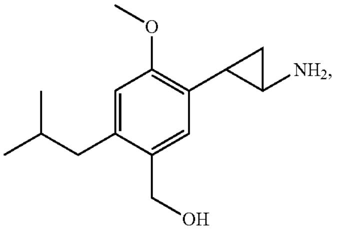

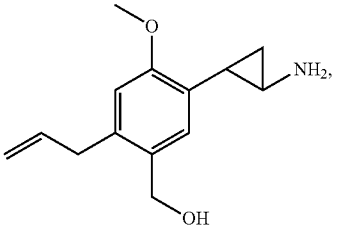

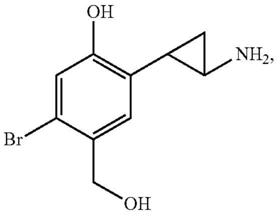

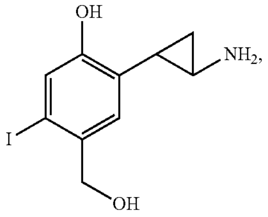

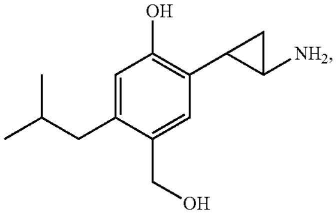 and

-continued

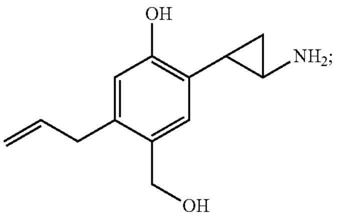

or a pharmaceutically acceptable salt, stereoisomer, hydrate, solvate, or isotopic derivative thereof.

In some such embodiments, the compound is any of the 2-HO, 5-HM cyclopropyl compounds. In other such embodiments, the compound is any of the 2-MeO, 5-HM cyclopropyl compounds.

In some embodiments, the compound is a 2-HO or 2-MeO, 5-MM cyclopropyl compound. In embodiments, the compound is a 2-HO, 5-MM cyclopropyl compound. In some embodiments, the compound is a 2-MeO, 5-MM cyclopropyl compound. In some embodiments, the 2-HO or 2-MeO, 5-MM cyclopropyl compound is selected from the group consisting of:

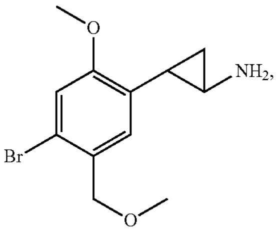

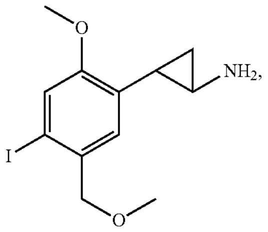

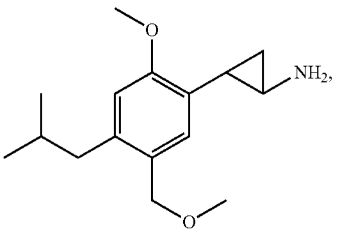

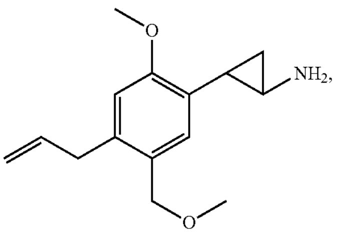

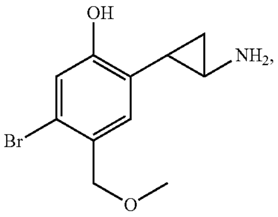

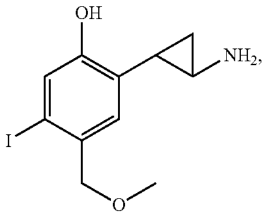

-continued

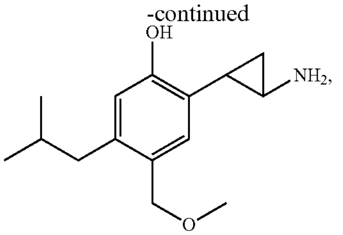

and

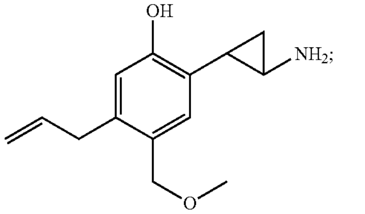

or a pharmaceutically acceptable salt, stereoisomer, hydrate, solvate, or isotopic derivative thereof.

In some such embodiments, the compound is any of the 2-HO, 5-MM cyclopropyl compounds. In other such embodiments, the compound is any of the 2-MeO, 5-MM cyclopropyl compounds.

In some embodiments, the compound is

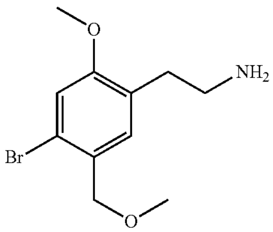

(2CB-5MM).

In some embodiments, the compound is

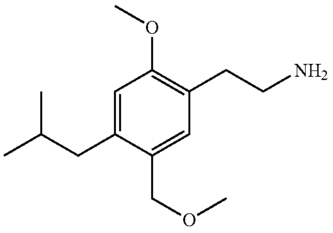 [SMILES: COCc1cc(CCN)c(OC)cc1CC(C)C]

(2C-iBu-5MM).

In some embodiments, the compound is

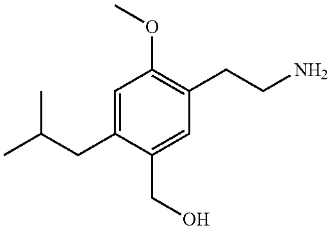 [SMILES: COc1cc(CC(C)C)c(CO)cc1CCN]

(2C-iBu-5HM).

In some embodiments, the compound is

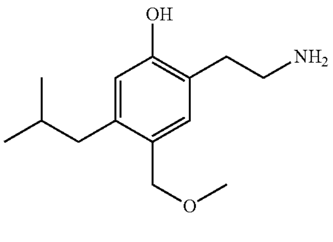 [SMILES: COCc1cc(CCN)c(O)cc1CC(C)C]

(2C-iBu-2OH-5MM).

In some embodiments, the compound is 2CB-5MM, 2C-iBu-5MM, 2C-iBu-5HM, or 2C-iBu-2OH-5MM.

In some embodiments, the compound is 2CB-5MM, 2C-iBu-5MM, or 2C-iBu-2OH-5MM. In some embodiments, the compound is 2CB-5MM or 2C-iBu-2OH-5MM. In some embodiments, the compound is 2C-iBu-5MM or 2C-iBu-5HM. In some embodiments, the compound is 2C-iBu-5MM or 2C-iBu-2OH-5MM.

Disclosure of a compound also encompasses the pharmaceutically acceptable salts of the compound. A "pharmaceutically acceptable salt" refers to salts prepared from pharmaceutically acceptable non-toxic acids or bases, and which may be synthesized by conventional chemical methods. Such salts may be prepared by reacting the free acid or base forms of the compound with a stoichiometric amount of the appropriate base or acid in water or in an organic solvent, or in a mixture of the two; exemplary nonaqueous solvents include ether, ethyl acetate, ethanol, isopropanol, and acetonitrile. For therapeutic use, salts of a compound are those wherein the counter-ion is pharmaceutically acceptable. One of skill can select from among available counterions those that are pharmaceutically acceptable. Selection of a given anion or cation for preparation of a salt may result in increased or decreased solubility of that salt. Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, amino-salicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentane-propionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, I-aspartate, I-camsylate, I-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc, and the like (see generally, Berge et al. *J Pharm Sci.* 1977; 66(1): 1-19).

Certain disclosed compounds may contain one or more ionizable groups (groups from which a proton can be removed (e.g., —COOH) or added (e.g., amines) or which can be quaternized (e.g., amines)). All possible ionic forms of such molecules and salts thereof are included herein.

A disclosed compound can exist in solid or liquid form. In the solid state, the compound may exist in crystalline or noncrystalline form, or as a mixture thereof. The skilled artisan will appreciate that pharmaceutically acceptable solvates may be formed for crystalline or non-crystalline compounds. In crystalline solvates, solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The subject matter described herein includes such solvates.

The skilled artisan will further appreciate that certain compounds described herein that exist in crystalline form, including the various solvates thereof, may exhibit polymorphism (i.e. the capacity to occur in different crystalline structures). These different crystalline forms are typically known as "polymorphs." The subject matter disclosed herein includes such polymorphs. Polymorphs include the different crystal packing arrangements of the same elemental composition of a compound. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. Various factors such as the recrystallization solvent, rate of crystallization, and storage temperature may cause a single crystal form to dominate. In addition, one polymorph may spontaneously convert to another polymorph under certain conditions.

The compounds described herein may contain one or more asymmetric centers and give rise to enantiomers, diastereomers, and other stereoisomeric forms. Each chiral center may be defined, in terms of absolute stereochemistry, as (R)- or (S)-. The disclosure includes all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. Various methods are known in the art for preparing optically active forms and determining activity. Such methods include standard tests described herein and other similar tests which are well known in the art. Examples of methods that can be used to obtain optical isomers of the compounds according to the present disclosure include selective crystallization, enzymatic resolution, asymmetric synthesis (including asymmetric chemical synthesis and asymmetric enzymatic synthesis), kinetic resolution, and chiral chromatography (including chiral liquid chromatography, gas chromatography, and high-performance liquid chromatography). When the compounds described herein contain olefinic double bonds or other centers of geometric asymmetry, and unless specified otherwise, it is intended that the compounds include both E and Z geometric isomers. Likewise, tautomeric forms are included.

The disclosure also includes compounds with at least one desired isotopic substitution of an atom, at an amount above the natural abundance of the isotope, i.e., isotopically enriched. Isotopes are atoms having the same atomic number but different mass numbers, i.e., the same number of protons but a different number of neutrons. Examples of isotopes that can be incorporated into disclosed compounds include isotopes of H, C, N, O, and Cl such as $^{2}H$, $^{3}H$, $^{11}C$, $^{13}C$, $^{14}C$, $^{15}N$, $^{17}O$, $^{18}O$, and $^{36}Cl$ respectively. Isotopically labeled compounds can be used in metabolic studies (e.g., with $^{14}C$), reaction kinetic studies (e.g., with $^{2}H$ or $^{3}H$), detection or imaging techniques, such as positron emission tomography (PET) or single-photon emission computed tomography (SPECT) including drug or substrate tissue distribution assays (e.g., with $^{18}F$), or in radioactive treatment of patients. In some embodiments, substitution with heavier isotopes such as deuterium, i.e., $^{2}H$, affords certain therapeutic advantages resulting from greater metabolic stability, for example increased in vivo half-life or reduced dosage requirements which may be preferred in some circumstances. Isotopically labeled compounds can be prepared by carrying out the procedures described herein or known to those in the art and by substituting a readily available isotopically labeled reagent for a non-isotopically labeled reagent.

The disclosure also includes prodrugs of disclosed compounds. A "prodrug" refers to a precursor of a biologically active agent, which may undergo a chemical or a metabolic conversion to become the biologically active agent. In vivo, a prodrug may be converted to the biologically active agent by the action of a metabolic process, an enzymatic process, or a degradative process, that removes the prodrug moiety to form the biologically active agent. Prodrugs include the addition of biologically labile or cleavable (protecting) groups on a functional moiety of the compound. Prodrugs include compounds that can be oxidized, reduced, aminated, deaminated, hydroxylated, dehydroxylated, hydrolyzed, alkylated, dealkylated, acylated, deacylated, phosphorylated, or dephosphorylated to produce the biologically active agent. Commonly used functional groups include esters, carbonates, carbamates, amides, phosphates, and sulfonamides. Such functional groups can be attached to a molecule via a linker that is designed to be cleaved under specific physiological conditions, such as enzymatic hydrolysis or pH-dependent cleavage. The choice of functional groups may depend on factors such as stability, ease of synthesis, enzymatic activity, and desired rate of prodrug conversion, but the choice of functional groups for disclosed compounds will be appreciated by those in the art.

Generally, the individual disclosed compounds will be administered as part of a pharmaceutical composition (also "composition" as shorthand, and used interchangeably herein, unless context indicates otherwise, with "pharmaceutical formulation" and "formulation"), and are prepared for inclusion in such composition as isolated or purified compounds. The terms "isolated," "purified," or "substantially pure," as used herein, refer to material that is substantially or essentially free from components that normally accompany the material when the material is synthesized, manufactured, or otherwise produced. An "isolated," "purified," or "substantially pure" preparation of a compound can accordingly be defined as a preparation having a chromatographic purity (of the desired compound) of greater than 90%, greater than 95%, greater than 96%, greater than 97%, greater than 98%, greater than 99%, greater than 99.5%, and greater than 99.9%, as determined by area normalization of an HPLC profile or other similar detection method.

A substantially pure compound is in some embodiments substantially free of any other active compounds which are not intended to be administered to a subject. In this context "substantially free" can be taken to mean that no active compounds other than the agent intended to be administered to the subject are detectable by HPLC or similar detection method, or are below a specified threshold of detection.

In some embodiments, the comparator for a disclosed compound is a 2C compound (e.g., 2C-C, 2C-B, 2C-E, and the like). In some embodiments, the comparator for a disclosed compound is 2C-iBu (2C-IB). In embodiments, the comparator for a disclosed compound is a 5-methoxyethyl compound (e.g., 2CB-5ME).

In some embodiments, the comparator for a disclosed compound is a corresponding compound with an identical substitution pattern, except for the substituent at the 5-position, such as a corresponding 2C compound. For example, in some embodiments, the comparator for

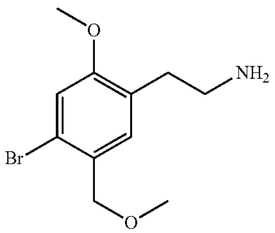

(2CB-5MM) is 2C-B.

In some embodiments, the comparator for 2CB-5MM is

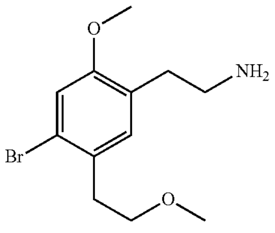 [SMILES: COCCc1cc(CCN)c(OC)cc1Br]

(2CB-5ME). In some embodiments, the comparator for

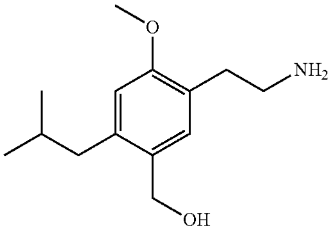 [SMILES: COc1cc(CC(C)C)c(CO)cc1CCN]

(2C-iBu-5HM) is

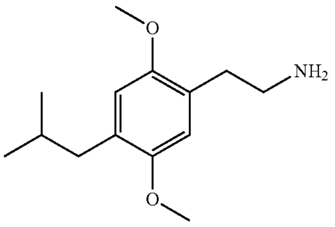 [SMILES: COc1cc(CC(C)C)c(OC)cc1CCN]

(2C-iBu). In some embodiments, the comparator for

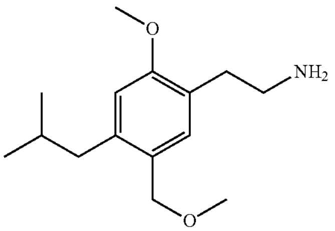 [SMILES: COCc1cc(CCN)c(OC)cc1CC(C)C]

(2C-iBu-5MM) is 2C-iBu.

In some embodiments, the comparator for a disclosed compound is a corresponding compound with an identical substitution pattern, except for the substituents at the 2- and 5-positions. For example, in some embodiments, the comparator for

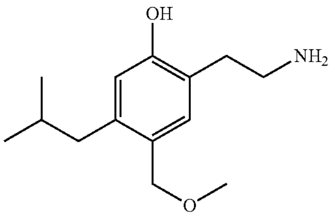 [SMILES: COCc1cc(CCN)c(O)cc1CC(C)C]

(2C-iBu-2OH-5MM) is 2C-iBu.

In some embodiments, a compound may have two or more comparators, including two comparators. For example, in some embodiments the comparators for 2C-iBu-5MM are 2C-iBu and 2CB-5ME.

In some embodiments, the comparator is a phenethylamine having an identical substitution pattern, except the substituent at the 5-position is a hydroxy, methoxy, or other alkoxy. In some embodiments, the comparator is a phenethylamine having an identical substitution pattern, except for the substituents at the 5-position and 2-position. In some embodiments, the comparator is a phenethylamine having an identical substitution pattern, except for the substituents at the 5-position and 4-position. In some embodiments, the comparator is a phenethylamine having an identical substitution pattern, except for the substituents at the 4-position and 2-position. In embodiments, the comparator is a phenethylamine having an identical substitution pattern, except for the substituents at the 5-position and alpha position. In embodiments, the comparator is a phenethylamine having an identical substitution pattern, except the substituent at the 4-position is a different halogen. In embodiments, the comparator is a phenethylamine having an identical substitution pattern, except the substituent at the 4-position is a different alkyl. In embodiments, the comparator is a phenethylamine having an identical substitution pattern, except for the substituent at the alpha-position. In embodiments, the comparator is a phenethylamine having a methyl substituent at the alpha-position, i.e., an amphetamine (or "DOx") compound. In embodiments, the comparator is a phenethylamine having an identical substitution pattern, except for a methyl substituent at the alpha-position. In embodiments, the comparator is a phenethylamine having an ethyl substituent at the alpha-position, i.e., a "4C-x" (or "Ariadne"-type) compound. In embodiments, the comparator is a phenethylamine having an identical substitution pattern, except for an ethyl substituent at the alpha-position. Other comparators will be appreciated by those of skill.

In some embodiments, the comparator is a phenethylamine having an identical substitution pattern, except the substituent at the 5-position is a different methoxyalkyl or hydroxyalkyl. In some embodiments, the comparator is a phenethylamine having an identical substitution pattern, except the substituent at the 2-position is a methoxy, and the substituent at the 5-position is a different methoxyalkyl or hydroxyalkyl. In some embodiments, the comparator is a phenethylamine having an identical substitution pattern, except the substituent at the 4-position is a different halogen, and the substituent at the 5-position is a different methoxyalkyl or hydroxyalkyl. In some embodiments, the comparator is a phenethylamine having an identical substitution pattern, except the substituent at the 4-position is a different alkyl, and the substituent at the 5-position is a different methoxyalkyl or hydroxyalkyl. In some embodiments, the comparator is a phenethylamine having an identical substitution pattern, except the substituent at the 5-position is a methoxyethyl or hydroxyethyl. In some embodiments, the comparator is a phenethylamine having an identical substitution pattern, except the substituent at the 2-position is a methoxy, and the substituent at the 5-position is a methoxyethyl or hydroxyethyl. In some embodiments, the comparator is a phenethylamine having an identical substitution pattern, except the substituent at the 4-position is a different halogen, and the substituent at the 5-position is a methoxyethyl or hydroxyethyl. In some embodiments, the comparator is a phenethylamine having an identical substitution pattern, except the substituent at the 4-position is a different alkyl, and the substituent at the 5-position is a methoxyethyl or hydroxyethyl.

C. METHODS OF PREPARING DISCLOSED COMPOUNDS

In general, disclosed compounds can be synthesized using known techniques in synthetic organic chemistry that are within the understanding and capabilities of one of ordinary skill in the relevant art.

Disclosed compounds can be synthesized from a substituted phenyl precursor (e.g., wherein X is a halogen (e.g., Cl, Br, I); and $R^2$, $R^4$, and $R^5$ are as defined for Formula (1)):

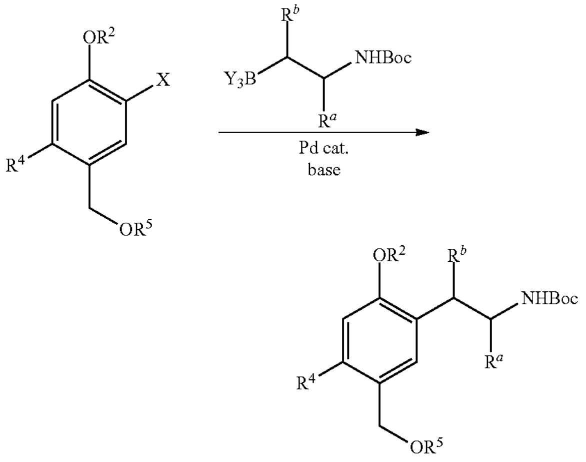

In this exemplary synthesis, a Boc-protected alkylamino side chain is installed using palladium-catalyzed cross coupling with a boron (R-$BY_3$) reagent (e.g., an organotrifluoroborane or the like). Compounds wherein $R^a$ and $R^b$ together with the intervening atoms form a 3- to 6-membered cycloalkyl can be synthesized according to the same approach, wherein $R^a$ and $R^b$ of the boron reagent (together with the intervening atoms) form a cycle; for example, potassium ((1R,2R)-2-(ethoxycarbonyl)cyclopropyl)trifluoroborate can be used to install a cyclopropylamine side chain. In some embodiments, a suitably substituted phenyl precursor is commercially available. If no substituted phenyl precursor having a desired $R^2$, $R^4$, or $R^5$ group is commercially available, such precursors can be synthesized as described in EXAMPLES 1-3.

Compounds wherein $R^N$ is —$CH_2$—Ar can be synthesized by reductive amination of a disclosed compound wherein $R^N$ is H, as follows:

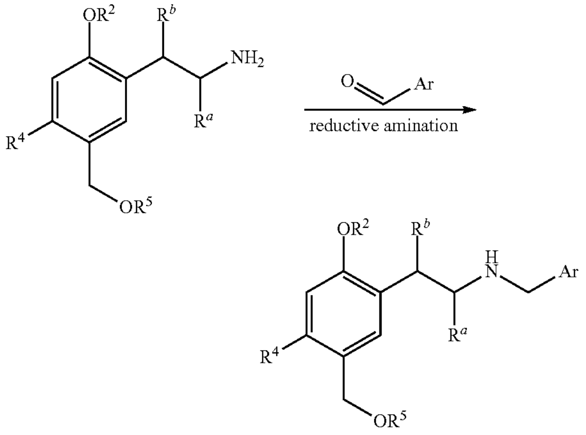

The reductive amination may be conducted according to standard techniques. For example, the starting materials may first be reacted to form an imine intermediate, which is then reduced by sodium borohydride in a second step. Alternatively, the reductive amination can be done in one step using sodium triacetoxyborohydride or sodium cyanoborohydride as the reducing agent.

Compounds wherein $R^b$ and $R^N$ together with the intervening atoms form a 4- to 8-membered heterocyclyl can be synthesized from a substituted phenyl precursor (e.g., wherein X is a halogen (e.g., Cl, Br, I); and $R^2$, $R^4$, and $R^5$ are as defined for Formula (1)):

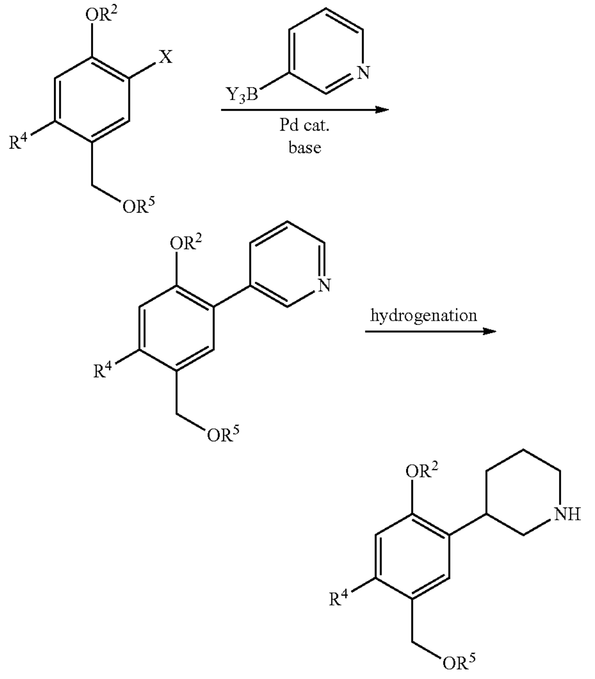

In this exemplary synthesis, palladium-catalyzed cross coupling with a pyridine-based boron ($R\text{-}BY_3$) reagent (e.g., an organotrifluoroborane, boronic acid, or the like) is used to attach a pyridine moiety to the substituted phenyl precursor. Subsequent hydrogenation of the pyridine (using, e.g., hydrogen gas and a metal catalyst) results in a substituted phenylpiperidine compound of Formula (1). If no substituted phenyl precursor having a desired $R^2$, $R^4$, or $R^5$ group is commercially available, such precursors can be synthesized as described in EXAMPLES 1-4.

The $R^4$ substituent corresponds to the 4-position of "classical" 2C-X and DOx phenethylamine psychedelics. Typically, the 4-substituent is introduced by substitution of the corresponding 4-substituted phenethylamine (e.g., as in the halogenation of 2C-H to yield 2C-B, 2C-I, etc.), or by substitution of the aryl group a suitable precursor prior to the introduction of the ethylamino side chain (e.g., as in the case of the 2C-T series). In general, similar approaches can be used for disclosed compounds, and appropriate modifications, substitutions, changes, and variations of these known synthetic procedures can be made by those skilled in the art without undue experimentation. Exemplary synthetic procedures may be found in, e.g., Shulgin and Shulgin, PiHKAL: A Chemical Love Story, Transform Press (1991).

Additional methods for synthesis of disclosed compounds and any necessary starting materials are either described in the art or will be readily apparent to the skilled artisan in view of general references well-known in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995) and may be used to synthesize the disclosed compounds.

Specific examples of the synthesis of certain compounds are in EXAMPLES 1-4. The schemes provided are merely illustrative of exemplary synthetic routes that are useful to prepare disclosed compounds.

D. PROPERTIES OF DISCLOSED COMPOUNDS

In some aspects, disclosed compounds have one or more favorable physicochemical properties. Examples of advantageous physical compounds include high aqueous solubility and/or low photoreactivity.

In embodiments, disclosed compounds are highly water soluble. Aqueous solubility affects the bioavailability and environmental fate of chemical substances (Letinski et al. *BMC Chem.* 2021; 15(1):52). In embodiments, the aqueous solubility of a disclosed compound refers to a maximum concentration at which the compound dissolves in water to form a solution at a specific temperature. In embodiments, aqueous solubility may be determined at a temperature of about 20° C. to 25° C. In embodiments, aqueous solubility is assessed by visible or microscopic inspection of undissolved material. Solubility may be expressed as the concentration of a solute in a saturated solution, and molarity is a standard unit of representation. One skilled in the art will recognize methods of determining aqueous solubility, e.g., stepwise dilution protocols, spectrophotometric quantification, and lyophilization parameters, such as described in Letinski et al. 2021; Birch et al. *Analytica Chimica Acta.* 2019; 1086:16-28; Loftsson & Hreinsdöttir *AAPS PharmSciTech.* 2006 Jan. 13; 7(1):E29-E32.

In embodiments, a disclosed compound has an aqueous solubility of between about 1 and 50 mM, about 10 and 100 mM, about 25 and 250 mM, or about 50 and 400 mM. In embodiments, a disclosed compound has an aqueous solubility of between about 100 and 125 mM, or between about 350 and 375 mM.

In embodiments, a disclosed compound has an aqueous solubility of about 1 mM, 5, 10, 15, 20, 25, 30, 35, 40, 45, 50, 55, 60, 65, 70, 75, 80, 85, 90, 95, 100, 105, 110 mM or greater than about 110 mM, wherein all values are expressed in mM, and including all values, ranges, or subranges in between. In embodiments, a disclosed compound has an aqueous solubility of at least about 100 mM, including at least about 105 mM, 110, 115, 120, 125, 130, 135, 140, 145, 150, 175, 200, 225, 250, 275, 300, 325, 350, 375 mM, or greater than about 375 mM, wherein all values are expressed in mM, and including all values, ranges, and subranges in between.

In embodiments, a compound has an aqueous solubility of about 43.46 mM. In embodiments, the aqueous solubility is about 110.18 mM. In embodiments, the aqueous solubility is about 364.8 mM.

In embodiments, a disclosed compound remains chemically stable in aqueous solution for at least about 1 hour, 2 hours, 3 hours, 4 hours, 5 hours, 6 hours, 7 hours, 8 hours, 9 hours, 10 hours, 11 hours, 12 hours, 24 hours, 36 hours, 48 hours, or greater than at least about 48 hours, including all values, ranges, and subranges in between. In embodiments, a disclosed compound remains chemically stable in aqueous solution for at least about 24 hours, 36 hours, 48 hours, 72 hours, 1 week, 2 weeks, 3 weeks, 4 weeks, 2 months, 3 months, 4 months, 5 months, 6 months, 7 months, 8 months, 9 months, 10 months, 11 months, 12 months, or greater than about 12 months, including all values, ranges, and subranges in between.

In embodiments, a disclosed compound exhibits greater aqueous solubility relative to one or more structurally related reference compounds or comparators, for example a compound having a common core scaffold and sharing one or more functional groups. A comparator may include a comparator described herein, such as for certain disclosed compounds, 2C-B, 2C-IB, 2CB-ME, and the like. In embodiments, a disclosed compound is at least 2×, 5×, or 10× more soluble than one or more reference compounds or comparators.

In embodiments, disclosed compounds are freely soluble or highly soluble in aqueous solutions, such as purified water, buffered saline, or other pharmaceutically acceptable aqueous carriers. In embodiments, high aqueous solubility contributes to improved formulation options, increased bioavailability, and/or ease of administration. In embodiments, high aqueous solubility allows disclosed compounds to be formulated with less of, or without the use of co-solvents, surfactants, or other solubilizing agents.

Light often provokes changes in physicochemical properties of active compounds and can also impact the stability of the final product (Coelho et al. *Int'l J Pharmaceutics.* 2018; 541(1-2):19-25). In embodiments, disclosed compounds have reduced photoliability. Photoliability refers to the susceptibility of a compound to undergo chemical degradation upon exposure to light (Ahmad et al. *Int'l J Photoenergy.* 2016; 2016(1): 8135608). In embodiments, disclosed compounds have increased photostability. Photostability refers to a compound that is resistant to degradation and maintains its chemical structure and potency under light exposure (Coelho et al., 2018; Allain et al. *J Pharm Sci.* 2019; 108(3):1172-1176). One of skill will recognize methods of determining photoliability and photostability, e.g., as described in Ahmad et al., 2016; Q1B Photostability Testing of New Drug Substances and Products. ICH. November 1996).

When a compound absorbs light, it may become photoreactive, potentially generating reactive oxygen species (ROS) and/or causing cellular damage (de Jager et al. *Adv Exp Med Biol.* 2017; 996:15-23). In embodiments, a disclosed compound exhibits low absorbance in the ultraviolet (UV) and visible spectral range (e.g., approximately 290-700 nm). In embodiments, a disclosed compound exhibits reduced photoreactivity. Reduced photoreactivity lowers the risk of direct phototoxicity, including phototoxic effects that may occur in vivo, upon exposure to light during administration, or during storage. A number of in vitro assays are known in the art for assessing the photoreactivity and phototoxicity potential of chemicals, including pharmaceuticals.

FDA guidelines provide that a compound having a molar extinction coefficient (MEC) at its Amax (maximum absorbance wavelength) of below about 1,000 $L \cdot mol^{-1} \cdot cm^{-1}$ (i.e., $M^{-1} \cdot cm^{-1}$) is considered insufficiently photoreactive to produce phototoxic effects under standard physiological or environmental exposure conditions. In embodiments, a disclosed compound has an MEC of less than 1,000 $L \cdot mol^{-1} \cdot cm^{-1}$.

In embodiments, a disclosed compound having an MEC of less than about 1,000 $M^{-1} \cdot cm^{-1}$ has an MEC of less than about 900 $M^{-1} \cdot cm^{-1}$, 800, 700, 600, 500, 400, 300, 200, or less than about 100 $M^{-1} \cdot cm^{-1}$, including all values, ranges, and subranges in between. In embodiments, a compound has an MEC of less than about 800 $M^{-1} \cdot cm^{-1}$. In embodiments, a compound has an MEC of less than about 400 $M^{-1} \cdot cm^{-1}$. In embodiments, a compound has an MEC of less than about 350 $M^{-1} \cdot cm^{-1}$. In embodiments, a compound has an MEC of less than about 300 $M^{-1} \cdot cm^{-1}$. In embodiments, a compound has an MEC of less than about 3,800 $M^{-1} \cdot cm^{-1}$. In embodiments, a compound has an MEC of less than about 4,000 $M^{-1} \cdot cm^{-1}$.

In embodiments, a disclosed compound exhibits reduced photoliability relative to one or more reference compounds or comparators. In embodiments, a compound has an MEC that is at least 2×, 3×, 4×, 5×, 6×, 7×, 8×, 9×, or 10× lower than a reference compound or comparator, including values in between.

In embodiments, one or more physical properties of a compound, such as solubility, photoliability, photostability, and/or formulation compatibility, are improved relative to a reference compound or comparator.

In embodiments, a head twitch response (HTR) assay is conducted using known rodent behavioral pharmacology protocols, for example as described in Laberstadt & Geyer. *Psychopharmacol* (Berl). 2013; 227 (4):727-739; Glatfelter et al., *ACS Pharmacol. Transl. Sci.* 2022; 5:321-330; and de la Fuente Revenga et al., *Sci. Rep.* 2019; 9(1):14247. HTR is defined as a rapid, lateral head movement that occurs in response to administration of $5\text{-}HT_{2A}$ receptor agonists and other serotonergic compounds (Laberstadt & Geyer, 2015).

In embodiments, a disclosed compound is characterized as HTR-negative, i.e., does not induce a head twitch response (HTR), such as by not demonstrating a statistically significant increase in HTR counts relative to vehicle control when tested using a standard head-twitch assay in a rodent model.

In embodiments, a compound is HTR-negative in a rodent behavioral model across a dose range of between about 0.01 and 50 mg/kg, about 0.01 and 40 mg/kg, or about 0.01 and 30 mg/kg. In embodiments, a compound is HTR-negative in a rodent behavioral model at a dose of at least or about 0.01 mg/kg, 0.02 mg/kg, 0.03 mg/kg 0.04 mg/kg, 0.05 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, or greater than about 40 mg/kg, including all values, ranges, and subranges in between.

In embodiments, a disclosed compound exhibits HTR counts within 2-fold, 1.5-fold, or equivalent to vehicle-treated controls across one or more tested dose amounts. In embodiments, the absence of an HTR indicates reduced or absent activation of the $5\text{-}HT_{2A}$ receptor. In embodiments, the absence of an HTR indicates reduced or absent such activation of the $5\text{-}HT_{2A}$ receptor as mediates hallucinogenic or subjective psychedelic effects in humans, i.e., partial agonism or biased agonism (ligand bias), or functional selectivity. In some embodiments, a compound may preferentially activate non-hallucinogenic $5\text{-}HT_{2A}$ signaling pathways.

In embodiments, compounds that are HTR-negative may exhibit a reduced likelihood of inducing perceptual disturbances, hallucinations, or dissociative symptoms in subjects, including humans. In embodiments, compounds that are HTR-negative are beneficial in populations where perceptual disturbances, hallucinations, dissociative symptoms, or other similar central nervous system effects are contraindicated (e.g., patients with psychosis, dementia, or pediatric populations). In embodiments, the absence of HTR supports functional selectivity or agonism towards non-hallucinogenic 5-HT signaling pathways. In embodiments, compounds that are HTR-negative may be administered chronically, in higher doses, or in outpatient settings.

E. PHARMACEUTICAL COMPOSITIONS

In some aspects are provided compositions, such as pharmaceutical compositions, comprising a disclosed compound. "Pharmaceutical compositions" may include a disclosed compound together in an amount (for example, in a unit dosage form) with a pharmaceutically acceptable carrier, diluent, or excipient. In some embodiments, a composition may comprise more than one carrier, diluent, and/or excipient. Compositions can be prepared by standard pharmaceutical formulation techniques such as disclosed in, e.g., Remington: Science & Practice of Pharm. (2020) 23th ed., Acad. Press., Cambridge, Mass.; The Merck Index (1996) 12th ed., Merck Pub. Group, Whitehouse, N.J.; Pharm. Principles of Solid Dosage Forms (1993), Tech. Pub. Co., Inc., Lancaster, Pa.; Ansel & Stoklosa, Pharm. Calculations (2001) 11th ed., Lipp. Williams & Wilkins, Baltimore, Md.; & Poznansky et al. Drug Delivery Sys. (1980), R. L. Juliano, ed., Oxford, N.Y., pp. 253-315).

"Pharmaceutically acceptable," such as to describe a carrier, diluent, excipient, or other ingredient, means it is generally safe and, within the scope of sound medical judgment, suitable for use in subjects without undue toxicity, irritation, allergic response, or complication, commensurate with a reasonable risk/benefit ratio.

Pharmaceutical compositions comprising a disclosed compound can be administered by a variety of routes including oral, mucosal (e.g., buccal, sublingual), rectal, topical, transdermal, subcutaneous, intravenous, intramuscular, inhaled, intranasal, and ocular. In embodiments, the compounds employed in the methods of this disclosure are effective as oral, mucosal (e.g., buccal, sublingual), rectal, topical, transdermal, subcutaneous, intravenous, intramuscular, inhaled, and intranasal compositions, and are formulated for such administration. In some embodiments, the compounds employed in the methods of this disclosure are effective as ocular (e.g., ophthalmic, intraocular, intravitreal, and periocular, including subconjunctival, retrobulbar, peribulbar, suprachoroidal, and sub-Tenon's) compositions, and are formulated for such administration.

The disclosed compositions can be formulated in a unit dosage form, each dosage containing a therapeutically effective amount of the active ingredients, for example in the dosage amounts disclosed below. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof, of the compound to be administered. For example, a composition may be administered as a single capsule or in multiple capsules.

Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein. Unit dosage forms further include compounds for transdermal administration, such as "patches" that contact the epidermis (including the mucosa) for an extended or brief period of time.

In embodiments, a composition is formulated in a pharmaceutically acceptable oral dosage form. Oral dosage forms include oral liquid dosage forms (such as tinctures, drops, emulsions, syrups, elixirs, suspensions, and solutions, and the like) and oral solid dosage forms. A pharmaceutical composition may be prepared as a formulation suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

In embodiments, disclosed pharmaceutical compositions may be formulated into a topical formulation (e.g., a topical dosage form). Topical formulations include transmucosal and transdermal formulations, such as aerosols, emulsions, sprays, ointments, salves, gels, pastes, lotions, liniments, oils, and creams; and may include a pharmaceutically acceptable excipient. Pharmaceutically acceptable excipients for topical formulations include penetration enhancers, carriers, diluents, emulsifiers, stabilizers, solvents and cosolvents, viscosity modifying agents (e.g., thickeners), adhesion modifying agents (e.g., tackifiers), preservatives, antioxidants, adhesive polymers, solubilizing agents, colorants, binders, humectants, surfactants, gelling agents, and other such ingredients as will be generally known to one of skill.

In some embodiments, the topical formulation comprises a penetration enhancer. Without being bound by theory, penetration enhancers are generally characterized by their ability to increase the permeability of biological barriers, such as scalp skin. In some embodiments, including a penetration enhancer in the formulation increases the bioavailability of the active agent(s) by improving the ability of the active agent(s) to diffuse into the skin tissue. Penetration enhancers include fatty acids and oils such as castor oil, coconut oil, medium chain triglycerides (MCT), jojoba oil, sunflower oil, argan oil, almond oil, olive oil, mineral oil, petroleum jelly, cocoa butter, shea butter, or other esters, triglycerides, or functional derivatives thereof. In some embodiments, the penetration enhancer is 1,2-lauryl ether, aprotinin, azone, benzalkonium chloride, benzalkonium bromide, cetylpyridinium chloride, cetyltrimethyl ammonium, cyclodextrin, dextran sulfate, glycol, lauric acid, lauric acid, propylene, lysophosphatidylcholine, menthol, phosphatidylcholine, polyoxyethylene, polysorbate 80, sodium EDTA, chitosan, sodium glycocholate, sodium deoxyglycocholate, sodium lauryl sulfate, sodium salicylate, sodium taurocholate, dimethyl sulfoxide, or a combination thereof. In embodiments, the penetration enhancer is selected from a group comprising lower chain alcohol with a carbon chain length of 1 to 5, sodium glycocholate, sodium deoxycholate, sodium taurocholate, sodium glycodeoxycholate, sodium taurodeoxycholate, oleic acid, capric acid, lauric acid, lecithin, myristic acid, palmitic acid, lysophosphatidyl-choline, phosphatidylcholine, azone, cyclodextrin, sodium lauryl sulphate, Polyoxyethylene-9-lauryl ether, Poly-oxythylene-20-cetyl ether, Benzalkonium chloride, cetylpyridinium chloride, Vitamin E TPGS, Caprylocaproyl polyoxylglycerides, Stearoyl Macrogolglycerides, Propylene Glycol Dicaprylocaprate or mixtures thereof.

In some embodiments, a topical formulation may comprise a penetration enhancer at a concentration of about 0.01%, 0.02%, 0.05%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 55%, 60%, 61%, 62%, 63%, 64%, 65%, 66%, 67%, 68%, 69%, 70%, 75%, 75%, and about 80% of the formulation, on a weight or volume basis.

In some embodiments, the topical formulation comprises a carrier. Carriers can be designed to give controlled release profiles, improved circulation times and better penetration across the epithelium. In some embodiments, the carrier is a hydrophobic drug carrier. Hydrophobic drug carriers can have the advantage of exhibiting slow sustained release and may adhere well to biological surfaces. Hydrophobic drug carriers can have slow (i.e., extended) release kinetics, or may also be constructed to have a rapid or immediate release profile. New techniques include the development of hydrophilic coatings on hydrophobic nanoparticles to improve their transport across tissue surfaces while retaining the slow-release profiles. These include polyethylene glycol and chitosan coatings (see, e.g., de la Fuente, et al. *Nanomedicine* 2008; 3:845-857). Any of a variety of pharmaceutically acceptable carriers may be used including, without limitation, aqueous media such as water, saline, glycine, hyaluronic acid and the like; solid carriers such as starch, magnesium stearate, mannitol, sodium saccharin, talcum, cellulose, glucose, sucrose, lactose, trehalose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); Remington: The Science and Practice of Pharmacy (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003).

In embodiments, the topical formulation comprises an emulsifier. The emulsifier may be an anionic, cationic, or neutral emulsifier. In certain embodiments, the emulsifier is an anionic emulsifier selected from the group consisting of alkyl sulfate, aralkyl sulfates, alkyl ethoxy ether sulfates, alkaryl sulphonates, alkyl succinates, alkyl sulfosuccinates, N-alkoyl sarconsinates, isethionates, N-acyl taurate, sodium lauryl sulfate, sodium laureth sulfate, sodium oleyl succinate, sodium dodecylbenzenesulfonate, and sodium lauryl sarconsinate. Exemplary non-ionic or neutral emulsifiers include sorbitan ester, ethoxylated sorbitan ester, ethoxylated alkyl ether, ethoxylated fatty acid ether, fatty alcohol, ethoxylated fatty alcohol, and esters of glycerin and fatty acids. In certain embodiments, the emulsifiers are synthetic or natural polymers. In certain embodiments, the emulsifier includes silicon. In certain embodiments, the emulsifier is a silicone (e.g., dimethicone, phenyltrimethicone, PEG dimethicone, PPG dimethicone, etc.).

In embodiments, the topical formulation comprises an antioxidant. Without being bound by theory, antioxidants generally can delay or inhibit the oxidative decomposition of components of the topical formulations, which may thereby improve the stability and extend the shelf-life thereof. The antioxidant may be amino acids (e.g., glycine, histidine, tyrosine, tryptophan) and derivatives thereof, imidazoles (e.g., urocanic acid) and derivatives thereof peptides, such as D,L-carnosine, D-carnosine, L-carnosine and derivatives thereof (e.g., anserine), carotenoids, carotenes (e.g., β-carotene, lycopene) and derivatives thereof, chlorogenic acid and derivatives thereof, liponic acid and derivatives thereof (e.g., dihydroliponic acid), aurothioglucose, propylthiouracil and other thiols (e.g., thiorodoxin, glutathione, cysteine, cystine, cystamine and the glycosyl, N-acetyl, methyl, ethyl, propyl, amyl, butyl, and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulfoximine compounds (e.g., buthionine sulfoximines, homocysteine sulfoximines, buthionine sulfones, penta, hexa and heptathionine sulfoximine), in very low tolerated doses (e.g., pmol to μmol/kg), and furthermore (metal)chelators (e.g., α-hydroxy-fatty acids, palmitic acid, phytic acid, lactoferrin), α-hydroxy acids (e.g., citric acid, lactic acid, malic acid), humic acid, gallic acid, bile extracts, bilirubin, biliverdin, EDTA and derivatives thereof, unsaturated fatty acids and derivatives thereof (e.g., γ-linolenic acid, linoleic acid, oleic acid), folic acid and derivatives thereof, ubiquinone and ubiquinol and derivatives thereof vitamin C and derivatives thereof (e.g., sodium ascorbate, ascorbyl palmitate, magnesium ascorbyl phosphate, ascorbyl acetate), tocopherol and derivatives (e.g., vitamin E acetate, tocotrienol), vitamin A and derivatives (vitamin A palmitate) and coniferyl benzoate of benzoic resin, rutinic acid and derivatives thereof, α-glycosylrutin, ferulaic acid, furfurylideneglucitol, carnosine, butylhydroxytoluene, butylhydroxyanisole, nordihydroguajak resin acid, nordihydroguaiaretic acid, trihydroxybutyrophenone, uric acid and derivatives thereof, mannose and derivatives thereof, zinc and derivatives thereof (e.g., ZnO, $ZnSO_4$), selenium and derivatives thereof (e.g., selenium methionine), stilbenes and derivatives thereof (e.g., stilbene oxide, trans-stilbene oxide). In embodiments, the antioxidant is α-tocopherol, ascorbyl palmitate, butylated hydroxyanisole, butylated hydroxytoluene, methionine, citric acid, ascorbic acid, sodium ascorbate, sodium thiosulfate, sodium bisulfite, sodium metabisulfite, ascorbyl palmitate, thioglycerol, propyl gallate, cysteine, or a combination thereof. In embodiments, the antioxidant is a cyclodextrin, D-α-tocopherol, rosmarinic acid, or a combination thereof.

In embodiments, the topical formulation comprises a thickener. The thickener may be crosslinked polyacrylic acids and derivatives thereof, polysaccharides and derivatives thereof, such as xanthan gum, agar agar, alginates or tyloses, cellulose derivatives (e.g., carboxymethylcellulose or hydroxycarboxymethyl-cellulose), fatty alcohols, monoglycerides and fatty acids, polyvinyl alcohol and PVP.

In embodiments, the topical formulation comprises a cosmetically and/or dermo-cosmetically active substance. A cosmetically and/or dermo-cosmetically active substance may be a color-imparting active substance, skin- or hair-pigmenting composition, tinting composition, tanning composition, bleach, keratin-hardening substance, antimicrobial active substance, light filter active substance, repellent active substance, substance having hyperemic activity, substance having keratolytic or keratoplastic activity, antiphlogistic agent, substance having keratinizing activity, antioxidant active substance or substance active as a free radical scavenger, skin-moisturizing substance or skin humectant, refatting active substance, substance having antierythematous or antiallergic activity, branched fatty acid, and any mixture thereof.

In embodiments, the topical formulation comprises a perfume oil. Natural fragrances are extracts of blossoms (lily, lavender, rose, jasmine, neroli, ylang-ylang), stalks and leaves (geranium, patchouli, petitgrain), fruits (anise, coriander, caraway, juniper), fruit peels (bergamot, lemon, orange), roots (mace, *angelica*, celery, cardamom, costus, iris, calmus), woods (pinewood, sandalwood, guajak wood, cedar wood, rosewood), herbs and grasses (tarragon, lemongrass, sage, thyme), needles and branches (spruce, fir, pine, dwarf pine), resins and balsams (*Galbanum*, elemi, benzoin, myrrh, olibanum, opoponax). Typical synthetic fragrance compounds are products of the type consisting of the esters, ethers, aldehydes, ketones, alcohols and hydrocarbons. Essential oils of low volatility, which are generally used as aroma components, are also suitable as perfume oils, e.g., sage oil, chamomile oil, clove oil, balm oil, mint oil, cinnamon leaf oil, lime tree blossom oil, juniper oil, vetiver oil, oliban oil, *Galbanum* oil, labolanum oil and lavandin oil. Bergamot oil, dihydromyrcenol, lilial, lyral, citronellol, phenylethyl alcohol, α-hexylcinnamaldehyde, geraniol, benzylacetone, cyclamenaldehyde, linalool, Boisambrene® Forte, ambroxan, indole, hedione, sandelice, lemon oil, mandarin oil, orange oil, allylamyl glycolate, cyclovertal, lavandin oil, muscatel sage oil, G39 damascone, Bourbon geranium oil, cyclohexyl salicylate, Vertofix® Coeur, iso-E-Super®, Fixolide® NP, evemyl, iraldein gamma, phenylacetic acid, geranyl acetate, benzyl acetate, rose oxide, romillate, irotyl and floramat.

In embodiments, the topical formulation comprises a solvent, and optionally a cosolvent. Any solvent(s) and cosolvent(s) may be collectively referred to as a "solvent system." Without being bound by theory, the solvent system chosen can affect the stability, bioavailability, and overall efficacy of the formulation. In embodiments, the solvent system is capable of dissolving or solubilizing the active agent(s) and any included excipients at the desired concentration(s), and is stable and compatible with the active agent(s) and any other excipients) in the formulation. In some embodiments, a solvent system comprises more than one solvent, and the ratio of cosolvents is optimized, for example to increase the penetration or bioavailability of an active agent. Preferred solvent systems are safe and non-toxic for human consumption. In embodiments, potential adverse effects, such as irritation or allergic reactions, are considered and minimized during selection of solvents included in the solvent system. Solvents that may be included in topical formulations may include, without limitations, water, ethanol, polyhydric alcohols (e.g., glycerin), 1,3-butylene glycol, propylene glycol, hexylene glycol, propane diol, ethylene glycol, diethylene glycol, dipropylene glycol, diglycerin, sorbitol, other sugars which are liquid at room temperature, water-soluble alkoxylated nonionic polymers such as polyethylene glycol, and combinations thereof. Solvents may be present, individually or in total (if more than one solvent is included), in the formulation in an amount ranging from about 0.1 wt % to about 95 wt % (calculated as the total weight of solvents in the formulation divided by the total weight of the formulation).

In embodiments, the topical formulation comprises a viscosity modifying agent. In some embodiments, the viscosity modifying agent is a thickener. Common thickeners include but are not limited to: acrylates, carbomers, cellulose matrices, silicones, carrageenans, gums, resins, polysaccharides, and high melting point waxes and oils such as beeswax, coconut oil, palm oil, soybean oil, stearic acid, rapeseed, cocoa butter, shea butter, gums, rosins, resins, paraffins, and petroleum jelly. In some embodiments, the viscosity modifying agent is a carbohydrate. Exemplary carbohydrates include monosaccharides, disaccharides, oligosaccharides, and polysaccharides. Exemplary polysaccharides include cellulose, methylcellulose, hydroxypropylmethylcellulose, chitin, galactoarabinan, polygalactose, and polyarabinose. Exemplary glycerides includes hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid monoglyceride, malic acid diglyceride, and mixture thereof. In some embodiments, the viscosity modifying agent is a polymer. The polymer may be a natural or synthetic polymer. Natural polymers include polysaccharides, nucleic acid, and proteins. Synthetic polymers include polyesters, polyureas, polycarbonates, polyvinyl alcohol, polyamides, polyethers, polyesters, polyamines, polytyrosines, polyanhydrides, polyphosphazenes, polyacrylamides, polyacrylates, polymethacrylates, polyvinylpyrrolidone (PVP), etc. Exemplary thickening agents include alginate derivatives, preneutralized carbomer 430, hydrophilic silicas, polysaccharides, xanthan gum, guar guar, agar agar, carboxymethylcellulose, hydroxyethylcellulose, polyacrylates, polyacrylamides, PVP, and salts.

In embodiments, the topical formulation comprises an adhesion modifying agent. In embodiments, the topical formulation comprises an adhesive polymer. Adhesive polymers have physicochemical properties that allow prolonged binding to tissue surfaces. In some embodiments, inclusion of an adhesive polymer in the formulation increases the amount of time that an active agent is in contact with, and can diffuse across, a barrier (e.g., skin). In some embodiments, the adhesive polymer is chitosan, gelatin guar gum, lectins, sodium alginate, soluble starch, tragacanth, xanthan gum deacetylated gum, polyacrylic acid, polyvinyl alcohol, hydroxypropylmethylcellulose, hydroxyethylcellulose, hydroxypropyl cellulose, sodium carboxymethylcellulose, a thiomer, polycarbophil, hyaluronic acid, dermatan sulfate, or a combination thereof. In some embodiments, the adhesion modifying agent is a tackifier. Common tackifiers include but are not limited to gums, resins (natural or modified), carbomers, or other natural or synthetic polymers.

In embodiments, the topical formulation comprises a preservative. Preservatives can be used to inhibit microbial growth or increase stability of the formulation, thereby prolonging the shelf life of the formulation. Suitable preservatives are known in the art and include EDTA, EGTA, benzalkonium chloride or benzoic acid or benzoates (e.g., sodium benzoate), vitamin A, vitamin C (ascorbic acid), citric acid, vitamin E, and tocopherol.

In embodiments, the topical formulation comprises a solubilizing agent. Without being bound by theory, solubilizing agents generally form complexes with active ingredients which can have different physicochemical properties than the active ingredient alone. The properties of the complexes can increase the solubility of the active agent(s) in the formulation. In some embodiments, the solubilizing agent is a water-soluble organic solvent, a non-ionic surfactant, a water insoluble lipid, an organic liquid, a cyclodextrin, or a phospholipid. In some embodiments the solubilizing agent is a water-soluble enhancing agent. In some embodiments, the water-soluble enhancing agent is polyethylene glycol 300, polyethylene glycol 400, ethanol, propylene glycol, xanthan gum, glycerin, N-methyl-2-pyrrolidone, dimethylacetamide, dimethylsulfoxide, or a combination thereof. In some embodiments, the solubilizing agent is propylene glycol. In some embodiments, the solubilizing agent is xanthan gum. In some embodiments the solubilizing agent is a non-ionic surfactant. In some embodiments, the non-ionic surfactant is Cremophor EL, Cremophor RH 40, Cremophor RH 60, d-tocopherol polyethylene glycol 1000 succinate, polysorbate 20, polysorbate 80, Solutol HS 15, sorbitan monooleate, poloxamer 407, Labrafil M-1944CS, Labrafil M-2125CS, Labrasol, Gellucire 44/14, Softigen 767, mono- and di-fatty acid esters of PEG 300, 400, or 1750, or a combination thereof. In some embodiments the solubilizing agent is an organic liquid. In embodiments, the organic liquid is beeswax, d-alpha-tocopherol, oleic acid, or a medium-chain mono- or diglyceride. In some embodiments the solubilizing agent is a cyclodextrin. In some embodiments the solubilizing agent is a phospholipid. In embodiments, the phospholipid is hydrogenated soy phosphatidylcholine, distearoyl-phosphatidylglycerol, L-alpha-dimyristoyl-phosphatidylcholine, or L-alpha-dimyristoyl-phosphatidylglycerol. In some embodiments, the solubilizing agent is lecithin.

In embodiments, the topical formulation comprises a colorant. Suitable colorants and/or dyes and/or pigments include colors such as e.g., white, black, yellow, blue, green, pink, red, orange, violet, indigo, brown, and combinations thereof, pigments such as, e.g., Timica Extra Large Sparkles, titanium dioxide and chromium oxide greens, ultramarine blues and pinks and ferric oxides. Colorants and/or dyes and/or pigments may be present, individually or in total (if more than one colorant and/or dye and/or pigment is included), in disclosed formulations in an amount ranging from about 0.01 wt % to about 5 wt % (calculated as the total weight of colorants and/or dyes and/or pigments in the formulation divided by the total weight of the formulation). Colorants may be present, individually or in total (if more than one colorant is included), in disclosed formulations in an amount ranging from about 0.01 wt % to about 5 wt % (calculated as the total weight of colorants in the formulation divided by the total weight of the formulation).

In embodiments, the topical formulation comprises a binder. Suitable binders include polyvinyl-pyrrolidone (PVP), marine colloids, carboxyvinyl polymers, starches, cellulosic polymers such as hydroxyethylcellulose, carboxymethylcellulose (carmellose), hydroxypropylmethylcellulose, hydroxyethylpropyl-cellulose, hydroxybutyl methyl cellulose, and salts thereof (e.g., carmellose sodium), natural gums such as karaya, xanthan, carrageenans, gellan gum, locust bean gum, gum arabic and tragacanth, chitosan, colloidal magnesium aluminum silicate, and colloidal silica. Binders may be present, individually or in total (if more than one binder is included), in disclosed formulations in an amount ranging from about 0.01 wt % to about 5 wt % (calculated as the total weight of binders in the formulation divided by the total weight of the formulation).

In embodiments, the topical formulation comprises a humectant. Humectants, such as low molecular weight polyethylene glycol (e.g., PEG6-PEG12), may be present, individually or in total (if more than one humectant is included), in the formulation in an amount of up to about 10 wt %, up to about 5 wt %, up to about 3 wt %, up to about 1 wt %, or up to about 0.1 wt % (calculated as the total weight of humectants in the formulation divided by the total weight of the formulation).

In embodiments, the topical formulation comprises a surfactant. The surfactants that can be included in the formulation may be anionic, nonionic, or amphoteric compounds. Suitable examples of anionic surfactants are one or more of higher alkyl sulfates such as potassium or sodium lauryl sulfate, higher fatty acid monoglyceride monosulfates, such as the salt of the monosulfated monoglyceride of hydrogenated coconut oil fatty acids, alkyl sulfonates such as sodium dodecyl benzene sulfonate, higher fatty sulfoacetates, higher fatty acid esters of 1,2 dihydroxypropane sulfonate. Examples of water soluble nonionic surfactants are condensation products of ethylene oxide with various hydrogen-containing compounds that are reactive therewith and have long hydrophobic chains (e.g., aliphatic chains of about 12 of 20 carbon atoms), which condensation products contain hydrophilic polyoxyethylene moieties, such as condensation products of poly (ethylene oxide) with fatty acids, fatty alcohols, fatty amides and other fatty moieties, and with propylene oxide and polypropylene oxides, e.g., Pluronic materials such as Pluronic F127. Exemplary suitable alkyl polyglycoside (APG) surfactant(s) that may be used in the formulation may comprise APG C8-C10, APG C10-C16, decyl glucoside, coco-glucoside, anionic APG carboxylate, sodium lauryl glucose carboxylate, lauryl glucoside, D-glucopyranose (oligomeric, CIO-16 glycosides, carboxymethyl ethers, sodium salts), C12-C16 fatty alcohol glycoside, and combinations thereof. Exemplary APG surfactant(s) that may be used may have an industry designation of Plantaren® 2000 N UP/MB, Plantapon® LGC Sorb, Plantaren® 1200 N UP/MB, and Plantaren® 818 UP/MB. Surfactants may be present, individually or in total (if more than one surfactant is included) in the formulation in an amount ranging from about 0.01 wt % to about 10 wt % (calculated as the total weight of surfactants in the formulation divided by the total weight of the formulation).

In embodiments, the topical formulation comprises a gelling agent. Exemplary gelling agent(s) used in disclosed formulations may comprise pectins, starches, and gelatin forms derived from animals or from plants (e.g., pork gelatin). The pectin in the formulation may include, e.g., high methoxyl pectin, low methoxyl pectin, or a combination thereof. In some embodiments, the pectin is amidated pectin. In other embodiments, the pectin is non-amidated pectin. In certain embodiments, the pectin is a combination of amidated pectin and non-amidated pectin. The gelatin in the formulation may include Type A gelatin, Type B gelatin, a hide or skin gelatin (e.g., calf skin, pig skin) and/or a bone gelatin (e.g., calf bone, pig bone) used alone or in combination. Gelling agent(s) may be present, individually or in total (if more than one gelling agent is included) in the formulation in an amount ranging from about 0.1 wt % to about 20 wt % (calculated as the total weight of gelling agents in the formulation divided by the total weight of the formulation).

In some embodiments, a composition is formulated as an oral solid dosage form. Oral solid dosage forms include lozenges, troches, tablets, capsules, caplets, powders, pellets, multiparticulates, beads, spheres, and any combinations thereof. Oral solid dosage forms may be formulated as immediate release, controlled release, sustained release, extended release, or modified release formulations. In some embodiments, an oral solid dosage form is in the form of any of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, capsules made from animal-derived gelatin or plant-derived HPMC, and sprinkle capsules), a solid dispersion, a solid solution, a bioerodible dosage form, a controlled release formulation, a pulsatile release dosage form, a multiparticulate dosage form, pellets, granules, or an aerosol. In some embodiments, the composition is in the form of a powder. In embodiments, the composition is in the form of a tablet, e.g., a fast-melt tablet. Compositions may be administered as a single capsule or in a multiple capsule dosage form. In embodiments, the composition is administered in two, three, four, or more capsules or tablets.

Oral solid dosage forms may contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Oral solid dosage forms may comprise pharmaceutically acceptable additives such as a compatible carrier, complexing agent, ionic dispersion modulator, disintegrating agent, surfactant, lubricant, colorant, moistening agent, plasticizer, stabilizer, penetration enhancer, wetting agent, anti-foaming agent, alone or in combination, as well as supplementary active compound(s).

Supplementary active compounds include preservatives, antioxidants, antimicrobial agents including biocides and biostats such as antibacterial, antiviral and antifungal agents. Preservatives can be used to inhibit microbial growth or increase stability of the active ingredient thereby prolonging the shelf life of the formulation. Suitable preservatives are known in the art and include EDTA, EGTA, benzalkonium chloride or benzoic acid or benzoates, such as sodium benzoate. Antioxidants include vitamin A, vitamin C (ascorbic acid), vitamin E, tocopherols, other vitamins or provitamins, and compounds such as alpha lipoic acid.

In some embodiments, a disclosed composition is formulated as an oral liquid dosage form. Oral liquid dosage forms include tinctures, drops, emulsions, syrups, elixirs, suspensions, and solutions, and the like. These oral liquid dosage forms may be formulated with any pharmaceutically acceptable excipient for the preparation of liquid dosage forms, and with solvents, diluents, carriers, excipients, and the like chosen as appropriate to the solubility and other properties of the active agents and other ingredients. Solvents include water, glycerin, simple syrup, alcohol, medium chain triglycerides (MCT), and combinations thereof.

Liquid dosage forms for oral administration may be in the form of pharmaceutically acceptable emulsions, syrups, elixirs, suspensions, and solutions, which may contain an inactive diluent, such as water. Compositions may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Liquid formulations also may be prepared as single dose or multi-dose beverages. Suspensions may include oils. Such oils include peanut oil, sesame oil, cottonseed oil, corn oil, and olive oil. Suitable oils also include carrier oils such as MCT and long chain triglyceride (LCT) oils. Suspension preparation may also contain esters of fatty acids such as ethyl oleate, isopropyl myristate, fatty acid glycerides, and acetylated fatty acid glycerides. Suspension formulations may include alcohols, (such as ethanol, isopropyl alcohol, hexadecyl alcohol), glycerol, and propylene glycol. Ethers, such as poly(ethylene glycol), petroleum hydrocarbons such as mineral oil and petrolatum, and water may also be used in suspension formulations. Suspension can thus include an aqueous liquid or a non-aqueous liquid, an oil-in-water liquid emulsion, or a water-in-oil emulsion.

In some embodiments, formulations are provided comprising the disclosed compositions and at least one dispersing agent or suspending agent for oral administration to a subject. The formulation may be a powder and/or granules for suspension, and upon admixture with water, a substantially uniform suspension is obtained. The aqueous dispersion can comprise amorphous and non-amorphous particles consisting of multiple effective particle sizes such that a drug is absorbed in a controlled manner over time.

Dosage forms for oral administration can be aqueous suspensions selected from the group including pharmaceutically acceptable aqueous oral dispersions, emulsions, solutions, and syrups (see, e.g., Singh et al., *Encyclopedia Pharm. Tech.,* 2nd Ed., 754-757 (2002)). In addition to disclosed compounds, liquid dosage forms may comprise additives, e.g., one or more (a) disintegrating agents, (b) dispersing agents, (c) wetting agents, (d) preservatives, (e) viscosity enhancing agents, (f) sweetening agents, and/or (g) flavoring agents.

Compositions include those suitable for intramuscular, subcutaneous, intraperitoneal, or IV injection, comprising physiologically acceptable sterile aqueous or non-aqueous solutions, dispersions, suspensions or emulsions, liposomes, and sterile powders for reconstitution into sterile injectable solutions or dispersions.

In some embodiments, a disclosed pharmaceutical composition may be formulated for ocular including ophthalmic administration, such as formulated as or prepared as an ocular or ophthalmic formulation.

Ophthalmic formulations of the disclosure include topical formulations, such as eye drops, gels, and ointments; and may comprise excipients suitable for topical formulations, e.g., penetration enhancers, carriers, diluents, emulsifiers, stabilizers, solvents and cosolvents, viscosity modifying agents (e.g., thickeners), adhesion modifying agents (e.g., tackifiers), preservatives, antioxidants, adhesive polymers, solubilizing agents, colorants, binders, humectants, surfactants, gelling agents, and other such ingredients described herein and as will be generally known to one of skill in the art.

An ophthalmic formulation may contain one or more viscosity-modifying agents and have a viscosity that feels comfortable to the eye and does not cause blurring of the vision. For example, an ophthalmic formulation may have a viscosity of 1.0 to 100,000 cP (e.g., from about 2.0 to 90,000 cP or from about 2.5 to 75,000 cP). Viscosity-modifying agents include substances that have the ability to cause thickening (increase the viscosity) of ophthalmic formulations. Viscosity modifying agents include xanthan gum, edetate, methyl-cellulose, carboxymethylcellulose, hydroxypropyl methylcellulose, hydroxyethyl cellulose, polyethylene glycol, propylene glycol alginate, chitosan, and tragacanth. Hydrogels may be used as viscosity-enhancing excipients, particularly in artificial tears. Compatible viscosity-adjusting agents can be used in all formulations mentioned herein. Concentrations of viscosity-modifying agents in ophthalmic formulations of the disclosure can range from about 0.1% to about 10% by weight (e.g., between 1% and 5% by weight). Sorbitol may be used as a combined tonicity-adjusting and viscosity-modifying excipient. Sorbitol may be used in ophthalmic formulations of the disclosure in a concentration range from about 0.1% to about 10% (e.g., from 2% to 5% by weight).

An ophthalmic formulation may comprise a penetration enhancer, for example to aid penetration of the active compound(s) into and across the skin or eyelid skin. Exemplary penetration enhancers for ophthalmic formulations include an aliphatic alcohol, fatty acid (including salts thereof), fatty acid ester, polyalcohol alkyl ether, polyoxyethylene alkyl ether, glyceride, polyalcohol medium chain fatty acid ester, polyoxyethylene sorbitan fatty acid ester, alkyl lactate ester, terpene, and organic amine. In some embodiments, the penetration enhancer is any of ethanol, glycerol, diethylene glycol, propylene glycol, polyethylene glycol and higher aliphatic alcohols (e.g., a saturated or unsaturated higher aliphatic alcohol having 12 to 22 carbon atoms such as oleyl alcohol, lauryl alcohol and stearyl alcohol), capric acid, myristic acid, palmitic acid, lauric acid, stearic acid, isostearic acid, oleic acid, linoleic acid, and linolenic acid (including salts thereof); an ester of a fatty acid such as myristic acid, palmitic acid, lauric acid, stearic acid, isostearic acid, oleic acid, linoleic acid, linolenic acid, propionic acid, butyric acid, isobutyric acid, valeric acid, pivalic acid, caproic acid, heptanoic acid, malonic acid, succinic acid, glutaric acid, adipic acid, pimelic acid, crotonic acid, sorbic acid, maleic acid, fumaric acid, and sebacic acid with a lower aliphatic alcohol such as methanol, ethanol, propanol, isopropanol, butanol, pentanol, hexanol, heptanol and octanol, isopropyl myristate, isopropyl palmitate, diisopropyl adipate and diethyl sebacate; an ether of a polyalcohol such as glycerol, ethylene glycol, propylene glycol, 1,3-butylene glycol, diglycerol, polyglycerol, diethylene glycol, polyethylene glycol, dipropylene glycol, polypropylene glycol, sorbitan, sorbitol, methyl glucoside, oligosaccharide and reduced oligosaccharide with alkyl alcohol; polyoxy-ethylene lauryl ether, polyoxyethylene cetyl ether, polyoxyethylene stearyl ether and polyoxyethylene oleyl ether, glycerol ester of fatty acid having 6 to 18 carbon atoms (e.g., monoglyceride, diglyceride, triglyceride and a mixture thereof), glyceryl monolaurate, glyceryl monomyristate, glyceryl monostearate, glyceryl monooleate, glyceryl dilaurate, glyceryl dimyristate, glyceryl distearate, glyceryl trilaurate, glyceryl trimyristate and glyceryl tristearate, ethylene glycol monocaprylate, propylene glycol monocaprylate, glycerin monocaprylate, mono 2-ethylene glycol ethylhexanoate, mono 2-propylene glycol ethylhexanoate, di(2-propylene)glycol ethylhexanoate, propylene glycol, dicaprylate, polyoxyethylene sorbitan monolaurate, polyoxyethylene sorbitan monostearate and polyoxyethylene sorbitan monooleate, methyl lactate, ethyl lactate, methyl 2-methoxy propionate, ethyl 2-methoxypropionate, monoethanolamine, triethanol-amine, creatinine and meglumine. In embodiments, the ophthalmic formulation comprises a hydrating agent. Hydrating agents may facilitate penetration of the active compound(s) through the cell or junctions of the barriers including mucosal, mucocutaneous, and stratum corneum layers. Exemplary hydrating agents include hyaluronic acid (or a salt thereof, e.g., sodium hyaluronate), water, saline solution, PVP, propylene glycol, glycerol, sorbitol, polyethylene glycol, dexpanthenol, pantothenic acid, ectoin, carboxyvinyl polymer, carmellose sodium, and povidone.

In some embodiments, the ophthalmic formulation comprises a surfactant. Surfactants may facilitate dissolution and/or absorption of formulation components, and include, e.g., any of an anionic surfactant, cationic surfactant, nonionic surfactant and amphoteric surfactant. Exemplary surfactants include, e.g., any of a fatty acid salt, alkyl sulfate, polyoxyethylene alkyl sulfate, alkylsulfo carboxylate salt, alkylether carboxylate salt, amine salt, quaternary ammonium salt, polysorbate 80, poloxamer, polyoxyethylene hydrogenated castor oil, polyoxyethylene fatty acid ester, polyoxyethylene alkyl ether, polyoxyethylene sorbitan fatty acid ester, alkyl betaine, dimethylalkylglycine, and lecithin.

In some embodiments, the ophthalmic formulation comprises a gum and/or resin, e.g., any of a sodium polyacrylate, cellulose ether, calcium alginate, carboxyvinyl polymer, ethylene-acrylic acid copolymer, vinyl pyrrolidone polymer, vinyl alcohol-vinyl pyrrolidone copolymer, nitrogen-substituted acrylamide polymer, polyacrylamide, cationic polymer such as cationic guar gum, dimethylacrylic ammonium polymer, acrylic acid-methacrylic acid copolymer, polyoxyethylene-polypropylene copolymer, polyvinyl alcohol, pullulan, agar, gelatine, chitosan, polysaccharide from tamarindo seed, xanthan gum, carageenan, high-methoxyl pectin, low-methoxyl pectin, guar gum, acacia gum, microcrystalline cellulose, arabinogalactan, karaya gum, tragacanth gum, alginate, albumin, casein, curdlan, gellan gum, dextran, cellulose, polyethyleneimine, high polymerized polyethylene glycol, cationic silicone polymer, synthetic latex, acrylic silicone, trimethylsiloxysilicate, and fluorinated silicone resin.

In some embodiments, the ophthalmic formulation comprises a pH adjuster. A pH adjuster may be used to adjust the pH of the formulation to a desired range, e.g., 4-10, 5-8, or another to maximize the skin penetration of the compound(s) in the composition. In embodiments, the pH adjuster is any of hydrochloric acid, citric acid, sodium citrate, acetic acid, sodium acetate, ammonium acetate, succinic acid, tartaric acid, L-sodium tartrate, sodium hydrate, potassium hydrate, sodium carbonate, sodium hydrogencarbonate, lactic acid, calcium lactate, sodium lactate, sodium fumarate, sodium propionate, boric acid, ammonium borate, maleic acid, phosphoric acid, sodium hydrogen phosphate, malic acid, adipic acid, triethanolamine, diisopropanolamine, meglumine, monoethanolamine, sulfuric acid, and aluminum potassium sulfate.

In some embodiments, the ophthalmic formulation comprises a stabilizer. Exemplary stabilizers include, e.g., sodium bisulfite, sodium sulfite, sodium pyrosulfite, sodium formaldehyde sulfoxylate, L-ascorbic acid, erythorbic acid, L-cysteine, thioglycerol, butylated hydroxyanisole (BHA), butylated hydroxytoluene (BHT), propyl gallate, ascorbyl palmitate, alpha-tocopherol, nordihydroguaiaretic acid, disodium edetate, tetrasodium edetate dehydrate, sodium citrate, sodium polyphosphate, sodium metaphosphate, gluconic acid, phosphoric acid, citric acid, ascorbic acid and/or succinic acid.

Additional ophthalmic formulations of the disclosure include contact lenses. In some embodiments, a disclosed compound or pharmaceutical composition is incorporated into a contact lens for ocular drug delivery. The contact lens may be a hydrogel contact lens or a molecularly imprinted contact lens. Another exemplary contact lens drug delivery system known to those of skill in the art is the experimental SIGHT (Sustained Innovative Glaucoma and Ocular Hypertension Treatment) treatment, which seeks to treat mild to moderate glaucoma and ocular hypertension (see Clinical Trial NCT04747808). The SIGHT drug-eluting lens for glaucoma treatment incorporates the FDA-approved drug bimatoprost into contact lenses that are formulated for controlled drug release. The SIGHT lens comprises drug and barrier layers on the lens surface to control the diffusion release kinetics of the drug. Ophthalmic formulations of the disclosure include those of similar material design as the SIGHT lens, as well as others generally known to those of skill in the art (e.g., as described in Franco, et al., *Polymers,* 2021, 13, 1102).

A disclosed pharmaceutical composition may comprise any excipient (e.g., a surfactant, carrier, antioxidant, and the like) at a concentration of about 0.01%, about 0.02%, about 0.05%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 35%, about 40%, about 45%, about 50%, about 55%, about 60%, about 61%, about 62%, about 63%, about 64%, about 65%, about 66%, about 67%, about 68%, about 69%, about 70%, about 75%, about 75%, or about 80% of the formulation, on a weight or volume basis.

F. PHARMACEUTICAL COMBINATIONS

The disclosed compositions are not limited to compositions of a single compound, or limited to a single carrier, diluent, and/or excipient. Compositions also include combinations of multiple compounds (including additional active compounds), and/or multiple carriers, diluents, and excipients. Pharmaceutical compositions for example may comprise a compound of Formula (1) together with one or more other active agents in combination, together with one or more pharmaceutically-acceptable carriers, diluents, and/or excipients, and additionally with one or more other active agents. Additional exemplary embodiments include compositions comprising two compounds of Formula (1), or compositions comprising any other two disclosed compounds.

A pharmaceutical composition may be prepared to increase an existing therapeutic effect, provide an additional therapeutic effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

"Therapeutic effects" in embodiments include antioxidant, anti-inflammatory, analgesic, anti-neuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, and stimulant effects.

"Synergistic effects" include increases in potency, bioactivity, bioaccessibility, bioavailability, and/or therapeutic effect, defined as greater than the additive contributions of the components acting alone. Numerous methods are known to those of skill to determine whether there is synergy as to a particular effect, i.e., whether, when two or more components are mixed together, the effect is greater than the sum of the effects of the individual components applied alone, thereby producing "1+1>2." Suitable methods include isobologram (or contour) analysis (Huang. *Front Pharmacol.* 2019; 10: 1222), or the equation of Loewe additivity (Loewe & Muischnek. *Arch Exp Pathol Pharmacol.* 1926; 114: 313-326). A synergistic effect also may be calculated using methods such as the Sigmoid-Emax equation (Holford & Scheiner. *Clin Pharmacokinet.* 1981; 6: 429-453) and the median-effect equation (Chou & Talalay. *Adv Enzyme Regul.* 1984; 22: 27-55). The corresponding graphs associated with the equations referred to above are the concentration-effect curve and combination index curve, respectively. Each equation referred to above may be applied to experimental data to generate a corresponding graph to aid in assessing the effects of the drug combination.

In some embodiments, wherein a pharmaceutical composition comprises an additional active compound, the additional active compound is selected from the group consisting of: amino acids, antioxidants, anti-inflammatory agents, analgesics, antineuropathic and antinociceptive agents, antimigraine agents, anxiolytics, antidepressants, antipsychotics, anti-PTSD agents, dissociatives, cannabinoids, immunostimulants, anti-cancer agents, antiemetics, orexigenics, antiulcer agents, antihistamines, antihypertensives, anticonvulsants, antiepileptics, bronchodilators, neuroprotectants, nootropics, empathogens, psychedelics, plasticity-inducing agents (e.g., psychoplastogens and neuroplastogens), monoamine oxidase inhibitors, tryptamines, terpenes, phenethylamines, sedatives, stimulants, serotonergic agents, and vitamins. In some embodiments, the additional active compound acts to increase a therapeutic effect, provide an additional therapeutic effect, decrease an unwanted effect, increase stability or shelf-life, improve bioavailability, induce synergy, increase plasticity (e.g., neural plasticity), or alter pharmacokinetics or pharmacodynamics. In some embodiments, the additional therapeutic effect is an antioxidant, anti-inflammatory, analgesic, antineuropathic, antinociceptive, antimigraine, anxiolytic, antidepressant, antipsychotic, anti-PTSD, dissociative, immunostimulant, anti-cancer, antiemetic, orexigenic, antiulcer, antihistamine, antihypertensive, anticonvulsant, antiepileptic, bronchodilator, neuroprotective, empathogenic, psychedelic, sedative, or stimulant effect.

In some embodiments, an additional active compound is a tryptamine. A tryptamine may have the structure below, wherein $R^{N1}$, $R^{N2}$, $R^{\alpha}$, $R^{\beta}$, $R^2$, $R^4$, $R^5$, $R^6$, and $R^7$ are as defined herein or known in the art:

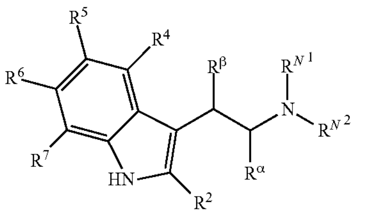

In some embodiments, $R^{N1}$, $R^{N2}$, $R^{\alpha}$, $R^{\beta}$, $R^2$, $R^4$, $R^5$, $R^6$, and $R^7$ are each independently hydrogen, deuterium, halogen (F, Cl, Br, or I), OH, phosphoryloxy, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. Additionally, any two of $R^{N1}$, $R^{N2}$, $R^{\alpha}$, $R^{\beta}$, $R^2$, $R^4$, $R^5$, $R^6$, and $R^7$ and the intervening atoms can be taken together to form an optionally substituted optionally substituted cycloalkyl, optionally substituted cycloalkenyl, optionally substituted aryl, or optionally substituted heterocyclyl. In embodiments, the tryptamine is a quaternary salt, in which an additional $R^{N3}$ is connected to the nitrogen to which $R^{N1}$ and $R^{N2}$ are bound; wherein $R^{N3}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl.

In some embodiments, the additional active compound is a tryptamine selected from the group consisting of psilocybin, psilocin, psilacetin, DBT, DET, DiPT, α,O-DMS, DMT, 2,α-DMT, α,N-DMT, DPT, EiPT, AET, 4-HO-DBT, 4-HO-DET, 4-HO-DiPT, 4-HO-TMT, 4-HO-DMT, 5-HO-DMT (i.e., bufotenine), 4-HO-DPT, 4-HO-MET, 4-HO-MiPT, 4-HO-MPT, 4-HO-pyr-T, ibogaine, MBT, 4,5-MDO-DiPT, 5,6-MDO-DiPT, 4,5-MDO-DMT, 5,6-MDO-DMT, 5,6-MDO-MiPT, 2-Me-DET, 5-Br-DMT, 5-Cl-DMT, 5-F-DMT, 4,5-MDO-DMT, 4,5-MDO-DiPT, 2-Me-DMT, melatonin, 5-MeO-DET, 5-MeO-DiPT, 5-MeO-DALT, 5-MeO-DMT, 4-MeO-MiPT, 5-MeO-MiPT, 5,6-MeO-MiPT, 5-MeO-NMT, 5-MeO-pyr-T, 5-MeO-TMT, 5-MeS-DMT, MiPT, α-MT (i.e., AMT), NET, NMT, pyr-T, tryptamine, or α,N,O-TMS, or a pharmaceutically acceptable salt, hydrate, solvate, prodrug, stereoisomer, or tautomer thereof, or a combination thereof. As known in the art, the systematic naming of tryptamines, such as herein, involves the use of prefixes and suffixes to indicate substitutions on the indole ring and/or the side chain of the tryptamine core structure. For example, EiPT stands for ethyl isopropyl tryptamine, also known as N-ethyl-N-isopropyltryptamine (i.e., N-ethyl-N-[2-(1H-indol-3-yl)ethyl]propan-2-amine). Examples of these tryptamines and others that may in embodiments be included in a disclosed composition as an additional active compound are known to those of skill, and include the compounds disclosed in Shulgin & Shulgin, TiHKAL: The Continuation, Transform Press (1997) ("TiHKAL").

In embodiments, the additional active compound is a complex tryptamine or other indolamine, including iboga alkaloids such as ibogaine, and its analogs, metabolites, and derivatives. In embodiments, the tryptamine is a beta-carboline, such as beta-carboline, harmaline, harmine, harmane, harmalol, tetrahydroharmine, 9-methyl-R-carboline, pinoline, and 6-MeO-THH.

In some embodiments, the additional active compound is a phenethylamine. A phenethylamine may have the structure below, wherein $R^{N1}$, $R^{N2}$, $R^{\alpha}$, $R^{\beta}$, and each of $R^2$—$R^6$ are as defined herein or known in the art:

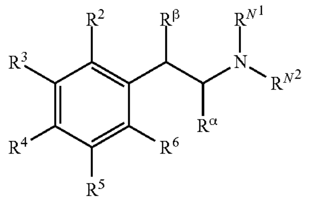

In some embodiments, $R^{N1}$, $R^{N2}$, $R^{\alpha}$, $R^{\beta}$, and each of $R^{2-6}$ are independently hydrogen, deuterium, halogen, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. In some embodiments, $R^3$ and $R^4$ are joined together to form an optionally substituted heterocyclyl, such as a dioxole (as with MDMA), a furan, a tetrahydrofuran, a thiophene, a pyrrole, a pyridine, a pyrrolidine, an ethylene oxide, an ethylenimine, a trimethylene oxide, a pyran, a piperidine, an imidazole, a thiazole, a dioxane, a morpholine, or a pyrimidine. In some embodiments, $R^3$ and $R^4$ are joined together to form an optionally substituted aryl, such as a phenyl. In some embodiments, the phenethylamine comprises a quaternary ammonium cation wherein each of $R^{N1}$, $R^{N2}$, and an additional $R^{N3}$ are independently an alkyl group or an aryl group, and with all other substituents as above. In some embodiments, the phenethylamine is a quaternary salt, in which an additional $R^{N3}$ is connected to the nitrogen to which $R^{N1}$ and $R^{N2}$ are bound; wherein $R^{N3}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl.

In some embodiments, the additional active compound is a phenethylamine selected from the group consisting of mescaline, α-ethylmescaline, escaline, symbescaline, meta-escaline, allylescaline, methallylescaline, asymbescaline, cyclopropylmescaline, phenescaline, 4-desoxymescaline, isomescaline, proscaline, metaproscaline, isoproscaline, thiomescaline, thioescaline, thioproscaline, thiobuscaline, a thiomescaline analog (e.g., 3-TM, 4-TM), buscaline, a thioisomescaline (e.g., 2-TIM, 3-TIM, 4-TIM), Aleph (i.e., DOT), a thiometaescaline (e.g., 3-TME, 4-TME, 5-TME), a thiotrisescaline (e.g., 3-T-TRIS, 4-T-TRIS), a thiosymbescaline (e.g., 3-TSB, 4-TSB), Aleph-2, Aleph-4, Aleph-6, Aleph-7, Ariadne, Beatrice (i.e., MDO-D, MDOM), BIS-TOM, BOB, BOD, BOH, BOHD, BOM, 4-Br-3,5-DMA, 2-Br-4,5-MDA, MDEA, 3C-BZ, a 2C-X compound (e.g., 2C-B, 2C-B-AN, 2C-B-FLY, 2C-B-BUTTERFLY, 2C-B-FLY-NBOMe, 2C-B-FLY-NB2EtO5Cl, 2C-Bn, 2C-Bu, 2C-B-5-HEMIFLY, 2C-C, 2C-C-3, 2C-CN, 2C-CP, 2C-D, 2C-E, 2C-EF, 2C-F, 2C-G, 2C-G-1, 2C-G-2, 2C-G-3, 2C-G-4, 2C-G-5, 2C-G-6, 2C-G-N, 2C-H, 2C-1, 2CB-Ind, 2C-iP, 2C-N, 2C-NH2, 2C-PYR, 2C-PIP, 2C-O, 2C-O-4, 2C-MOM, 2C-P, 2C-Ph, 2C-Se, 2C-T, 2C-T-2, 2C-T-3, 2C-T-4, 2C-T-5, 2C-T-6, 2C-T-7, 2C-T-8, 2C-T-9, 2C-T-10, 2C-T-11, 2C-T-12, 2C-T-13, 2C-T-14, 2C-T-15, 2C-T-16, 2C-T-17, 2C-T-18, 2C-T-19, 2C-T-21, 2C-T-21.5, 2C-T-22, 2C-T-23, 2C-T-24, 2C-T-25, 2C-T-27, 2C-T-28, 2C-T-30, 2C-T-31, 2C-T-32, 2C-T-33, 2C-DFM, 2C-TFM, 2C-TFE, 2C-YN, 2C-V, 2C-AL, CPM, psi-2C-T-4, 2C-Se), 3C-BZ, 3C-E, 4-D, beta-D, 2,4-DMA, 2,5-DMA, 3,4-DMA, DMCPA, DME, DMMDA, DMMDA-2, DMPEA, DOAM, DOB, DOBU, DOC, DOEF, DOET, DOI, DOM (i.e., STP), psi-DOM, DON, DOPR, EEE, EEM, EME, EMM, ETHYL-J, ETHYL-K, F-2, F-22, FLEA, GANESHA, a GANESHA analog (e.g., G-3, G-4, G-5, G-N), HOT-2, HOT-7, HOT-17, IDNNA, IRIS, BDB, LOPHOPHINE, 4-MA (i.e., PMA), MADAM-6, MDA, MDMA, MDAL, MDBU, MDBZ, MDCPM, MDDM, MDE, MDHOET, MDIP, MDMC, MDMEO, MDMEOET, MDMP, MDOH, MDPEA, MDPH, MDPL, MDPR, MEDA, MEE, MEM, MEPEA, META-DOB, META-DOT, METHYL-DMA, METHYL-DOB, METHYL-J (i.e., MBDB), METHYL-K, METHYL-MA (i.e., PMMA), METHYL-MMDA-2, MMDA, MMDA-2, MMDA-3a, MMDA-3b, MME, MPM, ORTHO-DOT, PEA, PROPYNYL, tetra-methoxyamphetamine, 3-TASB, 4-TASB, 5-TASB, 3-TE, 4-TE, TMA, TMA-2, TMA-3, TMA-4, TMA-5, TMA-6, 2T-MMDA-3a, 4T-MMDA-2, TMPEA, 2-TOET, 5-TOET, 2-TOM, 5-TOM, TOMSO, 4-MTA, MDAI, 5-methyl-MDA, 5-APB, 6-APB, and DiFMDA, or a pharmaceutically acceptable salt, hydrate, solvate, prodrug, stereoisomer, or tautomer thereof, or a combination thereof. As known in the art, the systematic naming of phenethylamines, such as herein, involves the use of prefixes and suffixes to indicate substitutions on the phenyl ring and/or side chain of the phenethylamine core structure. For example, MDBZ stands for methylenedioxybenzylamphetamine (i.e., 3,4-methylenedioxy-N-benzylamphetamine). Exemplary phenethylamines that, in embodiments, may be included in a composition as an additional active compound are known to those of skill, and include the compounds in Shulgin & Shulgin, PiHKAL: A Chemical Love Story, Transform Press (1991) ("PiHKAL"); and Shulgin A T, The Shulgin Index Vol. 1: Psychedelic Phenethylamines & Related Compounds, Transform Press (2011).

In some embodiments, the additional active compound is an ergoline. In some embodiments, the additional active compound is an ergot alkaloid. In some embodiments, the additional active compound is a lysergamide. A lysergamide may have the structure below, wherein $R^{N1}$, $R^{N2}$, $R^1$, $R^2$, $R^4$, $R^6$, $R^7$, $R^8$, $R^9$, $R^{12}$, $R^{13}$, and $R^{14}$ are as defined herein or known in the art:

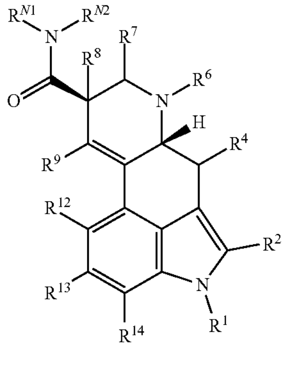

In some embodiments, $R^{N1}$, $R^{N2}$, $R^1$, $R^2$, $R^4$, $R^6$, $R^7$, $R^8$, $R^9$, $R^{12}$, $R^{13}$, and $R^{14}$ are each independently hydrogen, deuterium, halogen, optionally substituted alkyl, optionally substituted alkenyl, optionally substituted alkynyl, optionally substituted cycloalkyl, optionally substituted cycloalkenyl, optionally substituted aryl, or optionally substituted heterocyclyl. Additionally, any two of $R^{N1}$, $R^{N2}$, $R^1$, $R^2$, $R^4$, $R^6$, $R^7$, $R^8$, $R^9$, $R^{12}$, $R^{13}$, and $R^{14}$ and the intervening atoms can be taken together to form an optionally substituted optionally substituted cycloalkyl, optionally substituted cycloalkenyl, optionally substituted aryl, or optionally substituted heterocyclyl. In some embodiments, the lysergamide is a quaternary salt, in which an additional $R^{6A}$ is connected to the nitrogen to which $R^6$ is bound; wherein $R^{6A}$ is optionally substituted alkyl, optionally substituted alkoxy, optionally substituted alkyl, optionally substituted alkenyl, optionally substituted alkynyl, optionally substituted cycloalkyl, optionally substituted cycloalkenyl, optionally substituted aryl, or optionally substituted heterocyclyl.

In some embodiments, the additional active compound is a lysergamide selected from the group consisting of lysergic acid diethylamide (i.e., LSD, LSD-25, LAD, Delysid), 6-ethyl-6-nor-lysergic acid diethylamide (ETH-LAD), 6-propynyl-6-nor-lysergic acid diethylamide (PARGY-LAD), 6-allyl-6-nor-lysergic acid diethylamide (AL-LAD), 6-propyl-6-nor-lysergic acid diethylamide (PRO-LAD), 6-isopropyl-6-nor-lysergic acid diethylamide (IP-LAD), 6-cylopropyl-6-nor-lysergic acid diethylamide (CIP-LAD), 6-butyl-6-nor-lysergic acid diethylamide (BU-LAD), 6-(2-fluoroethyl)-6-nor-lysergic acid diethylamide (FLUORO-ETH-LAD), 1-acetyl-lysergic acid diethylamide (i.e., ALD, ALD-52, N-acetyl-LSD), 1-propionyl-lysergic acid diethylamide (1P-LSD), 1-butyryl-lysergic acid diethylamide (1B-LSD), 1-valeryl-lysergic acid diethylamide (1V-LSD), 1-(cyclopropylmethanoyl)-lysergic acid diethylamide (1 cP-LSD), 1-(1,2-dimethylcyclobutane-1-carbonyl)-lysergic acid diethylamide (1D-LSD), 1-propionyl-6-allyl-6-nor-lysergic acid diethylamide (1P-AL-LAD), 1-(cyclopropylmethanoyl)-6-allyl-6-nor-lysergic acid diethylamide (1 cP-AL-LAD), 1-propionyl-6-ethyl-6-nor-lysergic acid diethylamide (1P-ETH-LAD), lysergic acid 2,4-dimethylazetidide (i.e., LA-SS-Az, LSZ), lysergic acid piperidide (LSD-Pip), and lysergic acid methylisopropyl amide (MIPLA).

Other tryptamines, phenethylamines, and lysergamides useful as additional active compounds for purposes of the disclosure and thus contemplated for inclusion therein will be as generally known in the art (see, e.g., PiHKAL; TiHKAL; Grob & Grigsby, Handbook of Medical Hallucinogens, 2021; Luethi & Liechti. *Arch Toxicol.* 2020; 94: 1085-1133; Nichols. *Pharmacol Revi.* 2016; 68(2): 264-355; Glennon. *Pharmacol Biochem Behav.* 1999; 64: 251-256; each of which is incorporated by reference as if fully set forth herein).

G. DOSE AND DOSAGE

In some embodiments, pharmaceutical compositions comprise a therapeutically effective amount or an effective amount of a disclosed compound, such as for administration to a subject.

Administration of pharmaceutical compositions in a "therapeutically effective amount," or an "effective amount" to a subject means administration of an amount of composition sufficient to achieve the desired effect. When an "effective amount" means an amount effective in treating the stated disorder or symptoms in a subject, "therapeutic effect" would be understood to mean the responses(s) in a mammal after treatment that are judged to be desirable and beneficial. Depending on the symptom(s), condition, disease, or disorder to be treated, and depending on the particular constituent (s) in the compositions administered, those responses shall differ, but would be readily understood by those of skill, in view of the disclosure and the general knowledge of the art (e.g., for a mental health disorder, by reference to the symptoms listed in the Diagnostic and Statistical Manual of Mental Disorders, 5th Edition (DSM-5) for the stated disorder).

In embodiments, a pharmaceutical composition comprises a disclosed compound in an amount so that a single dose is (in a milligram dosage amount calculated based on the kilogram weight of the patient), e.g., 0.25 mg/kg or less (including a dose of 0.10 mg/kg or less, 0.05 mg/kg or less, 0.01 mg/kg or less, and 0.005 mg/kg or less), at least 0.50 mg/kg, at least 0.55 mg/kg, at least 0.60 mg/kg, at least 0.65 mg/kg, at least 0.70 mg/kg, at least 0.75 mg/kg, at least 0.80 mg/kg, at least 0.85 mg/kg, at least 0.90 mg/kg, at least 0.95 mg/kg, at least 1.0 mg/kg, at least 1.1 mg/kg, at least 1.2 mg/kg, at least 1.3 mg/kg, or at least 1.4 mg/kg, at least 1.5 mg/kg, at least 1.6 mg/kg, at least 1.7 mg/kg, at least 1.8 mg/kg, at least 1.9 mg/kg, at least 2.0 mg/kg, at least 2.1 mg/kg, at least 2.2 mg/kg, at least 2.3 mg/kg, at least 2.4 mg/kg, at least 2.5 mg/kg, at least 2.6 mg/kg, at least 2.7 mg/kg, at least 2.8 mg/kg, at least 2.9 mg/kg, or at least 3.0 mg/kg, and amounts within these ranges.

"Disclosed compound," broadly, and in some embodiments, includes any compound of Formula (1) or any other Formula herein, such as Formula (2), Formula (3), and Formulae (I)-(XXI); any compound of any of Group A, Group B, or Group C; any compound of Table 1; any specific compound described by structure; any additional active compound, such as any phenethylamine, tryptamine, or lysergamide; and any other compound herein. In embodiments, a disclosed compound is a compound of Formula (1). In embodiments, a disclosed compound is a compound of Formula (2). In embodiments, a disclosed compound is a compound of Formula (3). In embodiments, a disclosed compound is a compound of Formula (I). In embodiments, a disclosed compound is a compound of Formula (II). In embodiments, a disclosed compound is a compound of Formula (III). In embodiments, a disclosed compound is a compound of Formula (IV). In embodiments, a disclosed compound is a compound of Formula (V). In embodiments, a disclosed compound is a compound of Formula (VI). In embodiments, a disclosed compound is a compound of Formula (VII). In embodiments, a disclosed compound is a compound of Formula (VIII). In embodiments, a disclosed compound is a compound of Formula (IX). In embodiments, a disclosed compound is a compound of Formula (X). In embodiments, a disclosed compound is a compound of Formula (XI). In embodiments, a disclosed compound is a compound of Formula (XII). In embodiments, a disclosed compound is a compound of Formula (XIII). In embodiments, a disclosed compound is a compound of Formula (XIV). In embodiments, a disclosed compound is a compound of Formula (XV). In embodiments, a disclosed compound is a compound of Formula (XVI). In embodiments, a disclosed compound is a compound of Formula (XVII). In embodiments, a disclosed compound is a compound of Formula (XVIII). In embodiments, a disclosed compound is a compound of Formula (XIX). In embodiments, a disclosed compound is a compound of Formula (XX). In embodiments, a disclosed compound is a compound of Formula (XXI). In embodiments, a disclosed compound is a compound of Group A. In embodiments, a disclosed compound is a compound of Group B. In embodiments, a disclosed compound is a compound of Group C. In embodiments, a disclosed compound is a compound of Table 1. In embodiments, a disclosed compound is any of 2CB-5MM, 2C-iBu-5MM, 2C-iBu-5HM, and 2C-iBu-2OH-5MM. In embodiments, the disclosed compound is 2CB-5MM. In embodiments, the disclosed compound is 2C-iBu-5MM. In embodiments, the disclosed compound is 2C-iBu-5HM. In embodiments, the disclosed compound is 2C-iBu-2OH-5MM.

In some embodiments, a pharmaceutical composition comprises a disclosed compound in an amount so that a single dose is (in a milligram dosage amount calculated based on the kilogram weight of the patient) between about 0.001 mg/kg and 0.1 mg/kg, such as about 0.001 mg/kg, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, and about 0.1 mg/kg, as well as ranges between these values. In some embodiments, a single dose is between about 0.1 mg/kg and 1.0 mg/kg, such as about 0.1 mg/kg, about 0.2 mg/kg, about 0.3 mg/kg, about 0.4 mg/kg, about 0.5 mg/kg, about 0.6 mg/kg, about 0.7 mg/kg about 0.8 mg/kg about 0.9 mg/kg, and about 1.0 mg/kg, as well as ranges between these values.

In some embodiments, a pharmaceutical composition comprises a disclosed compound in an amount so that a single dose is (in a milligram dosage amount calculated based on the kilogram weight of the patient) about 20 μg/kg body weight or less (e.g., less than 20 μg/kg, less than 15 μg/kg, less than 10 μg/kg, or less than 5 μg/kg body weight, e.g., from 1 to 20 μg/kg body weight, e.g., from 1 to 5 μg/kg, from 5 to 10 μg/kg, from 10 to 15 μg/kg, or from 15 to 20 μg/kg, e.g., about 5 μg/kg, about 10 μg/kg, about 15 μg/kg, or about 20 μg/kg).

In some embodiments, a pharmaceutical composition comprises a disclosed compound in an amount so that a single dose is (in a milligram dosage amount calculated based on the kilogram weight of the patient) about less than about 20 ng/mL (e.g., 0.05 to 20 ng/mL, e.g., 0.1 to 15 ng/mL, 0.5 to 10 ng/mL, or 1 to 5 ng/mL, e.g., 0.05 to 0.1 ng/mL, 0.1 to 0.2 ng/mL, 0.2 to 0.3 ng/mL, 0.3 to 0.4 ng/mL, 0.4 to 0.5 ng/mL, 0.5 to 1.0 ng/mL, 1.0 to 5 ng/mL, 5 to 10 ng/mL, 10 to 15 ng/mL, or 15 to 20 ng/mL, e.g., about 0.05 ng/mL, 0.1 ng/mL, 0.2 ng/mL, 0.5 ng/mL, 1.0 ng/mL, 2.0 ng/mL, 2.5 ng/mL, 5.0 ng/mL, 7.5 ng/mL, 10 ng/mL, 12 ng/mL, 15 ng/mL, or 20 ng/mL). In some embodiments, the circulating drug plasma level of the compound is below the limit of detection (e.g., 0.1 ng/mL or less).

In some embodiments, a pharmaceutical composition comprises a disclosed compound in an amount so that a single dose is (whether or not present in a unit dosage form), e.g., 25 mg or less (including a dose of 10 mg or less, 5 mg or less, 1 mg or less, and 0.5 mg or less), at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 225 mg, or at least 250 mg, as well as amounts within these ranges.

In some embodiments, a pharmaceutical composition comprises a disclosed compound in an amount so that a single dose is (whether or not present in a unit dosage form) between about 0.1 mg and 1.0 mg, such as about 0.1 mg, about 0.2 mg, about 0.3 mg, about 0.4 mg, about 0.5 mg, about 0.6 mg, about 0.7 mg, about 0.8 mg, about 0.9 mg, and about 1.0 mg, as well as ranges between these values. In some embodiments, a single dose is between about 1 mg and 10 mg, such as about 1 mg, about 2 mg, about 3 mg, about 4 mg, about 5 mg, about 6 mg, about 7 mg, about 8 mg, about 9 mg, and about 10 mg, as well as ranges between these values. In some embodiments, a single dose is between about 10 mg and 100 mg.

It will be appreciated that dosages may vary depending upon whether the treatment is therapeutic or prophylactic, the onset, progression, severity, frequency, duration, probability of or susceptibility of the symptom to which treatment is directed, clinical endpoint desired, previous, simultaneous or subsequent treatments, general health, age, gender, and race of the subject, bioavailability, potential adverse systemic, regional or local side effects, the presence of other disorders or diseases in the subject, and other factors that will be appreciated by the skilled artisan (e.g., medical or familial history).

Dose amount, frequency or duration may be increased or reduced, as indicated by the clinical outcome desired, status of the pathology or symptom, any adverse side effects of the treatment or therapy, or concomitant medications. One of skill together with the teachings of this disclosure will appreciate the factors that may influence the dosage, frequency, and timing required to provide an amount sufficient or effective for providing a therapeutic effect or benefit, and to do so depending on the type of therapeutic effect desired, as well as to avoid or minimize adverse effects.

In some embodiments, the dose administered is determined by a physician, in light of relevant circumstances, such as the disorder to be treated, the route of administration, the composition or formulation administered, the age, weight, and response of the patient, the severity of the patient's symptoms, and the like. Disclosed dosages are consequently exemplary and not limiting. In some instances, dosages below the lower limit of a disclosed range may be sufficient, and in other cases dosages above a range may be administered.

Doses may be divided into several smaller doses for administration, and taken together or separately.

In some embodiments, such as where a composition is a single unit dosage form, suggested dosage amounts are known by reference to the format of the preparation itself. In some embodiments, such as where a composition is in a multiple dosage form, suggested dosage amounts are known by reference to the means of administration, or by reference to the packaging and labeling, package insert(s), marketing materials, training materials, and/or other information and knowledge available to those of skill or to the public.

H. KITS

In some aspects are further provided pharmaceutical kits ("kits") containing a disclosed pharmaceutical composition, suggested administration guidelines or prescribing information therefor, and a suitable container. Individual unit dosage forms can be included in multi-dose kits or containers. Pharmaceutical compositions can be packaged in single or multiple unit dosage forms for uniformity of dosage and ease of administration.

Kits may comprise suitable packaging. A kit may comprise one or more containers comprising any disclosed compound. Each component (if there is more than one component) can be packaged in separate containers or some components can be combined in one container where cross-reactivity and shelf life permit. A kit may comprise compositions in unit dosage form, bulk packages (e.g., multi-dose packages), or sub-unit doses. For example, kits may comprise sufficient dosages of a compound as disclosed herein and/or an additional pharmaceutically active compound useful for a disease detailed herein to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies). Information pertaining to dosing and proper administration (if needed) may be printed onto a multi-dose kit directly (e.g., on a blister pack or other interior packaging holding disclosed compositions). Kits also may comprise package inserts and/or printed instructions (e.g., on exterior packaging) for administering their contents and their appropriate therapeutic use.

I. METHODS OF USE

In some aspects, provided herein are methods of using the disclosed compounds. In some embodiments, disclosed compounds are used to modulate neurotransmission. In some embodiments, disclosed compounds are used to treat a condition, such as a disease or a disorder. In some embodiments, disclosed compounds are used in the manufacture of a medicament for the therapeutic and/or the prophylactic treatment of a condition, such as a disease or a disorder. In some embodiments, disclosed compounds are administered as part of therapy. In some embodiments, disclosed compounds are administered along with psychotherapy, psychological support, or patient monitoring. In some embodiments, disclosed compounds are administered in a therapeutically effective amount to a subject having a condition, such as a disease or a disorder. In some embodiments, the condition is a mental health disorder. In some embodiments, the condition is a neurodegenerative disorder. In some embodiments, the condition is a pain disorder. In some embodiments, disclosed compounds are administered to a subject that is healthy.

Herein, the terms "subject," "user," "patient," and "individual" are used interchangeably, and refer to any mammal, including murines, simians, mammalian farm animals, mammalian sport animals, and mammalian pets, such as canines and felines, although preferably humans. Such terms will be understood to include one who has an indication for which a compound, composition, or method described herein may be efficacious, or who otherwise may benefit by the invention. In general, all of the compounds, compositions, and disclosed methods will be appreciated to work for all individuals, although individual variation is to be expected, and will be understood. The disclosed methods also can be modified to treat multiple patients at once, including couples or families. Hence, these terms will be understood to also mean two or more individuals.

Compounds and compositions may be administered to a subject orally, mucosally, rectally, subcutaneously, intravenously, intramuscularly, intranasally, or by inhalation. Compounds and compositions may be administered to a subject topically or transdermally. Compounds and compositions may be administered to a subject ocularly, including ophthalmically, i.e., via ophthalmic administration, including via topical administration to the surface of the eye. In embodiments, when administered through any such routes, the compounds and compositions are useful in methods for treating a subject in need of such treatment.

In some embodiments, a disclosed compound may be useful as a locally active therapeutic agent. Systemic administration of therapeutically active agents may directly or indirectly affect multiple organs and tissues throughout the body. Consequently, systemic administration of a compound may give rise to a greater number or extent of adverse effects (e.g., side effects) at a therapeutically active dose. For example, certain psychedelics have been shown to exert potent anti-inflammatory effects, but are also psychoactive or have other effects on the central nervous system (CNS) that may be undesired or unnecessary in the context of treating certain medical conditions (e.g., skin or muscle inflammation). Hence, it may be desired to administer a compound that exhibits minimal penetration into the CNS, but has therapeutic effects (e.g., anti-inflammatory effects) in tissues and organs in which the compound is directly administered, or in tissues and organs proximal to the site of administration. Such compounds may be referred to as "locally active," because their action is localized to the area to which (or close to which) they are applied.

Without being bound by theory, disclosed compounds may be substrates for an enzyme. Inactivation (e.g., hydrolysis) of such compounds (e.g., by an enzyme) may prevent systemic action, thereby localizing their therapeutic effects to (or close to) the site of administration. In some embodiments, other features of disclosed compounds may prevent systemic action. In some embodiments, features of disclosed compounds may prevent penetration into the CNS (e.g., prevent crossing the blood-brain barrier). In some embodiments, administration of a disclosed compound in a disclosed topical formulation exerts therapeutic (e.g., anti-inflammatory) effects locally, without causing systemic effects. In some embodiments, administration of a disclosed compound in a disclosed topical formulation exerts therapeutic (e.g., anti-inflammatory) effects systemically, without causing psychoactive or other effects associated with penetration into the CNS.

a. Modulating Neurotransmission

In some embodiments, disclosed compounds modulate neurotransmission in a subject, such as following administration of a therapeutically effective amount to said subject.

In embodiments, modulating neurotransmission by administering a disclosed compound to a subject treats a disease or disorder in the subject. In embodiments, modulating neurotransmission comprises regulating levels of monoamines in, for example, the CNS and peripheral tissues. In embodiments, modulating neurotransmission by administering a disclosed compound to a subject treats a disease or disorder therein.

In some embodiments, disclosed compounds activate serotonin receptors. In some embodiments, disclosed compounds agonize and/or antagonize serotonin receptors (5-HT receptors, such as the 5-$HT_2$ receptor). The 5-$HT_2$ receptor family consists of the three distinct receptor subtypes: 5-$HT_{2A}$, 5-$HT_{2B}$, and 5-$HT_{2C}$. 5-$HT_{2A}$ and 5-$HT_{2C}$ receptors are more highly expressed in the brain than the 5-$HT_{2B}$ subtype. Psilocin and other related psychoactive tryptamines exert their psychoactive effects primarily by acting as 5-$HT_{2A}$ receptor agonists. However, many of these tryptamines (including psilocin) are also agonists at the 5-$HT_{2B}$ and 5-$HT_{2C}$ receptors, owing to high sequence homology among the three 5-$HT_2$ receptor subtypes (Nichols. *Pharmacol. Rev.* 2016; 68: 264-355). Activation of all 5-$HT_2$ receptor subtypes may result in reduced efficacy or detrimental side effects. For example, activation of 5-$HT_{2C}$ receptors has been shown to functionally oppose effects of 5-$HT_{2A}$ receptor activation (id.), while activation of 5-$HT_{2B}$ receptors in cardiac muscle tissue has been linked to heart valve disease (Hutcheson et al. *Pharmacol Ther.* 2011; 132(2): 146-157). In embodiments, it may be desired for a compound, especially one that may be used regularly or over a relatively long time period, to have reduced activity (e.g., agonism) of 5-$HT_{2B}$. In some embodiments, disclosed compounds agonize or partially agonize 5-HT receptors, such as any one or more of an 5-$HT_1$ receptor, such as 5-$HT_{1A}$ and 5-$HT_{1B}$, an 5-$HT_2$ receptor, such as 5-$HT_{2A}$, 5-$HT_{2B}$, and 5-$HT_{2C}$, and 5-$HT_6$.

In some embodiments, a disclosed compound has an in vitro $EC_{50}$ (agonist mode) for any one or more of 5-$HT_{1A}$, 5-$HT_{1B}$, 5-$HT_{2A}$, 5-$HT_{2C}$, and 5-$HT_6$ that is less than 10 μM, less than 5 μM, less than 1 μM, less than 0.5 μM, or less than 0.1 μM. In embodiments, a disclosed compound has an in vitro $EC_{50}$ (agonist mode) for 5-$HT_{2A}$ that is less than 1 μM, less than 0.5 μM, less than 0.1 μM, less than 0.05 μM, less than 0.01 μM, less than 0.005 μM, or less than 0.001 μM. In embodiments, a disclosed compound has an in vitro $EC_{50}$ (agonist mode) for 5-$HT_{2C}$ that is less than 1 μM, less than 0.5 μM, less than 0.1 μM, less than 0.05 μM, less than 0.01 μM, less than 0.005 μM, or less than 0.001 μM.

In some embodiments, disclosed compounds show greater potency at 5-$HT_{2A}$ relative to another 5-HT receptor. In some embodiments, disclosed compounds show greater potency at 5-$HT_{2A}$ relative to any one or more of an 5-$HT_1$ receptor, another 5-$HT_2$ receptor, such as 5-$HT_{2B}$ and 5-$HT_{2C}$, a 5-$HT_5$ receptor, a 5-$HT_6$ receptor, and a 5-$HT_7$ receptor.

Determining agonism and antagonism, and measuring $EC_{50}$ and $IC_{50}$, respectively, may be determined according to methods available to one of skill in the art. In one example, measuring Gq-mediated calcium flux is a known method for assessing modulation, e.g., activation, of 5-$HT_{2A}$, a widely recognized target of psychedelic compounds. See, e.g., Klein et al. *ACS Pharmacol Transl Sci.* 2020; 4(2): 533-542; Flanagan et al. *ACS Pharmacol Transl Sci.* 2020; 4(2): 488-502; Toro-Sazo et al. *PLoS One.* 2019; 14(1): e0209804; Halberstadt et al. *Psychopharmacol* (Berl). 2019; 236(2): 799-808. As would be recognized by one of skill, a partial agonist is one that shows reduced maximum efficacy ($E_{MAX}$) relative to a full agonist ($E_{MAX}$=100%), e.g., serotonin in the example of a 5-HT receptor.

Certain therapeutic benefits of disclosed compounds derives, at least in part, from selective activation of a serotonin receptor (e.g., 5-$HT_{2A}$, 5-$HT_{2C}$). In some embodiments, disclosed compounds have increased therapeutic efficacy, improved safety profiles, and reduced side effects because of optimization for selective serotonin receptor activation. In some embodiments, a disclosed compound has increased selectivity for the 5-$HT_{2A}$ receptor over another serotonin receptor (e.g., the 5-$HT_{2B}$ receptor, or the 5-$HT_{2C}$ receptor). In some embodiments, a disclosed compound has increased selectivity for the 5-$HT_{2A}$ receptor over the 5-$HT_{2B}$ receptor. In some embodiments, a disclosed compound has increased selectivity for the 5-$HT_{2A}$ receptor over the 5-$HT_{2C}$ receptor. In some embodiments, selectivity is defined as functional activity selectivity, calculated by the ratio of the half-maximal effective concentration ($EC_{50}$) of a disclosed compound for one receptor (e.g., the 5-$HT_{2A}$ receptor) as compared to another receptor (e.g., a serotonin receptor, such as the 5-$HT_{2B}$ receptor, or the 5-$HT_{2C}$ receptor). For example, if a hypothetical compound had a 5-$HT_{2A}$ $EC_{50}$ of 0.2 μM and a 5-$HT_{2B}$ $EC_{50}$ of 1.0 μM, the compound could be said to have a 5-fold functional activity selectivity for the 5-$HT_{2A}$ receptor over the 5-$HT_{2B}$ receptor. In some embodiments, selectivity can be defined as affinity selectivity, defined by the ratio of binding affinity (e.g., as assessed by K) for one receptor (e.g., the 5-$HT_{2A}$ receptor) as compared to another receptor (e.g., a serotonin receptor, such as the 5-$HT_{2B}$ receptor, or the 5-$HT_{2C}$ receptor). For example, if a hypothetical compound had a 5-$HT_{2A}$ K of 0.1 μM and a 5-$HT_{2B}$ $EC_{50}$ of 1.0 μM, the compound could be said to have a 10-fold affinity selectivity for the 5-$HT_{2A}$ receptor over the 5-$HT_{2B}$ receptor.

In some embodiments, a disclosed compound has an affinity selectivity of about 1.1-fold, 1.5-fold, 1.6-fold, 2-fold, 5-fold, 10-fold, 20-fold, 30-fold, 50-fold, 70-fold, 80-fold, 90-fold, 100-fold, 150-fold, or at least 150-fold selectivity for the 5-$HT_{2A}$ receptor over the 5-$HT_{2B}$ receptor. In embodiments, a disclosed compound has improved affinity selectivity for the 5-$HT_{2A}$ receptor over the 5-$HT_{2B}$ receptor, relative to a comparator.

In embodiments, a disclosed compound has a functional activity selectivity of about 1.1-fold, 1.5-fold, 1.6-fold, 2-fold, 5-fold, 10-fold, 20-fold, 30-fold, 50-fold, 70-fold, 80-fold, 90-fold, 100-fold, 150-fold, or at least 150-fold selectivity for the 5-$HT_{2A}$ receptor over the 5-$HT_{2B}$ receptor. In embodiments, a disclosed compound has improved affinity selectivity for the 5-$HT_{2A}$ receptor over the 5-$HT_{2B}$ receptor, relative to a comparator.

In some embodiments, a disclosed compound has an affinity selectivity of about 1.1-fold, 1.5-fold, 1.6-fold, 2-fold, 5-fold, 10-fold, 20-fold, 30-fold, 50-fold, 70-fold, 80-fold, 90-fold, 100-fold, 150-fold, or at least 150-fold selectivity for the 5-$HT_{2C}$ receptor over the 5-$HT_{2B}$ receptor.

In embodiments, a disclosed compound has improved affinity selectivity for the 5-$HT_{2C}$ receptor over the 5-$HT_{2B}$ receptor, relative to a comparator.

In embodiments, a disclosed compound has a functional activity selectivity of about 1.1-fold, 1.5-fold, 1.6-fold, 2-fold, 5-fold, 10-fold, 20-fold, 30-fold, 50-fold, 70-fold, 80-fold, 90-fold, 100-fold, 150-fold, or at least 150-fold selectivity for the 5-$HT_{2C}$ receptor over the 5-$HT_{2B}$ receptor. In embodiments, a disclosed compound has improved affinity selectivity for the 5-$HT_{2C}$ receptor over the 5-$HT_{2B}$ receptor, relative to a comparator.

b. Modulating Neuroplasticity

In some embodiments, a disclosed compound modulates neurotransmission in a subject, such as following administration of a therapeutically effective amount to the subject. In some embodiments, modulating neurotransmission contributes to the therapeutic effects of a compound in a subject. In some embodiments, modulating neurotransmission by administering a compound to a subject treats a disease or disorder therein.

Neurotransmission can refer to the transfer of information between neurons. Information is emitted by a neuron when an action potential occurs, resulting in the release of neurotransmitters into a synapse. Neurotransmission can thus be quantified by measuring parameters of action potential firing in a population of neurons. In some embodiments, neurotransmission is quantified by measuring the general action potential firing activity (Obien et al. *Front Neurosci.* 2015; 8: 423; Morin et al. *J Biosci Bioeng.* 2005; 100(2): 131-143). General action potential firing activity parameters include spike rate, burst rate, and/or spike contrast. In embodiments, neurotransmission is quantified by measuring burst structure. Burst structure parameters include burst spike number, burst duration, and/or burst amplitude. In some embodiments, neurotransmission is quantified by measuring oscillatory behavior. Oscillatory behavior is measured as the standard deviation of spike rate, burst rate, and/or burst amplitude. In some embodiments, neurotransmission is quantified by measuring the synchronicity of activity of a neuron population. Synchronicity is measured as the coefficient of variation in spike rate, burst rate, and/or burst duration across a neuron population. Synchronicity is also measured as synchronicity share, synchronicity distance, and/or spike simplex.

In some embodiments, a disclosed compound modulates spike rate. Spike rate is the number of action potentials per second. In some embodiments, a disclosed compound modulates burst rate. Neurons may send out a series of action potentials in rapid succession, known as a burst. Burst rate is the number of bursts per second. In some embodiments, a disclosed compound modulates spike contrast. Spike contrast is a measure of variability in neuronal activity, measured as the difference between the number of spikes occurring in the first half and second half of a recording duration (e.g., 700 ms). In embodiments, a compound modulates burst spike number, i.e., the number of spikes per burst. In embodiments, a compound modulates burst duration, i.e., the mean duration of detected bursts. In embodiments, neurotransmission is measured as the burst amplitude, which is obtained as an integral function with a decay calculated over the timestamps of bursts. The burst amplitude is the peak value of the integral, which increases with highly frequent and numerous spiking.

In some embodiments, a disclosed compound modulates oscillatory behavior. Oscillatory behavior is a measure of variability in a parameter, measured as the standard deviation of a parameter over time within the experimental episode. In some embodiments, a compound modulates the synchronicity of activity in a neuron population. Synchronicity is a measure of the relative variability in activity across a neuron population. In some embodiments, a compound modulates synchronicity share. Synchronicity share is the average number of units involved in population bursts, higher values reflecting a higher degree of synchronicity in bursts occurring amongst populations of neurons. In some embodiments, a compound modulates synchronicity distances. Synchronicity distances are defined as the average distance of burst starts within a population burst from the population burst center, lower values reflecting a stronger synchronicity of a network. In some embodiments, a compound modulates spike simplex. Spike simplex is a measure of connectivity and complexity in a neuronal network, higher values reflecting higher synchronicity among neurons.

In embodiments, administration of a disclosed compound increases neuroplasticity. Neuroplasticity, also known as neural plasticity or brain plasticity, refers to the brain's ability to change and adapt in response to experiences, learning, and environmental factors. Without being bound by theory, neuroplasticity may occur through several mechanisms. Neuroplasticity in some embodiments includes synaptic plasticity, which involves the strengthening or weakening of connections (synapses) between neurons. Synaptic plasticity may be associated with learning and memory. Neuroplasticity in some embodiments includes structural plasticity, which involves changes in the physical structure of neurons, such as the growth of new dendritic branches or the formation of new synapses. In embodiments, increasing neuroplasticity contributes to the therapeutic effects of administering a disclosed compound to a subject. In embodiments, increasing neuroplasticity refers to increasing synaptic plasticity. In embodiments, increasing neuroplasticity refers to increasing structural plasticity. In embodiments, increasing neuroplasticity by administering a disclosed compound to a subject treats a disease or disorder in the subject.

Neuroplasticity can be defined in terms of neuritogenesis, spinogenesis, and synaptogenesis. Neuritogenesis refers to a process by which neurons generate and extend their neurites (i.e., to form axons and dendrites). Neuritogenesis is vital in neural development and the formation of neuronal circuits. Spinogenesis refers to the formation of dendritic spines, small protrusions on the dendrites of neurons. Dendritic spines are vital for synaptic connections and play a role in synaptic transmission and plasticity. Synaptogenesis refers to the formation of synapses, vital for the establishment and refinement of neural circuits, and a fundamental process underlying learning, memory, and information processing in the brain.

In some embodiments, a disclosed compound increases neuritogenesis. Neuritogenesis can be measured in terms of total neurite length, maximum neurite length, number of neurite nodes, and/or number of neurite extremities. In some embodiments, a compound increases total neurite length. In some embodiments, a compound increases maximum neurite length. In some embodiments, a disclosed compound increases the number of neurite nodes. In some embodiments, a compound increases the number of neurite extremities.

In some embodiments, administration of a disclosed compound increases the number of dendritic branches, the number of dendritic crossings, the density of dendritic spines, the density of synapses (i.e., number of synapses per neuron), and/or the total dendritic length. These can be measured using a Sholl analysis or another technique known in the art (Ly et al. *ACS Pharmacol Transl Sci.* 2020; 4(2): 452-460).

c. Treatment

In some aspects are provided methods of treating a medical condition, such as a disease or a disorder, by administrating a disclosed compound or composition. In some embodiments, disclosed compounds and compositions are accordingly used to treat a medical condition, such as a disease or disorder.

Also provided are the use of disclosed compounds in the manufacture of a medicament, including to treat a medical condition, such as a disease or disorder. Also provided are methods of administering disclosed compounds to a subject having a condition, such as a disease or disorder, thereby treating said condition.

Herein, unless context indicates otherwise, the terms "disease," "disorder," and "condition" are used interchangeably and are intended to be interpreted broadly to encompass any pathological or non-pathological state. These terms may include subjects with or without a formal diagnosis, including those who do not meet established diagnostic criteria as well as those who do. For example, an inflammatory "disease," "disorder," or "condition" may refer to states associated with or characterized by inflammation, including diagnosable inflammatory diseases, acute or chronic inflammatory disorders, inflammatory syndromes, subclinical inflammatory states, and both localized and systemic inflammatory responses. These terms further encompass states in which inflammation is a contributing factor, consequence, or mechanistic component, whether or not inflammation is the primary clinical focus, and whether or not the condition is formally recognized as an inflammatory disease. In some embodiments, reference to a "disease," "disorder," or "condition" refers to a specific, diagnosable medical entity, including but not limited to those classified by established diagnostic criteria or medical coding systems (e.g., ICD, DSM). As an example, in some embodiments, reference to an inflammatory "disease," "disorder," or "condition" refers to a disease, disorder, or condition having a specific clinical diagnosis, including formally recognized medical conditions characterized by inflammation.

In some embodiments, disclosed compounds and compositions are administered to a subject by one or more routes of administration, including, e.g., oral, mucosal, rectal, subcutaneous, intravenous, intramuscular, intranasal, inhaled, ocular, ophthalmic, intraocular, periocular, topical, and transdermal routes.

In some embodiments are provided methods of treating and/or preventing a condition in a mammal, preferably a human, the method comprising administering to the mammal an amount, preferably a therapeutically effective amount, of a disclosed compound or a disclosed pharmaceutical composition.

"Treating" and "treatment" includes causing a desired biological or pharmacological effect, and may include any one or more of, or a specific subset of, including depending on whether "treatment" includes "prevention": (a) preventing a condition from occurring in a subject who may be predisposed to the condition but has not yet received a diagnosis; (b) inhibiting a condition, i.e. arresting its development; (c) relieving a condition, i.e., causing regression thereof; (d) protecting from or relieving a symptom or pathology caused by or related to a condition; (e) reducing, decreasing, inhibiting, ameliorating, or preventing the onset, severity, duration, progression, frequency or probability of one or more symptoms or pathologies associated with a condition; and (f) preventing or inhibiting of a worsening or progression of symptoms or pathologies associated with a condition or comorbid with a condition. Other such measurements, benefits, and surrogate or clinical endpoints, alone or in combination, are understood in the art. In some embodiments, treatment includes prevention. In some other embodiments, treatment does not include prevention.

In embodiments, disclosed compounds are used to treat a central nervous system (CNS) disorder. Broadly, CNS disorders include diseases of the nervous system (e.g., movement disorders, neurodegenerative disorders) as well as mental, behavioral, and neurodevelopmental disorders, such as those in the DSM-5, Merck Manual, ICD-11, or other such diagnostic resources known to one of skill.

i. Mental, Behavioral, or Neurodevelopmental Disorders

In some embodiments, disclosed compounds are used to treat a mental, behavioral, or neurodevelopmental disorder. In some embodiments, disclosed compounds are administered, such as in a therapeutically effective amount, to a subject having a mental, behavioral, or neurodevelopmental disorder, thereby treating said mental, behavioral, or neurodevelopmental disorder. In some methods herein, the disclosed compositions, when administered in a therapeutically effective amount, provide beneficial therapeutic effects for the treatment of a mental, behavioral, or neurodevelopmental disorder.

The ICD-11, which is incorporated by reference herein in its entirety, defines "mental, behavioral, or neurodevelopmental disorders" as syndromes characterized by clinically significant disturbance in cognition, emotional regulation, or behavior that reflects a dysfunction in the psychological, biological, or developmental processes that underlie mental and behavioral functioning. Such disorders include neurodevelopmental disorders, schizophrenia or other primary psychotic disorders, catatonia, mood disorders, anxiety or fear-related disorders, obsessive-compulsive or related disorders, disorders specifically associated with stress, dissociative disorders, feeding (or eating) disorders, elimination disorders, disorders of bodily distress or bodily experience, disorders due to substance use or addictive behaviors, impulse control disorders, disruptive behavior or dissocial disorders, personality disorders (and related traits), paraphilic disorders, factitious disorders, neurocognitive disorders, mental or behavioral disorders associated with pregnancy, childbirth or the puerperium, sleep-wake disorders, sexual dysfunctions, and gender incongruence.

A mental, behavioral, or neurodevelopmental disorder where otherwise undefined, will be understood to refer to the disorder as defined in the ICD-11. Within the category of mental, behavioral, or neurodevelopmental disorders, a mental disorder (or "mental health disorder") generally refers to a disease condition that involves negative changes in emotion, mood, thinking, and/or behavior. In general, mental health disorders are characterized by clinically significant disturbances in an individual's cognition, emotion, behavior, or a combination thereof, resulting in impaired functioning, distress, or increased risk of suffering.

Although the terms "mental disorder" and "mental health disorder," as well as terms that define specific diseases and disorders, generally shall refer to the criteria in the ICD-11, or a patient with a diagnosis based thereon, it will be appreciated that disclosed methods are equally applicable to patients having an equivalent underlying disorder, whether that disorder is diagnosed based on the criteria in ICD-11, ICD-10, DSM-5, or DSM-IV (each of which is incorporated by reference herein in its entirety) whether the diagnosis is based on other clinically acceptable criteria, or whether the patient has not yet had a formal clinical diagnosis.

In some embodiments, disclosed compounds are used to treat a mental health disorder. In some embodiments, compounds are administered, such as in a therapeutically effective amount, to a subject having a mental health disorder, thereby treating said mental health disorder. In some methods, the compounds, when administered in a therapeutically effective amount, provide beneficial therapeutic effects for the treatment of a mental health disorder. In some embodiments, the compounds and compositions are used to reduce the symptoms of a mental health disorder. The symptoms of the mental health disorder to be treated shall be able to be determined by one of skill, by reference to the general understanding of the art regarding that disorder.

In some embodiments, measures of therapeutic efficacy include reports by a subject or an observer. In some embodiments, measures of therapeutic efficacy include responses to a questionnaire. Non-limiting representative examples of applicable measures of symptom improvement include the Generalized Anxiety Disorder Scale-7 (GAD-7), Montgomery-Asberg Depression Rating Scale (MADRS), Global Assessment of Functioning (GAF) Scale, Clinical Global Impression (CGI), Substance Abuse Questionnaire (SAQ), Mini International Neuropsychiatric Interview 5 (MINI 5), Columbia Suicide Severity Rating Scale (C-SSRS), Patient Health Questionnaire (PHQ-9), Pittsburgh Sleep Quality Index (PSQI), Interpersonal Reactivity Index (IRI), Short Form (36) Health Survey (SF-36), Self-Compassion Scale (SCS), Trauma History Questionnaire (THQ), Beck Depression Index (BDI), and related subject- or observer-reported measures.

Disclosed compounds are useful in some embodiments to treat a neurodevelopmental disorder. In some embodiments, a "neurodevelopmental disorder" is a neurological and/or cognitive disorder that arises during the developmental period that involves significant difficulties in the acquisition and execution of specific neurological functions (e.g., intellectual, motor, language, or social functions). In some embodiments, the neurodevelopmental disorder is a disorder of intellectual development, a developmental speech or language disorder, autism spectrum disorder, a developmental learning disorder, a developmental motor coordination disorder, attention deficit hyperactivity disorder, or stereotypic movement disorder.

Disclosed compounds are useful in some embodiments to treat schizophrenia or another primary psychotic disorder. In general, these disorders are characterized by significant impairments in reality and alterations in behavior manifest in positive symptoms like persistent delusions, persistent hallucinations, disorganized thinking and speech, grossly disorganized behavior, as well as experience of negative symptoms such as blunted or flat affect and avolition and psychomotor disturbances. In some embodiments, a disclosed compound is used to treat schizophrenia, schizoaffective disorder, schizotypal disorder, acute and transient psychotic disorder, delusional disorder, or a substance-induced psychotic disorder.

Disclosed compounds are useful in some embodiments to treat catatonia. In some embodiments, "catatonia" refers to a category of syndromes characterized by the co-occurrence of several symptoms of decreased, increased, or abnormal psychomotor activity. In some embodiments, the catatonia is associated with another mental disorder. In some embodiments, the catatonia is induced by substances or medications.

Disclosed compounds are useful in embodiments to treat a mood disorder. As defined in the ICD-11, mood disorders are categorized according to the specific type(s) of mood episodes, and their pattern over time. The primary types of mood episodes are depressive episodes, manic episodes, mixed episodes, and hypomanic episodes. In some embodiments, the mood disorder is a bipolar or related disorder (e.g., bipolar type I disorder, bipolar type II disorder, cyclothymic disorder), a depressive disorder, or a substance-induced mood disorder. In embodiments, the mood disorder is a depressive disorder. In embodiments, the depressive disorder is single-episode depressive disorder, major depressive episode disorder, persistent depressive disorder (formally known as dysthymia), disruptive mood dysregulation disorder, premenstrual dysphoric disorder, postpartum depression, substance/medication-induced depressive disorder, depressive disorder due to another medical condition, seasonal affective disorder, mixed depressive and anxiety disorder, or an unspecified depressive disorder. In embodiments, depression is assessed through the Patient Health Questionnaire-9 (PHQ-9) screening tool, Montgomery-Asberg Depression Rating Scale (MADRS), Hamilton Depression Rating Scale, Beck Depression Inventory (BDI-II), Zung Self-Rating Depression Scales (SDS), Major Depression Inventory (MDI), Center for Epidemiologic Studies Depression Scale (CED-D), Rome Depression Inventory (RDI), Hamilton Rating Scale for Depression (HRSD), and Carroll Rating Scale (CRS).

Disclosed compounds are useful in some embodiments to treat an anxiety or fear-related disorder. An "anxiety disorder" refers to a class of mental disorders that induce excessive or abnormal fear, dread, or worry. In some embodiments, the anxiety disorder is selected from the group consisting of generalized anxiety disorder, panic disorder, agoraphobia, specific phobia, social anxiety disorder, separation anxiety disorder, selective mutism, or a substance-induced anxiety disorder.

Disclosed compounds are useful in some embodiments to treat an obsessive-compulsive or related disorder. In general, these disorders are characterized by repetitive thoughts and behaviors, such as cognitive phenomena (obsessions, intrusive thoughts and preoccupations). In some embodiments, the disorder is characterized by a compulsive need to accumulate possessions and distress related to discarding them (i.e., hoarding disorder). In some embodiments, the disorder is body-focused and can be characterized by recurrent and habitual actions (hair-pulling, skin-picking). In some embodiments, the disorder is obsessive-compulsive disorder, body dysmorphic disorder, olfactory reference disorder, hypochondriasis, hoarding disorder, a body-focused repetitive behavior disorder, or a substance-induced obsessive-compulsive disorder.

Disclosed compounds are useful in some embodiments to treat a disorder associated with stress. In some embodiments, the disorder associated with stress has an identifiable stressor that is a causal factor, like exposure to a stressful or traumatic event, or a series of such events or adverse experiences. Stressors may be within the normal range of life experiences (e.g., divorce, socioeconomic problems), or from a threatening or traumatizing experience. In general, the nature and duration of the symptoms that arise in response to the stressor can distinguish the disorder from everyday stress. In embodiments, a disclosed compound is used to treat post-traumatic stress disorder, complex post-traumatic stress disorder, prolonged grief disorder, adjustment disorder, reactive attachment disorder, or disinhibited social engagement disorder.

Disclosed compounds are useful in some embodiments to treat a dissociative disorder. Dissociative disorders can be characterized by involuntary disruption or discontinuity in the normal integration of one or more of the following: identity, sensations, perceptions, affects, thoughts, memories, control over body movements, or behavior. In some subjects, dissociative disorder symptoms can be severe, and may result in impairment in personal, social, educational, occupational or other areas of functioning. In some embodiments, a compound is used to treat dissociative neurological symptom disorder, dissociative amnesia (including amnesia with dissociative fugue and without dissociative fugue), trance disorder, possession trance disorder, dissociative identity disorder, partial dissociative identity disorder, or depersonalization-derealization disorder.

Disclosed compounds are useful in some embodiments to treat a feeding or eating disorder. Feeding or eating disorders generally involve abnormal eating or feeding behaviors that are not explained by another health condition, and are not developmentally appropriate or culturally sanctioned. These disorders can involve preoccupation with food as well as body weight and shape concerns. In embodiments, a disclosed compound is used to treat anorexia nervosa (including anorexia with significantly low body weight, anorexia with dangerously low body weight, or anorexia in recovery with normal body weight), bulimia nervosa, binge eating disorder, avoidant-restrictive food intake disorder, pica, or rumination-regurgitation disorder.

Disclosed compounds are useful in some embodiments to treat an elimination disorder. Elimination disorders include the repeated voiding of urine into clothes or bed, and the repeated passage of feces in inappropriate places once the individual has reached a developmental age when continence is ordinarily expected. In embodiments, a disclosed compound is used to treat enuresis (including nocturnal enuresis, diurnal enuresis, and nocturnal and diurnal enuresis) or encopresis (including both with encopresis constipation or overflow incontinence, and encopresis without constipation or overflow incontinence).

Disclosed compounds are useful in some embodiments to treat a disorder of bodily distress or bodily experience. Disorders of bodily stress typically involve bodily symptoms that the subject finds distressing and to which the subject devotes excessive attention. Bodily integrity dysphoria typically involves a disturbance in the person's experience of the body manifested by persistent discomfort or intense feelings of body configuration. In some embodiments, a disclosed compound is used to treat a bodily distress disorder (including mild, moderate, and severe bodily distress disorder) or body integrity dysphoria.

Disclosed compounds are useful in some embodiments to treat a disorder due to substance use or addictive behaviors. Disorders due to substance use or addictive behaviors are mental and/or behavioral disorders that develop predominantly as a result of the use of psychoactive substances (including medications and illegal or illicit substances), or specific repetitive rewarding and reinforcing behaviors. In some embodiments, a disclosed compound is used to treat disorders due to substance use (i.e., a substance use disorder, or SUD). In some embodiments, the substance use disorder is associated with alcohol, *cannabis*, synthetic cannabinoids, opioids, sedatives, hypnotics or anxiolytics, cocaine, stimulants (e.g., amphetamines, methamphetamines, methcathinone, synthetic cathinones, caffeine), hallucinogens, nicotine, volatile inhalants, MDMA or MDA, dissociative drugs like ketamine and phencyclidine, or another substance (including medications and non-psychoactive substances). In some embodiments, the substance use disorder is selected from alcohol use disorder, *cannabis* use disorder, caffeine use disorder, phencyclidine use disorder, inhalants use disorder, opioids use disorder, sedatives use disorder, hypnotics use disorder, anxiolytics use disorder, stimulants use disorder, and tobacco use disorder. In some embodiments, the substance use disorder is alcohol use disorder. In some embodiments, the substance use disorder is *cannabis* use disorder. In some embodiments, the substance use disorder is caffeine use disorder. In some embodiments, the substance use disorder is phencyclidine use disorder. In some embodiments, the substance use disorder is inhalant use disorder. In some embodiments, the substance use disorder is opioids use disorder. In some embodiments, the substance use disorder is sedatives use disorder. In some embodiments, the substance use disorder is hypnotics use disorder. In some embodiments, the substance use disorder is anxiolytics use disorder. In some embodiments, the substance use disorder is stimulants use disorder. In some embodiments, the substance use disorder is tobacco use disorder. In some embodiments, the substance use disorder is alcohol use disorder, wherein said alcohol use disorder is selected from alcohol abuse, alcohol dependence, and alcoholism. In some embodiments, the disorder is associated with another addictive behavior (e.g., gambling disorders, gaming disorder). In some embodiments, a substance use disorder can be screened using a Screening to Brief Intervention (S2BI), Alcohol, Smoking, and Substance Involvement Screening Test (ASSIST), Brief Screener for Alcohol, Tobacco, and other Drugs (BSTAD), Tobacco, Alcohol, Prescription medication, and other Substance use (TAPS), the Opioid Risk Tool—OUD (ORT-OUD) Chart, Drug Abuse Screen Test (DAST-10), and Tobacco, Alcohol, Prescription medication, and other Substance use (TAPS).

Disclosed compounds are useful in some embodiments to treat an impulse control disorder. Such disorders may be characterized by a repeated failure to resist an impulse, drive, or urge to perform an act that is rewarding to a subject despite negative long-term consequences, such as harm to the subject or a significant impairment in important areas of functioning. In embodiments, impulse control behaviors include fire-setting, stealing, inappropriate sexual behavior, and explosive outbursts. In embodiments, a compound is used to treat pyromania, kleptomania, compulsive sexual behavior disorder, or intermittent explosive disorder.

Disclosed compounds are useful in some embodiments to treat a disruptive behavior disorder or a dissocial disorder. Such disorders may be broadly characterized by persistent behavior problems that range from persistently defiant, disobedient, provocative or spiteful behaviors to behaviors that violate the rights of others or norms, rules, or laws. In some embodiments, a disclosed compound is used to treat oppositional defiant disorder (including oppositional defiant disorder with chronic irritability-anger and oppositional defiant disorder without chronic irritability-anger) or conduct-dissocial disorder (including childhood-onset conduct-dissocial disorder and adolescent-onset conduct-dissocial disorder).

Disclosed compounds are useful in some embodiments to treat a personality disorder. Personality disorders may be generally characterized by problems in perceiving one's identity, self-worth, accuracy of self-view, and self-discretion that is manifest in patterns of cognition, emotional experience, emotional expression, and maladaptive behavior. In embodiments, a compound is used to treat a mild, moderate, or severe personality disorder. In embodiments, a compound is used to treat a prominent personality trait or patterns (e.g., negative affectivity, detachment, dissociality, disinhibition, anankastia, borderline pattern). In some embodiments, the personality disorder is antisocial personality disorder, avoidant personality disorder, borderline personality disorder, dependent personality disorder, histrionic personality disorder, masochistic or sadistic behavior, narcissistic personality disorder, obsessive-compulsive personality disorder, paranoid personality disorder, psychopathy, sociopathy, schizoid personality disorder, or schizotypal personality disorder.

Disclosed compounds are useful in some embodiments to treat a paraphilic disorder. Paraphilic disorders can be characterized by persistent and intense patterns of atypical sexual arousal, the focus of which involves others whose age or status renders them unwilling or unable to consent. In some embodiments, a disclosed compound is used to treat exhibitionistic disorder, voyeuristic disorder, pedophilic disorder, coercive sexual sadism disorder, frotteuristic disorder, other paraphilic disorders involving non-consenting individuals, or paraphilic disorders involving solitary behavior or consenting individuals.

Disclosed compounds are useful in some embodiments to treat a factitious disorder. Such disorders may be characterized by intentionally feigning, falsifying, inducing or aggravating medical, psychological, or behavior signs and symptoms or injury to oneself or another person. Subjects with factitious disorders may seek treatment or otherwise present themselves or another person as ill, injured, or impaired. In embodiments, a compound is used to treat factitious disorder imposed on self or a factitious disorder imposed on another.

Disclosed compounds are useful in some embodiments to treat a neurocognitive disorder. Such disorders may be characterized by primary clinical defects in cognitive functioning that are acquired (rather than developmental); thus, the subject experiences a decline from a previously attained level of functioning. In some embodiments, a compound is used to treat delirium. In some embodiments, the delirium is associated with another disease or disorder. In some embodiments, the delirium is associated with a psychoactive substance (including medications and illicit or illegal substances). In some embodiments, a compound is used to treat mild neurocognitive disorder. In some embodiments, a compound is used to treat an amnestic disorder. In some embodiments, the amnestic disorder is associated with another disease or disorder. In some embodiments, the delirium is associated with a psychoactive substance (including medications and illicit or illegal substances). In some embodiments, a compound is used to treat dementia. In some embodiments, the dementia is associated with Alzheimer's disease, Parkinson's disease, cerebrovascular disease, Lewy body disease, a psychoactive substance (including medications and illicit or illegal substances). In some embodiments, a compound is used to treat a behavioral or psychological disturbance associated with dementia. In some embodiments, dementia is assessed using a Functional Activities Questionnaire (FAQ), Ascertain Dementia 8 (AD8), Mini-Cog, Mini-Mental State Exam (MMSE), the Montreal Cognitive Assessment (MoCA), and the Neuropsychiatric Inventory Questionnaire (NPI-Q).

Disclosed compounds are useful in some embodiments to treat a mental or behavioral disorder associated with pregnancy, childbirth, or the puerperium. In some embodiments, the syndrome associated with pregnancy or the puerperium involves significant mental and behavioral features, including a depressive symptom. In some embodiments, the disorder includes psychotic symptoms. In some embodiments, a disclosed compound is used to treat mental or behavioral disorders associated with pregnancy, childbirth or the puerperium, with psychotic symptoms. In embodiments, a disclosed compound is used to treat mental or behavioral disorders associated with pregnancy, childbirth or the puerperium, without psychotic symptoms.

Disclosed compounds are useful in some embodiments to treat a sleep-wake disorder. In general, sleep-wake disorders are associated with difficulty initiating or maintaining sleep (e.g., insomnia), excessive sleepiness (e.g., hypersomnolence disorders), respiratory disturbance during sleep (e.g., sleep-related breathing disorders (SRBDs), such as obstructive sleep apnea (OSA), central sleep apnea (CSA), sleep-related hypoventilation disorders, sleep-related hypoxemia disorder, snoring, catathrenia, Cheyne-Stokes breathing, and sleep-disordered breathing), disorders of the sleep-wake schedule (e.g., circadian rhythm sleep-wake disorders), abnormal movements during sleep, or problematic behavioral or psychological events that occur while falling asleep, during sleep, or upon arousal from sleep (e.g., parasomnia disorders). In embodiments, a compound is used to treat an insomnia disorder, a hypersomnolence disorder, a sleep-related breathing disorder, a circadian rhythm sleep-wake disorder, or a parasomnia disorder.

Disclosed compounds are useful in some embodiments to treat sexual dysfunction. Sexual dysfunctions can be defined as syndromes wherein a subject may have difficulty experiencing personally satisfying, non-coercive sexual activities. In some embodiments, a disclosed compound is used to treat hypoactive sexual desire dysfunction, sexual arousal dysfunction, orgasmic dysfunction, ejaculatory dysfunction, or sexual dysfunction associated with pelvic organ prolapse.

ii. Neurodegenerative Disorders

Disclosed compounds are useful in some embodiments to treat a neurodegenerative disorder. In some embodiments, compounds are administered, such as in a therapeutically effective amount, to a subject having a neurodegenerative disorder. In some methods, the compounds, when administered in a therapeutically effective amount, provide beneficial therapeutic effects for the treatment of a neurodegenerative disorder.

The term "neurodegenerative disorder" refers to a class of progressive, chronic, and debilitating conditions characterized by the gradual loss of structure and function of neurons within the central nervous system (CNS) or peripheral nervous system (PNS). These disorders involve the degeneration, impairment, or death of neuronal cells, leading to a decline in cognitive, motor, and/or sensory abilities.

Neurodegenerative disorders can be classified according to primary clinical features, e.g., dementia, parkinsonism, or motor neuron disease, anatomic distribution of neurodegeneration, e.g., frontotemporal degenerations, extrapyramidal disorders, or spinocerebellar degenerations, or principal molecular abnormality (Dugger & Dickson. *Cold Spring Harb Perspect Biol.* 2017: 9(7); a028035). These disorders may involve various etiologies, including but not limited to, presence of pathogenic proteins, age, environmental stressors, and genetic predisposition (Armstrong. *Folia Neuropathologica.* 2020: 58(2); 93-112).

In some embodiments, the neurodegenerative disorder is any of Alzheimer's disease, amyotrophic lateral sclerosis or Charcot's disease, chronic traumatic encephalopathy, corticobasal degeneration, dementias including vascular dementia, Huntington's disease, Lytico-Bodig disease, mild cognitive impairment, multiple sclerosis, a motor neuron disease, neuromyelitis optica spectrum disorder, Parkinson's disease or Parkinsonisms, prion diseases, progressive supranuclear palsy, and traumatic brain injury including mild TBI.

iii. Pain and Pain Disorders

Disclosed compounds are useful in some embodiments to treat pain or a pain disorder. In some embodiments, disclosed compounds are administered, such as in a therapeutically effective amount, to a subject having a pain disorder. In some methods herein, the disclosed compositions, when administered in a therapeutically effective amount, provide beneficial therapeutic effects for the treatment of a pain disorder.

A "pain disorder" refers to a class of medical conditions characterized by the experience of persistent or recurrent physical or psychological pain, either localized or widespread, that significantly impairs an individual's daily functioning and quality of life. These disorders may involve various etiologies, including but not limited to nociceptive, neuropathic, psychogenic, idiopathic or radicular origins.

Disclosed compounds are useful in some embodiments to treat neuropathic pain. In embodiments, a compound is used to treat psychogenic pain. In embodiments, a compound is used to treat idiopathic pain. In embodiments, a compound is used to treat radicular pain.

Pain disorders may manifest as acute or chronic pain, and they can affect different parts of the body, such as musculoskeletal, neurological, gastrointestinal, or visceral systems. Pain can be expressed as, but is not limited to, post-herpetic pain, trigeminal pain, occipital pain, or pudendal pain. In embodiments, a disclosed compound is used to treat pain associated with chemotherapy (e.g., chemotherapy associated neuropathy). In embodiments, a compound is used to treat arthritis, back pain, central pain, chronic fatigue syndrome, cluster headaches, migraine headaches, phantom limb pain, complex regional pain syndrome, compression mononeuropathy, diabetic neuropathy, fibromyalgia, focal neuropathy, herniated disc pain, or sciatica.

Pain may be assessed using the Pain, Enjoyment, and General Activity Scale (PEG), the Numeric Rating Scale (NRS), the Visual Analog Scale (VAS), Behavioral Pain Scale (BPS), and the Faces Pain Scale-Revised (FPS-R).

iv. Inflammation and Inflammatory Conditions

Inflammation is an essential immune response to tissue insults such as microbial infection, acute injury, chemical irritants or other such dysregulation of normal tissue functioning. The inflammatory process is a feature of the innate immune system, whereby molecular patterns of tissue damage are recognized and responded to by a variety of inflammatory agents such as cytokines and chemokines. Inflammatory agents act directly to remove harmful stimuli and initiate various signaling responses to return damaged tissue to a homeostatic state. Although this response is often self-terminating, the resolution of inflammation may fail for multiple reasons, extending the inflammation response into a chronic stage (Ahmed. *Front Biol.* 2011; 6(4): 274-281). Chronic inflammation is associated with or underlies a variety of pathological conditions, including major cardiovascular and neuropsychiatric disorders (Nichols. *Cardiovasc Psych Neurol.* 2009; 475108).

Recent evidence suggests a significant role of the 5-$HT_{2A}$ serotonin receptor subtype in mediating the termination of the inflammatory response. 5-$HT_{2A}$ receptors are found throughout the body, including in both the central nervous system and peripheral tissues (Flanagan & Nichols. *Int Rev of Psychiatry.* 2018; 30(4): 363-375). In the brain, 5-$HT_{2A}$ receptors are involved in cognitive function and working memory, mediate the effects of psychedelic compounds, and have been implicated in mechanisms underlying neuropsychiatric disorders such as schizophrenia (Nichols. *Cardiovasc Psychiatry Neurol.* 2009; 475108). In the periphery, 5-$HT_{2A}$ receptors are found in multiple immune-related tissues, organs, and cells, such as the spleen, thymus, and circulating lymphocytes, as well as in components of both the innate and adaptive immune systems (Stefulj et al. *Brain Behav Immun.* 2000; 14(3): 219-24; Closz-Tayarani et al. *Int Immunol.* 2003; 15(2): 233-40). Research on 5-$HT_{2A}$ receptors at these tissues have elucidated their role in modulating the immune response (Flanagan & Nichols. *Int Rev Psychiatry.* 2018; 30(4): 363-375).

Due to their significant action on 5-$HT_{2A}$ receptors in the brain, multiple studies have been performed to assess the effect of psychedelic compounds on the inflammation modulating effects of 5-$HT_{2A}$ receptors. One such study found that (R)-2,4-dimethoxy-4-iodoamphetamine ((R)-DOI) is able to potently repress TNF-α induced inflammation. This study found the same effect, albeit slightly less potent, induced by the psychedelic compounds 2C-BCB, LA-SS-Az and LSD (Yu et al. *J Pharmacol Exp Ther.* 2008; 327: 316-323). Notably, the potency required to achieve anti-inflammatory effects of some psychedelic compounds is at levels in the low picomolar range, approximately 500× more potent than conventional corticosteroids at their target. Anti-inflammatory doses of psychedelics also can be below the threshold for producing subjective or behavioral effects, meaning they may exhibit anti-inflammatory effects without triggering a psychedelic "trip."

This work, and subsequent in vitro and in vivo studies have demonstrated that (R)-DOI inhibits TNF-α induced expression of genes encoding intracellular adhesion molecule-1 (ICAM1), vascular cell adhesion molecule-1 (VCAM1), and inflammatory cytokines IL-6 and IL-13, and chemokines monocyte chemotactic protein-1 (MCP1). (R)-DOI also blocks activation and nuclear translocation of NF-κB, nitric oxide synthase activity, and downregulates asthma-associated protein arginase-1 (Nau et al. PLoS One. 2013; 8(10): e75426; Flanagan & Nichols. *Int Rev Psychiatry.* 2018; 30(4): 363-375; Flanagan et al. *ACS Pharmacol Transl Sci.* 2024; 7(2): 478-492). Further, some psychedelic compounds potently suppress select key proinflammatory biomarkers, while leaving others unaffected. For the biomarkers where suppression is evident, suppression is potent and returns levels to baseline, not suppressed below baseline levels, even at relatively high doses of drug (Nichols. *Neuropharmacol.* 2022; 219: 109232). Thus, some psychedelics can reduce expression of certain key inflammatory components, while leaving the immune response largely intact. This is a unique mechanism of action among known anti-inflammatory and immunomodulatory agents, and may be advantageous as it is predicted to have fewer side effects such as opportunistic infections that are associated with broad immunosuppressants like corticosteroids (id.).

Although there is great therapeutic potential for psychedelics as anti-inflammatory agents, there is considerable variation in the efficacy of different psychedelics. It has been hypothesized that chemical structural diversity among psychedelics may result in functional selectivity at the 5-$HT_{2A}$ receptor, whereby certain ligands engage specific subsets of amino acid residues in the binding pocket of the receptor that induce stable conformational states that couple to different anti-inflammatory signal transduction affectors. This hypothesis is supported by the differential peripheral effects of (R)-DOI and (R)-DOTFM, wherein the former induces anti-inflammatory effects in a mouse model of asthma while the latter does not (Flanagan et al. *ACS Pharmacol Transl Sci.* 2024). This finding supports earlier work that determined the primary pharma-cophore for anti-inflammatory phenethylamine 5-$HT_{2A}$ receptor agonists to be 2,5-dimethoxyphenethylamine (2C-H) (Flanagan T W, et al. *ACS Pharmacol Transl Sci.* 2020; 4(2): 488-502). However, structure-activity relationships of anti-inflammatory agents with 5-$HT_{2A}$ receptor agonist properties remain unclear.

In some embodiments, a disclosed compound is a potent anti-inflammatory agent that acts on specific inflammation mediators, thereby returning chronically inflamed tissue to a healthy state. In some embodiments, the anti-inflammatory effect is enacted without broadly suppressing the immune system, and can therefore be beneficial to treat inflammatory disease where steroids are contraindicated, or the condition is steroid resistant.

In some embodiments, administration of a disclosed compound decreases an inflammatory response. In embodiments, the inflammatory response is quantified by a change in the level of an inflammation response biomarker. In embodiments, the level of an inflammation response biomarker represents the expression level of an inflammation response gene. For example, an increased level of an inflammation response biomarker in a subject can be compared to a baseline level of the same biomarker, the increase indicative of increased expression of the inflammation response gene encoding the biomarker. In embodiments, increased expression of an inflammation response gene is associated with chronic inflammation. In embodiments, decreased expression of an inflammation response gene is associated with chronic inflammation.

In some embodiments, a disclosed compound exhibits potent anti-inflammatory properties. In some embodiments, administration of a disclosed compound suppresses several pro-inflammatory markers (e.g., mRNA encoding IL6, IL1b, GMCSF, Arg1, and IL5). In some embodiments, administration of a disclosed compound suppresses pro-inflammatory markers to baseline levels. Without being bound by theory, disclosed compounds may exert their anti-inflammatory effects due to functional selectivity at the 5-$HT_{2A}$ receptor, whereby the compound engages certain amino acid residues within receptor, stabilizing it in a conformation that triggers anti-inflammatory signal transduction pathway effectors.

In some embodiments, the biomarker of inflammation response gene expression is mRNA. In some embodiments, the biomarker of inflammation response gene expression is a protein. In some embodiments, the inflammation response gene is TNFα, Arg-1, IL-4, IL-5, IL-6, IL-8, IL-9, IL-1β, I-IA, IL-12, IL-13, IFNα, IFNb, IFNg, TGF-β, IL-15, IL-17, IL-20, IL-22, LTA, IL-23, IL-18, VCAM1, ICAM1, MCP1, MMP-9, Muc5ac, Gm-csf, CCL2, CCL5, CCL3, CCL4, CCL11, CD11a, CD3, CD4, CD8, or CRP. In some embodiments, the inflammation response gene encodes an inflammatory agent. An inflammatory agent is a protein that activates an inflammatory response. Inflammatory agents include the proteins IL-1β, TNFα, IL-15, IL-17, Arg-1, and IL-18. In some embodiments, the inflammation response gene encodes an anti-inflammatory agent. An anti-inflammatory agent is a protein that reduces an inflammatory response. Anti-inflammatory agents include the proteins IL-1, IL-4, IL-10, IL-11, and IL-13. In some embodiments, the inflammation response gene encodes an agent that may be inflammatory or anti-inflammatory. For example, leukemia inhibitory factor, interferon-alpha, IL-6, and transforming growth factor (TGF-β) can act as either inflammatory or anti-inflammatory cytokines under various circumstances (Zhang & An. *Int Anesthesiol Clin.* 2007; 45(2): 27-37).

In some embodiments, the inflammation response gene is ICAM1. In embodiments, the biomarker of inflammation response comprises an ICAM1 gene product. In embodiments, the biomarker comprises ICAM1 mRNA. In embodiments, the biomarker comprises the ICAM1 protein. In embodiments, the inflammation response gene is VCAM1. In embodiments, the biomarker of inflammation response comprises a VCAM1 gene product. In embodiments, the biomarker comprises VCAM1 mRNA. In embodiments, the biomarker comprises the VCAM1 protein. In embodiments, the inflammation response gene is MCP1. In embodiments, the biomarker of inflammation response comprises a MCP1 gene product. In embodiments, the biomarker comprises MCP1 mRNA. In embodiments, the biomarker comprises the MCP1 protein. In embodiments, the inflammation response gene is IL-5. In embodiments, the biomarker of inflammation response comprises a IL-5 gene product. In embodiments, the biomarker comprises IL-5 mRNA. In embodiments, the biomarker comprises the IL-5 protein. In embodiments, the inflammation response gene is IL-6. In embodiments, the biomarker of inflammation response comprises a IL-6 gene product. In embodiments, the biomarker comprises IL-6 mRNA. In embodiments, the biomarker comprises the IL-6 protein.

In some embodiments, the inflammation response gene is IL-9. In embodiments, the biomarker of inflammation response comprises a IL-9 gene product. In embodiments, the biomarker comprises IL-9 mRNA. In embodiments, the biomarker comprises the IL-9 protein. In embodiments, the inflammation response gene is IL-15. In embodiments, the biomarker of inflammation response comprises a IL-15 gene product. In embodiments, the biomarker comprises IL-15 mRNA. In embodiments, the biomarker comprises the IL-15 protein. In embodiments, the inflammation response gene is IL-1β. In embodiments, the biomarker of inflammation response comprises a IL-1β gene product. In embodiments, the biomarker comprises IL-1β mRNA. In embodiments, the biomarker comprises the IL-1β protein. In embodiments, the inflammation response gene is Arg-1. In embodiments, the biomarker of inflammation response comprises a Arg-1 gene product. In embodiments, the biomarker is Arg-1 mRNA. In embodiments, the biomarker comprises the Arg-1 protein.

In some embodiments, the inflammation response gene is Gm-csf. In embodiments, the biomarker of inflammation response comprises a Gm-csf gene product. In embodiments, the biomarker comprises Gm-csf mRNA. In embodiments, the biomarker comprises the Gm-csf protein. In embodiments, the inflammation response gene is Muc5ac. In embodiments, the biomarker of inflammation response comprises a Muc5ac gene product. In embodiments, the biomarker comprises Muc5ac mRNA. In embodiments, the biomarker comprises the Muc5ac protein. In embodiments, the inflammation response gene is MMP-9. In embodiments, the biomarker of inflammation response comprises a MMP-9 gene product. In embodiments, the biomarker comprises MMP-9 mRNA. In embodiments, the biomarker comprises the MMP-9 protein. In embodiments, the inflammation response gene is TGF-β. In embodiments, the biomarker of inflammation response comprises a TGF-β gene product. In embodiments, the biomarker comprises TGF-β mRNA. In embodiments, the biomarker comprises the TGF-β protein.

In some embodiments, the inflammation response biomarker comprises a cytokine. Cytokines are small signaling proteins that coordinate the interactions of different cell types involved in the amplification and regulation of the inflammatory response. In embodiments, the cytokine biomarker comprises IL-2, IFN-γ, TNFα, TNFβ, GM-CSF, IL-2, IL-3, IL-4, IL-5, IL-6, IL-9, IL-10, IL-13, IL-17, IL-25, IL-33, or TGF-β. In embodiments, the inflammation response biomarker comprises a chemokine. Chemokines are small signaling proteins that induce the movement of other cell types, such as toward a tissue injury site. In embodiments, the chemokine biomarker comprises CCL-1 to CCL-28, CXCL-1 to CXCL-16, IL-8, MCP1, RANTES, XCL1, XCL2, or $CX_3CL1$. In embodiments, the inflammation response biomarker comprises an enzyme. In embodiments, the enzyme biomarker comprises Arg-1. In embodiments, the biomarker of inflammation for a particular inflammatory disease, comorbidity, or patient demographic will be known to those of skill in the art (see Sreedhar et al. General Mechanisms of Immunity and Inflammation. In: Watanabe K & Arumugam S. eds. Japanese Kampo medicines for the treatment of common diseases: Focus on inflammation. Academic Press; 2017; Germolec et al. *Methods Mol Biol.* 2018; 1803: 57-79; Calder et al. *Br J Nutr.* 2013; 109 Suppl 1: S1-34).

In some embodiments, a disclosed compound causes the level of an inflammation response biomarker in a subject to become closer to a baseline level. "Baseline level" refers to the level of a biomarker observed in healthy populations not experiencing inflammation. Baseline levels differ among biomarkers and will be known in the art, or can be measured by standard techniques (Calder et al. *Br J Nutr.* 2013; 109 Suppl 1: S1-34).

In some embodiments, a disclosed compound (e.g., administration of a disclosed compound to a subject, such as in a disclosed pharmaceutical composition, and/or such as according to a disclosed method) reduces the level of an inflammatory biomarker. In embodiments, a compound does not reduce the level of an inflammatory biomarker below baseline. In embodiments, a compound reduces the level of an inflammatory biomarker (e.g., an mRNA biomarker, a cytokine biomarker, a chemokine biomarker) by about 1%, 5%, 10%, 20%, 30%, 40%, 50%, 60%, 70%, 80%, 90%, 95%, or 100%. In embodiments, a compound reduces the level of an inflammatory biomarker (e.g., an mRNA biomarker, a cytokine biomarker, a chemokine biomarker) to within about 1%, 5%, 10%, 20%, 30%, 40%, 50%, 60%, 70%, 80%, 90%, 95%, or 100% of its baseline level. In embodiments, a compound decreases the concentration of one or more inflammatory biomarkers in a sample by about 100 μg/mL, 90 μg/mL, 80 μg/mL, 70 μg/mL, 60 μg/mL, 50 μg/mL, 40 pg/mL, 30 μg/mL, 20 μg/mL, 10 μg/mL, 5 μg/mL, or 1 μg/mL. In embodiments, the sample is a tissue sample. In embodiments, the sample is a blood sample. In embodiments, the same is a plasma sample.

In some embodiments, a disclosed compound increases the level of an anti-inflammatory biomarker. In embodiments, a compound does not increase the level of a pro-inflammation biomarker above baseline. In embodiments, a compound increases the level of a pro-inflammation biomarker (e.g., an mRNA biomarker, a cytokine biomarker, a chemokine biomarker) by about 1%, 5%, 10%, 20%, 30%, 40%, 50%, 60%, 70%, 80%, 90%, 95%, or 100%. In embodiments, a compound increases the concentration of one or more anti-inflammatory biomarkers in a sample by about 100 μg/mL, 90 μg/mL, 80 μg/mL, 70 μg/mL, 60 μg/mL, 50 μg/mL, 40 pg/mL, 30 μg/mL, 20 μg/mL, 10 μg/mL, 5 μg/mL, or 1 μg/mL. In embodiments, the sample is a tissue sample. In embodiments, the sample is a blood sample. In embodiments, the same is a plasma sample.

In some embodiments, the dosage of a disclosed compound used to elicit an anti-inflammatory effect is sub-behavioral. In some embodiments, a disclosed compound is used to elicit an anti-inflammatory effect at dosage between about 0.001 and 0.01 mg/kg, between about 0.01 and 0.05 mg/kg, between about 0.05 mg/kg and 0.1 mg/kg, between about 0.1 mg/kg and 0.2 mg/kg, between about 0.4 mg/kg and 0.3 mg/kg, between about 0.3 mg/kg and 0.4 mg/kg, or between about 0.4 mg/kg and 0.5 mg/kg. In embodiments, administration of a disclosed compound at greater than 0.5 mg/kg is sub-behavioral, e.g., without hallucinogenic effects.

Disclosed compounds are useful in some embodiments to treat an inflammatory condition. In embodiments, a disclosed compound is used to reduce inflammation. In embodiments, a disclosed compound is used in the manufacture of a medicament to treat an inflammatory condition or to reduce inflammation.

In some embodiments, the inflammatory condition is an acute inflammatory disorder. In some embodiments, the inflammatory condition is a chronic inflammatory disorder. In some embodiments, the inflammatory condition is asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, conjunctivitis, Alzheimer's disease, or another inflammatory condition described herein.

Disclosed compounds are useful in some embodiments for treating an inflammatory condition in patients with autoimmune disorders or otherwise compromised immune systems. For example, a disclosed compound is useful for treating chronic inflammation in patients with type 1 diabetes, type 2 diabetes, multiple sclerosis, lupus, rheumatoid arthritis, psoriatic arthritis, reactive arthritis, Addison disease, Celiac disease, autoimmune encephalitis, gout, vasculitis, mixed connective tissue disease, undifferentiated connective tissue disease, myositis, scleroderma, Sjogren's syndrome, uveitis, inflammatory bowel disease (IBD), Guillain-Barre syndrome, psoriasis, Grave's disease, scleroderma (systemic sclerosis), dermatomyositis, Hashimoto thyroiditis, pernicious anemia, Alzheimer's disease, heart disease, cardiovascular disease, chronic hepatic and renal disease, fibromyalgia, allergies, or chronic obstructive pulmonary disease. In embodiments, a disclosed compound is useful for treating chronic inflammation in an immunocompromised chemotherapy patient.

Disclosed compounds are useful in some embodiments for treating an inflammatory condition in patients with a steroid-resistant disease or disorder. In some embodiments, the steroid-resistant disease or disorder is steroid resistant nephrotic syndrome (SRNS), steroid-resistant inflammatory bowel syndrome (IBS), steroid-resistant asthma, steroid-resistant acute graft-versus-host disease, steroid-resistant ulcerative colitis, steroid-resistant Crohn's disease, steroid-resistant chronic obstructive pulmonary disease (COPD), steroid-resistant pulmonary fibrosis, steroid-resistant leukemias, steroid-resistant rheumatoid arthritis, or steroid-resistant idiopathic nephrosis.

Disclosed compounds are useful in some embodiments for treating an inflammatory condition in a patient with a contraindication to a corticosteroid. Contraindications to corticosteroids can occur, for example, because of hypersensitivity to any component of a corticosteroid formulation, concurrent administration of live or live-attenuated vaccines (e.g., when using immunosuppressive doses), systemic fungal infection, osteoporosis, uncontrolled hyperglycemia, adrenal suppression, Cushing syndrome, diabetes mellitus, glaucoma, cataracts, joint infection, uncontrolled hypertension, herpes simplex keratitis, myopathy, certain psychiatric disturbances and/or disorders, and varicella infection. Additional exemplary contraindications include peptic ulcer disease, congestive heart failure, and viral or bacterial infections not controlled by anti-infective or antibacterial agents.

Disclosed compounds are useful in embodiments for treating skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, ocular inflammation, or brain inflammation.

In some embodiments, the inflammatory condition is any of acne vulgaris, acid reflux/heartburn, age-related macular degeneration (AMD), allergies, allergic rhinitis, Alzheimer's disease, amyotrophic lateral sclerosis, Anemia, appendicitis, arteritis, arthritis, including osteoarthritis, rheumatoid arthritis, juvenile idiopathic arthritis, spondyloarthropathy such as ankylosing spondylitis, reactive arthritis (Reiter syndrome), psoriatic arthritis, enteroarthritis associated with inflammatory bowel disease, Whipple and Behcet's disease, septic arthritis, gout (also known as gouty arthritis, crystalline synovitis, metabolic arthritis), pseudogout (calcium pyrophosphate deposition disease), and Still's disease. Arthritis can affect a single joint (monoarthritis), two to four joints (oligoarthritis), or five or more joints (polyarthritis).

In some embodiments, the inflammatory condition is any of long COVID, a food allergy, an ulcer, asthma, atherosclerosis, autoimmune disorder, balanitis, blepharitis, bronchiolitis, bronchitis, bullous pemphigoid, burns, bursitis, cancer, including NF-κB-induced inflammatory cancer; cardiovascular disease, including hypertension, endocarditis, myocarditis, heart valve dysfunction, congestive heart failure, myocardial infarction, diabetic heart abnormalities, vascular inflammation, including arteritis, phlebitis, and vasculitis; arterial occlusive disease, including arteriosclerosis and stenosis; inflammatory cardiac hypertrophy, peripheral arterial disease, aneurysm, embolism, incision, pseudoaneurysm, vascular malformation, vascular nevus, thrombosis, thrombophlebitis, varicose veins, stroke, cardiac arrest, and carditis; celiac disease, cellulitis, cervicitis, cholangitis, cholecystitis, chorioamnionitis, chronic obstructive pulmonary disease (COPD), cirrhosis, congestive heart failure, conjunctivitis, colitis, cyclophosphamide-induced cystitis, cystic fibrosis, cystitis, lacrimal inflammation, and dementia.

In some embodiments, the inflammatory condition is a dermatitis disorder. Without being bound by theory, dermatitis refers to inflammation of the skin which can occur chronically due to skin barrier dysfunction, abnormal inflammatory response, and persistent itching (Nakahara et al. *J Dermatol.* 2021; 48(2): 130-139; Beck et al. *JID Innov.* 2022; 2(5): 100131). Whereas common among dermatitis disorders include redness, persistent itching, and dry skin, further clinical phenotypes of dermatitis disorders are highly heterogeneous, reflecting the diversity and complexity of the underlying mechanisms leading to the disorder (Renert-Yuval et al. *J Allergy Clin Immunol.* 2021; 147(4): 1174-1190.e1). Many of the inflammatory agents involved in chronic inflammation are also involved in the inflammatory response to dermatitis disorders, including but not limited to CCL17, CCL18, CCL22, CCL27, IL-4, IL-13, IL-17A, IL-18, IL-19, IL-22, IL-26, IL-33, MMP12, and Th2 (Ahn et al. *Curr Opin Immunol.* 2020; 66: 14-21; Renert-Yuval et al. *J Allergy Clin Immunol.* 2021; 147(4): 1174-1190.e1; Furue et al. *Iran J Immunol.* 2019; 16(2): 97-107; Sroka-Tomaszewska & Trzeciak. *Int J Mol Sci.* 2021; 22(8): 4130; Fallon et al. *Nat Genetics.* 2009; 41: 602-608). Effective treatments of dermatitis disorders often target inflammatory pathways, thereby regulating the inflammatory response and ameliorating the symptoms of the dermatitis disorder (Wollenberg et al. *Br J Dermatol.* 2014; 170 Suppl 1: 7-11).

In some embodiments, the inflammatory condition is a dermatitis disorder, including atopic dermatitis, chronic photosensitivity dermatitis, eczema, atopic eczema, contact eczema, dryness eczema, seborrheic eczema, discoid eczema, varicose eczema, herpetic dermatitis, neurodermatitis, autosensitizing dermatitis, stasis dermatitis, purulent dermatitis, dyshidrotic eczema, follicular eczema, spongiotic dermatitis, hand dermatitis, diaper dermatitis, occupational contact dermatitis, and lichen planus-like atopic dermatitis.

In some embodiments, the dermatitis disorder is atopic dermatitis. In embodiments, the dermatitis disorder is chronic photosensitivity dermatitis. In embodiments, the dermatitis disorder is eczema. In embodiments, the dermatitis disorder is atopic eczema. In embodiments, the dermatitis disorder is contact eczema. In embodiments, the dermatitis disorder is dryness eczema. In embodiments, the dermatitis disorder is seborrheic eczema. In embodiments, the dermatitis disorder is discoid eczema. In embodiments, the dermatitis disorder is varicose eczema. In embodiments, the dermatitis disorder is herpetic dermatitis. In embodiments, the dermatitis disorder is neurodermatitis. In embodiments, the dermatitis disorder is herpetic dermatitis. In embodiments, the dermatitis disorder is autosensitizing dermatitis. In embodiments, the dermatitis disorder is stasis dermatitis. In embodiments, the dermatitis disorder is purulent dermatitis. In embodiments, the dermatitis disorder is dyshidrotic eczema. In embodiments, the dermatitis disorder is follicular eczema. In embodiments, the dermatitis disorder is spongiotic dermatitis. In embodiments, the dermatitis disorder is hand dermatitis. In embodiments, the dermatitis disorder is diaper dermatitis. In embodiments, the dermatitis disorder is occupational contact dermatitis. In embodiments, the dermatitis disorder is lichen planus-like atopic dermatitis.

In some embodiments, the inflammatory condition is any of dermatitis, including atopic dermatitis, chronic photosensitivity dermatitis, eczema, atopic eczema, contact eczema, dryness eczema, seborrheic eczema, sweating disorders, discoid eczema, venous eczema, herpetic dermatitis, neurodermatitis, and autosensitizing dermatitis, stasis dermatitis, purulent sweaty, lichen planus, psoriasis, including psoriasis vulgaris, nail psoriasis, prickly psoriasis, scalp psoriasis, inverse psoriasis, pustular psoriasis, erythrodermic psoriasis, and psoriatic arthritis; rosacea, and scleroderma, including morphea; pharmacologically induced inflammation, including from legal or illegal drugs, and chemicals; chronic neurogenic inflammation, including primary and secondary neural inflammation; dermatomyositis, diabetes, diabetic neuropathy, diabetic retinopathy, diabetic nephropathy, diabetic ulcer, digestive system disease, emphysema, encephalitis, endocarditis, endometritis, enterocolitis, epicondylitis, epididymis, fasciitis, fibromyalgia, fibrosis, connectitis, gastritis, gastroenteritis, gingivitis, glomerulonephritis, glossitis, heart disease, heart valvular dysfunction, hepatitis, purulent spondylitis, Huntington's disease, hyperlipidemic pancreatitis, hypertension, ileitis, infection, including lymphangitis, lymphadenitis, bacterial cystitis, bacterial encephalitis, pandemic influenza, viral encephalitis, and viral hepatitis (types A, B, and C); inflammatory bowel disease, including Crohn's disease; inflammatory heart enlargement, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), migraine, multiple sclerosis, myelitis, myocarditis, myositis, nephritis, non-alcoholic steatohepatitis, obesity, umbilitis, ovitis, testitis, osteochondritis, osteopenia, osteomyelitis, osteoporosis, osteomyelitis, otitis, pancreatitis, Parkinson's disease, parotitis, pelvic inflammatory disease, pemphigus vulgaris, pericarditis, Peritonitis, pharyngitis, phlebitis, pleurisy, interstitial pneumonia, polycystic nephritis, polymyositis, proctitis, prostatitis, psoriasis, pulpitis, pyelonephritis, portal vein, renal failure, reperfusion injury, retinitis, rheumatic fever Rhinitis, fallopianitis, sarcoidosis, salivary glanditis, sepsis, including bacteremia and viremia; sinusitis, spastic colon, stenosis, stomatitis, stroke, inflammation associated with surgical complications, synovitis, tendonitis, tendonitis, tendonitis, thrombophlebitis, tonsillitis, trauma, traumatic brain injury, graft rejection, including graft versus host disease (GVHD); a Th1-mediated inflammatory disease, trigonitis, tuberculosis, tumor, urethritis, bursitis, uveitis, vaginitis, vasculitis, including Buerger's disease, cerebral vasculitis, Churg-Strauss arteritis, cryoglobulinemia, essential cryoglobulin vasculitis, giant cells arteritis, golfer vasculitis, Henoch-Schonlein purpura, hypersensitivity vasculitis, Kawasaki disease, microscopic polyarteritis/polyvasculitis, nodular polyarteritis, rheumatoid polymuscular muscle pain (PMR), rheumatic vasculitis, Takayasu arteritis, Wegener's granulomatosis, systemic lupus erythematosus (SLE), relapsing polychondritis, Behcet's disease; ulcerative colitis such as ulcerative proctitis, left side colitis, total colitis, and fulminant colitis; and vulvitis.

A reduction in inflammation, such as chronic systemic inflammation, may be measured according to various methods available to one of skill. Inflammatory biomarkers may be detected from biological specimens, for example, a subject's blood, such as plasma or serum, or saliva. In one example, inflammation may be detected by measuring high-sensitivity C-reactive protein (CRP) and white blood cell count from a blood test. CRP may also be detected in a saliva sample. Salivary CRP is not synthesized locally in the mouth and may reflect more systemic levels of inflammation compared to other inflammatory biomarkers, such as cytokines (Szabo & Slavish, *Psychoneuroendocrin.* 2021; 124: 105069). Additionally clinical pathology data, e.g., hematology data on erythrocyte parameters, platelet count, total number of leukocytes, and leukocyte differentials and morphology, coagulation data on clotting times and fibrinogen, and clinical chemistry data on total protein, albumin and globulin, liver enzymes, renal parameters, electrolytes, and bilirubin can provide an initial indication of the presence and potentially the location of inflammation, in the absence of specific data on immune tissues (e.g., Germolec et al. *Methods Mol Biol.* 2018; 1803: 57-79; Luo et al. *Clin Lab.* 2019; 65(3)).

v. Ophthalmic Diseases and Disorders

In some embodiments, a compound is used to treat an ophthalmic disease or disorder. Ophthalmic diseases and disorders often result from infection and/or inflammation of ocular tissue, and are the leading cause of corneal blindness and visual morbidity worldwide (Bourne et al. *Lancet Glob Health.* 2013; 1(6): e339-49). Repeated episodes of infection or inflammation triggers a chronic inflammatory disease process that can result in vascularization and subsequent vision threatening scarring of the cornea (Vaidyanathan et al. *Med Hypothesis Discov Innov Ophthalmol.* 2019; 8(3): 163-176). Corticosteroids are often used to control the ophthalmic inflammatory response, however, this treatment is immunosuppressive and can result in uncontrolled pathogen replication, loss of an intact corneal epithelial barrier, increased ocular pressure and eventual deterioration of vision (Fung et al. *Clin Exp Ophthalmol.* 2020; 48(3): 366-401). By contrast, modulation with 5-HT receptor agonists is shown to have anti-inflammatory and anti-vascularization properties, and the ability to decrease ophthalmic pressure (Foster et al. *Invest Ophthalmol Vis Sci.* 2020; 61(7): 429).

Disclosed compounds are useful in some embodiments to reduce, or ameliorate, or prevent an ophthalmic disease or disorder, non-limiting examples of which are described herein.

In some embodiments, administration of a disclosed compound reduces intraocular pressure in a subject. In some embodiments, a disclosed compound is used to treat ocular hypertension.

The range for normal intraocular pressure is generally considered to be between 10 and 21 mmHg. This pressure is primarily determined by the balance between how much aqueous humour is produced in the eye and how much is drained away. Factors such as the thickness and stiffness of the cornea also play a role in influencing this pressure. Typically, intraocular pressure averages around 15 to 16 mmHg, with potential variations of up to 6 mmHg. For instance, during nighttime, this pressure often drops due to reduced aqueous humour production. Moreover, intraocular pressure can change in response to several physiological factors, including exercise, heart rate, breathing, fluid consumption, and the use of certain systemic or topical medications. Elevated intraocular pressure can lead to optic nerve damage, a condition known as glaucoma. If there's no optic nerve damage, the term ocular hypertension is used. Various factors can contribute to increased intraocular pressure, including conditions like orbital swelling, traumatic hyphema, blockage in the pupil, retained surgical materials, inflammation within the eye, or the use of corticosteroids. High intraocular pressure is a significant risk factor for glaucoma, and conversely, glaucoma frequently involves an increase in intraocular pressure. Symptoms that may arise from elevated intraocular pressure or from a combination of glaucoma and increased pressure include optic nerve damage, bleeding of the optic disc, defects in the nerve fiber layer, notching, a vertically elongated cup, uneven or progressive enlargement of the optic cup, diminished field of vision, seeing halos, blurry vision, and eye discomfort, among others.

Disclosed compounds are useful in some embodiments to treat glaucoma. In some embodiments, the glaucoma is open-angle glaucoma, normal-tension glaucoma, angle-closure glaucoma, congenital glaucoma, neovascular glaucoma, pigmentary glaucoma, exfoliation glaucoma, uveitic glaucoma, or glaucoma caused by another factor (e.g., cataracts, tumors, eye injury).

Disclosed compounds are useful in some embodiments to treat allergic conjunctivitis, including vernal keratoconjunctivitis and atopic keratoconjunctivitis; dry eye syndrome and meibomian gland dysfunction; cataracts; keratoconus; bullous and other keratopathy; Fuch's endothelial dystrophy; ocular cicatricial pemphigoid; conditions associated with photoreactive keratotomy (PRK) healing and other corneal healing; conditions associated with tear lipid degradation or lacrimal gland dysfunction; uveitis, including anterior uveitis, intermediate uveitis, posterior uveitis, panuveitis, non-infectious uveitis, and infectious uveitis; keratitis; scleritis; iritis; cyclitis; ocular graft versus host disease; optic neuritis; ocular Stevens Johnson Syndrome; blepharitis; ocular rosacea, with or without meibomian gland dysfunction; post cataract; persistent corneal erosion; and inflammation associated with corneal trauma, corneal transplantation, and refractive surgery.

In some embodiments, the ophthalmic disease or disorder is an inflammatory disorder. In some embodiments, the ophthalmic disease or disorder is macular degeneration (e.g., age-related macular degeneration), keratoconjunctivitis, conjunctivitis, keratitis, diabetic retinopathy, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neo-vascularization, choroidal neovascularization, retinochoroidal neovascularization, or a combination thereof.

In some embodiments, the ophthalmic disease is macular degeneration. In embodiments, the ophthalmic disease is keratoconjunctivitis. In embodiments, the ophthalmic disease is conjunctivitis. In embodiments, the ophthalmic disease is keratitis. In embodiments, the ophthalmic disease is diabetic retinopathy. In embodiments, the ophthalmic disease is retinopathy of prematurity. In embodiments, the ophthalmic disease is polypoidal choroidal vasculopathy. In embodiments, the ophthalmic disease is ischemic proliferative retinopathy. In embodiments, the ophthalmic disease is retinitis pigmentosa. In embodiments, the ophthalmic disease is cone dystrophy. In embodiments, the ophthalmic disease is proliferative vitreoretinopathy. In embodiments, the ophthalmic disease is retinal artery occlusion. In embodiments, the ophthalmic disease is retinal vein occlusion. In embodiments, the ophthalmic disease is Leber's disease. In embodiments, the ophthalmic disease is retinal detachment. In embodiments, the ophthalmic disease is retinal pigment epithelial detachment. In embodiments, the ophthalmic disease is rubeosis iridis. In embodiments, the ophthalmic disease is corneal neovascularization. In embodiments, the ophthalmic disease is retinal neovascularization. In embodiments, the ophthalmic disease is choroidal neovascularization. In embodiments, the ophthalmic disease is retinochoroidal neovascularization.

vi. Other Administration Considerations

In some embodiments, such as when administered to a subject for the treatment of a mental health disorder, a disclosed compound is administered together with therapy. "Therapy" herein is intended to be understood broadly, and includes psychotherapy, such as psychosocial or behavioral therapy, e.g., any of (or adapted from any of) cognitive behavioral therapy (e.g., as in Crits-Christoph et al. *Arch Gen Psychiatry.* 1999; 56(6): 493-502), interpersonal therapy (e.g., as in Barry et al. *Psychol Addict Behav.* 2009; 23(1): 168-174), contingency management based therapy (e.g., as in Barry et al. *Psychol Addict Behav.* 2009; 23(1): 168-174; in Petry et al. *J Consult Clin Psychol.* 2005; 73(2): 354-359.; or in Adams et al. *Case Reports in Psychiatry.* 2012; 2012: Article ID 731638), motivational interviewing based therapy (e.g., as in Stotts et al. *J Consult Clin Psycho.* 2001; 69(5): 858-862), meditation based therapy, such as transcendental meditation based therapy (e.g., as in Rohsenow et al. *J Consult Clin Psychol.* 2000; 68(3):515-520), or a therapeutic approach such as used by the Multidisciplinary Association for Psychedelic Studies (MAPS) (e.g., as in Mithoefer. Manual for MDMA-Assisted Psychotherapy in the Treatment of Post-traumatic Stress Disorder. 7th ed. Multidisciplinary Association for Psychedelic Studies; 2015) (see also, e.g., Schenberg. *Front Pharmacol.* 2018; 9: 733; Johnson et al. *J Psychopharmacol.* 2008; 22(6): 603-620). Therapy may be conducted periodically, such as more than once a week, every about one week, every about two weeks, every about three weeks, and the like.

In embodiments, a compound is administered together with standardized psychological treatment or support, including any modality of psychotherapy or counseling, including both in person and virtual sessions, and including sessions involving a human therapist as well as a virtual or artificial intelligence (AI) "therapist."

In some embodiments, disclosed compounds are administered together with the subject performing or participating in one or more therapeutically beneficial activities, such as breathing exercises, meditation and concentration practices, focusing on an object or mantra, listening to music, physical exercise, stretching or bodywork, journaling, grounding techniques, positive self-talk, or engaging with a pet or animal, and the like.

Disclosed compounds in some embodiments are administered without or with reduced risk of side effects that would require supervision or monitoring, and thus do not require such supervision or monitoring.

A disclosed compound may be administered to a subject if the subject meets certain or all inclusion criteria, does not meet certain or all exclusion criteria, does not meet certain or all withdrawal criteria, and/or satisfies one or more other limitations of a disclosed or claimed embodiment, such as a method of use.

In embodiments, a personalized approach (i.e., "personalized" or "precision" medicine) may be utilized, based on individual characteristics, including drug metabolism (e.g., CYP2D6 or CYP3A4) or individual genetic variation. The term "genetic variation" refers to a change in a gene sequence relative to a reference sequence (e.g., a commonly-found and/or wild-type sequence). Genetic variation may be recombination events or mutations such as substitution/deletion/insertion events like point and splice site mutations.

In embodiments, the genetic variation is a genetic variation in one or more cytochrome P450 (CYP or CYP450) enzymes that affects drug metabolism, such as of a disclosed compound, e.g., CYP1A2, CYP2C9, CYP2D6, CYP2C19, CYP3A4 and CYP3A5. Other CYP enzymes include CYP1A1, CYP1B1, CYP2A6, CYP2A13, CYP2B6, CYP2C8, CYP2C9, CYP2C18, CYP2E1, CYP2G1, CYP2J2, CYP2R1, CYP2S1, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

In some embodiments, a disclosed composition is taken together with a compound that is metabolized by the same CYP enzyme(s) as the disclosed compound, so as to permit a lower dose to be taken, increase the effective bioavailability of one or both, or otherwise affect drug metabolism or pharmacokinetics. In some embodiments, the dose of a disclosed compound is adjusted, such as reduced, when administered to a subject known to be a poor metabolizer of the compound, or increased when administered to a subject known to be a rapid metabolizer. In some embodiments, a patient is tested using ordinary means known to those of skill to determine if the patient is a poor or rapid metabolizer for one or more such CYP enzymes.

In some embodiments, the genetic variation is a genetic variation in metabotropic glutamate receptor type 5 (mGluR5), which has been implicated in mood and anxiety symptoms in humans. In embodiments, the genetic variation is one or more single nucleotide polymorphisms (SNPs) in the FKBP5 gene that are associated with elevated levels of FKBP51 protein relative to persons lacking such SNPs. The FKBP5 gene is associated with responses to stress and trauma, and such SNPs are correlated with susceptibility to PTSD and depressive and anxiety disorders. In embodiments, a genetic variation is an inclusion criteria for administration of a compound. In embodiments, a genetic variation is an exclusion criteria for administration of a compound.

In some embodiments, the subject being treated, i.e., being administered a disclosed compound, has altered epigenetic regulation of a gene, the expression of which is associated with a mental health condition or susceptibility to a mental health treatment, such as the SIGMAR1 gene for the non-opioid sigma-1 receptor.

J. EXAMPLES

The following examples are illustrative only and shall not be used to limit the scope of the disclosure.

Example 1: Synthesis of 2-(4-bromo-2-methoxy-5-(methoxymethyl)phenyl)ethan-1-amine (Compound 4)

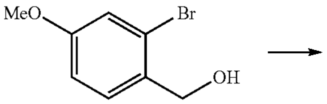

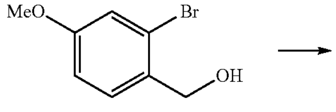

1

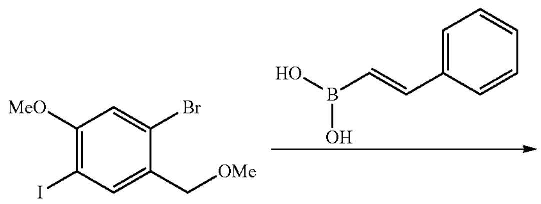

2

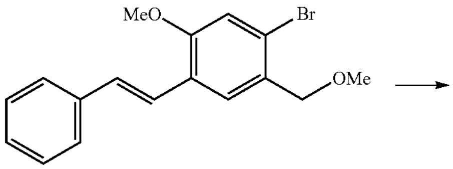

3

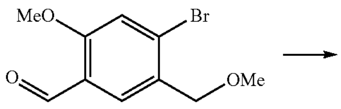

4

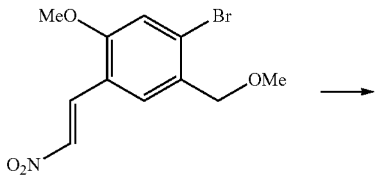

5

-continued

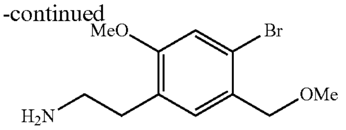

6

Step 1: 2-Bromo-4-methoxy-1-(methoxymethyl)benzene

To a solution of (2-bromo-4-methoxy-phenyl)methanol (3.70 g, 17.0 mmol) in THF (50 mL) was added NaH (1.00 g, 25.0 mmol, 60.0% purity) at 0° C. The mixture was stirred at 0° C. for 30 minutes, followed by $CH_3I$ (2.70 g, 19.0 mmol, 1 mL). The mixture was stirred at 25° C. for 2 hours, quenched by sat. aq. $NH_4Cl$ (10 mL) at 0° C. and extracted with EtOAc (100 mL*3). The combined organic layers were dried over $Na_2SO_4$, filtered, concentrated and purified by column chromatography ($SiO_2$, Petroleum ether:EtOAc=1:0 to 5:1) to yield 2-bromo-4-methoxy-1-(methoxymethyl)benzene (2.90 g, 12.0 mmol, 72.6% yield) as a pale yellow oil. $^1H$ NMR (400 MHz, acetonitrile-$d_3$) δ=7.38 (d, J=8.5 Hz, 1H), 7.20 (d, J=2.5 Hz, 1H), 6.95 (dd, J=2.5, 8.5 Hz, 1H), 4.45 (s, 2H), 3.81 (s, 3H), 3.38 (s, 3H) ESI [M-OMe]=199.1/201.1.

Step 2: 1-Bromo-4-iodo-5-methoxy-2-(methoxymethyl)benzene

To a solution of 2-bromo-4-methoxy-1-(methoxymethyl) benzene (990 mg, 4.00 mmol) in EtOH (10 mL) was added AgOTf (1.30 g, 5.00 mmol) and 12 (1.60 g, 6.40 mmol, 1 mL). The mixture was stirred at 20° C. for 2 hours, concentrated, quenched by $H_2O$ (20 mL) and extracted with DCM (60 mL*3). The combined organic layers were dried over $Na_2SO_4$, filtered and concentrated to yield 1-bromo-4-iodo-5-methoxy-2-(methoxy-methyl)benzene (2.00 g, crude) as a yellow oil. ESI [M-OMe]=324.9/326.9.

Step 3: (E)-1-Bromo-5-methoxy-2-(methoxymethyl)-4-styrylbenzene

To a solution of 1-bromo-4-iodo-5-methoxy-2-(methoxymethyl)benzene (1.10 g, 3.00 mmol), (E)-styrylboronic acid (572 mg, 4.00 mmol) in THF (16 mL), $H_2O$ (4 mL) was added Pd(dppf)$Cl_2$ (235 mg, 322 μmol) and $K_3PO_4$ (2.00 g, 9.00 mmol). The mixture was stirred at 80° C. for 2 hours under $N_2$ atmosphere, quenched by $H_2O$ (10 mL) and extracted with EtOAc (60 mL*3). The combined organic layers were dried over $Na_2SO_4$, filtered, concentrated and purified by column chromatography ($SiO_2$, Petroleum ether:EtOAc=1:0 to 97:3) to yield (E)-1-bromo-5-methoxy-2-(methoxymethyl)-4-styrylbenzene (640 mg, 2.00 mmol, 29.8% yield) as a yellow oil. ESI [M-OMe] =301.1/303.1.

Step 4: 4-Bromo-2-methoxy-5-(methoxymethyl)benzaldehyde

A mixture of 1-bromo-5-methoxy-2-(methoxymethyl)-4-[(Z)-styryl]benzene (600 mg, 1.80 mmol) in DCM (6 mL) was stirred at −78° C. for 1 hr under ozone atmosphere. The reaction mixture was quenched by $H_2O$ (5 mL) at 0° C. and extracted with DCM (15 mL*3). The combined organic layers were dried over $Na_2SO_4$, filtered, concentrated and purified by column chromatography ($SiO_2$, Petroleum ether: EtOAc=1:0 to 97:3) to yield 4-bromo-2-methoxy-5-(methoxymethyl)benzaldehyde (150 mg, 578 μmol, 32.1% yield) as a white gum. LCMS (ESI+): m/z 259.1, 261.1 $[M+H]^+$ Step 5: (E)-1-Bromo-5-methoxy-2-(methoxymethyl)-4-(2-nitrovinyl)benzene To a solution of 4-bromo-2-methoxy-5-(methoxymethyl) benzaldehyde (100 mg, 385 μmol) in AcOH (5 mL) was added nitromethane (47.0 mg, 771 μmol, 42 μL) and $NH_4OAc$ (89.0 mg, 1.00 mmol). The mixture was stirred at 120° C. for 2 h, quenched by sat. aq. $Na_2CO_3$ (3 mL) and extracted with DCM (20 mL*2). The combined organic layers was dried over $Na_2SO_4$, filtered, concentrated and purified by prep-TLC ($SiO_2$, Petroleum ether:EtOAc=5:1) to yield (E)-1-bromo-5-methoxy-2-(methoxymethyl)-4-(2-nitrovinyl)benzene (80.0 mg, 264 μmol, 68.6% yield) as a yellow gum. ESI [M-OMe]=270.0/272.0.

Step 6: 2-(4-Bromo-2-methoxy-5-(methoxymethyl) phenyl)ethan-1-amine (Compound 4)

To a solution of 1-bromo-5-methoxy-2-(methoxymethyl)-4-[(E)-2-nitrovinyl]benzene (80.0 mg, 264 μmol) in THF (1 mL) was added $BH_3$-THF (1 M, 529 μL) at 0° C. under $N_2$ atmosphere. The mixture was stirred at 60° C. for 12 h, quenched by MeOH (10 mL) and 1 N HCl (2 mL) at 0° C. and stirred at 60° C. for 0.5 h. The mixture was concentrated and purified by prep-HPLC (column: Phenomenex luna C18 100*40 mm*5 um; mobile phase: [$H_2O$(0.04% HCl)-ACN]; gradient: 5%-30% B over 8.0 mins) to yield 2-(4-bromo-2-methoxy-5-(methoxymethyl) phenyl)ethan-1-amine (9.00 mg, 31.0 μmol, 11.7% yield, 94.4% purity) as a white solid. $^1H$ NMR (400 MHz, DMSO-$d_6$) δ=7.69 (br s, 2H), 7.25 (d, J=12.1 Hz, 2H), 4.38 (s, 2H), 3.83 (s, 3H), 3.34 (br s, 3H), 2.96 (br d, J=8.3 Hz, 2H), 2.82 (br d, J=8.3 Hz, 2H) LCMS (ESI+): m/z 274.0/276.0 [M+H]*.

Example 2: Synthesis of 2-[4-isobutyl-2-methoxy-5-(methoxymethyl)phenyl]ethanamine HCl (Compound 8)

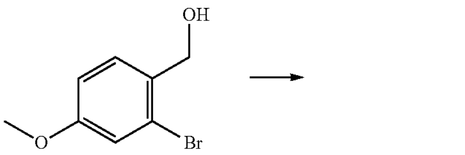

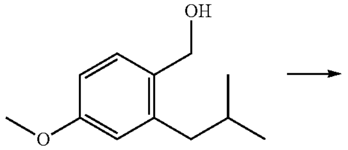

1

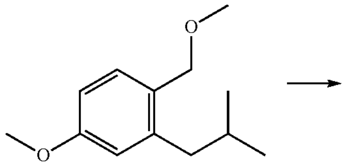

2

-continued

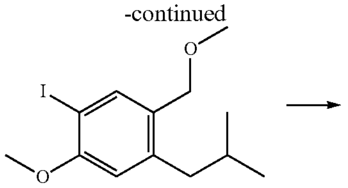

3

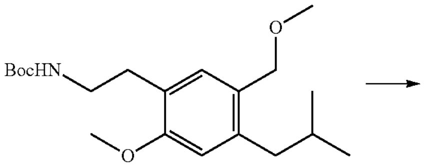

4

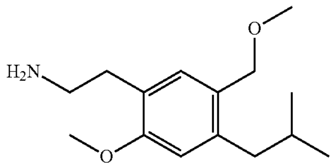

5

Step 1: (2-Isobutyl-4-methoxy-phenyl)methanol

To a solution of (2-Br-4-methoxy-phenyl)methanol (7.10 g, 32.7 mmol, 1 eq), isobutylboronic acid (5 g, 49.1 mmol, 1.5 eq) and $Cs_2CO_3$ (32.0 g, 98.1 mmol, 3 eq) in toluene (200 mL) and $H_2O$ (20 mL) was added Pd(dppf)$Cl_2$ (2.39 g, 3.27 mmol, 0.1 eq), then the mixture was stirred at 100° C. for 1 h, under an atmosphere of nitrogen. The reaction was concentrated under reduced pressure to give a residue. The residue was purified by column chromatography (silica gel, petroleum ether/ethyl acetate=1/0-10/1) to give (2-isobutyl-4-methoxy-phenyl)methanol (4.7 g, 24.2 mmol, 74.0% yield) as a yellow oil. LCMS (ESI) $[M+H]^+$ m/z: 194.1.

Step 2: 2-Isobutyl-4-methoxy-1-(methoxymethyl)benzene

To a solution of (2-isobutyl-4-methoxy-phenyl)methanol (1.21 g, 6.25 mmol, 1 eq) in DMF (30 mL) was added NaH (275 mg, 6.87 mmol, 60% purity, 1.1 eq) at 0° C. and the mixture was stirred at 0° C. for 0.5 h. MeI (1.77 g, 12.5 mmol, 2 eq) was added dropwise the above mixture at 0° C., the mixture was stirred at 25° C. for 0.5 h. The reaction was added into water (10 mL), then extracted with ethyl acetate (3*20 mL). The combined organic layers were washed with brine (3*20 mL) and dried over anhydrous sodium sulfate, filtered, and concentrated under reduced pressure to give a residue. The residue was purified by column chromatography (silica gel, petroleum ether/ethyl acetate=1/0 to 20/1) to give 2-isobutyl-4-methoxy-1-(methoxymethyl) benzene (1.06 g, 5.09 mmol, 81.5% yield) as a white liquid. $^1H$ NMR (400 MHz, methanol-$d_4$) δ=7.21 (d, J=8.6 Hz, 1H), 6.76-6.69 (m, 2H), 4.40 (s, 2H), 3.77 (s, 3H), 3.34 (s, 3H), 2.52 (d, J=7.2 Hz, 2H), 1.87 (quind, J=6.8, 13.6 Hz, 1H), 0.93 (s, 3H), 0.92 (s, 3H). LCMS (ESI) $[M+H]^+$ m/z: 208.1.

Step 3: 1-Iodo-4-isobutyl-2-methoxy-5-(methoxymethyl)benzene

To a solution of 2-iBu-4-MeO-1-(methoxymethyl)benzene (900 mg, 4.32 mmol, 1 eq) in EtOH (35 mL) was added AgOTf (1.22 g, 4.75 mmol, 1.1 eq) the mixture was stirred at 20° C. for 1 h, and then $I_2$ (1.21 g, 4.75 mmol, 1.1 eq) was added at 20° C. The resulting mixture was stirred at 20° C. for 1 h. The reaction was added into saturated sodium bicarbonate solution (100 mL), then extracted with ethyl acetate (3*100 mL) and dried over anhydrous $Na_2SO_4$, filtered, and concentrated under reduced pressure to give a residue. The residue was purified by prep-TLC ($SiO_2$, petroleum ether: ethyl acetate=20:1) to give 1-iodo-4-isobutyl-2-methoxy-5-(methoxymethyl)benzene (1.34 g, 4.01 mmol, 92.8% yield) as a colorless oil. LCMS (ESI) $[M+H]^+$ m/z: 334.0.

Step 4: Tert-butyl N-[2-[4-isobutyl-2-methoxy-5-(methoxymethyl) phenyl]ethyl]carbamate To a solution of 1-iodo-4-isobutyl-2-methoxy-5-(methoxymethyl) benzene (1.34 g, 4.01 mmol, 1 eq), potassium 2-(tert-butoxycarbonylamino)ethyl-trifluoro-boranuide (2.01 g, 8.02 mmol, 2 eq) and $Cs_2CO_3$ (3.92 g, 12.03 mmol, 3 eq) in toluene (50 mL) and $H_2O$ (10 mL) was added Pd(dppf)$Cl_2$—$CH_2Cl_2$ (327 mg, 401 μmol, 0.1 eq), then the mixture was stirred at 90° C. for 12 h. The reaction was concentrated under reduced pressure to give a residue. The residue was purified by column chromatography (silica gel, petroleum ether/ethyl acetate=1/0 to 10/1) to give tert-butyl N-[2-[4-isobutyl-2-methoxy-5-(methoxymethyl) phenyl] ethyl]carbamate (970 mg, 2.76 mmol, 68.8% yield) as a yellow oil. $^1$H NMR (400 MHz): δ=0.92 (s, 3H), 0.94 (s, 3H), 1.41 (s, 9H), 1.87 (dquin, 1H, J=13.5, 6.8 Hz), 2.52 (d, 2H, J=7.3 Hz), 2.73 (t, 2H, J=7.2 Hz), 3.19-3.25 (m, 2H), 3.34 (s, 3H), 3.81 (s, 3H), 4.39 (s, 2H), 6.48 (br s, 1H), 6.72 (s, 1H), 7.06 (s, 1H). LCMS (ESI) $[M+H]^+$ m/z: 351.2.

Step 5: 2-[4-Isobutyl-2-methoxy-5-(methoxymethyl) phenyl]ethanamine (Compound 8)

Tert-butyl N-[2-[4-isobutyl-2-MeO-5-(methoxymethyl) phenyl]ethyl]carbamate (300 mg, 854 μmol, 1 eq) was dissolved in HCl/MeOH (4M, 12 mL, 5.62 eq), and then the mixture was stirred at 25° C. for 15 min. The reaction mixture was concentrated to get a residue. The residue was purified by prep-HPLC (HCl condition; column: 3_Phenomenex Luna C18 75*30 mm*3 μm; mobile phase: [$H_2O$ (0.04% HCl)-ACN]; gradient: 20%-50% B over 8.0 min) to give 2-[4-iBu-2-MeO-5-(methoxymethyl)phenyl] ethanamine (120 mg, 415 μmol, 48.6% yield, 99.5% purity, HCl) as a white solid. checked by $^1$H NMR (400 MHz, DMSO-de) 5=7.88 (br s, 3H), 7.08 (s, 1H), 6.77 (s, 1H), 4.32 (s, 2H), 3.79 (s, 3H), 3.27 (s, 3H), 2.98-2.91 (m, 2H), 2.83-2.77 (m, 2H), 2.46 (d, J=7.3 Hz, 2H), 1.84 (td, J=6.9, 13.4 Hz, 1H), 0.89 (d, J=6.6 Hz, 6H). LCMS (ESI) $[M+H]^+$ m/z: 251.2.

Example 3: Synthesis of [5-(2-Aminoethyl)-2-isobutyl-4-methoxy-phenyl]methanol HCl (Compound 26)

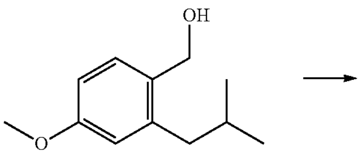

-continued

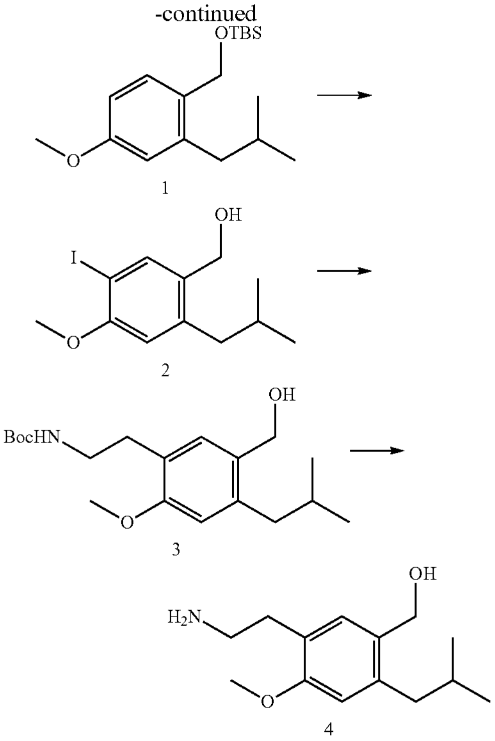

Step 1: Tert-butyl-[(2-isobutyl-4-methoxyphenyl) methoxy]dimethylsilane (2-Isobutyl-4-methoxyphenyl)methanol (2 g, 10.3 mmol, 1 eq) was dissolved in THF (40 mL) and then to the mixture was added imidazole (1.54 g, 22.7 mmol, 2.2 eq), and then to the mixture was added TBSCl (3.10 g, 20.6 mmol, 2 eq) below 20° C., and then the mixture was stirred at 25° C. for 1 h. The mixture was quenched by $NaHCO_3$ (200 mL), and then extracted with EtOAc (50 mL*3), and then the organic phase was concentrated in vacuum. The residue was purified by flash chromatography (silica gel, petroleum ether/ethyl acetate=50/1 to 10/1) to give tert-butyl-[(2-isobutyl-4-methoxyphenyl)methoxy]dimethylsilane (2.2 g, 7.13 mmol, 69.3% yield) as a yellow oil. LCMS (ESI+) m/z: 308.2 [M+H]*.

Step 2: (5-iodo-2-isobutyl-4-methoxyphenyl)methanol

Tert-butyl-[(2-isobutyl-4-methoxyphenyl)methoxy]dimethyl-silane (2.2 g, 7.13 mmol, 1 eq) was dissolved in EtOH (40 mL), and then to the mixture was added AgOTf (2.02 g, 7.84 mmol, 1.1 eq), the mixture was stirred at 25° C. for 20 min, and then to the mixture was added 12 (1.99 g, 7.84 mmol, 1.1 eq), and then the mixture was stirred at 25° C. for 30 min. The mixture was quenched by saturated $NaHCO_3$ solution (150 mL), and then extracted with EtOAc (50 mL*3), and then the organic phase was concentrated in vacuum to give (5-iodo-2-isobutyl-4-methoxy-phenyl) methanol (2.2 g, crude) as a yellow oil. LCMS (ESI+) m/z: 320.0 [M+H]*.

Step 3: Tert-butyl N-[2-[5-(hydroxymethyl)-4-isobutyl-2-methoxyphenyl]ethyl]carbamate (5-I-2-iBu-4-methoxyphenyl)methanol (2.4 g, 7.50 mmol, 1 eq) and potassium 2-(tert-butoxycarbonyl-amino)

ethyl-trifluoro-boranuide (3.76 g, 15.0 mmol, 2 eq) was dissolved in toluene (50 mL) and $H_2O$ (10 mL), and then to the mixture was added $Cs_2CO_3$ (7.33 g, 22.5 mmol, 3 eq) and Pd(dppf)$Cl_2$—$CH_2Cl_2$ (612.16 mg, 749.61 μmol, 0.1 eq), and the mixture was degassed and purged with $N_2$ 3 times, then stirred at 90° C. for 12 h under $N_2$. The mixture was concentrated in vacuum. The residue was purified by flash chromatography (silica gel, petroleum ether/ethyl acetate=10/1-3/1) to give tert-butyl N-[2-[5-(hydroxymethyl)-4-iBu-2-MeO-phenyl]ethyl]carbamate (1.2 g, 3.56 mmol, 47.4% yield) as a yellow oil. $^1$H NMR (400 MHz, chloroform-d) 6=7.14-7.08 (m, 1H), 6.67-6.62 (m, 1H), 4.63 (s, 2H), 3.87-3.78 (m, 3H), 3.46-3.23 (m, 2H), 2.82-2.73 (m, 2H), 2.58-2.51 (m, 2H), 1.97-1.79 (m, 1H), 1.43 (s, 9H), 0.99-0.90 (m, 6H). LCMS (ESI+) m/z: 337.2 [M+H]*.

Step 4: [5-(2-Aminoethyl)-2-isobutyl-4-methoxyphenyl]methanol (Compound 26)

Tert-butyl N-[2-[5-(hydroxymethyl)-4-isobutyl-2-methoxyphenyl]ethyl]carbamate (300 mg, 889 μmol, 1 eq) was dissolved in HCl/EtOAc (4M, 12 mL, 5.34 eq), and then the mixture was stirred at 25° C. for 15 min. The suspension was filtered, and the filter cake was washed by EtOAc (2 mL*3), and then the filter cake was dissolved in $H_2O$ (5 mL). The solution was lyophilized to give [5-(2-aminoethyl)-2-isobutyl-4-methoxyphenyl]methanol (140 mg, 502 μmol, 56.48% yield, 98.191% purity, HCl) as a white solid. $^1$H NMR (400 MHz, $D_2O$) δ=7.21-7.06 (m, 1H), 6.97-6.80 (m, 1H), 4.59-4.51 (m, 2H), 3.89-3.72 (m, 3H), 3.21-3.07 (m, 2H), 2.96-2.82 (m, 2H), 2.58-2.42 (m, 2H), 1.87-1.68 (m, 1H), 0.91-0.73 (m, 6H)$^1$H NMR (400 MHz, DMSO-$d_6$) δ=7.90 (br s, 3H), 7.14 (s, 1H), 6.72 (s, 1H), 4.93 (t, J=5.2 Hz, 1H), 4.43 (d, J=5.1 Hz, 2H), 3.83-3.75 (m, 3H), 2.97-2.89 (m, 2H), 2.85-2.77 (m, 2H), 2.45 (br d, J=7.2 Hz, 2H), 1.89-1.77 (m, 1H), 0.96-0.80 (m, 6H). LCMS (ESI+) m/z: 237.2 [M+H]*.

Example 4: Synthesis of 2-(2-aminoethyl)-5-isobutyl-4-(methoxymethyl)phenol (Compound 116)

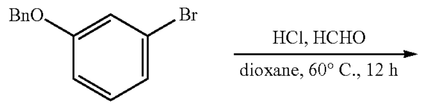

1

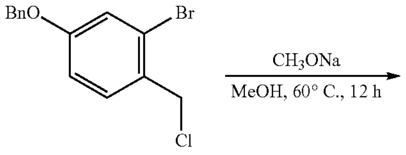

2

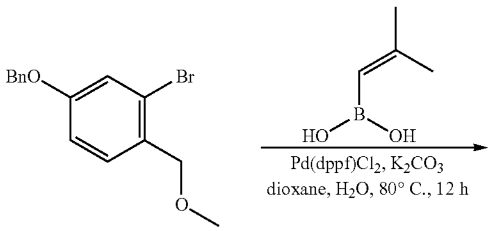

3

-continued

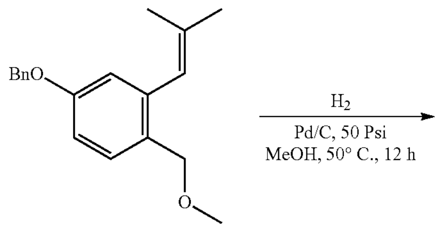

4

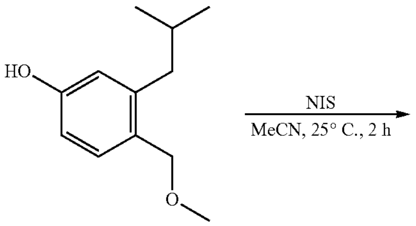

5

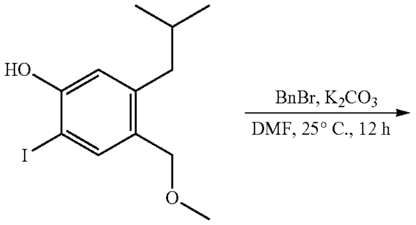

6

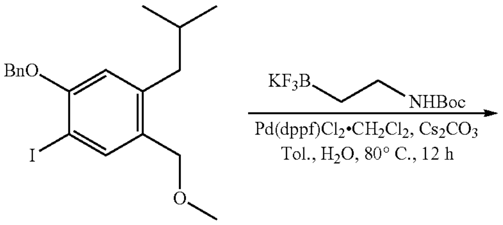

7

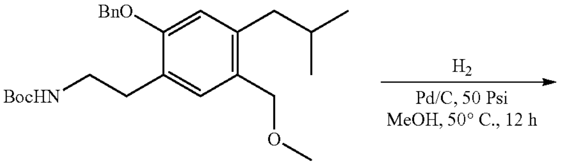

8

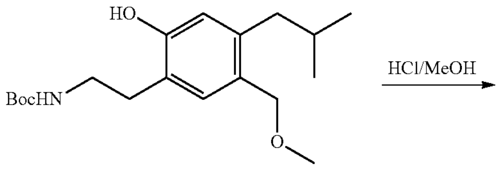

9

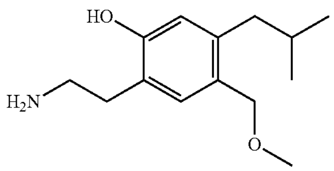

Step 1: 4-benzyloxy-2-bromo-1-(chloromethyl)benzene (2)

To a solution of 1-benzyloxy-3-bromo-benzene (10.0 g, 38.0 mmol, 1 eq) in dioxane (100 mL) were added HCl (12 M, 41.7 mL, 13.18 eq) and HCHO (4.55 g, 152 mmol, 3.99 eq). The mixture was stirred at 60° C. for 12 hours. TLC indicated 1-benzyloxy-3-bromo-benzene remained, and one major new spot with larger polarity was detected. The reaction mixture was quenched by addition aq. $NaHCO_3$ (10 mL) at 0° C., and then extracted with EtOAc (5.00 mL*3). The combined organic layers were dried over $Na_2SO_4$, filtered and concentrated under reduced pressure to give 4-benzyloxy-2-Br-1-(chloromethyl)benzene (11.0 g, 35.3 mmol, crude) as a yellow oil.

Step 2: 4-benzyloxy-2-bromo-1-(methoxymethyl)benzene (3)

To a solution of 4-benzyloxy-2-Br-1-(chloromethyl)benzene (11.0 g, 35.3 mmol, 1 eq) in MeOH (60.0 mL) was added $CH_{30}Na$ (10.2 g, 189 mmol, 5.35 eq). The mixture was stirred at 50° C. for 3 h. TLC indicated 4-benzyloxy-2-Br-1-(chloromethyl)benzene was consumed completely and one new spot formed. The reaction mixture was concentrated under reduced pressure to remove MeOH. The residue was diluted with water (200 mL) and extracted with EtOAc (150 mL*3). The combined organic layers were washed with brine (200 mL), dried over $Na_2SO_4$, filtered and concentrated under reduced pressure to give a residue. The residue was purified by column chromatography ($SiO_2$, petroleum ether/ethyl acetate=1/0, Rf=0.29) to give 4-benzyloxy-2-bromo-1-(methoxymethyl)benzene (24.0 g, 78.1 mmol, crude) as yellow oil. $^1H$ NMR (400 MHz, Chloroform-d) δ 7.36-7.27 (m, 5H), 7.25-6.97 (m, 1H), 6.86-6.69 (m, 1H), 4.98-4.94 (m, 2H), 4.38 (s, 2H), 3.34 (s, 3H).

Step 3: 4-benzyloxy-1-(methoxymethyl)-2-(2-methylprop-1-enyl)benzene (4)

A mixture of 4-benzyloxy-2-bromo-1-(methoxymethyl) benzene (10.0 g, 32.6 mmol, 1 eq), 2-methyl-prop-1-enyl-boronic acid (6.51 g, 65.1 mmol, 2 eq), $K_2CO_3$ (6.75 g, 48.8 mmol, 1.5 eq) and $Pd(dppf)Cl_2$ (2.38 g, 3.26 mmol, 0.1 eq) in dioxane (120 mL) and $H_2O$ (30.0 mL) was degassed and purged three times with $N_2$, and then the mixture was stirred at 100° C. for 12 h under $N_2$ atmosphere. TLC showed 4-benzyloxy-2-bromo-1-(methoxymethyl)benzene was consumed completely and one new spot was detected. The residue was diluted with $H_2O$ (20.0 mL) and extracted with EtOAc (15.0 mL*3). The combined organic layers were washed with brine (20.0 mL), dried over $Na_2SO_4$, filtered and concentrated under reduced pressure to give a residue. The residue was purified by column chromatography ($SiO_2$, petroleum ether/ethyl acetate=1/0 to 30/1, Rf=0.55) to give 4-benzyloxy-1-(methoxymethyl)-2-(2-methylprop-1-enyl) benzene (7.00 g, 24.8 mmol, 76.2% yield) as a yellow oil. $^1H$ NMR (400 MHz, CHLOROFORM-d) δ 7.42-7.38 (m, 2H), 7.37-7.32 (m, 2H), 7.29-7.25 (m, 1H), 7.23 (d, J=1.4 Hz, 1H), 6.80 (dd, J=2.6, 8.4 Hz, 1H), 6.75 (d, J=2.5 Hz, 1H), 6.26 (s, 1H), 5.03 (s, 2H), 4.31 (s, 2H), 3.32 (s, 3H), 1.87 (d, J=1.0 Hz, 3H), 1.62 (d, J=0.8 Hz, 3H).

Step 4: 3-isobutyl-4-(methoxymethyl)phenol (5)

A mixture of 4-benzyloxy-1-(methoxymethyl)-2-(2-methylprop-1-enyl)benzene (7.00 g, 24.8 mmol, 1 eq) and Pd/C (2.64 g, 10% purity) in MeOH (70.0 mL) was stirred under $H_2$ (50 psi) at 50° C. for 12 h. TLC indicated 4-benzyloxy-1-(methoxymethyl)-2-(2-methylprop-1-enyl)benzene was consumed completely and one new spot formed. The reaction mixture was filtered. The filter liquor was concentrated to give a residue. The residue was purified by column chromatography ($SiO_2$, petroleum ether/ethyl acetate=1/0 to 10/1, Rf=0.46) to give 3-isobutyl-4-(methoxymethyl)phenol (3.00 g, 14.3 mmol, 57.7% yield, 92.6% purity) as a colorless oil. $^1H$ NMR (400 MHz, Chloroform-d) δ 7.10 (d, J=9.0 Hz, 1H), 6.57-6.53 (m, 2H), 4.97 (br s, 1H), 4.32 (s, 2H), 3.29 (s, 3H), 2.41 (d, J=7.3 Hz, 2H), 1.84-1.73 (m, 1H), 0.86 (s, 3H), 0.84 (s, 3H).

Step 5: 2-iodo-5-isobutyl-4-(methoxymethyl)phenol (6)

To a solution of 3-isobutyl-4-(methoxymethyl)phenol (3.00 g, 15.4 mmol, 1 eq) in MeCN (30.0 mL) was added NIS (4.17 g, 18.5 mmol, 1.2 eq). The mixture was stirred at 25° C. for 2 hours. TLC showed 3-isobutyl-4-(methoxymethyl)phenol was consumed completely and one new spot formed. The reaction mixture was concentrated under reduced pressure to remove MeCN. The residue was diluted with $H_2O$ (50.0 mL) and extracted with EtOAc (30.0 mL*3). The combined organic layers were washed with brine (50.0 mL), dried over $Na_2SO_4$, filtered and concentrated under reduced pressure to give a residue. The residue was purified by column chromatography ($SiO_2$, petroleum ether/ethyl acetate=1/0 to 5/1, Rf=0.53) to give 2-iodo-5-isobutyl-4-(methoxymethyl)phenol (1.80 g, 5.62 mmol, 36.4% yield) as a yellow oil.

Step 6: 2-iodo-5-isobutyl-4-(methoxymethyl)phenol (7)

To a solution of 2-iodo-5-isobutyl-4-(methoxymethyl) phenol (1.80 g, 5.62 mmol, 1 eq) in DMF (20.0 mL) was added BnBr (962 mg, 5.62 mmol, 1 eq) and $K_2CO_3$ (1.17 g, 8.43 mmol, 1.5 eq). The mixture was stirred at 25° C. for 12 hours. LCMS showed 2-iodo-5-isobutyl-4-(methoxymethyl) phenol was consumed completely and one main peak with desired mass was detected. The reaction mixture was diluted with water (100 mL) and extracted with EtOAc (60.0 mL*3). The combined organic layers were washed with brine (100 mL), dried over $Na_2SO_4$, filtered and concentrated under reduced pressure to give a residue. The residue was purified by column chromatography ($SiO_2$, petroleum ether/ethyl acetate=1/0 to 5/1, Rf=0.71) to give 1-benzyloxy-2-iodo-5-isobutyl-4-(methoxymethyl)benzene (1.20 g, 2.92 mmol, 52.0% yield) as a yellow oil. $^1H$ NMR (400 MHz, CHLOROFORM-d) δ 7.66 (s, 1H), 7.61 (br d, J=7.0 Hz, 1H), 7.41 (br d, J=7.3 Hz, 2H), 7.30 (s, 1H), 7.23 (d, J=7.3 Hz, 1H), 6.55 (s, 1H), 5.07 (s, 2H), 4.27 (s, 2H), 3.29 (s, 3H), 2.38 (d, J=7.3 Hz, 2H), 1.71 (quind, J=6.8, 13.5 Hz, 1H), 0.80 (s, 3H), 0.79 (s, 3H) LCMS: (ESI+): m/z=411.2 $[M+H]^+$.

Step 7: 2-iodo-5-isobutyl-4-(methoxymethyl)phenol (8)

A mixture of 1-benzyloxy-2-iodo-5-isobutyl-4-(methoxymethyl)benzene (1.10 g, 2.68 mmol, 1 eq), 2-(tert-butoxycarbonylamino)ethyl-trifluoro-boron;potassium hydride (807 mg, 3.22 mmol, 1.2 eq), $Cs_2CO_3$ (2.62 g, 8.04 mmol, 3 eq) and $Pd(dppf)Cl_2 \cdot CH_2Cl_2$ (219 mg, 268 μmol, 0.1 eq) in toluene (40 mL) and $H_2O$ (10 mL) was degassed and purged with $N_2$ for 3 times, and then the mixture was stirred at 85° C. for 12 hours under $N_2$ atmosphere. TLC indicated 1-benzyloxy-2-iodo-5-isobutyl-4-(methoxymethyl)benzene was consumed completely and one new spot formed. The reaction mixture was concentrated under reduced pressure to remove toluene. The residue was diluted with $H_2O$ (50.0 mL) and extracted with EtOAc (30.0 mL*3). The combined organic layers were washed with brine (50.0 mL), dried over $Na_2SO_4$, filtered and concentrated under reduced pressure to give a residue. The residue was purified by column chromatography ($SiO_2$, petroleum ether/ethyl acetate=1/0 to 5/1, Rf=0.31) to give tert-butyl N-[2-[2-benzyloxy-4-isobutyl-5-(methoxymethyl)phenyl]ethyl]carbamate (500 mg, 1.08 mmol, 40.2% yield, 92.2% purity) as a colorless oil.

Step 8: 2-iodo-5-isobutyl-4-(methoxymethyl)phenol (9)

A mixture of tert-butyl N-[2-[2-benzyloxy-4-isobutyl-5-(methoxymethyl)phenyl]ethyl]carbamate (500 mg, 1.17 mmol, 1 eq) and Pd/C (124 mg, 10% purity) in MeOH (10.0 mL) was stirred under $H_2$ (50 psi) at 50° C. for 12 hours. LC-MS showed tert-butyl N-[2-[2-benzyloxy-4-isobutyl-5-(methoxymethyl)phenyl]ethyl]carbamate was consumed completely and one main peak with desired mass was detected. The reaction mixture was filtered. The filter liquor was concentrated to give a residue. The residue was purified by prep-HPLC (column: CD24-WePure Biotech XPT C18 150*25*7 μm; mobile phase: [$H_2O$(0.05% HCl)-ACN]; gradient:35%-65% B over 12.0 min) to give tert-butyl N-[2-[2-hydroxy-4-isobutyl-5-(methoxymethyl)phenyl] ethyl]carbamate (120 mg, 348.32 μmol, 29.79% yield, 97.95% purity) as a white solid. LCMS: (ESI+): m/z=360.2 $[M+Na]^+$ Step 9: 2-(2-aminoethyl)-5-isobutyl-4-(methoxymethyl)phenol (Compound 116)

To a solution of tert-butyl N-[2-[2-hydroxy-4-iBu-5-(methoxymethyl)phenyl]ethyl]carbamate (110 mg, 326 μmol, 1 eq) was added HCl/MeOH (2 M, 2.00 mL, 12.3 eq). The mixture was stirred at 25° C. for 2 hours. LCMS showed tert-butyl N-[2-[2-hydroxy-4-iBu-5-(methoxymethyl)phenyl]ethyl]carbamate was consumed completely and one main peak with desired mass was detected. The reaction mixture was concentrated and the residue was purified by prep-HPLC (column: CD24-WePure Biotech XPT C18 150*25*7 μm; mobile phase: [$H_2O$(0.05% HCl)-ACN]; gradient: 10%-40% B over 12.0 min) to give 2-(2-aminoethyl)-5-iBu-4-(methoxy-methyl)phenol (70 mg, 245 μmol, 75.01% yield, 95.6% purity, HCl) as a white solid. $^1H$ NMR (400 MHz, Methanol-$d_4$) δ 7.07 (s, 1H), 6.66 (s, 1H), 4.37 (s, 2H), 3.21-3.09 (m, 2H), 2.98-2.80 (m, 2H), 2.46 (d, J=7.3 Hz, 2H), 1.84 (td, J=6.8, 13.5 Hz, 1H), 0.93 (d, J=6.6 Hz, 6H) LCMS: (ESI+): m/z=238.2 $[M+H]^+$.

Example 5: Physical Properties of Exemplary Compounds: Aqueous Solubility and Photoliability Purpose: Aqueous solubility studies were conducted to evaluate the dissolution of exemplary compounds in water. Additionally, photostability testing was performed to assess the susceptibility of exemplary compounds for degradation upon exposure to light.

Methods: The aqueous solubility of exemplary compounds 2CB-5MM (Compound 4), 2CiBu-5MM (Compound 8) 2CiBu-5HM (Compound 26), 2CiBu-2OH-5MM (Compound 116), and reference compound 2C-iBu were tested by sequentially diluting a known mass in water. Aqueous solubility was determined by the presence or absence of undissolved material upon microscopic inspection. Photoabsorption was determined from a dilution of the resulting solutions and assessed using wavelengths between 290 nm and 700 nm. The molar extinction coefficient (MEC) was calculated based on the wavelength of maximal absorption within this band range. In accordance with FDA guidelines, MEC below 1,000 $L\cdot mol^{-1}\cdot cm^{-1}$ were considered insufficiently photoreactive to result in direct phototoxicity.

Results: Detected aqueous solubility and photoliability for exemplary compounds and reference compound 2C-iBu are provided in Table 2.

TABLE 2

Results of Aqueous Solubility and Photoliability Assessments

| | 2CB-5MM (Compound 4) | 2CiBu-5MM (Compound 8) | 2CiBu-5HM (Compound 26) | 2CiBu-2OH-5MM (Compound 116) | 2C-iBu |
|---|---|---|---|---|---|
| Max Solubility (mM) | 43.46 | 364.8 | 44.36 | 110.18 | 31.18 |
| MEC ($L\cdot mol^{-1}\cdot cm^{-1}$) | 781.9 | 283.6 | 340.7 | 380.8 | 3683.8 |

Exemplary compounds 2CiBu-5MM (Compound 8) and 2CiBu-2OH-5MM (Compound 116) exhibited significantly higher aqueous solubility than reference compound 2C-iBu. Specifically, Compound 8 was over ten times more soluble than 2C-iBu under the same conditions.

Regarding photoliability, 2C-iBu exhibited the highest MEC at approximately 3684 $L\cdot mol^{-1}\cdot cm^{-1}$. MEC values above 1000 $L\cdot mol^{-1}\cdot cm^{-1}$ are considered photoreactive and liable to pose a risk of direct phototoxicity, such as by absorbing light and harming surrounding cells. The MEC value for 2C-iBu was approximately an order of magnitude greater than exemplary compounds 2CiBu-5MM, 2CiBu-5HM, and 2CiBu-2OH-5MM. None of the tested exemplary compounds exhibited an MEC value in excess of 1000 $L\cdot mol^{-1}\cdot cm^{-1}$, indicating a reduced risk of phototoxicity. Together, the exemplary compounds exhibited greater aqueous solubility and reduced phototoxicity relative to reference compound 2C-iBu. Such physical characteristics provide advantageous properties, e.g., benefits related to enhanced bioavailability, ease of formulation, and reduced risk of adverse events, such as phototoxicity, and are unexpected in view of reference compound 2C-iBu.

Example 6: In Vitro Serotonin Receptor Functional Activity Assay

Purpose: The potential of exemplary compounds of the disclosure as serotonergic modulators was determined by quantifying intracellular inositol monophosphate (IP-1) accumulation. The IP-1 assay provides a sensitive measure of receptor-mediated signaling, which enables identification and characterization of compounds with agonist or antagonist properties. Exemplary compounds 2CB-5MM (Compound 4), 2CIB-5MM (Compound 8), and 2CIB-5HM (Compound 26) were assessed along with comparators 2-CB and 2CB-5ME.

Methods (5-$HT_{2A}$ and 5-$HT_{2C}$ IP-One Functional Activity Assays): Intracellular accumulation of IP-1 was measured using an IP-One HTRF assay kit (Cat. #62IPAPEJ, Cisbio) at WuXi AppTec Co. Ltd. (Hong Kong) Discovery Biology Unit according to their standard protocols. Briefly, the reference compounds and screening compounds were 3.16-fold serially diluted in 100% DMSO for 10 points using Bravo. 70 nL of compounds were added to the assay plate using Echo555. Added 14 μL/7500 cells/well of 5-$HT_{2A}$-expressing HEK293 or 5-$HT_{2C}$-expressing HEK293 to the assay plate and incubate for 60 min at 37° C. Added 3 μL of IP-1 d2 Reagent working solution and 3 μL of IP-1 Tb Cryptate Antibody working solution to all wells. The plates were incubated for 1 hour at room temperature and read for fluorescence at 620 nm and 665 nm on an EnVision Multi-mode Plate Reader (PerkinElmer). The ratio of the acceptor and donor emission signals (665/620) were calculated for each individual well and substituted into the standard curve to obtain the log concentration of IP level. After converting to the antilog base IP-1, the average background control signal was subtracted from each well and values were normalized to the maximal response of 5-HT at 3 μM (100%). % MAX was calculated by taking the average normalized maximal response for each compound at the highest concentration tested. The data were analyzed using the four-parameter nonlinear regression curve-fitting function in GraphPad Prism 5 (GraphPad Software, San Diego, CA) to generate potency ($EC_{50}$) values. The represented plots show normalized IP-1 values versus compound concentrations; the corresponding numerical data are parameter estimates for the concentration-response curve using the four-parameter nonlinear regression curve-fitting function in GraphPad Prism 10.

Methods (5-$HT_{2B}$ IP-One Functional Activity Assays): Intracellular accumulation of IP-1 was measured using an IP-One HTRF) assay kit (Cat. #62IPAPEJ, Cisbio) at WuXi AppTec Co. Ltd. (Hong Kong) Discovery Biology Unit according to their standard protocols. Briefly, 5-$HT_{2B}$/HEK293 were plated in a 384-well plate and incubated at 37° C. and 5% $CO_2$ overnight. The reference compounds and screening compounds were 3.16-fold serially diluted in 100% DMSO for 10 points using Bravo. 70 nL of compounds were added to the cell plate using Echo555. Incubated for 60 minutes at 37° C. Added 3 μL of IP-1 d2 Reagent working solution and 3 μL of IP-1 Tb Cryptate Antibody working solution to all wells. The plates were incubated for 1 hour at room temperature and read on for fluorescence at 620 nm and 665 nm on an EnVision Multi-mode Plate Reader (PerkinElmer). The ratio of the acceptor and donor emission signals (665/620) were calculated for each individual well and substituted into the standard curve to obtain the log concentration of IP level. After converting to the antilog base IP-1, the average background control signal was subtracted from each well and values were normalized to the maximal response of 5-HT at 3 μM (100%). % MAX was calculated by taking the average normalized maximal response at the highest concentration tested. Data were analyzed using the four-parameter nonlinear regression curve-fitting function in GraphPad Prism 5 (GraphPad Software, San Diego, CA) to generate potency ($EC_{50}$) values. Parameter constraint "Top=100" was used in the analysis of 5-$HT_{2B}$ IP-1. Represented plots show normalized IP-1 values versus compound concentrations; the corresponding numerical data are parameter estimates for the concentration-response curve using the 4-parameter nonlinear regression curve-fitting function in GraphPad Prism 10. "Top=100" parameter constraint was not enabled for the represented plot analysis.

Results: FIGS. 1A-1E show the dose-response curves of exemplary compounds 2CB-5MM (FIG. 1A), 2CIB-5MM (FIG. 1B), and 2CIB-5HM (FIG. 1C), and comparators 2CB (FIG. 1D) and 2CB-5ME (FIG. 1E), from the IP-1 accumulation assay. Each plot represents the response elicited by each test concentration of agonist, expressed as a percentage of the maximal effect (Emax) produced by serotonin (the reference full agonist). This normalization allows for direct comparison of the efficacy of each compound relative to serotonin. Table 3 presents the $EC_{50}$ values for each compound.

TABLE 3

5-HT Potency ($EC_{50}$) of Exemplary Compounds and Comparators in IP-1 Accumulation Assays

| Human 5-HT Receptor Subtype | $EC_{50}$ Values of Tested Compounds: 2CB-5MM | 2CIB-5MM | 2CIB-5HM | 2CB | 2CB-5ME |
|---|---|---|---|---|---|
| 5-$HT_{2A}$ | $5.91*10^{-8}$ | $3.41*10^{-7}$ | $4.66*10^{-7}$ | $2.09*10^{-8}$ | $2.27*10^{-7}$ |
| 5-$HT_{2B}$ | $7.86*10^{-8}$ | $8.25*10^{-7}$ | $1.12*10^{-6}$ | $2.32*10^{-7}$ | $1.31*10^{-7}$ |
| 5-$HT_{2C}$ | $2.25*10^{-7}$ | n.t. | n.t. | $3.99*10^{-8}$ | $2.65*10^{-7}$ |

The 5-$HT_{2A}$ receptor signaling activity of exemplary compounds of the disclosure is consistent with known serotonergic agonists 2CB and 2CB-5ME, as evidenced by IP-1 accumulation profiles. Interestingly, the comparator compounds exhibited enhanced activation of 5-$HT_{2B}$ over 5-$HT_{2A}$ Activation of the 5-$HT_{2B}$ receptor is strongly associated with cardiac liabilities, particularly drug-induced valvular heart disease (VHD). Surprisingly, selective activation of 5-$HT_{2B}$ over 5-$HT_{2A}$ was not exhibited by exemplary compounds of the disclosure, in contrast to known compounds. Together, the data indicate that the tested exemplary compounds are capable of robust serotonergic activity at human 5-$HT_{2A}$ receptors, with reduced selectivity for 5-$HT_{2B}$.

Example 7: Calcium Flux Assay

Purpose: The agonist activity of test compounds at 5-$HT_{2A}$ and 5-$HT_{2B}$ receptors was determined using a calcium flux assay.

Methods: Briefly, Human Embryonic Kidney (293T) cells transiently expressing human 5-$HT_{2A}$ receptors or human 5-$HT_{2B}$ receptors were seeded in 200 μL DMEM supplemented with 1% (v/v) dialyzed fetal bovine serum (Gibco, Cat. #A33820-01) onto black 96-well poly-D-lysine coated plates with clear bottoms (40 000 cells/well) and maintained overnight in a humidified atmosphere at 37° C. and 5% CO2. The following day, media was aspirated and replaced with 100 μL HBSS supplemented with 20 mM HEPES (pH 7.4), loaded with 5 μM Fluo-2 AM HA (ION Biosciences, San Marcos, TX) and 2.5 mM water-soluble probenecid (Thermo Fisher Scientific, Waltham, MA). Plates were incubated for 1 hour at 37° C., washed once with 100 μL HBSS-HEPES, and maintained in 100 μL HBSS-HEPES supplemented with 2.5 mM water-soluble probenecid. The plates of dye-loaded cells were placed into a FlexStation 3 microplate reader (Molecular Devices, Sunnyvale, CA) set at 37° C. to monitor fluorescence (excitation, 485 nm; emission, 525 nm; cutoff, 515 nm).

Plates were read for 30 s (2 s interval) to establish baseline fluorescence and then administered 50 μL of 2,7-dimethyl-4-hydroxy-DET and read for an additional 120 s. After obtaining a calcium flux trace, the mean baseline fluorescence (F) was subtracted from peak fluorescence (ΔF) in each well and the product normalized by F (ΔF/F). The data were analyzed using the four-parameter nonlinear regression curve-fitting function in GraphPad Prism 10.2.3 (GraphPad Software, San Diego, CA), to generate potency ($EC_{50}$) and maximal response values. Maximal response values were normalized to the maximum 5-HT response (100%) and minimum 5-HT response (0%) on the same plate. Each concentration point was tested in triplicate.

Results: Table 4 shows the dose-response curves for 2C-B, 2CB-5MM, 2C-iBu, 2C-iBu-5MM, and 2C-iBu-2OH-5MM. FIGS. 2A-2E show the dose response curves of exemplary compounds 2CB-5MM (FIG. 2A), 2C-iBU-5MM (FIG. 2B), 2C-iBu-2OH-5MM (FIG. 2C), and comparators 2C-B (FIG. 2D) and 2C-iBu (FIG. 2E), from the calcium flux assay.

TABLE 4

Calcium Flux Assay Results

| Compound | Potency ($EC_{50}$) (Emax) | |
|---|---|---|
| | $5\text{-HT}_{2A}$ | $5\text{-HT}_{2B}$ |
| 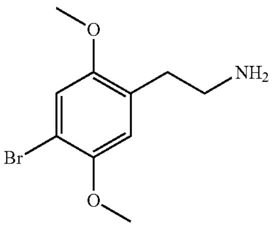<br>(2C-B) | 0.62 nM (105.2%) | 9.98 nM (92.7%) |
| 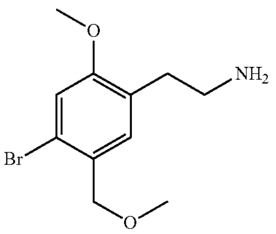<br>(2CB-5MM) | 0.68 nM (114%) | 23.43 nM (94.0%) |
| 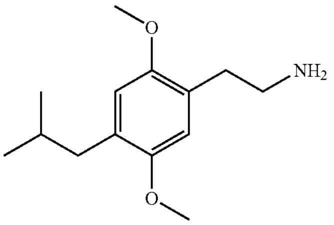 [SMILES: COc1cc(CC(C)C)c(OC)cc1CCN]<br>(2C-iBu) | 21.94 nM (92.6%) | 22.34 nM (89.1%) |
| 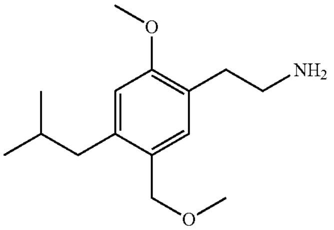 [SMILES: COCc1cc(CCN)c(OC)cc1CC(C)C]<br>(2C-iBu-5MM) | 42.15 nM (111%) | 497.20 nM (45.7%) |

TABLE 4-continued

Calcium Flux Assay Results

| Compound | Potency ($EC_{50}$) (Emax) | |
|---|---|---|
| | $5\text{-HT}_{2A}$ | $5\text{-HT}_{2B}$ |
| 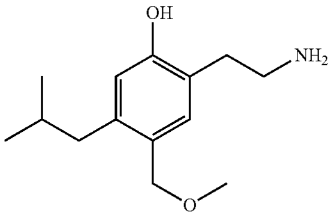 [SMILES: COCc1cc(CCN)c(O)cc1CC(C)C]<br>(2C-iBu-20H-5MM) | 55.93 nM (115%) | Unstable nM (2.64%) |

Comparator compounds 2CB and 2C-iBu exhibited near maximal activation of the $5\text{-HT}_{2B}$ receptor. In contrast, certain exemplary compounds, such as 2C-iBu-5MM and 2C-iBu-2OH-5MM, exhibited unexpectedly reduced $5\text{-HT}_{2B}$ receptor activation, as represented by their relatively high $EC_{50}$ values and low Emax values. Reduced $5\text{-HT}_{2B}$ receptor activation can provide significant advantages, such as reduced off-target effects and a lower risk of $5HT_{2B}$-mediated valvular heart disease, thereby contributing to an improved therapeutic index.

Example 8: Serotonin Receptor (5-HTR) Binding Activity of 2CiBu-5MM (Compound 8)

Purpose: The 5-HTR binding affinity of exemplary compounds of the disclosure was evaluated using in vitro radioligand binding assays, thereby characterizing its potential for receptor engagement and selectivity.

Methods: In vitro binding assays were performed by Eurofins Discovery using human recombinant receptors expressed in mammalian cell lines. The $5\text{-HT}_{2A}$ and $5\text{-HT}_{2C}$ receptors were expressed in HEK-293 cells, and the $5\text{-HT}_{2B}$ receptor was expressed in CHO cells. For the $5\text{-HT}_{2A}$ assay, $^{125}$I-DOI was used at a final concentration of 0.1 nM, with nonspecific binding determined using 1 μM (±)-DOI. Incubation was carried out for 60 minutes at room temperature. For the $5\text{-HT}_{2B}$ assay, $^{125}$I-DOI was used at 0.2 nM, with nonspecific binding defined using 1 μM (±)-DOI, and incubation was also performed at room temperature for 60 minutes. For the $5\text{-HT}_{2C}$ assay, $^{125}$I-DOI was used at a final concentration of 0.1 nM, with nonspecific binding determined using 10 μM (±)-DOI, and incubation was performed at 37° C. for 60 minutes.

All assays were conducted in triplicate, and specific binding was quantified by scintillation counting.

Specific binding was expressed as a percentage of control-specific binding, and percent inhibition was calculated using the formula: % Inhibition=100−[(Measured Binding/Control Binding)×100]. Half-maximal inhibitory concentrations ($IC_{50}$) were determined by non-linear regression analysis of the inhibition curves using the Hill equation: $Y=D+[(A-D)/(1+(C/C_{50})^{nH})]$, where Y represents specific binding, A is the minimum asymptote (lower plateau), D is the maximum asymptote (upper plateau), C is the compound concentration, $C_{50}$ is the $IC_{50}$ value (i.e., the concentration producing 50% inhibition), and nH is the Hill coefficient indicating the slope factor. Inhibition constants (K) were calculated using the Cheng-Prusoff equation: $K_i=IC_{50}/(1+[L]/K_D)$, where [L] is the concentration of radioligand and $K_D$ is the dissociation constant of the radioligand for the receptor. $K_D$ values used in these calculations were previously established for each receptor under the assay conditions: 0.3 nM for 5-$HT_{2A}$, 0.2 nM for 5-$HT_{2B}$, and 0.9 nM for 5-$HT_{2C}$. Data analysis was performed using software developed at Cerep and validated against SigmaPlot 4.0 for Windows.

Results: Experimental values are provided in Table 5.

TABLE 5

In vitro 5-HTR binding activity of exemplary compound and reference compound R-DOI

| Human Serotonin Receptor Subtype | 2CiBu-5MM (Compound 8) $IC_{50}$ (M) | $K_i$ (M) | nH | R-DOI $IC_{50}$ (M) | $K_i$ (M) | nH |
|---|---|---|---|---|---|---|
| 5-$HT_{2A}$ | $5.7*10^{-8}$ | $4.3*10^{-8}$ | 0.6 | $2.6*10^{-10}$ | $2.0*10^{-10}$ | 0.7 |
| 5-$HT_{2B}$ | $2.7*10^{-7}$ | $1.3*10^{-7}$ | 0.7 | $2.3*10^{-9}$ | $1.2*10^{-9}$ | 0.7 |
| 5-$HT_{2C}$ | $1.4*10^{-8}$ | $1.2*10^{-8}$ | 0.9 | $4.4*10^{-10}$ | $4.0*10^{-10}$ | 1.0 |

Lower $IC_{50}$ and K values represent greater binding affinity. Comparison was with known 5-HTR agonist $^{125}$I-DOI. The affinity of 2CiBu-5MM was potent yet reduced across the tested human 5-HTR subtypes.

Regarding the Hill coefficient (nH), 2CiBu-5MM exhibited negative cooperativity at each tested serotonin receptor, indicating that the compound decreased receptor affinity for further ligand binding. The nH provides insight into ligand-receptor interactions: An nH value equal to 1 indicates non-cooperative binding, where each ligand binds independently to the receptor, and an nH value of less than 1 indicates negative cooperativity, where the binding of one ligand decreases the affinity for subsequent ligands.

The combination of high affinity (low Ki) and negative cooperativity indicates that exemplary compound 2CiBu-5MM is effective at engaging the receptor at low concentrations, and initial binding events reduce the affinity of subsequent binding events. Negative cooperativity can serve as a regulatory mechanism, preventing overstimulation of the receptor, thereby modulating receptor activity as ligand concentration increases.

Example 9: In Vitro Pharmacology of Compounds 4, 8, and 116: Binding, Enzyme, and Uptake Assays Purpose: The pharmacology of compounds 2CB-5MM (Compound 4), 2CiBu-5MM (Compound 8), and 2CiBu-2OH-5MM (Compound 116) was evaluated using in vitro binding, enzyme, and uptake assays.

Methods—Binding Assays: In vitro binding assays were performed using human recombinant receptors expressed in mammalian cell lines. Receptors were expressed in either HEK-293 or CHO cells depending on the target, and assay conditions (radioligand, concentration, nonspecific competitor, temperature, and incubation time) were optimized for each receptor. Detailed assay parameters, including cell line, ligand identity, and assay conditions, are provided in Table 6. All assays were conducted in triplicate, and specific binding was quantified by scintillation counting as the detection method for each listed assay.

Specific binding was expressed as a percentage of control-specific binding, and percent inhibition was calculated using the formula in Ex. 8 above. Half-maximal inhibitory concentrations ($IC_{50}$) were determined by non-linear regression analysis of the inhibition curves using the Hill equation (see Ex. 8). Inhibition constants ($K_i$) were calculated using the Cheng-Prusoff equation (see Ex. 8). $K_D$ values used in these calculations had been previously established for each receptor under the assay conditions (see Table 6). Data analysis was performed using software developed at Cerep and validated against SigmaPlot 4.0 for Windows.

TABLE 6

Binding assay conditions

| Assay | Source | Ligand | Conc. | $K_D$ | Non-Specific | Incubation |
|---|---|---|---|---|---|---|
| RECEPTORS | | | | | | |
| $A_{2A}$ (h) (agonist radioligand) | human recomb. (HEK-293 cells) | [$^3$H]CGS 21680 | 6 nM | 27 nM | NECA (10 μM) | 120 min RT |
| $alpha_{1A}$ (h) (antag. radioligand) | human recomb. (CHO cells) | [$^3$H]prazosin | 0.1 nM | 0.1 nM | epinephrine (0.1 mM) | 60 min RT |
| $alpha_{1D}$ (h) (antag. radioligand) | human recomb. (CHO cells) | [$^3$H]prazosin | 0.2 nM | 0.15 nM | phentolamine (10 μM) | 60 min RT |
| $alpha_{2A}$ (h) (antag. radioligand) | human recomb. (CHO cells) | [$^3$H]RX 821002 | 1 nM | 0.8 nM | (−)epinephrine (100 μM) | 60 min RT |
| $beta_1$ (h) (agonist radioligand) | human recomb. (HEK- 293 cells) | [$^3$H](−)CGP 12177 | 0.3 nM | 0.39 nM | alprenolol (50 μM) | 60 min RT |
| $beta_2$ (h) (antagonist radioligand) | human recomb. (CHO cells) | [$^3$H](−)CGP 12177 | 0.3 nM | 0.15 nM | alprenolol (50 μM) | 120 min RT |
| $CB_2$ (h) (agonist radioligand) | human recomb. (CHO cells) | [$^3$H]WIN 55212-2 | 0.8 nM | 1.5 nM | WIN 55212-2 (5 μM) | 120 min 37° C. |
| $CB_1$ (h) (agonist radioligand) | human recomb. (Chem-RBL cells) | [$^3$H]CP 55940 | 2 nM | 0.9 nM | AM281 (10 μM) | 30 min 22° C. |
| $CCK_1$ ($CCK_A$) (h) (agonist radioligand) | human recomb. (CHO cells) | [$^{125}$I]CCK-8s | 0.08 nM | 0.24 nM | CCK-8s (1 μM) | 60 min RT |
| $D_1$ (h) (antagonist radioligand) | human recomb. (CHO cells) | [$^3$H]SCH 23390 | 0.3 nM | 0.2 nM | SCH 23390 (1 μM) | 60 min RT |
| $D_{2S}$ (h) (agonist radioligand) | human recomb. (HEK- 293 cells) | [$^3$H]7-OH-DPAT | 1 nM | 0.68 nM | butaclamol (10 μM) | 60 min RT |
| $ET_A$ (h) (agonist radioligand) | human recomb. (CHO cells) | [$^{125}$I]endothelin-1 | 0.03 nM | 0.03 nM | endothelin-1 (100 nM) | 120 min 37° C. |
| $H_1$ (h) (antagonist radioligand) | human recomb. (HEK-293 cells) | [$^3$H]pyrilamine | 1 nM | 1.7 nM | pyrilamine (1 μM) | 60 min RT |
| $H_2$ (h) (antagonist radioligand) | human recomb. (CHO cells) | [$^{125}$I]APT | 0.075 nM | 2.9 nM | tiotidine (100 μM) | 120 min RT |

TABLE 6-continued

| Binding assay conditions | | | | | | |
|---|---|---|---|---|---|---|
| Assay | Source | Ligand | Conc. | $K_D$ | Non-Specific | Incubation |
| $M_1$ (h) (antagonist radioligand) | human recomb. (CHO cells) | [$^3$H]pirenzepine | 2 nM | 13 nM | atropine (1 μM) | 60 min RT |
| $M_2$ (h) (antagonist radioligand) | human recomb. (CHO cells) | [$^3$H]AF-DX 384 | 2 nM | 4.6 nM | atropine (1 μM) | 60 min RT |
| $M_3$ (h) (antagonist radioligand) | human recomb. (CHO cells) | [$^3$H]4-DAMP | 0.2 nM | 0.5 nM | atropine (1 μM) | 60 min RT |
| N neuronal α4β2 (h) (agonist radioligand) | human recomb. (SH-SY5Y cells) | [$^3$H]cytisine | 0.6 nM | 0.3 nM | nicotine (10 μM) | 120 min 4° C. |
| delta (DOP) (h) (agonist radioligand) | human recomb. (Chem-1 RBL) | [$^3$H]DALE | 0.5 nM | 0.6 nM | naltrexone (10 μM) | 60 min RT |
| kappa (KOP) (h) (agonist radioligand) | human recomb. (RBL cells) | [$^3$H]U69593 | 0.5 nM | 0.6 nM | naloxone (10 μM) | 60 min RT |
| μ (MOP) (h) (agonist radioligand) | human recomb. (HEK- 293 cells) | [$^3$H]DAMGO | 0.5 nM | 0.35 nM | naloxone (10 μM) | 120 min RT |
| 5-$HT_{1A}$ (h) (agonist radioligand) | human recomb. (HEK- 293 cells) | [$^3$H]8-OH-DPAT | 0.5 nM | 0.5 nM | 8-OH-DPAT (10 μM) | 60 min RT |
| 5-$HT_{1B}$ (h) (antagonist radioligand) | human recomb. (Chem-1 RBL cells) | [$^3$H]GR125743 | 1 nM | 0.8 nM | Serotonine (30 μM) | 60 min 37° C. |
| 5-$HT_{2A}$ (h) (agonist radioligand) | human recomb. (HEK-293 cells) | [$^{125}$I](±)DOI | 0.1 nM | 0.3 nM | (±)DOI (1 μM) | 60 min RT |
| 5-$HT_{2B}$ (h) (agonist radioligand) | human recomb. (CHO cells) | [$^{125}$I](±)DOI | 0.2 nM | 0.2 nM | (±)DOI (1 μM) | 60 min RT |
| 5-$HT_{2C}$ (h) (agonist radioligand) | human recomb. (HEK-293 cells) | [$^{125}$I](±)DOI | 0.1 nM | 0.9 nM | (±)DOI (10 μM) | 60 min 37° C. |
| GR (h) (agonist radioligand) | human endog. (IM-9 cells) | [$^3$H]dexamethasone | 1.5 nM | 1.5 nM | triamcinolone (10 μM) | 24 hr 4° C. |
| AR (h) (agonist radioligand) | human endog. (LNCaP cells) | [$^3$H]methyltrienolone | 1 nM | 0.8 nM | testosterone (1 μM) | 4 hr 22° C. |
| $V_{1a}$ (h) (agonist radioligand) | human recomb. (CHO cells) | [$^3$H]AVP | 0.3 nM | 0.5 nM | AVP (1 μM) | 60 min RT |
| ION CHANNELS | | | | | | |
| BZD (central) (agonist radioligand) | rat cerebral cortex | [$^3$H]flunitrazepam | 0.4 nM | 2.1 nM | diazepam (3 μM) | 60 min 4° C. |
| NMDA (antagonist radioligand) | rat cerebral cortex | [$^3$H]CGP 39653 | 5 nM | 23 nM | L-glutamate (100 μM) | 60 min 4° C. |
| 5-$HT_3$ (h) (antagonist radioligand) | human recomb. (CHO cells) | [$^3$H]BRL 43694 | 0.5 nM | 1.15 nM | MDL 72222 (10 μM) | 120 min RT |
| $Ca^{2+}$ channel (L, dihydropyridine site) (antag. radioligand) | rat cerebral cortex | [$^3$H]nitrendipine | 0.25 nM | 0.27 nM | nitrendipine (1 μM) | 90 min RT |
| Potassium Channel hERG (human) - [3H]Dofetilide | human recomb. (HEK- 293 cells) | [$^3$H]Dofetilide | 3 nM | 6.6 nM | Terfenadine (25 μM) | 60 min RT |
| $K_V$ channel (antag. radioligand) | rat cerebral cortex | [$^{125}$I]α-dendro-toxin | 0.01 nM | 0.04 nM | α-dendrotoxin (50 nM) | 60 min RT |
| $Na^+$ channel (site 2) (antag. radioligand) | rat cerebral cortex | [$^3$H]batracho-toxin | 10 nM | 31 nM | veratridine (300 μM) | 60 min 37° C. |
| TRANSPORTERS | | | | | | |
| NE transporter (h) (antag. radioligand) | human recomb. (CHO cells) | [$^3$H]nisoxetine | 1 nM | 2.9 nM | desipramine (1 μM) | 120 min 4° C. |
| DA transporter (h) (antag. radioligand) | human recomb. (CHO cells) | [$^3$H]BTCP | 4 nM | 4.5 nM | BTCP (10 μM) | 120 min 4° C. |
| 5-HT transporter (h) (antag. radioligand) | human recomb. (CHO cells) | [$^3$H]imipramine | 2 nM | 1.7 nM | imipramine (10 μM) | 60 min RT |
| OTHER ENZYMES | | | | | | |
| MAO-A (antagonist radioligand) | rat cerebral cortex | [$^3$H]Ro 41-1049 | 10 nM | 14 nM | clorgyline (1 μM) | 60 min 37° C. |

Methods—Enzyme and Uptake Assays: In vitro enzyme and uptake assays were conducted by Eurofins Discovery using human recombinant enzymes expressed in various mammalian and insect cell lines. Enzymatic activity was measured using appropriate substrates or tracers under conditions optimized for each target, as detailed in Table 7. Reactions were incubated at room temperature for a defined duration and terminated according to established protocols. The measured components (either enzymatic products or remaining substrate) were quantified using fluorimetry, photometry, scintillation counting, or LANCE technology, depending on the assay. Assay-specific parameters, including substrate identity, cell line source, incubation time, and detection method, are provided in Table 7.

All measurements were performed in technical replicates to ensure reproducibility and data quality.

Results were expressed both as a percentage of control-specific activity and as percent inhibition of control-specific activity. Percent activity was calculated as (measured specific activity/control specific activity)×100, and percent inhibition as 100−[(measured specific activity/control specific activity)×100], based on values obtained in the presence of test compounds. $IC_{50}$ and $EC_{50}$ values, along with Hill coefficients (nH), were determined by nonlinear regression analysis of inhibition or concentration-response curves generated from mean replicate values. Hill curve fitting was performed as previously described using software developed at Cerep and validated against SigmaPlot® 4.0 for Windows® (© 1997 by SPSS Inc.).

TABLE 7

Enzyme & Uptake Assay Conditions

| Assay | Source | Substrate/ Stimulus/Tracer | Incubation | Measured Component | Detection Method |
|---|---|---|---|---|---|
| COX1(h) | human recomb. (recombinant) | Arachidonic acid (3 μM) + ADHP (25 μM) | 3 min RT | Resorufin (oxidized ADHP) | Fluorimetry |
| COX2(h) | human recomb. (Sf9 cells) | arachidonic acid (1.2 μM) + ADHP (25 μM) | 5 min RT | Resorufin (oxidized ADHP) | Fluorimetry |
| PDE3A(h) | human recomb. (Sf21 cells) | [3H]cAMP + cAMP (0.5 μM) | 15 min RT | [3H]5'AMP | Scintillation counting |
| PDE4D2(h) | human recomb. (Sf9 cells) | [3H]cAMP + cAMP (0.5 μM) | 20 min RT | [3H]5'AMP | Scintillation counting |
| Lck kinase (h) | human recomb. (insect cells) | ATP + Uligh-Poly GAT[EAY(1:1:1)]n (25 nM) | 10 min RT | phospho-Ulight-Poly GAT[EAY(1:1:1)]n | LANCE |
| Acetylcholin-esterase (h) | human recomb. (HEK-293 cells) | Acetylcholine (400 μM) | 30 min RT | 5 thio 2 nitrobenzoic acid | Photometry |

Results: Radioligand binding data demonstrated that Compounds 4,8, and 116 exhibit high levels of specific binding at 5-$HT_{2A}$, 5-$HT_{2B}$, and 5-$HT_{2C}$ receptors, with greater than 95% inhibition of control-specific binding in each case. These results indicate strong target engagement at serotonin receptor subtypes relevant to central nervous system signaling. Additional profiling across a broad receptor panel showed comparatively lower levels of binding at muscarinic receptors, ion channels, and other off-target sites tested, as summarized in Table 8. The observed binding profile suggests a degree of receptor selectivity under the tested conditions.

Enzyme and uptake profiling further characterized the biochemical activity of the compounds. Each compound was assessed across a panel that included phosphodiesterases, cyclooxygenases, kinases, and key neurotransmitter transporters. Differential inhibition was observed among the compounds, with notable activity detected at specific phosphodiesterase isoforms. These findings (summarized in Table 9) provide additional support for the compounds' utility in modulating receptor and enzyme targets relevant to neurological and inflammatory signaling pathways.

TABLE 8

Target Binding Assays

| Radioligand Binding Assay | 2CB-5MM (Compound 4) | 2CiBu-5MM (Compound 8) | 2CiBu-20H-5MM (Compound 116) | 2CB-5ME (Comparator) |
|---|---|---|---|---|
| | Mean Percent Inhibition of Control Specific Binding | | | |
| $A_{2A}$(h) (agonist radioligand) | 12.2% | 1.1% | 11.0% | −21.3% |
| $alpha_{1A}$(h) (antagonist radioligand) | 29.4% | 7.6% | 51.6% | 33.6% |
| $alpha_{1D}$(h) (antagonist radioligand) | 9.5% | 0.5% | 11.8% | 10.0% |
| $alpha_{2A}$(h) (antagonist radioligand) | 80.2% | 88.5% | 79.4% | 73.0% |
| $beta_1$(h) (agonist radioligand) | 19% | 36.0% | 84.5% | 26.2% |
| $beta_2$(h) (antagonist radioligand) | 18.8% | 38.3% | 42.1% | 31.8% |
| BZD (central) (agonist radioligand) | −1.8% | 6.6% | 8.3% | −3.0% |
| $CB_2$(h) (agonist radioligand) | −14.9% | 17.8% | −6.0% | −22.8% |
| $CB_1$(h) (agonist radioligand) | −10.4% | −5.6% | −1.9% | 4.0% |
| $CCK_1$ ($CCK_A$) (h) (agonist radiolig.) | −11.5% | 12.2% | −0.1% | 3.3% |
| $D_1$(h) (antagonist radioligand) | 21.1% | −1.4% | 4.0% | 28.1% |
| $D_{2S}$(h) (agonist radioligand) | 89.4% | 12.9% | 46.6% | 83.0% |
| $ET_A$(h) (agonist radioligand) | −6.5% | −1.5% | −9.0% | −3.5% |
| NMDA (antagonist radioligand) | 4.7% | 12.0% | −24.3% | 3.5% |
| $H_1$(h) (antagonist radioligand) | 7.3% | 0.6% | 5.7% | 7.3% |
| $H_2$(h) (antagonist radioligand) | −14.7% | −16.5% | 12.5% | −0.6% |
| MAO-A (antagonist radioligand) | 9.3% | 4.1% | 7.0% | 5.4% |
| $M_1$(h) (antagonist radioligand) | 43.4% | 52.6% | 4.9% | 55.4% |
| $M_2$ (h) (antagonist radioligand) | 10.0% | 16.0% | 14.9% | 21.5% |
| $M_3$(h) (antagonist radioligand) | 29.2% | 31.8% | 10.6% | 47.9% |
| N neuronal alpha4beta2 (h) (agonist radioligand) | −0.1% | −2.6% | −10.0% | 7.4% |
| delta (DOP) (h) (agonist radiolig.) | 8.5% | 11.9% | 19.5% | 9.7% |
| kappa (h) (KOP) (agonist radiolig.) | 11.4% | 29.8% | 28.2% | 11.2% |
| μ (MOP) (h) (agonist radioligand) | 31.1% | 31.5% | 24.4% | 28.6% |
| 5-$HT_{1A}$(h) (agonist radioligand) | 95.1% | 76.5% | 34.8% | 98.2% |
| 5-$HT_{1B}$ (h) (antagonist radioligand) | 74.2% | 57.3% | 12.6% | 91.4% |

TABLE 8-continued

| Target Binding Assays | | | | |
|---|---|---|---|---|
| Radioligand Binding Assay | 2CB-5MM (Compound 4) | 2CiBu-5MM (Compound 8) | 2CiBu-20H-5MM (Compound 116) | 2CB-5ME (Comparator) |
| | Mean Percent Inhibition of Control Specific Binding | | | |
| 5-$HT_{2A}$(h) (agonist radioligand) | 98.9% | 96.6% | 97.6% | 98.8% |
| 5-$HT_{2B}$(h) (agonist radioligand) | 102.4% | 96.6% | 94.9% | 104.1% |
| 5-$HT_{2C}$(h) (agonist radioligand) | 99.3% | 97.2% | n.t. | 99.3% |
| 5-$HT_3$(h) (antagonist radioligand) | 11.6% | 2.6% | −3.9% | −1.6% |
| GR (h) (agonist radioligand) | −7.2% | −3.9% | −3.1% | −0.5% |
| AR(h) (agonist radioligand) | −9.2% | 3.0% | −9.9% | −7.7% |
| $V_{1a}$(h) (agonist radioligand) | 5.5% | 5.3% | 4.8% | 11.2% |
| $Ca^{2+}$ channel (L, dihydropyridine site) (antagonist radioligand) | 2.7% | −4.6% | 8.4% | 0.2% |
| Potassium Channel hERG(h) ([3H] Dofetilide) | 13.9% | 4.4% | 9.7% | 8.5% |
| $K_V$ channel (antagonist radiolig.) | 0.7% | −4.2% | 12.7% | −4.3% |
| Na+ channel (site 2) (antagonist radioligand) | 21.6% | 70.4% | 66% | 46.9% |
| norepinephrine transporter(h) (antagonist radioligand) | 0.2% | −5.4% | 17.4% | 11.4% |
| dopamine transporter(h) (antagonist radioligand) | 10.7% | 7.7% | 22.3% | 6.2% |
| 5-HT transporter (h) (antagonist radioligand) | −1.3% | 4.9% | 15.0% | 8.6% |

n.t. = not tested

*Sodium Channel Site2 (Non-selective) Rat Ion Channel Batrachotoxin Mass Spectr. Binding

TABLE 9

| Enzyme & Uptake Assays | | | | |
|---|---|---|---|---|
| Assay Type | 2CB-5MM (Compound 4) | 2CiBu-5MM (Compound 8) | 2CiBu-20H-5MM (Compound 116) | 2CB-5ME (Comparator) |
| | Mean Percent Inhibition of Control Specific Binding | | | |
| COX1(h) | 0.3% | 13.8% | −37.4% | −4.7% |
| COX2(h) | −8.0% | −7.0% | 10.2% | −10.4% |
| PDE3A (h) | 14.5% | 8.2% | 35.1% | −4.6% |
| PDE4D2 (h) | −0.5% | 3.0% | 67.4% | −5.7% |
| Lck kinase (h) | 5.9% | −6.6% | 12.8% | 23.3% |
| acetylcholinesterase (h) | −3.5% | 8.0% | 4.4% | −3.2% |

Example 10: In Vitro Permeability Assay

Purpose: The MDR1-MDCKII permeability assay is predictive of a compound's ability to cross biological barriers. Accordingly, an in vitro permeability assay was conducted to evaluate the ability of compounds to traverse cellular barriers that mimic physiological membranes, such as the blood brain barrier.

Methods: In vitro permeability studies were performed using confluent monolayers of MDR1-transfected Madin-Darby Canine Kidney (MDR1-MDCKII) cells cultured under standard conditions. Cells were seeded onto permeable supports and maintained until they formed tight monolayers suitable for bidirectional transport studies. The assay was conducted at 37° C. using Hanks' balanced salt solution (HBSS) adjusted to pH 7.4 on both the apical and basolateral sides. For apical-to-basolateral (A-B) permeability, samples were collected at 0 and 60 minutes, whereas for basolateral-to-apical (B-A) permeability, samples were collected at 0 and 40 minutes. The concentration of each compound in the donor and receiver chambers was determined by HPLC-MS/MS, and all results were expressed in terms of peak area.

The apparent permeability coefficient ($P_{app}$) for each compound was calculated using the formula:

$$P_{app}\ (\text{cm/s}) = (V_R \times C_{R,end})/(\Delta t \times A \times (C_{D,mid} - C_{R,mid}))$$

where $V_R$ was the volume of the receiver chamber, $C_{R,end}$ was the concentration of the compound in the receiver chamber at the final time point, At was the incubation time, and A was the surface area of the cell monolayer. The midpoint donor concentration ($C_{D,mid}$) was calculated as the average of the donor concentrations at time 0 and the end time point, while $C_{R,mid}$ was calculated as one-half of $C_a$R,end.

Compound recovery was also evaluated using the following formula:

$$\text{Recovery (\%)} = [(V_D \times C_{D,end}) + (V_R \times C_{R,end})]/(V_D \times C_{D0}) \times 100$$

where $V_D$ and $V_R$ were the volumes of the donor and receiver chambers, respectively, $C_{D,end}$ and $C_{R,end}$ were the compound concentrations at the final time point in their respective compartments, and $C_{D0}$ was the initial concentration in the donor chamber. Monolayer integrity was assessed following the permeability assay using fluorescein as a paracellular marker compound. Fluorescein was added to the apical chamber and sampled in the basolateral chamber after incubation. Monolayers with fluorescein $P_{app}$ values below $1.5\times10^{-6}$ cm/s were considered intact. Only data from wells that met this integrity threshold were included in the final analysis.

Results: Apical-to-basolateral (A-B) permeability, basolateral-to-apical (B-A) permeability, and percent recovery of compounds are provided in Table 10. Observed permeability profiles were consistent with those expected of compounds capable of traversing physiologically relevant barriers, including the blood-brain barrier.

TABLE 10

Permeability and Recovery of 2CB-5MM and 2CiBu-5MM and Reference Compound 2CB-5ME

| | 2CB-5MM (Compound 4) | 2CiBu-5MM (Compound 8) | 2CB-5ME (Comparator) |
|---|---|---|---|
| A-B Permeability ($10^{-6}$ cm/s) | 29.9 | 24.8 | 32.9 |
| A-B Percent Recovery | 78% | 76% | 75% |
| B-A Permeability ($10^{-6}$ cm/s) | 14.5 | 13.3 | 13.8 |
| B-A Percent Recovery | 83% | 79% | 79% |

The tested compounds exhibited greater A-B movement than the reverse, indicating facilitated transport or efficient passive diffusion in the A-B direction. B-A permeability of exemplary compounds was approximately half that of A-B permeability, suggesting that the compounds are not substrates for active efflux transporters, such as permeability glycoprotein (P-gp). The high percent recovery values observed support the stability of the test compounds and the validity of the permeability results.

Example 11: 2C-iBu-5MM Inhibits Airway Hyperresponsiveness in Allergic Mice

Purpose: Exemplary compound 2C-iBu-5MM (Compound 8) was evaluated for its ability to inhibit airway hyperresponsiveness (AHR) in a murine model of allergic asthma induced by ovalbumin (OVA). Prevention of AHR, which was quantified via whole-body plethysmography post-methacholine exposure, serves as a functional in vivo biomarker for anti-inflammatory efficacy.

Methods: Experiments were conducted in accordance with the methods of Flanagan et al., ACS Pharmacol Transl Sci. 2020 Aug. 13; 4(2):488-502 with modifications. Briefly, Balb/c mice were sensitized to OVA via IP injection. Mice were then exposed repeatedly to aerosolized OVA to induce acute allergic airway inflammation. Airway responsiveness was assessed using non-invasive whole-body plethysmography (WBP) and methacholine challenge. Lung tissue was analyzed to quantify inflammation and mucus production.

Mice were separated into three experimental groups: 1) Naive mice were not exposed to OVA sensitization and challenge, 2) OVA mice were sensitized and challenged with the allergen OVA to induce allergic airway inflammation and hyperresponsiveness, and 3) 0.5 mg/kg exemplary compound+OVA. The exemplary compound was administered to mice via intraperitoneal injection. Respiratory parameters were measured 48 hours after the final OVA exposure. Airway responsiveness to methacholine was measured using noninvasive whole-body plethysmography (WBP) in unrestrained mice.

Baseline PenH values were recorded for each experimental group, followed by exposure to aerosolized saline or increasing concentrations of methacholine, to assess the sensitivity and reactivity of airways due to its bronchoconstricting activity. PenH values were recorded, and data were analyzed using software. The PenH measurement estimates bronchoconstriction in unrestrained rodents during WBP. It is calculated from pressure signals related to the respiratory cycle, reflecting differences between the main and reference chambers. Experiments (Nau et al. Am J Physiol. Lung Cellular Mol Physiol. 2015; 308(2):L191-198; Flanagan et al. Life Sci. 2019; 236:116790; Hamelmann et al. Am. J. Respir. Crit. Care Med. 1997; 156:766-775; Djuric et al. Brain, Behav. Immun. 1998; 12(4):272-284) have shown PenH to be a reliable, sensitive measure of bronchoconstriction and a superior measure in assessing the degree of broncho-constriction compared to other derived parameters such as box pressure or box flow (e.g., Djuric et al., op cit.).

Figure 3:
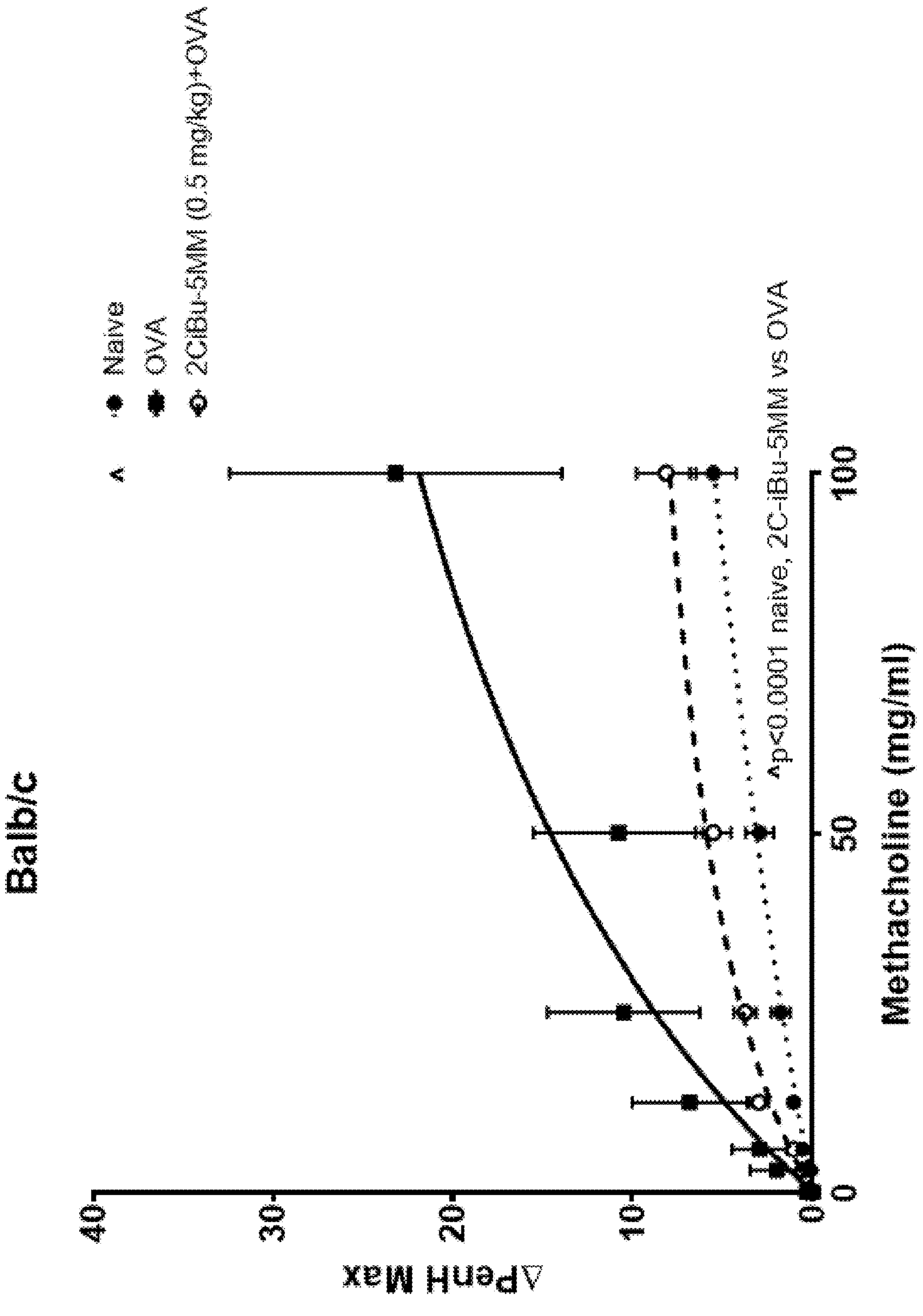
FIG. 3 shows a dose response curve of response of PenH, a measure of airway resistance, to increasing methacholine concentrations in naive mice, mice exposed to ovalbumin (OVA), and mice treated with 0.5 mg/kg exemplary compound 2C-iBu-5MM (Compound 8) and OVA, as described in Example 11.

Results: FIG. 3 shows the relationship between maximum enhanced pause (ΔPenH) at increasing levels of methacholine for each experimental group. Higher PenH values indicate greater airway obstruction or hyperresponsiveness. The highest PenH values were detected from the OVA group, indicating increased airway constriction in response to methacholine. In contrast, the lowest delta PenH values were measured from the naive group, indicative of relatively reduced inflammation and hyperresponsivity. Surprisingly, treatment with 2C-iBu-5MM mitigated the hyperresponsivity associated with OVA exposure. Mice treated with the exemplary compound exhibiting PenH values comparable to that of naive mice. Inhibition of PenH is considered a proxy to anti-inflammatory effects due to its correlation with asthma pathophysiology, e.g., reduced eosinophil infiltration, Th2 cytokine production, and airway remodeling. Whereas exaggerated bronchoconstriction was observed in the OVA group, treatment with compound 2C-iBu-5MM reduced PenH values to levels representative of normal airway function, indicating its potent anti-inflammatory effects.

Example 12: Assessment of HTR in Mice Administered Exemplary Compounds of the Disclosure Purpose: The mouse head-twitch response (HTR) is a behavioral test that reflects $5\text{-HT}_{2A}R$ activation and is predictive of human psychedelic effects (Halberstadt et al. *J Psychopharmacol.* 2011; 25(11):1548-1561). HTR is widely used as a behavioral surrogate for such effects as it can reliably distinguish psychedelic and non-psychedelic $5\text{-HT}_{2A}R$ agonists (Halberst. & Geyer, *Psychopharmacol* (*Berl*). 2013; 227(4):727-3).

Methods: HTR assays were performed in accordance with the methods described in Klein et al., *Neuropharmacol,* 2018; 142:231-239, with modifications, to assess HTRs and motor activity in male C57BL/6J mice treated with exemplary compounds of the disclosure. Test compounds: Exemplary compounds were dissolved in saline (0.9% NaCl) and administered in doses ranging from 0 to 30 mg/kg (mpk) intraperitoneally (i.p.) in 5 ul of vehicle per g of animal mass. R-DOI ((−)-R-2,5-dimethoxy-4-iodo-amphetamine) was used as positive control in the same vehicle and route of administration. Animals: C57BL/6J males were sourced from JAXS farms and maintained in a hygienic environment with controlled temperature and humidity in 12-hour light/dark cycles. Animals were provided free access to food and water except during testing.

Upon arrival at the vivarium, all animals were installed with magnetic ear tags bilaterally as previously described by de la Fuente et al., *J Neurosci Methods.* 2020 Jan. 16; 334:108595. Animals were allowed to acclimate to the tags for an additional week prior to initiating testing. For testing, each animal was placed individually in a cylinder with a magnetometer for acclimation during each session. After 30 min, either an exemplary compound or a vehicle control was administered to the animals, which were then returned to the magnetometer for an additional 60 min. Both periods (pre and post-article administration) were recorded. Tested exemplary compounds and their corresponding doses are provided in Table 11.

TABLE 11

Dosing Schedule for Exemplary Compounds in HTR Assays

| Exemplary Compound | Tested Doses | Group Size |
|---|---|---|
| 2CB-5MM (Compound 4) | 0, 0.03, 0.3, 1, 3, 10, 30 mpk | n = 6 per dose |
| 2CiBu-5MM (Compound 8) | 0, 0.3, 1, 3, 10, 30 mpk | |
| 2CiBu-20H-5MM (Compound 116) | 0, 0.03, 0.3, 1, 3, 10, 30 mpk | |
| 2C-iBu | 0, 0.1, 0.3, 1, 3, 10 mpk | |

Data Acquisition & Processing: Recording of changes in voltage signal in response to mouse head movement was performed in non-overlapping ~500-turn enameled wire (30 AWG) coils supported in closed plastic containers (inner dimensions, 11 cm diameter×14 cm tall) with both terminals of each coil connected to a phono preamplifier (Pyle PP444) as previously described by de la Fuente Revenga et al., *Sci Rep* 2019 Oct. 3; 9(1):14247. The amplified signal output was recorded at a 1000 Hz sampling rate using a NI USB-6001 (National Instruments) data acquisition system controlled through MATLAB (Mathworks, R2020a version, with NI myDAQ support package). The analog input range for each channel was ±10 V with an ADC (analog-digital conversion) of 16 bits. Raw signals were bandpass-filtered (70-110 Hz FIR filter). Filtered signals were rectified (absolute value×2), baseline-subtracted, and smoothed with a moving average.

Potential HTR events were identified as maxima in the processed signal, as described by de la Fuente et al., op cit. For spectral validation, unfiltered data segments (±2× event width around peaks) underwent spectral analysis. Events were confirmed as HTRs if they met: (1) maximum in the 70-110 Hz band of the spectrum exceeding a power threshold value of 0.005V2/Hz; (2) cumulative sum of all power values in the 70-110 Hz band in excess of 0.05 V2/Hz; (3) frequency corresponding to the absolute maximum within the operative frequency range of the spectrum >35 Hz; and (4) sum of zero-crossings of the derivative of the spectrum density <40(between 5-200 Hz). Regarding quality control, events were cross-validated with wavelet analysis (Halberstadt, 2020). Any discrepancies were visually inspected and corrected.

To quantify motor activity, baseline (smoothed vs. recorded) differences were binned. Activity was calculated as the area under the curve (AUC) of the baseline-corrected |V| signal, excluding confirmed HTR events. HTR and activity data for the 30 min preceding and the 60 min following administration were binned in 15 min fractions for representation of time-dependent effects. The sum of the first 30 min post-article administration was employed to analyze dose-dependence. Statistical analysis included one-way ANOVA w/Dunnett's post hoc correction for multiple comparisons and twotailed Student's t-test. $ED_{50}$ and $ID_{50}$ were estimated using non-linear regression in Prism 12.0 (GraphPad Software, San Diego, CA, USA). Inverted U-shape dose-responses were fitted to a third order polynomial equation for visualization purposes.

Figure 4A:
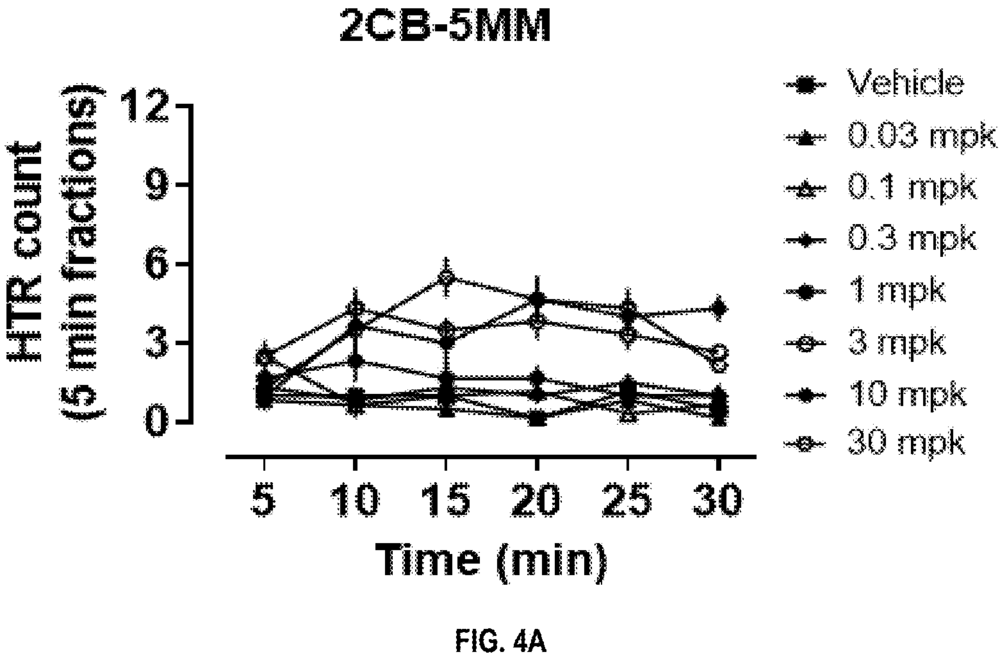
FIG. 4A shows the HTR count (5 min fractions) of exemplary compound 2CB-5MM at 0.03, 0.1, 0.3, 1, 3, 10, and 30 milligram per kilogram (mpk) over 30 minutes, as described in Example 12.
Figure 4B:
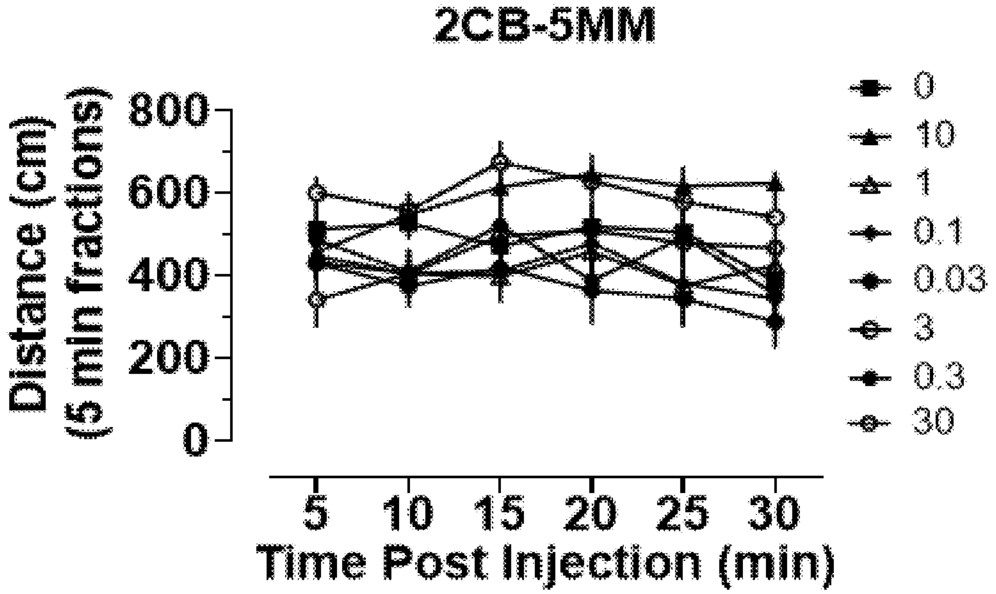
FIG. 4B shows the distance traveled (cm) induced by exemplary compound 2CB-5MM at 0.03, 0.1, 0.3, 1, 3, 10, and 30 mpk over 30 minutes, as described in Example 12.
Figure 5A:
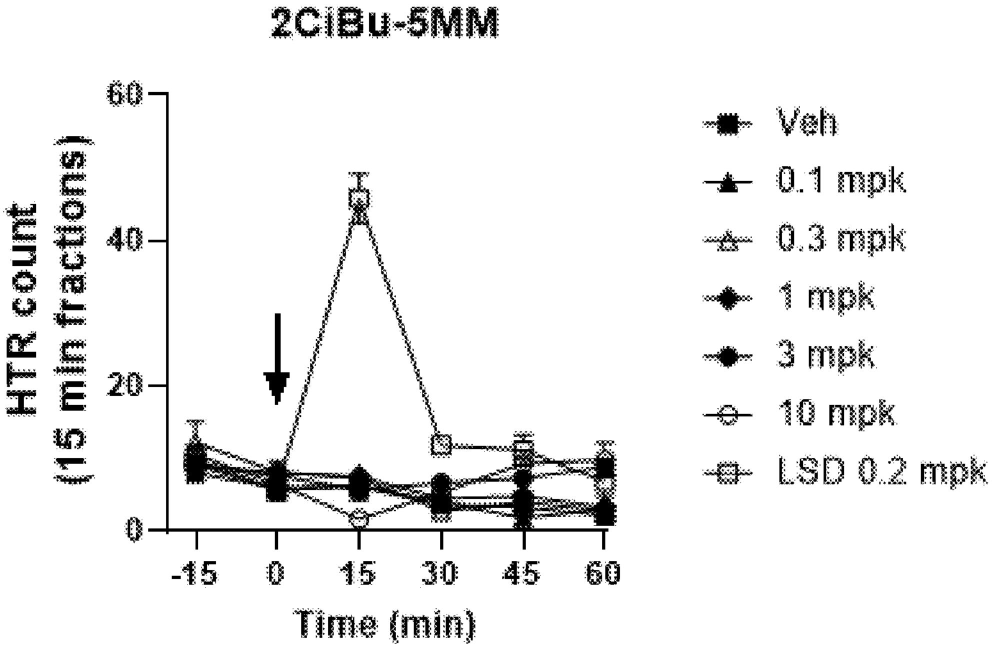
FIG. 5A shows the HTR count (15 min fractions) of exemplary compound 2CiBu-5MM at 0.1, 0.3, 1, 3, and 10 milligram per kilogram (mpk) and positive control LSD over 60 minutes, as described in Example 12.
Figure 5B:
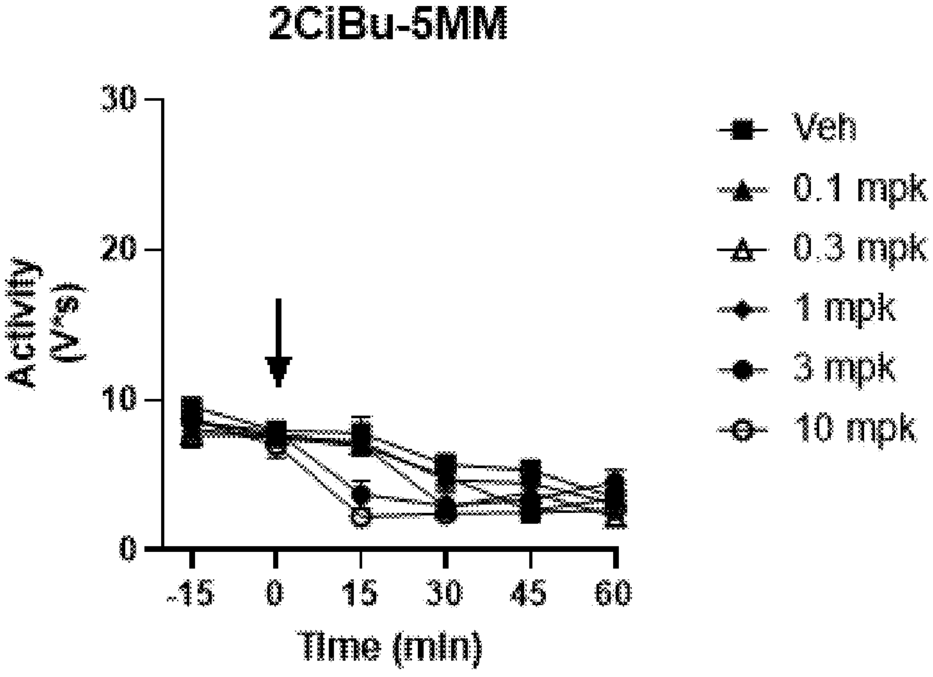
FIG. 5B shows the activity in volt-seconds (V*s over 30 minutes) of exemplary compound 2CiBu-5MM at 0.1, 0.3, 1, 3, and 10 mpk, as described in Example 12.

Results: None of the tested exemplary compounds (2CB-5MM, 2CiBu-5MM, and 2CiBu-2OH-5MM) produced meaningful or statistically significant changes in HTR, which refers to the discrete number of head twitch events observed within a defined period. Exemplary compound 2CB-5MM did not elicit a significant HTR at any tested dose, as shown by FIG. 4A. Distance traveled induced by 2CB-5MM remained consistent across doses, as shown in FIG. 4B. Distance traveled (cm) reflects gross locomotor activity, such as ambulation and exploration, and was measured in parallel to confirm that observed HTR changes are not confounded by sedation, hyperactivity, or non-specific motor effects. At the maximum tested dose of 30 mpk, 2CiBu-5MM (Compound 8) induced a subtle suppression of HTR during the first 15 min followed by a rebound in HTR counts during the last 30 min segment (FIG. 5A). An $EC_{50}$ of 5.926 mpk was calculated for 2CiBu-5MM based on HTR counts summed over a 30-60 min interval. Regarding dynamic behavioral activity, 2CiBu-5MM produced a statistically significant suppression of motor activity at the two highest doses tested of 10 and 30 mpk, as shown in FIG. 5B. However, motor activity returned to baseline by the end of the recording session, as reflected by a flattened curve over 60 min and an estimated $ID_{50}$>3 mpk (data not shown).

Figure 6A:
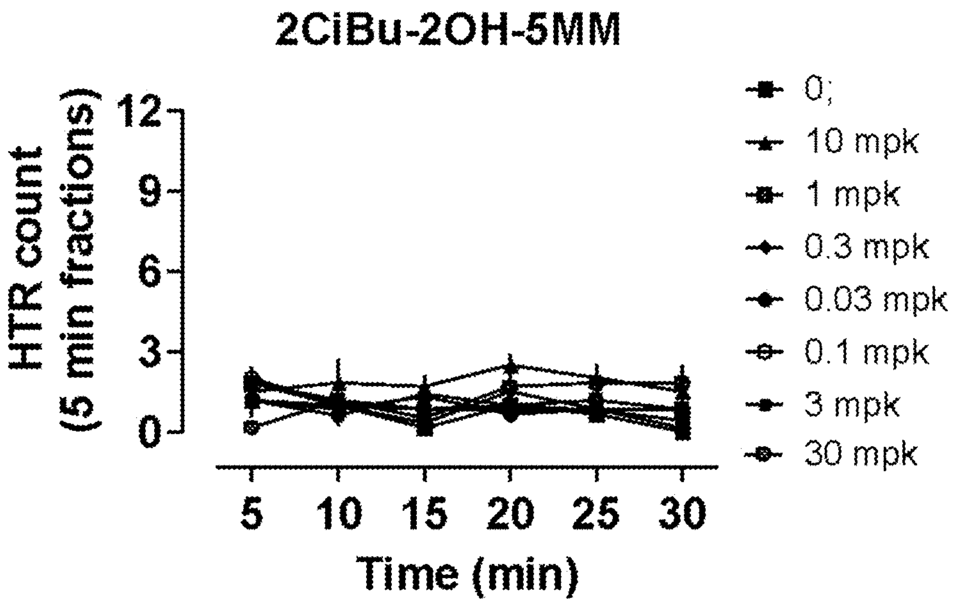
FIG. 6A shows the HTR count (5 min fractions) of exemplary compound 2CiBu-2OH-5MM at 0.03, 0.1, 0.3, 1, 3, 10, and 30 mpk over 30 minutes, as described in Example 12.
Figure 6B:
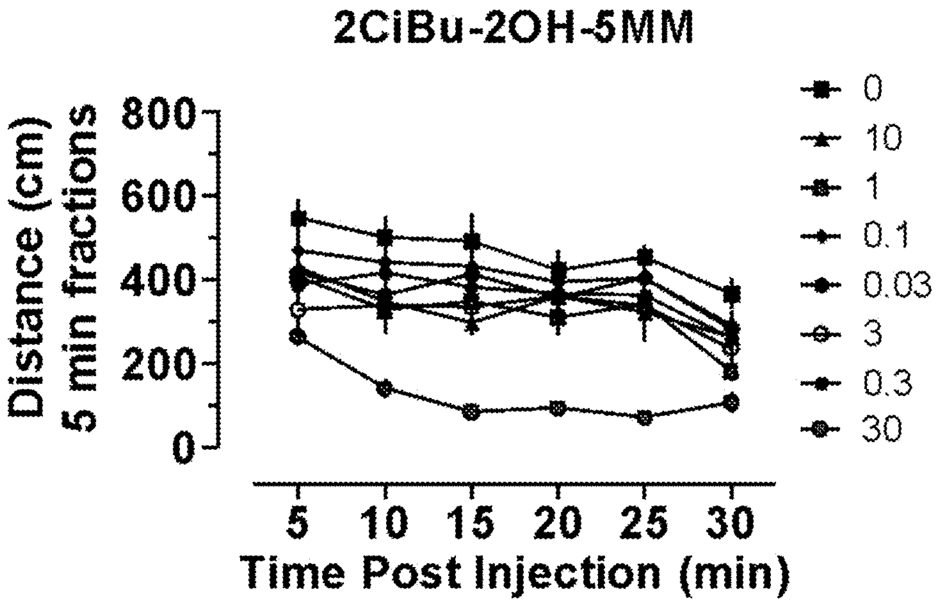
FIG. 6B shows the distance traveled (cm) induced by exemplary compound 2CiBu-2OH-5MM at 0.03, 0.1, 0.3, 1, 3, 10, and 30 mpk over 30 minutes, as described in Example 12.

Exemplary compound 2CiBu-2OH-5MM did not produce meaningful HTR across the tested dose range (0.0-30 mpk), as shown by FIG. 6A. 2CiBu-5MM HTR counts remained near baseline throughout the observation period. Distance traveled induced by 2CiBu-2OH-5MM remained consistent across doses. The highest tested dose (30 mpk) resulted in an overall reduction of locomotor activity, as shown in FIG. 6B.

Figure 7:
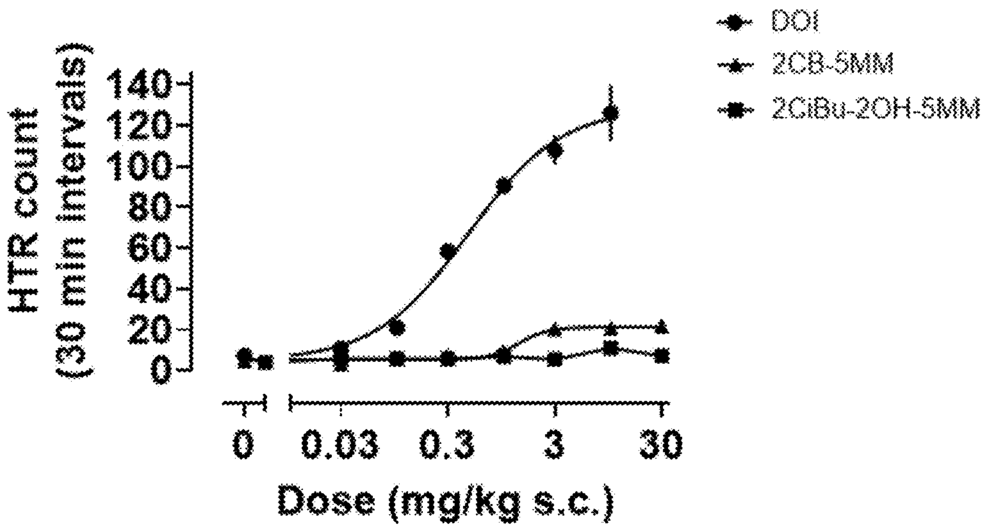
FIG. 7 shows the HTR count (30 min intervals) of exemplary compounds (2CB-5MM and 2CiBu-2OH-5MM) and positive control DOI at 0.03, 0.3, 3, and 30 mpk.
Figure 8A:
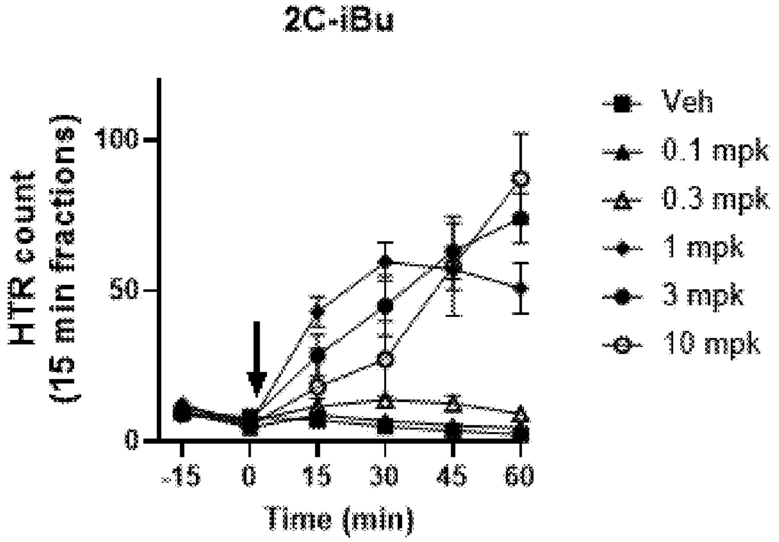
FIG. 8A shows the HTR count (15 min fractions) of reference compound 2C-iBu at 0.1, 0.3, 1, 3, and 10 mpk over 60 minutes, as described in Example 12.
Figure 8B:
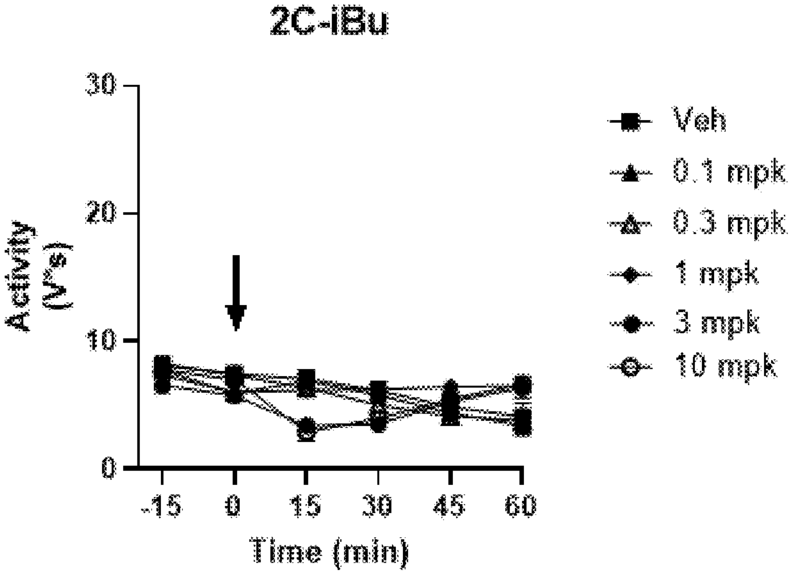
FIG. 8B shows the activity in volt-seconds (V*s) of reference compound 2C-iBu at 0.1, 0.3, 1, 3, and 10 mpk over 60 minutes, as described in Example 12.

FIG. 7 shows a comparative view of exemplary compounds 2CB-5MM and 2CiBu-2OH-5MM against positive control R-DOI. In contrast to the exemplary compounds, R-DOI induced HTR that gradually increased over time. The positive control's effect on HTR was matched with an increase in motor activity (data not shown). Reference compound 2C-iBu produced clear HTR time-course and inverted U-shape dose-response patterns with an $ED_{50}$ estimated at 0.42 mpk. Specifically, FIG. 8A illustrates the time-course of HTR counts over 60 minutes, showing dose-dependent increases peaking at intermediate doses. The doses of 1 and 3 mpk reached statistical significance whereas the highest dose tested of 10 mpk did not. This may be attributable to a delay on the peak of HTR at higher doses. 2C-iBu produced a modest but statistically significant effect on motor suppression at the doses of 3 and 10 mpk during the first 30 min post administration with an apparent return to baseline thereafter (FIG. 8B). The $ID_{50}$ was estimated at 2 mpk. 2C-iBu elicited a strong HTR effect at sub-mg doses, with a peak at 3 mpk and declining response at higher concentrations.

Reference compound 2CB-5ME did not produce statistically significant changes in HTR in the dose-response analysis. Unlike other HTR negative compounds, 2CB-5ME did not produce any level of HTR suppression at any of the tested doses. The compound did produce a very mild non-significant increase in activity at 3 mpk followed by a sharp decline with motor suppression reaching statistical significance at 30 mpk (data not shown). Accordingly, 2CB-5ME was inert with respect to both inducing and suppressing HTR, and 2CB-5ME may not interact with $5\text{-}HT_{2A}R$ or associated pathways in a way that affects HTR expression.

Tested compounds included both HTR positive and HTR negative representatives. Among the HTR negative compounds, 2CiBu-5MM (Compound 8) had an overall neutral effect compared to vehicle HTR occurrences, whereas reference compound 2C-iBu induced HTR activity. Classification as either HTR positive (compound induced HTR) and HTR negative (compound did not induce HTR) provides an in vivo correlate for serotonin receptor engagement and predicted psychedelic activity.

Considering certain arguable structural similarities between exemplary compounds and comparator compounds, such as 2C-iBu, HTR negative characterization is surprising in view of the comparators' potent HTR inducing effects. Characterization as HTR negative renders exemplary compounds less likely to trigger acute behavioral disturbances or psychotomimetic reactions. HTR negative compounds lack psychedelic liability, facilitating access for a wider treatment population. HTR negative compounds may be suitable for chronic, long-term administration in sensitive subject populations, including to avoid perceptual disturbances.

Example 13: Assessment of Ocular Inflammation Following Application of Compounds Purpose: Ocular inflammation and uveitis encompass potentially sight-threatening diseases with local and systemic etiologies. Cytokines, e.g. IL-6 (Ghasemi. *Ocul Immunol Inflamm.* 2018; 26(1): 37-50) and IL-8 (Ghasemi et al. *Ocul Immunol Inflamm.* 2011; 19(6): 401-412), and neuropeptides, e.g., substance P (Bignami et al. *Curr Drug Targets.* 2016; 17(11): 1265-1274), can contribute to ocular inflammation.

Methods: Ocular inflammation is assessed according to known methods with modifications. For example, ocular inflammation can be assessed in induced models of uveitis (see, e.g., PCT Pub. No. WO2015/074137A1, which describes an endotoxin-induced model in Example 1 and an LPS-induced model in Example 2), a chemical cauterization model of corneal inflammation (see, e.g., Example 4 of WO2015/074137A1), or in human subjects at risk of experiencing or currently experiencing such inflammation.

Results: Application of a compound, such as topical application, can prevent and/or reduce ocular inflammation. Reductions in ocular inflammation may lead to improvements in symptomatology associated with ocular inflammation, including but not limited to eye redness, pain, and alterations in sight, e.g., blurred vision.

Example 14: In Vivo Model for Assessing Atopic Dermatitis Following Application Purpose: Atopic dermatitis, or eczema, is characterized by chronic inflammation, and can result in inflammatory symptoms such as irritation of the skin. In some embodiments, disclosed compounds and compositions are useful for treating atopic dermatitis. The purpose of this study is to assess the therapeutic effects (e.g., inhibiting and/or reducing the various end-points associated with atopic dermatitis) of disclosed compounds in a mouse in vivo model of atopic dermatitis. The model for this study uses the flaky tail mouse strain, which carries a mutation in the gene for the epidermal protein filaggrin, which is comparable to the mutation underlying human atopic dermatitis or eczema (Fallon et al. *Nat Genetics.* 2009; 41: 602-608). Challenging these mice with topically applied ovalbumin results in a condition resembling atopic dermatitis. Mice typically exhibit eczema and increased skin levels of inflammatory biomarkers following ovalbumin application. Exemplary measures of efficacy include skin flakiness, skin levels of Type 2 helper T-cell (Th2) and cytokines, such as IL4, IL5 and IL10.

Methods: The protocol for application of ovalbumin to the skin of flaky tail mice is described in the literature (op cit.). In brief, abdomens of 3-5 week old mice are shaved 24 hours prior to cutaneous application of ovalbumin suspensions (50 pg in 50 μL PBS), which are applied to the abdomen as described previously.

There are two experimental groups: in the first, mice are pretreated with test compound prior to and during the application of ovalbumin to study the effects of preventing and inhibiting the development of atopic dermatitis. In the second group, mice are treated with test compound following 4-5 weeks of ovalbumin treatment (after atopic dermatitis symptoms have appeared) to study the effects of the compound in treating the symptoms. For each test compound, the compound is administered (e.g., IV, IM, IP, oral gavage) at several doses to study dose dependent effects. Following each experiment, mice are euthanized and skin punch biopsy specimens from each abdomen are harvested, snap frozen in liquid nitrogen, and homogenized with HTAB buffer. Samples are centrifuged, and supernatants are subjected to cytokine profiling by ELISA for the levels of biomarkers (e.g., Th2, IL4, IL5, and IL10) using protein standards for quantification.

Results: Results are expected to show that administration of a disclosed compound or composition prevents, inhibitors, and/or treats the symptoms atopic dermatitis.

Example 15: In Vivo Model for Assessing Intraocular Pressure Following Application Purpose: High intraocular pressure (IOP) is a significant risk factor and/or symptom of various ophthalmic diseases and disorders (e.g., glaucoma) and ocular pathologies. The purpose of this protocol is to assess the effects of administering a disclosed compound on intraocular pressure in an in vivo rat model.

Methods: To evaluate the IOP following a single or repeat dose of test article via topical ocular administration in male Brown Norway rats, the test compound will be administered directly to the ocular surface of both eyes using a calibrated positive displacement pipette. Baseline and subsequent IOP measurements will be completed using the TonoLab Rebound Tonometer. IOP measurements will be completed while the animal is fully awake. Three sets of 6 IOP measurements are recorded and averaged for each eye. Animals will receive a "loading dose" series of three administrations (10 μL of a solution of test compound per administration) over a 10-minute period, i.e., 10 μL every 2-3 minutes.

Results: Results may show that administration of a disclosed compound results in a reduction of IOP, which can indicate utility in treating ophthalmic diseases and disorders associated with elevated IOP.

Example 16: In Vitro Metabolic Stability

Purpose: The purpose of this study is to assess the metabolic stability of compounds in vitro. The liver is a major site of drug metabolism in the body, and liver microsomes, hepatocytes, and liver S9 fractions can be used to determine the in vitro intrinsic clearance of a compound (see, e.g., Ackley et al., Metabolic Stability Assessed by Liver Microsomes and Hepatocytes. In Yan & Caldwell (eds) Optimization in Drug Discovery. Methods Pharmacol Toxicol. Humana Press, and Richardson et al. Drug Metab Lett. 2016; 10(2): 83-90).

Methods: A liver microsomal stability assay is performed according to available methods, e.g., in accordance with the methods described in U.S. Pub. No. 2008/0045588 with modifications. Briefly, the assay is conducted at 1 mg/mL liver microsome protein with an NADPH-generating system in 2% $NaHCO_3$ (2.2 mM NADPH, 25.6 mM glucose 6-phosphate (G6P), 6 units per mL G6P dehydrogenase and 3.3 mM MgCl2). Test compounds are prepared as solutions in 20% acetonitrile-water and added to the assay mixture (final assay conc. of 5 μg/mL) and incubated at 37° C. Final concentration of acetonitrile should be <1%. Aliquots (50 μL) are taken out at 0, 15, 30, 45, and 60 min, and diluted with ice cold acetonitrile (200 μL) to stop the reactions. Samples are centrifuged at 12,000 RPM for 10 min to precipitate proteins. Supernatants are transferred to microcentrifuge tubes and stored for LC/MS/MS analysis of the degradation half-life of the test compounds.

Results: Results show a measurement of the in vitro intrinsic clearance of disclosed compounds. Such data provides a prediction of the metabolic stability and clearance of the compounds.

Example 17: Effects of Disclosed Compounds on Promoting Neurogenesis and Neuroplasticity Purpose: The effects of disclosed compounds on neurogenesis and neuroplasticity are measured in an in vitro dendritogenesis assay, an in vivo spinogenesis assay, and an ex vivo neuroplasticity assay.

Methods (In Vitro Dendritoqenesis Assay): Neurons are plated in 96-well format at a density of approximately 15,000 cells/well in wells containing 1% penicillin-streptomycin, 10% heat-inactivated fetal bovine serum, and 0.5 mM glutamine. After 24 h, the medium is replaced with Neurobasal containing B27 supplement, 1% penicillin-streptomycin, 0.5 mM glutamine, and 12.5 μM glutamate. After 3 days in vitro, the cells are treated with test compounds. Stock solutions of the compounds in DMSO are first diluted 100-fold in Neurobasal before an additional 10-fold dilution into each well (total dilution=1:1000; 0.1% DMSO concentration). Treatments are randomized. After 1 h, the media is removed and replaced with new Neurobasal media containing B27 supplement, 1% penicillin-streptomycin, 0.5 mM glutamine, and 12.5 μM glutamate. The cells grow for an additional 72 h. At that time, neurons are fixed by removing 80% of the media and replacing it with a volume of 4% aqueous paraformaldehyde equal to 50% of the working volume of the well. Then, the cells are incubated at room temperature for 20 min before the fixative is aspirated and each well washed twice with DPBS. Cells are permeabilized using 0.2% Triton X-100 in DPBS for 20 minutes at room temperature without shaking. Plates are blocked with antibody diluting buffer (ADB) containing 2% bovine serum albumin (BSA) in DPBS for 1 h at room temperature. Then, plates are incubated overnight at 4° C. with gentle shaking in ADB containing a chicken anti-MAP2 antibody (1:10, 000; EnCor, CPCA-MAP2). The next day, plates are washed three times with DPBS and once with 2% ADB in DPBS. Plates are incubated for 1 h at room temperature in ADB containing an anti-chicken IgG secondary antibody conjugated to Alexa Fluor 488 (1:500) and washed five times with DPBS. After the final wash, 100 μL of DPBS is added per well.

The wells are then imaged and analyzed. Plate controls (both positive and negative) are used to ensure that the assay is working properly as well as to visually determine appropriate numerical values for brightness/contrast and thresholding to be applied universally to the remainder of the randomized images.

Next, the brightness/contrast settings are applied, and approximately 1-2 individual pyramidal-like neurons per image (i.e., no bipolar neurons) that do not overlap extensively with other cells or extend far beyond the field of view are selected for analysis. All images are taken and analyzed by an experimenter blinded to treatment conditions. The number of crossings for each neuron at each distinct radius is averaged to produce an average Sholl plot for each treatment. For each treatment, neurons are selected from at least 6 wells spread across 2 plates (9 sites/well×3 wells/plate×2 plates).

Methods (In Vivo Spinogenesis Assay): Female C57BL/6J mice are treated with VEH (saline) or a disclosed compound (n=3/group). After 24 h, the animals are sacrificed via transcardial perfusion with oxygenated Ringer's solution, followed by a fixative (2% paraformaldehyde, 2.5% glutaraldehyde, 3 mM calcium chloride in 0.1 M cacodylate buffer). Brains are carefully removed from the skull and post-fixed overnight in the same fixative. Brains are then rinsed with PBS and 100 μm coronal sections spanning the prefrontal cortex are collected using a vibrating microtome. Regions of the infralimbic cortex are microdissected according to the Allen Brain Atlas (Lein et al. *Nature*. 2007; 445:168-176) and processed further for electron microscopy. Samples are then stained with buffered 1.5% reduced osmium tetroxide for 45 minutes, rinsed thoroughly, further stained with 1% aqueous uranyl acetate overnight at 4° C., dehydrated and embedded in Eponate 12™ epoxy resin.

A blockface that spans from the medical cortical surface to the corpus callosum is then trimmed and 150-250 serial ultrathin sections (55 nm) are collected onto silicon chips using diamond knives (Diatome) on an ultramicrotome. Serial sections on silicon chips are loaded into a scanning electron microscope for imaging. The apical tuft region is identified, and a series of images are collected from a region of interest identified on consecutive sections. Following image alignment, the datasets for each animal constitute volumes of at least 20×20×10 μm in dimension with voxel sizes of 8×8×55 nm. Cross sections of eight random dendrites are samples for the central section of each volume. Skeletons of the dendritic centerline and dendritic spines are traced by human experts. Dendritic spine densities (spines/micron) are calculated for each volume).

Methods (Ex Vivo Neuroplasticity Assay): This assay is conducted according to known procedures (see, e.g., Olson D E. J Exp Neurosci. 2018; 12:1179069518800508; Ly et al. *Cell Rep*. 2018; 23:3170-3182; and references therein). In brief, primary cortical neurons are prepared from timed pregnant wild-type C57BL/6JRccHsd mice at E18. Animals are sacrificed and embryos are dissected in Calcium and Magnesium free Hanks Balanced Salt Solution (CMF-HBSS) containing 15 mM HEPES and 10 mM $NaHCO_3$, pH 7.2. Embryos are decapitated, skin and skull gently removed and hemispheres are separated. After removing meninges and brain stem, the hippocampi are isolated, chopped with a sterile razor blade in Chop solution (Hibernate-E without Calcium containing 2% B-27) and digested in 2 mg/mL papain dissolved in Hibernate-E without Calcium for 30 minutes (±5 min) at 30° C. Hippocampi are triturated 10-15 times with a fire-polished silanized Pasteur pipette in Hibernate-E without Calcium containing 2% B-27, 0.01% DNase, 1 mg/mL BSA, and 1 mg/mL Ovomucoid Inhibitor. Undispersed pieces are allowed to settle by gravity for 1 min and the supernatant is centrifuged for 3 min at 228 g. The pellet is resuspended in Hibernate-E containing 2% B-27, 0.01% DNaseI, 1 mg/ml BSA, 1 mg/mL Ovomucoid Inhibitor and diluted with Hibernate-E containing 2% B-27. After the second centrifugation step (3 min at 228 g), the pellet is resuspended in nutrition medium (Neurobasal, 2% B-27, 0.5 mM glutamine, 1% Penicillin-Streptomycin).

Cells are counted in a hemacytometer and seeded in nutrition medium on poly-D-lysine pre-coated 96-well plates at a density of $2.6\times10^4$ cells/well. Cells are cultured at 37° C.; 95% humidity and 5% $CO_2$. All wells are handled the same way. The experiment is performed in adequate technical replicates for all groups.

On the day of preparation, mouse cortical neurons are seeded on poly-D-lysine pre-coated 96-well plates at a density of $2.6\times10^4$ cells per well. One day later, cells are treated with test compounds for three different time points (4 h, 8 h and 24 h), followed by a complete medium change. Additionally, cells are treated with 40 ng/mL of a positive control (Fibroblast Growth Factor, FGF) or vehicle control (VC) for 48 h. The experiment is carried out with several technical replicates per condition, and vehicle-treated cells as control.

Treated primary neurons are fixed on day 4 by addition of equal volume 4% paraformaldehyde (PFA) to the medium at room temperature (RT) for 30 minutes. Cells are rinsed two times with PBS and are permeabilized with 0.1% Triton X-100 in PBS for 30 minutes at RT. Next, cells are blocked for 90 min at RT with 20% horse serum, 0.1% Triton X-100 in PBS. Then, samples are incubated with the primary antibody against Beta Tubulin Isotype III at 4° C. overnight. The next day, the cells are further incubated for another 30 min at RT. After three washing steps with PBS, cells are incubated with a fluorescently labeled secondary antibody and DAPI (nucleus) for 1.5 hours at RT in the darkness. Cells are again rinsed four times with PBS and then imaged. From each well, images are taken at 10× magnification. Digital images from cortical neurons are analyzed using a software-supported automatic quantification method to measure the number of neurites, number of branches, total length of neurites and length of the longest neurite. Basic statistical analysis is performed. If appropriate, data are presented as mean±standard error of mean (SEM) and group differences are evaluated by e.g. one or two-way ANOVA or T-test. $EC_5O$ may be calculated as described elsewhere.

Results: Results are expected to show that administration of disclosed compounds increase dendritogenesis, spinogenesis, and/or neuroplasticity.

Example 18: Optic Nerve Crush Assay

The purpose of this study is to test disclosed compounds for potential neuroprotective effects in an optic nerve crush (ONC) model in rats. Animals will receive prophylactic dosing of the compounds (and optionally, one or more comparator compounds) 3 days prior to injury induction. Animals will undergo optical coherence tomography (OCT) exams starting at baseline, and again 7, 14, and 21 days after injury.

OCT will be used to measure the retinal nerve fiber layer (RNFL), inner plexiform layer (IPL), and total retinal thickness using a 9×9 spider plot. Animals will also undergo pupillary light reflex testing daily for up to 5 days post procedure and prior to anesthesia for OCT. At the conclusion of the study, whole eye samples will be collected and will undergo immunofluorescent staining using Brn3a and RBPMS to stain for retinal ganglion cells (RGCs) and counterstained with DAPI. From these, RGC loss will be calculated.

| Group ID | Model | Treatment | Dose | Route - Freq | Qty |
|---|---|---|---|---|---|
| 1 | ONC | TA 1 - Topical | TBD | Topical - BID | 8 |
| 2 | | TA 2 - Topical | TBD | Topical - BID | 8 |
| 3 | | TA 3 - IV* | TBD | IV - SID | 8 |
| 4 | | Vehicle - Topical | Vol. Matched | Topical - BID | 4 |
| 5 | N/A | Naive | N/A | N/A | 4 |
| Spares | TBD | TBD | TBD | TBD | 4 |
| | | TOTAL | | | 36 |

*IV dosing may be adjusted to IP if daily dosing is required, dependent on frequency needed and vet consult.

Results are expected to show that administration of disclosed compounds demonstrate protective effects, as determined by retinal ganglion cell counts, and other measures described herein.

NUMBERED EMBODIMENTS OF THE DISCLOSURE

Notwithstanding the appended claims, and among the other various exemplary and non-limiting aspects and embodiments described herein, are also the following numbered embodiments.

Embodiment 1. A compound of Formula (1) herein, wherein: $R^2$ is H or $C_1$-$C_6$ alkyl; $R^4$ is H, F, Cl, Br, I, CN, $NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkylthio, $C_1$-$C_6$ alkylthio, $C_3$-$C_6$ cycloalkylmethyl, or $-(CH_2)_{0-3}-C(O)-O-C_1$-$C_6$ alkyl; $R^5$ is H or $C_1$-$C_6$ alkyl; and $R^N$ is H or $-CH_2-Ar$; wherein Ar is 6- to 12-membered heterocyclyl or $C_6$-$C_{12}$ aryl optionally substituted by F, Cl, Br, I, OH, $C_1$-$C_6$ alkoxy, or phenyl; and $R^a$ is H or $C_1$-$C_6$ alkyl, and $R^b$ is H; or $R^a$ and $R^b$ together with the intervening atoms form a 3- to 6-membered cycloalkyl; or $R^N$ and $R^b$ together with the intervening atoms form a 4- to 8-membered heterocyclyl, and $R^a$ is H or $C_1$-$C_6$ alkyl; or a pharmaceutically acceptable salt, stereoisomer, hydrate, solvate, or isotopic derivative thereof.

Embodiment 2. The compound of embodiment 1, wherein $R^2$ is $C_1$-$C_6$ alkyl.

Embodiment 3. The compound of embodiment 1 or 2, wherein $R^2$ is methyl.

Embodiment 4. The compound of embodiment 1, wherein $R^2$ is H.

Embodiment 5. The compound of any one of embodiments 1-4, wherein $R^N$ is H.

Embodiment 6. The compound of any one of embodiments 1-4, wherein $R^N$ is $-CH_2-Ar$.

Embodiment 7. The compound of embodiment 1, having the structure of Formula (2) herein.

Embodiment 8. The compound of embodiment 1, having the structure of Formula (3) herein, wherein: X, Y, and Z are each independently H, F, Cl, Br, I, OH, $C_1$-$C_6$ alkoxy, or phenyl; or X and Y are taken together to form a 4- to 6-membered heterocyclyl, and Z is H, F, Cl, Br, I, OH, $C_1$-$C_6$ alkoxy, $C_3$-$C_6$ cycloalkyl, or phenyl; or Y and Z are taken together to form a 4- to 6-membered heterocyclyl, and X is H, F, Cl, Br, I, OH, $C_1$-$C_6$ alkoxy, $C_3$-$C_6$ cycloalkyl, or phenyl.

Embodiment 9. The compound of embodiment 8, wherein X is OH.

Embodiment 10. The compound of embodiment 8, wherein X is methoxy.

Embodiment 11. The compound of embodiment 8, wherein X is F, Cl, Br, or I.

Embodiment 12. The compound of embodiment 8, wherein X is phenyl.

Embodiment 13. The compound of embodiment 8, wherein X is $C_3$-$C_6$ cycloalkyl.

Embodiment 14. The compound of embodiment 8, or wherein X is cyclopropyl.

Embodiment 15. The compound of any one of embodiments 8-14, wherein Y and Z are H.

Embodiment 16. The compound of embodiment 8, wherein X and Y are taken together to form

(methylenedioxy), wherein * and ** indicate the points of connection between X and the rest of the compound, and between Y and the rest of the compound, respectively.

Embodiment 17. The compound of embodiment 8, wherein X and Y are taken together to form a dihydrofuranyl.

Embodiment 18. The compound of embodiment 17, wherein X and Y are taken together to for

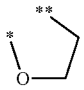 or 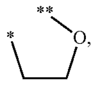

wherein * and ** indicate the points of connection between X and the rest of the compound, and between Y and the rest of the compound, respectively.

Embodiment 19. The compound of embodiment 8, wherein X and Y are taken together to form a furanyl.

Embodiment 20. The compound of embodiment 19, wherein X and Y are taken together to form

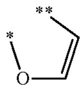 or 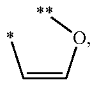

wherein * and ** indicate the points of connection between X and the rest of the compound, and between Y and the rest of the compound, respectively.

Further exemplary embodiments include those wherein, instead of X and Y being taken together to form the 4- to 6-membered heterocyclyl, Y and Z are taken together to form the 4- to 6-membered heterocyclyl.

Embodiment 21. The compound of any one of embodiments 1-20, wherein $R^a$ is H.

Embodiment 22. The compound of any one of embodiments 1-20, wherein $R^a$ is $C_1$-$C_6$ alkyl.

Embodiment 23. The compound of embodiment 22, wherein $R^a$ is methyl.

Embodiment 24. The compound of embodiment 22, wherein $R^a$ is ethyl.

Embodiment 25. The compound of any one of embodiments 1-24, wherein $R^4$ is F, Cl, Br, or I.

Embodiment 26. The compound of any one of embodiments 1-25, wherein $R^4$ is Br.

Embodiment 27. The compound of any one of embodiments 1-25, wherein $R^4$ is I.

Embodiment 28. The compound of any one of embodiments 1-24, wherein $R^4$ is $C_1$-$C_6$ alkyl.

Embodiment 29. The compound of embodiment 28, wherein $R^4$ is ethyl.

Embodiment 30. The compound of embodiment 28, wherein $R^4$ is isobutyl.

Embodiment 31. The compound of any one of embodiments 1-24, wherein $R^4$ is $-(CH_2)_{0-3}-C(O)-O-C_1$-$C_6$ alkyl.

Embodiment 32. The compound of embodiment 31, wherein $R^4$ is $-CH_2COOCH_3$.

Embodiment 33. The compound of embodiment 31, wherein $R^4$ is $-CH_2COOCH_2CH_3$.

Embodiment 34. The compound of any one of embodiments 1-24, wherein $R^4$ is $C_1$-$C_6$ alkenyl.

Embodiment 35. The compound of embodiment 34, wherein $R^4$ is allyl.

Embodiment 36. The compound of any one of embodiments 1-24, wherein $R^4$ is $C_1$-$C_6$ alkynyl.

Embodiment 37. The compound of embodiment 36, wherein $R^4$ is propargyl.

Embodiment 38. The compound of any one of embodiments 1-37, wherein $R^5$ is H.

Embodiment 39. The compound of any one of embodiments 1-38, wherein $R^5$ is $C_1$-$C_6$ alkyl.

Embodiment 40. The compound of embodiment 39, wherein $R^5$ is methyl.

Embodiment 41. A compound selected from Table 1 herein, or a pharmaceutically acceptable salt, stereoisomer, hydrate, solvate, or isotopic derivative thereof.

Embodiment 42. A compound selected from the group consisting of (herein, "Group A" compounds):

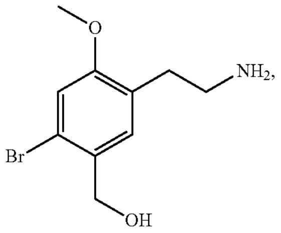
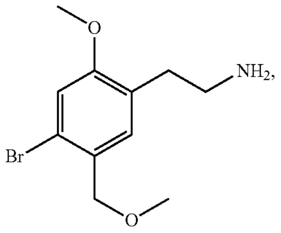
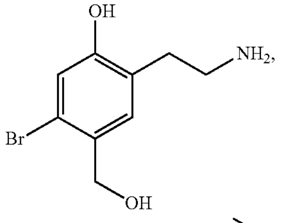
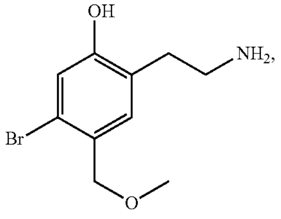
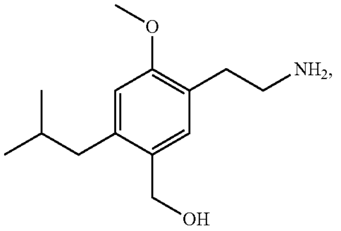

-continued
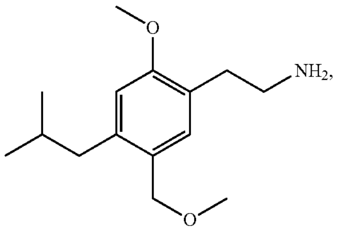
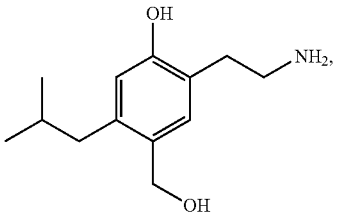
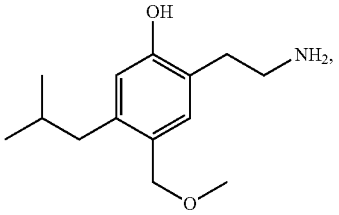
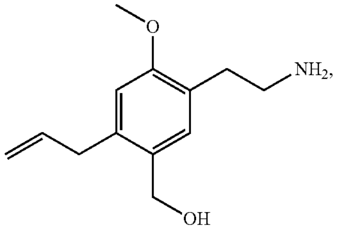
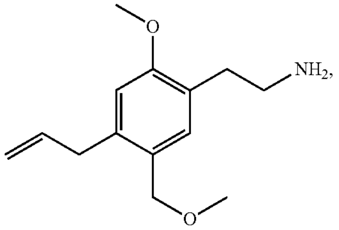
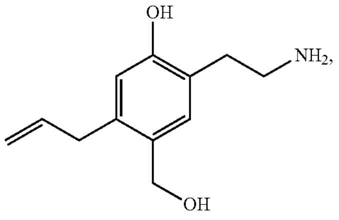
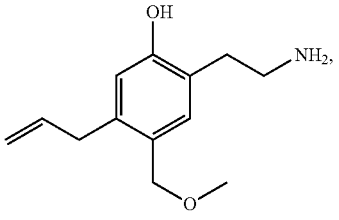
-continued
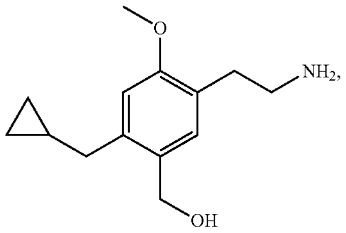
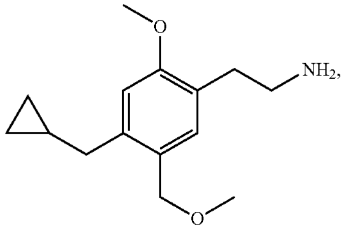
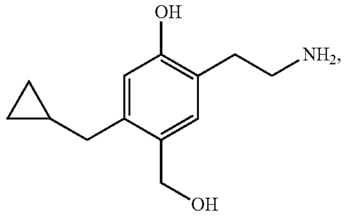
and
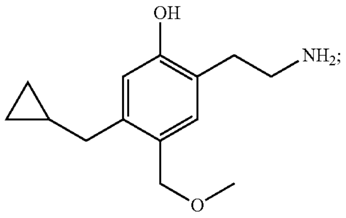
or a pharmaceutically acceptable salt, stereoisomer, hydrate, solvate, or isotopic derivative thereof.
Embodiment 43. A compound selected from the group consisting of (herein, "Group B" compounds):
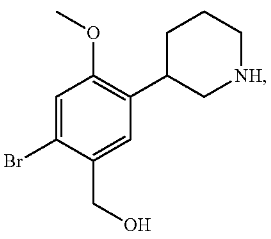
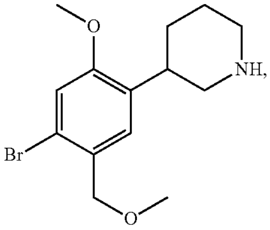
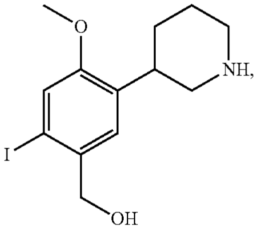
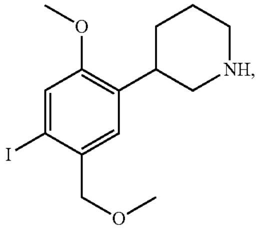

-continued
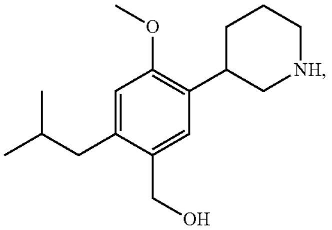
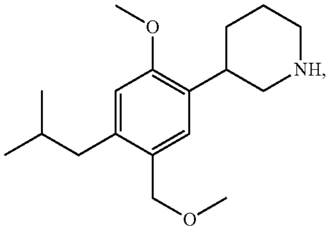
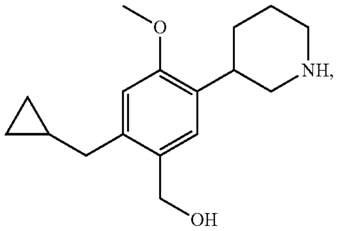
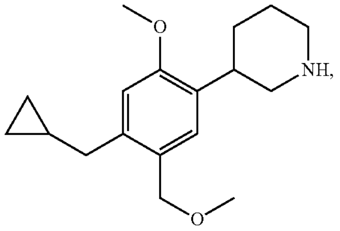
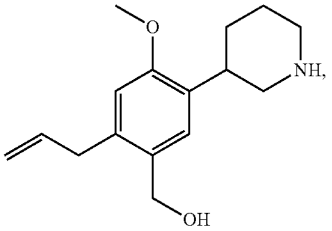
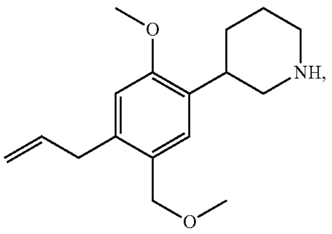
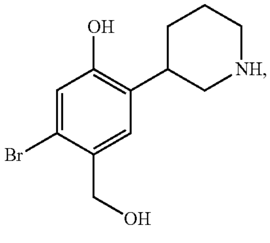
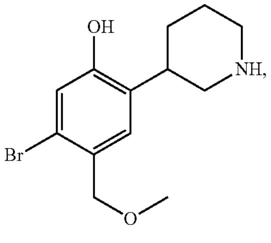
-continued
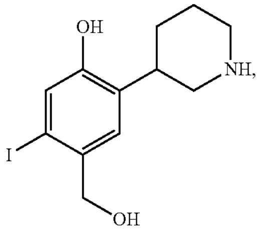
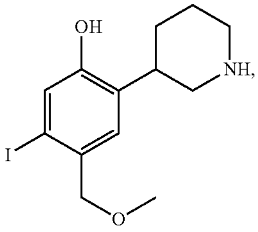
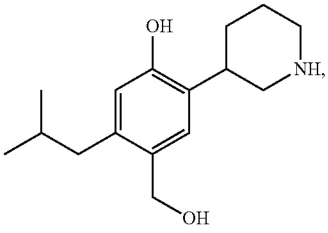
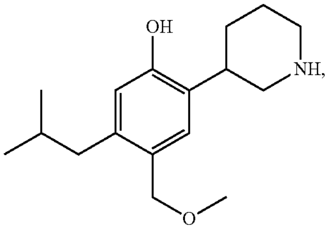
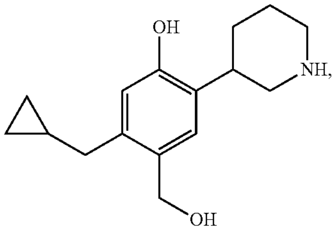
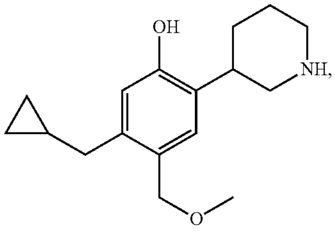
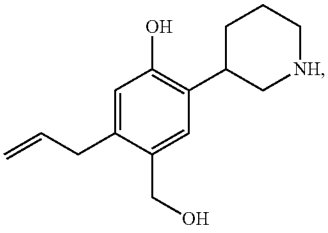
and
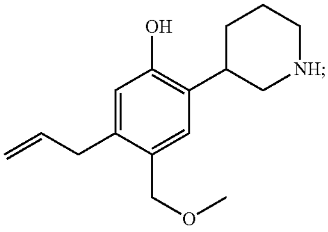 [SMILES: C=CCc1cc(O)c(C2CCCNC2)cc1COC]
or a pharmaceutically acceptable salt, stereoisomer, hydrate, solvate, or isotopic derivative thereof.

Embodiment 44. A compound selected from the group consisting of (herein, "Group C" compounds):

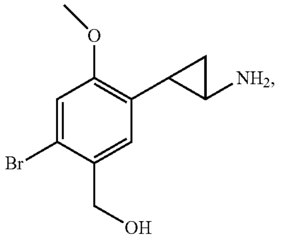

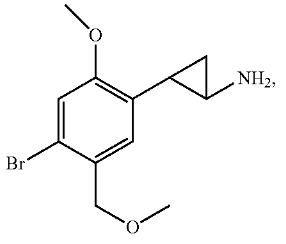

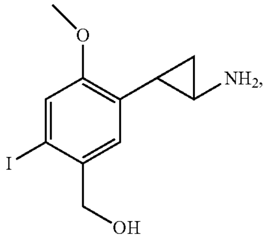

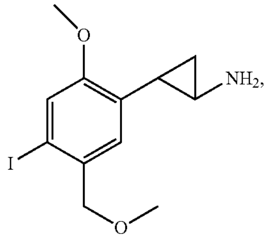

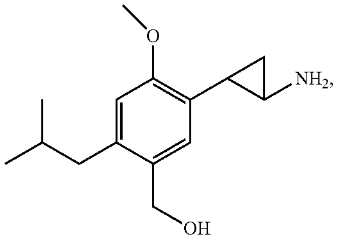

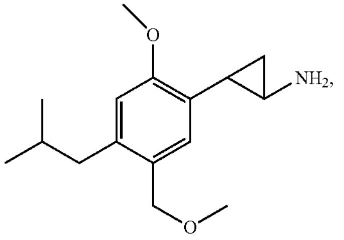

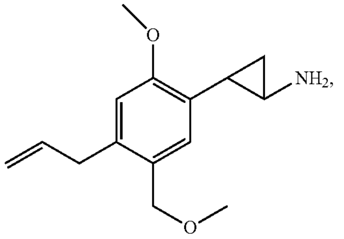

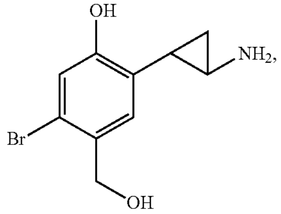

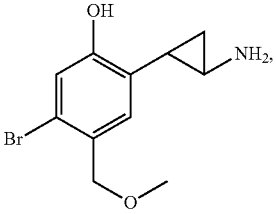

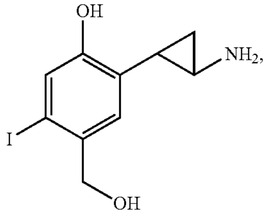

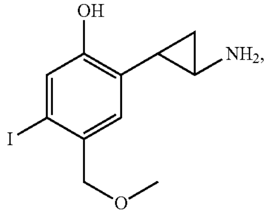

-continued

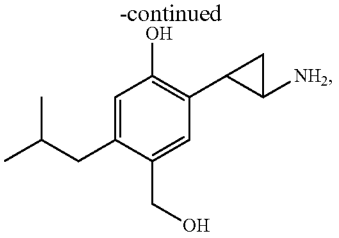

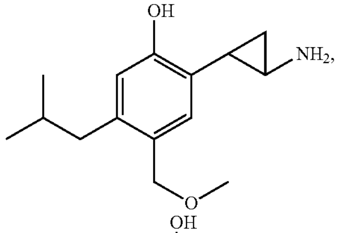

and

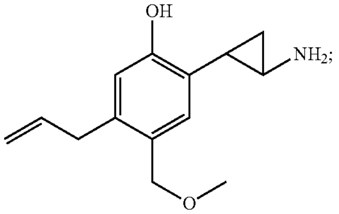

or a pharmaceutically acceptable salt, stereoisomer, hydrate, solvate, or isotopic derivative thereof.

Embodiment 44.1. The compound of anyone of embodiments 1-44, wherein the compound has aqueous solubility of at least about 100 mM.

Embodiment 44.2. The compound of any one of embodiments 1-44.1, wherein the compound has a molar extinction coefficient (MEC) at its Amax (maximum absorbance wavelength) of below about 1,000 $L \cdot mol^{-1} \cdot cm^{-1}$, below about 800 $L \cdot mol^{-1} \cdot cm^{-1}$, below about 400 $L \cdot mol^{-1} \cdot cm^{-1}$, or below about 300 $L \cdot mol^{-1} \cdot cm^{-1}$.

Embodiment 44.3. The compound of any one of embodiments 1-44.2, wherein the compound does not induce head twitch response in a rodent administered at least about 10 mg/kg of the compound.

Embodiment 44.4. The compound of any one of embodiments, 1-44.3, wherein the compound has an affinity selectivity of about 5-fold, 10-fold, or 20-fold for the $5\text{-}HT_{2A}$ receptor over the $5\text{-}HT_{2B}$ receptor.

Embodiment 45. A pharmaceutical composition comprising a therapeutically effective amount of the compound of any one of embodiments 1-44.4, and a pharmaceutically acceptable carrier, diluent, or excipient.

Embodiment 46. The composition of embodiment 45, suitable for oral, buccal, sublingual, intranasal, injectable, subcutaneous, intravenous, intraocular, topical, or transdermal administration.

Embodiment 47. The composition of embodiment 45 or 46, in unit dosage form.

Embodiment 48. The composition of embodiment 47, comprising the compound in a total amount of between about 0.01 and 100 mg.

Embodiment 49. The composition of any one of embodiments 45-48, formulated for topical administration.

Embodiment 50. The composition of embodiment 49, formulated as an aerosol, emulsion, spray, ointment, salve, gel, paste, lotion, liniment, oil, or cream.

Embodiment 51. The composition of embodiment 49 or 50, comprising one or more pharmaceutically acceptable excipients selected from the group consisting of penetration enhancers, carriers, diluents, emulsifiers, stabilizers, solvents and cosolvents, viscosity modifying agents (e.g., thickeners), adhesion modifying agents (e.g., tackifiers), preservatives, antioxidants, adhesive polymers, solubilizing agents, colorants, binders, humectants, surfactants, and gelling agents.

Embodiment 52. The composition of anyone of embodiments 45-51, further comprising a therapeutically effective amount of an additional active compound, or a pharmaceutically acceptable salt, solvate, or stereoisomer thereof.

Embodiment 53. The composition of embodiment 52, wherein the additional active compound is selected from the group consisting of amino acids, antioxidants, anti-inflammatory agents, analgesics, antineuropathic and antinociceptive agents, antimigraine agents, anxiolytics, antidepressants, antipsychotics, anti-PTSD agents, dissociatives, cannabinoids, immunostimulants, anti-cancer agents, antiemetics, orexigenics, antiulcer agents, antihistamines, antihypertensives, anticonvulsants, antiepileptics, bronchodilators, neuroprotectants, nootropics, empathogens, psychedelics, plasticity-inducing agents, monoamine oxidase inhibitors, tryptamines, terpenes, phenethylamines, sedatives, stimulants, serotonergic agents, NMDA modulators, NMDA antagonists, and vitamins.

Embodiment 54. A method of modulating neurotransmission in a subject, comprising administering to the subject the compound of any one of embodiments 1-44.4, or the composition of any one of embodiments 45-53.

Embodiment 55. The method of embodiment 54, wherein modulating neurotransmission comprises agonizing the $5\text{-HT}_{2A}$ or $5\text{-HT}_{2C}$ receptor.

Embodiment 56. A method of increasing neuroplasticity in a subject, comprising administering thereto the compound of any one of embodiments 1-44.4, or the composition of any one of embodiments 45-53.

Embodiment 57. A method of treating a medical condition in a subject in need of such treatment, the method comprising administering to the subject a therapeutically effective amount of the compound of any one of embodiments 1-44, or the composition of any one of embodiments 45-53.

Embodiment 58. The method of embodiment 57, wherein the medical condition is a disorder linked to dysregulation or inadequate functioning of serotonergic neurotransmission.

Embodiment 59. The method of embodiment 57 or 58, wherein the medical condition comprises a mental, behavioral, or neurodevelopmental disorder.

Embodiment 60. The method of embodiment 59, wherein the medical condition comprises a neurodevelopmental disorder, schizophrenia or another primary psychotic disorder, catatonia, a mood disorder, an anxiety or fear-related disorders, an obsessive-compulsive or related disorder, a disorder specifically associated with stress, a dissociative disorder, a feeding or eating disorder, an elimination disorder, a disorder of bodily distress or bodily experience, a disorder due to substance use or addictive behavior, an impulse control disorder, a disruptive behavior or dissocial disorder, a personality disorder, a paraphilic disorder, a factitious disorder, a neurocognitive disorder, a mental or behavioral disorder associated with pregnancy, childbirth or the puerperium, a sleep-wake disorder, or a sexual dysfunction.

Embodiment 61. The method of any one of embodiments 57-60, wherein the compound is administered together with one or more sessions of psychotherapy.

Embodiment 62. The method of embodiment 57, wherein the medical condition comprises inflammation or an inflammatory disorder.

Embodiment 63. The method of embodiment 62, wherein inflammation comprises skin inflammation, muscle inflammation, tendon inflammation, ligament inflammation, bone inflammation, cartilage inflammation, lung inflammation, heart inflammation, liver inflammation, pancreatic inflammation, kidney inflammation, bladder inflammation, gastric inflammation, intestinal inflammation, neuroinflammation, ocular inflammation, or brain inflammation.

Embodiment 64. The method of embodiment 62 or 63, wherein the inflammatory disorder comprises an acute inflammatory disorder.

Embodiment 65. The method of embodiment 62 or 63, wherein the inflammatory disorder comprises a chronic inflammatory disorder.

Embodiment 66. The method of any one of embodiments 62-65, wherein the inflammatory disorder comprises a steroid-resistant disorder.

Embodiment 67. The method of embodiment 62, wherein the inflammatory disorder is selected from the group consisting of asthma, chronic obstructive pulmonary disease, neuroinflammation, rheumatoid arthritis, atherosclerosis, psoriasis, type II diabetes, inflammatory bowel disease, Crohn's disease, multiple sclerosis, septicemia, conjunctivitis, and Alzheimer's disease.

Embodiment 68. The method of embodiment 67, wherein the inflammatory disorder comprises dermatitis.

Embodiment 69. The method of embodiment 68, wherein dermatitis comprises atopic dermatitis, chronic photosensitivity dermatitis, eczema, atopic eczema, contact eczema, dryness eczema, seborrheic eczema, discoid eczema, varicose eczema, herpetic dermatitis, neurodermatitis, autosensitizing dermatitis, stasis dermatitis, purulent dermatitis, dyshidrotic eczema, follicular eczema, spongiotic dermatitis, hand dermatitis, diaper dermatitis, occupational contact dermatitis, or lichen planus-like atopic dermatitis.

Embodiment 70. The method of anyone of embodiments 62-69, wherein the subject has a compromised immune system.

Embodiment 71. The method of anyone of embodiments 62-70, wherein the subject has an autoimmune disorder.

Embodiment 72. The method of any one of embodiments 62-71, wherein the subject has a contraindication to a corticosteroid.

Embodiment 73. The method of any one of embodiments 62-72, wherein treating inflammation or an inflammatory disorder comprises reducing the level of an inflammatory biomarker by about 1%, 5%, 10%, 20%, 30%, 40%, 50%, 60%, 70%, 80%, 90%, 95%, or 100%.

Embodiment 74. The method of embodiment 73, wherein the inflammatory biomarker comprises an inflammatory response gene product.

Embodiment 75. The method of embodiment 74, wherein the inflammatory response gene product comprises mRNA.

Embodiment 76. The method of embodiment 73, wherein the mRNA encodes Arg-1, ICAM1, VCAM1, MCP1, IL-6, IL-1β, GM-SCF, IL-5, IL-9, IL-15, Muc5ac, MMP9, or TGF-β.

Embodiment 77. The method of embodiment 76, wherein the inflammatory response gene product comprises a protein.

Embodiment 78. The method of embodiment 77, wherein the protein comprises Arg-1, ICAM1, VCAM1, MCP1, IL-6, IL-1β, GM-CSF, IL-5, IL-9, IL-15, Muc5ac, MMP9, or TGF-β.

Embodiment 79. The method of any one of embodiments 57-78, wherein the medical condition comprises an ophthalmic disorder.

Embodiment 80. The method of embodiment 79, wherein the ophthalmic disorder comprises an inflammatory disorder.

Embodiment 81. The method of any one of embodiments 57, 79, or 80, wherein the medical condition comprises macular degeneration, keratoconjunctivitis, conjunctivitis, keratitis, diabetic retinopathy, retinopathy of prematurity, polypoidal choroidal vasculopathy, ischemic proliferative retinopathy, retinitis pigmentosa, cone dystrophy, proliferative vitreoretinopathy, retinal artery occlusion, retinal vein occlusion, Leber's disease, retinal detachment, retinal pigment epithelial detachment, rubeosis iridis, corneal neovascularization, retinal neovascularization, choroidal neovascularization, or retinochoroidal neovascularization.

Embodiment 82. The method of any one of embodiments 57-81, wherein the medical condition comprises a neurodegenerative disorder.

Embodiment 83. The method of embodiment 82, wherein the neurodegenerative disorder is selected from the group consisting of Alzheimer's disease, amyotrophic lateral sclerosis or Charcot's disease, chronic traumatic encephalopathy, corticobasal degeneration, dementias including vascular dementia, Huntington's disease, Lytico-Bodig disease, mild cognitive impairment, multiple sclerosis, a motor neuron disease, neuromyelitis optica spectrum disorder, Parkinson's disease or Parkinsonisms, prion diseases, progressive supranuclear palsy, and traumatic brain injury.

Embodiment 84. A compound of any one of embodiments 1-44.4, or the composition of any one of embodiments 45-53, for use in the treatment of a medical condition.

Embodiment 85. Use of the compound of any one of embodiments 1-44.4, or the composition of any one of embodiments 45-53, for the manufacture of a medicament for the treatment of a medical condition.

The foregoing description, for purposes of explanation, uses specific nomenclature to provide a thorough understanding of the invention. However, it will be apparent to one skilled in the art that specific details are not required in order to practice the invention. Thus, the foregoing description of specific embodiments of the invention is presented for purposes of illustration and description. It is not intended to be exhaustive or to limit the invention to the precise compositions, formulations, methods, or the like disclosed; many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A compound having the following structure:

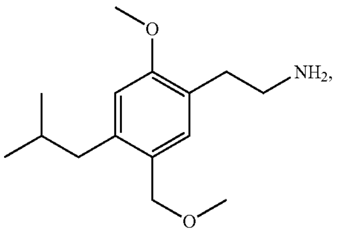 [SMILES: COCc1cc(CCN)c(OC)cc1CC(C)C]

or a pharmaceutically acceptable salt, hydrate, solvate, or isotopic derivative thereof.

2. A pharmaceutical composition comprising a therapeutically effective amount of the compound of claim 1, and a pharmaceutically acceptable carrier, diluent, or excipient.

3. The pharmaceutical composition of claim 2, wherein the composition is suitable for oral, buccal, sublingual, intranasal, injectable, subcutaneous, intravenous, topical, transdermal, ocular, ophthalmic, intraocular, or periocular administration.

4. The pharmaceutical composition of claim 2, wherein the composition is in a unit dosage form.

5. The pharmaceutical composition of claim 4, comprising the compound in a total amount of between about 0.01 mg and about 100 mg.

6. The pharmaceutical composition of claim 3, formulated for injectable administration.

7. The pharmaceutical composition of claim 3, formulated for topical administration.

8. The pharmaceutical composition of claim 3, formulated for ophthalmic administration.

9. The pharmaceutical composition of claim 3, formulated for intraocular administration.

* * * * *